US008338576B2

(12) United States Patent
Paralkar et al.

(10) Patent No.: US 8,338,576 B2
(45) Date of Patent: Dec. 25, 2012

(54) ANTIBODIES SPECIFIC FOR DKK-1 AND THEIR USES

(75) Inventors: Vishwas Madhav Paralkar, Madison, CT (US); Donna Marie Stone, Brisbane, CA (US); Mei Li, Westerly, RI (US); Jaume Pons, San Bruno, CA (US)

(73) Assignees: Rinat Neuroscience Corp., South San Francisco, CA (US); Pfizer Inc., New York, NY (US)

( * ) Notice: Subject to any disclaimer, the term of this patent is extended or adjusted under 35 U.S.C. 154(b) by 268 days.

(21) Appl. No.: 12/777,806

(22) Filed: May 11, 2010

(65) Prior Publication Data
US 2010/0291076 A1    Nov. 18, 2010

Related U.S. Application Data

(60) Provisional application No. 61/177,650, filed on May 12, 2009, provisional application No. 61/244,638, filed on Sep. 22, 2009.

(51) Int. Cl.
C07K 16/00 (2006.01)
C12P 21/08 (2006.01)
A61K 39/395 (2006.01)

(52) U.S. Cl. ............... 530/388.1; 530/387.1; 424/130.1; 424/141.1

(58) Field of Classification Search .................. None
See application file for complete search history.

(56) References Cited

U.S. PATENT DOCUMENTS

| | | | |
|---|---|---|---|
| 6,344,541 B1 | 2/2002 | Bass et al. |
| 6,673,549 B1 | 1/2004 | Furness et al. |
| 6,844,422 B1 | 1/2005 | Niehrs et al. |
| 6,916,648 B2 | 7/2005 | Goddard et al. |
| 6,962,797 B2 | 11/2005 | Goddard et al. |
| 7,057,017 B2 | 6/2006 | McCarthy |
| 7,138,508 B2 | 11/2006 | Niehrs et al. |
| 7,308,364 B2 | 12/2007 | Shaughnessy et al. |
| 7,371,736 B2 | 5/2008 | Shaughnessy |
| 7,446,181 B2 | 11/2008 | McCarthy |
| 7,459,437 B2 | 12/2008 | Shaughnessy |
| 7,579,168 B2 | 8/2009 | McCarthy |
| 7,642,238 B2 | 1/2010 | Shaughnessy |
| 7,645,451 B2 | 1/2010 | McCarthy |
| 7,668,659 B2 | 2/2010 | Shaughnessy et al. |
| 7,700,101 B2 | 4/2010 | Allen et al. |
| 7,709,611 B2 | 5/2010 | Li et al. |
| 7,723,478 B2 | 5/2010 | Bass et al. |
| 7,811,750 B2 | 10/2010 | Shaughnessy |
| 2002/0161178 A1 | 10/2002 | Bass et al. |
| 2003/0165501 A1 | 9/2003 | DeAlmeida et al. |
| 2003/0232364 A1 | 12/2003 | Shaughnessy et al. |
| 2005/0084494 A1 | 4/2005 | Prockop et al. |
| 2005/0196349 A1 | 9/2005 | Wu et al. |
| 2005/0227342 A1 | 10/2005 | Ashkenazi et al. |
| 2005/0261181 A1 | 11/2005 | Wu et al. |
| 2006/0127393 A1 | 6/2006 | Li et al. |
| 2007/0066558 A1 | 3/2007 | Shaughnessy |
| 2007/0077244 A1 | 4/2007 | Niehrs et al. |
| 2008/0085281 A1 | 4/2008 | Prockop et al. |
| 2008/0193449 A1 | 8/2008 | An et al. |
| 2008/0193515 A1 | 8/2008 | Shaughnessy et al. |
| 2008/0234139 A1 | 9/2008 | Shaughnessy et al. |
| 2008/0267950 A1 | 10/2008 | Shaughnessy et al. |
| 2008/0293578 A1 | 11/2008 | Shaughessy et al. |
| 2009/0092992 A1 | 4/2009 | McCarthy |
| 2010/0040619 A1 | 2/2010 | Li et al. |
| 2010/0216140 A1 | 8/2010 | McCarthy |
| 2010/0260754 A1 | 10/2010 | Chedid et al. |

FOREIGN PATENT DOCUMENTS

| | | |
|---|---|---|
| WO | WO-99/46281 A2 | 9/1999 |
| WO | WO-02/092015 A2 | 11/2002 |
| WO | WO-2005/112981 A2 | 12/2005 |
| WO | WO-2005/115354 A2 | 12/2005 |
| WO | WO-2007/084344 A2 | 7/2007 |
| WO | WO-2010/117980 A1 | 4/2010 |

OTHER PUBLICATIONS

Rudikoff, Giusti, Cook, and Sharff. Single amino acid substitution altering antigen-binding specificity. Proceedings of the National Academy of Science, 1982. vol. 79, p. 1979-1983.*

Mac Callum, Martin, and Thornton. Antibody-antigen interactions: contact analysis and binding site topography. Journal of Molecular Biology, 1996. vol. 262, pp. 732-745.*

De Pascalis, Iwahashi, Tamura, Padlan, Gonzales, Santos, Giuliano, Schuck, Schlom, and Kashmiri. Grafting of abbreviated complementarity determining regions containing specificity determining residues essential for ligand contact to engineer a less immunogenic humanized monoclonal antibody. Journal of Immunology, 2002. vol. 169, pp. 3076-3084.*

Casset, Roux, Mouchet, Bes, Chardes, Granier, Mani, Pugniere, Laune, Pau, Kaczorek, Lahana, and Rees. A peptide mimetic of an anti-CD4 monoclonal antibody by rational design. Biochemical and Biophysical Research Communications, 2003. vol. 307, pp. 198-205.*

(Continued)

Primary Examiner — Anne Gussow
(74) Attorney, Agent, or Firm — Jenny J. Yeh

(57) ABSTRACT

The present invention provides antibodies and fragments thereof that bind to Dkk-1 and, in particular, to humanized antibodies and fragments thereof that bind to Dkk-1 and, even more particularly to fully humanized antibodies and immunologically functional fragments that bind to Dkk-1. Also provided are antibodies and fragments thereof which compete with the binding of an anti-mouse Dkk-1 monoclonal antibody for binding to Dkk-1+ cells. Also provided are nucleic acids encoding anti-Dkk-1 antibodies or fragments thereof, as well as expression vectors and host cells incorporating these nucleic acids for the recombinant expression of anti-Dkk-1 antibodies and fragments thereof. Also provided are methods of preparing the antibodies and fragments thereof of the invention. Also provided are bone anabolic agents. Pharmaceutical compositions comprising the antibodies or fragments thereof of the invention are also provided. Further provided are methods of treating diseases, conditions and disorders, such as bone disorders, which result in a loss of bone. Methods of treating or preventing a loss of bone mass, methods of inducing increased bone mass, and methods of inducing Wnt activity are also provided.

8 Claims, 18 Drawing Sheets

OTHER PUBLICATIONS

Chen, Wiesmann, Fuh, Li, Christinger, Mc Kay, De Vos, and Lowman. Selection and analysis of an optimized anti-VEGF antibody: crystal structure of an affinity matured Fab in complex with antigen. Journal of Molecular Biology, 1999. vol. 293, pp. 865-881.*

Wu, Nie, Huse, and Watkins. Humanization of a murine monoclonal antibody by simultaneous optimization of framework and CDR residues. Journal of Molecular Biology, 1999. vol. 294, pp. 151-162.*

Vajdos, Adams, Breece, Presta, De Vos, and Sidhu. Comprehensive functional maps of the antigen-binding site of an anti-ErbB2 antibody obtained by shotgun scanning mutagenesis. Journal of Molecular Biology, 2002. vol. 320, pp. 415-428.*

Holm, Jafari, and Sundstrom. Functional mapping and single chain construction of the anti-cytokeratin 8 monoclonal antibody TS1. Molecular Immunology, 2007. vol. 44, pp. 1075-1084.*

Boyden et al. (May 2002) "High Bone Density Due to a Mutation in LDL-Receptor-Related Protein 5," *N. Engl. J. Med.* 346:1513-1521.

Cadigan et al. (Feb. 2006) "Wnt Signaling: Complexity at the Surface," *J. Cell Sci.* 119(Pt3):395-402.

Diarra et al. (Sep. 2005) "Dickkopf-1 is a Master Regulator of Joint Remodeling ," *Nature Medicine* 13(2):156-163.

Fedi et al. (Jul. 1999) "Isolation and Biochemical Characterization of the Human Dkk-1 Homologue, a Novel Inhibitor of Mammalian Wnt Signaling," *J. of Biol. Chem.* 274(27):19465-19472.

Fulciniti et al. (Jul. 2009) "Anti-DKK1 mAb (BHQ880) as a Potential Therapeutic Agent for Multiple Myeloma," *Blood* 114(2):371-379.

Glinka et al. (Jan. 1998) "Dickkopf-1 is a Member of a New Family of Secreted Proteins and Functions in Head Induction," *Nature* 391(6665):357-362.

Gregory et al. (May 2003) "The Wnt Signaling Inhibitor Dickkopf-1 Is Required for Reentry into the Cell cycle of Human Adult Stem Cells from Bone Marrow," *J. of Biol. Chem.* 278(30): 28067-28078.

Gong et al. (Nov. 2001) "LDL Receptor-Related Protein 5 (LRP5) Affects Bone Accrual and Eye Development," *Cell* 107(4):513-523.

Heath et al. (Nov. 2008) "Inhibiting Dickkopf-1 (Dkk1) Removes Suppression of Bone Formation and Prevents the Development of Osteolytic Bone Disease in Multiple Myeloma," *J of Bone Miner Res* 24(3):425-436.

Hillier et al. (Sep. 1996) "Generation and Analysis of 280,000 Human Expressed Sequence Tags," *Genome Research* 6(9):807-828.

International Search Report mailed Jul. 28, 2010 for PCT Application No. PCT/IB2010/052056 filed May 10, 2010, nine pages.

Krupnik et al. (Oct. 1999) "Functional and Structural Diversity of the Human Dickkopf Gene Family," *Gene* 238(2):301-313.

Little et al. (Jan. 2002) "A Mutation in the LDL Receptor-Related Protein 5 Gene Results in the Autosomal Dominant High-Bone-Mass Trait," *Am. J. Hum. Genet.* 70(1):11-19.

Niehrs (Dec. 2006) "Function and Biological Roles of the Dickkopf Family of Wnt Modulators," *Oncogene* 25(57):7469-7481.

Nusse (Nov. 2003) "Wnts and Hedgehogs: Lipid-Modified Proteins and Similarities in Signaling Mechanisms at the Cell Surface," *Development* 130(22):5297-5305.

Pinson et al. (Sep. 2000) "An LDL-Receptor-Related Protein Mediates Wnt Signalling in Mice," *Nature* 407(6803)535-8.

Tate et al. (1999) "Human Dickkopf as well as DAN Family Members, Cerbeus, and Gremlin, are Preferentially Expressed in Epithelial Malignant Cell Lines," *J. Biochem. Mol. Biol. & Biophys.* 3:239-242.

Terpos (Oct. 2006) "Antibodies to Dickkopf-1 Protein," *Expert Opin. Ther. Patents* 16(10):1453-1458.

Tian et al. (Dec. 2003) "The Role of the Wnt-Signaling Antagonist DKK1 in the Development of Osteolytic Lesions in Multiple Myeloma," *N. Engl. J. Med.* 349(26):2483-2494.

Yaccoby et al. (Mar. 2007) "Antibody-based Inhibition of DKK1 Suppresses Tumor-induced Bone Resorption and Multiple Myeloma Growth In Vivo," *Blood* 109(5):2106-2111.

Zhang et al. (Jun. 2004) "The LRP5 High-Bone-Mass G171V Mutation Disrupts LRP5 Interaction with Mesd," *Mol. Cell Biol.* 24(11):4677-4684.

International Preliminary Report on Patentability and Written Opinion of the International Searching Authority mailed Nov. 15, 2011 for PCT Application No. PCT/IB2010/052056 filed May 10, 2010, 7 pages.

* cited by examiner

Total BMD of Distal Femur

Bone Formation Rate of Distal Femur

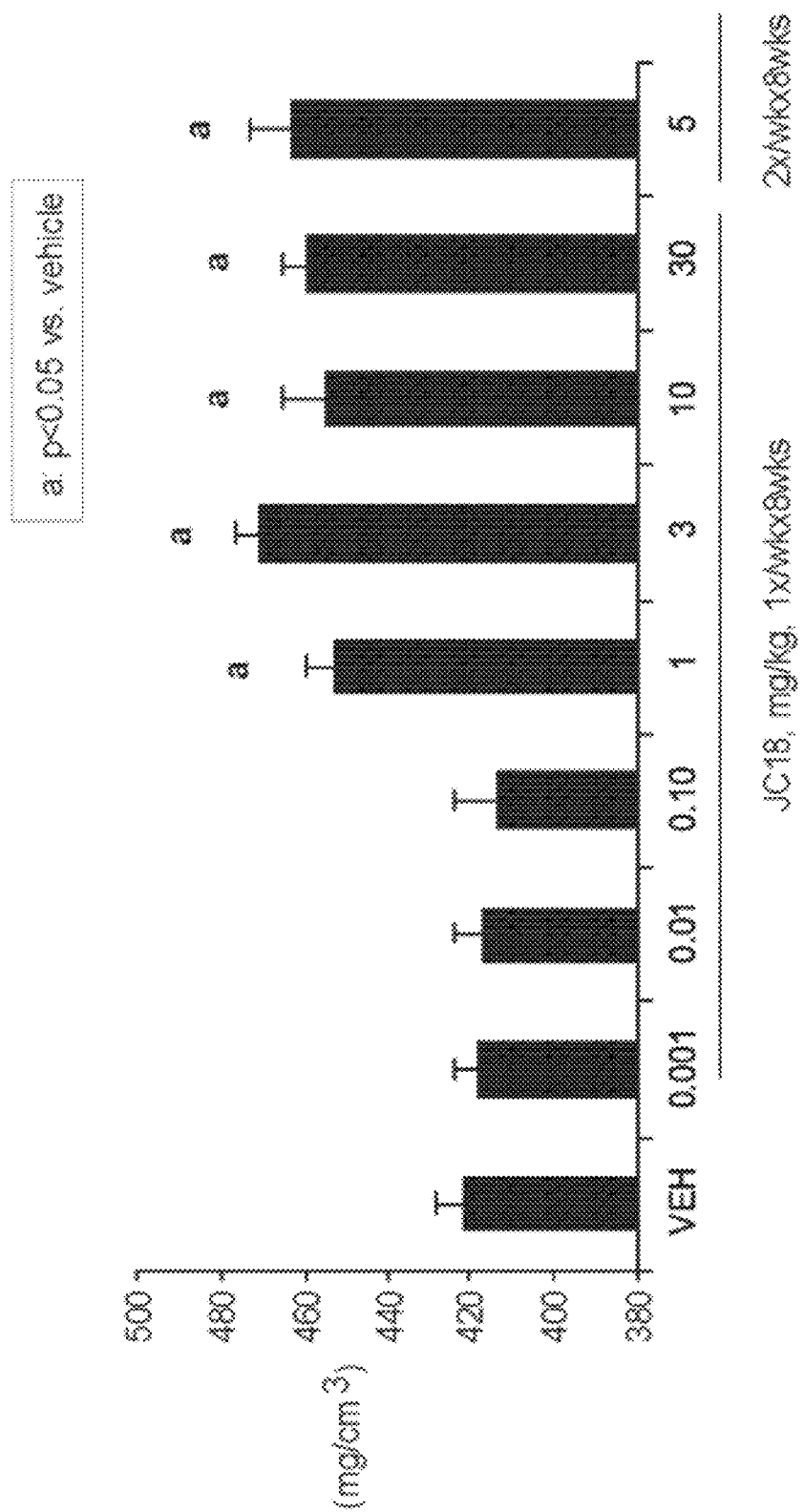

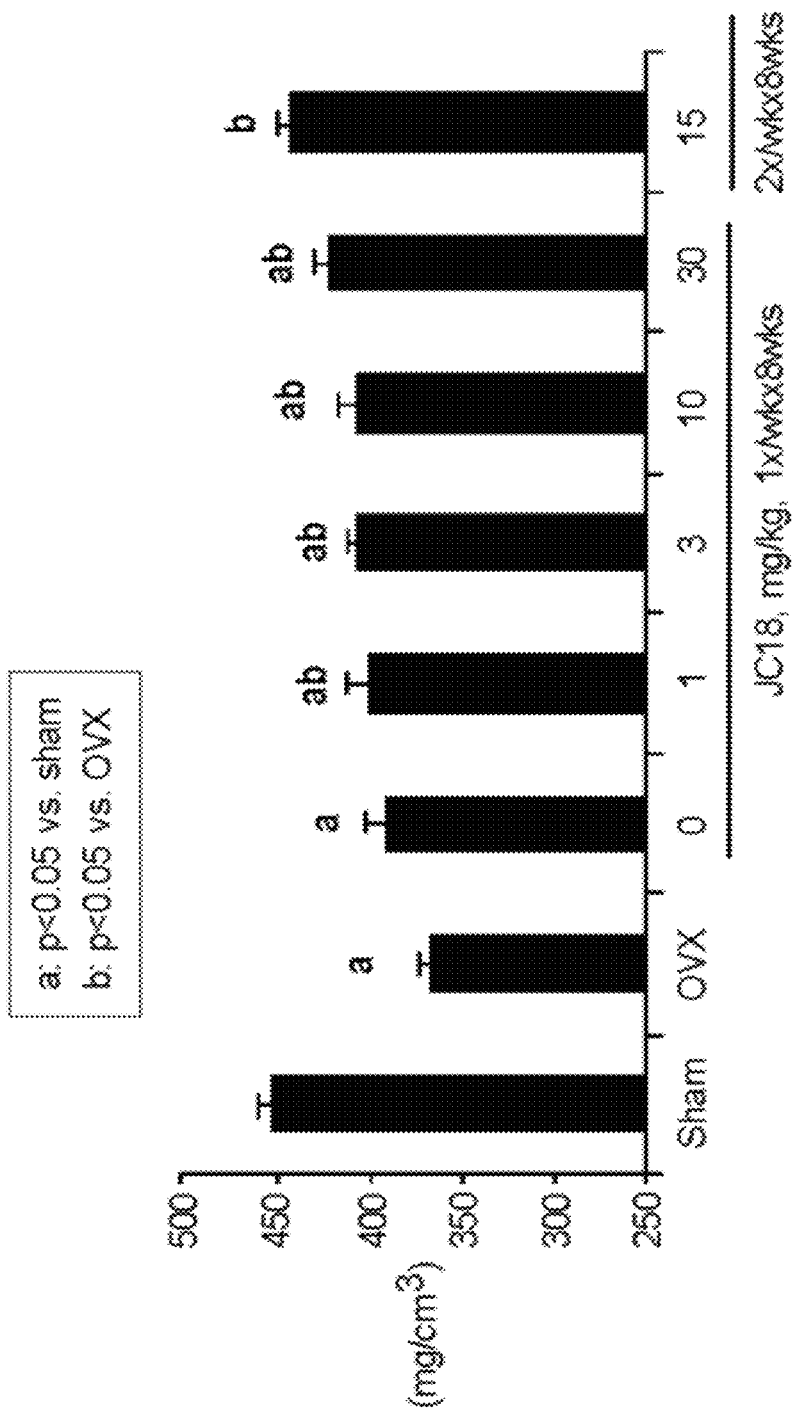

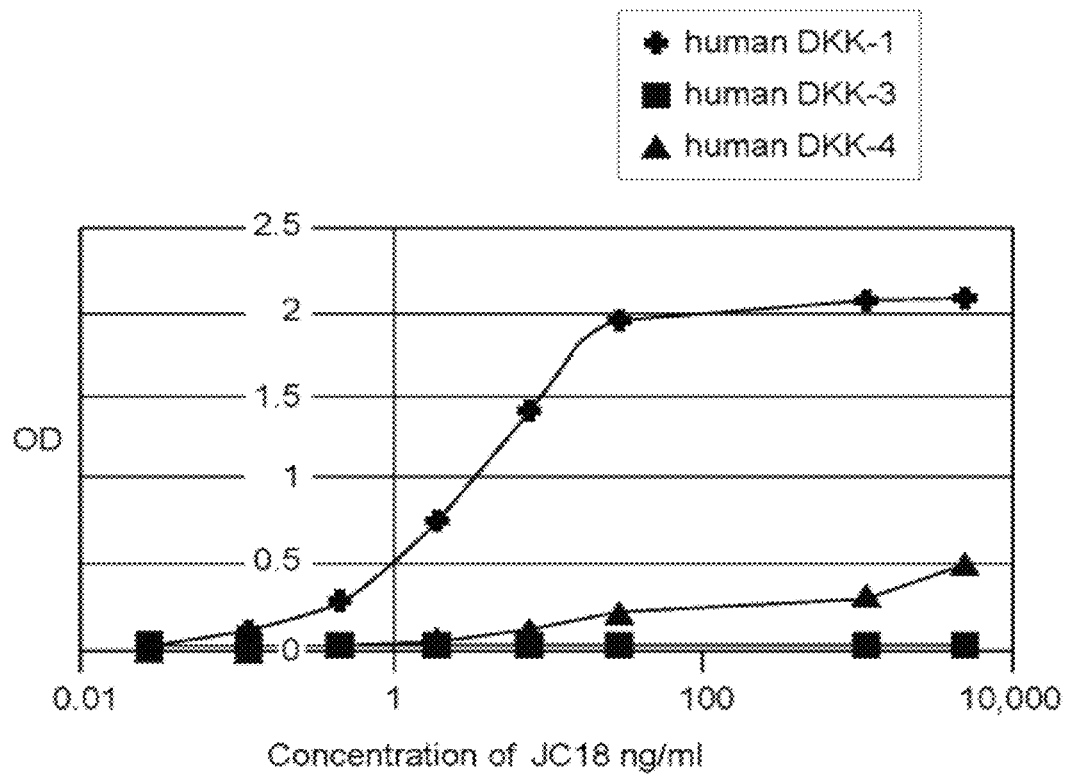

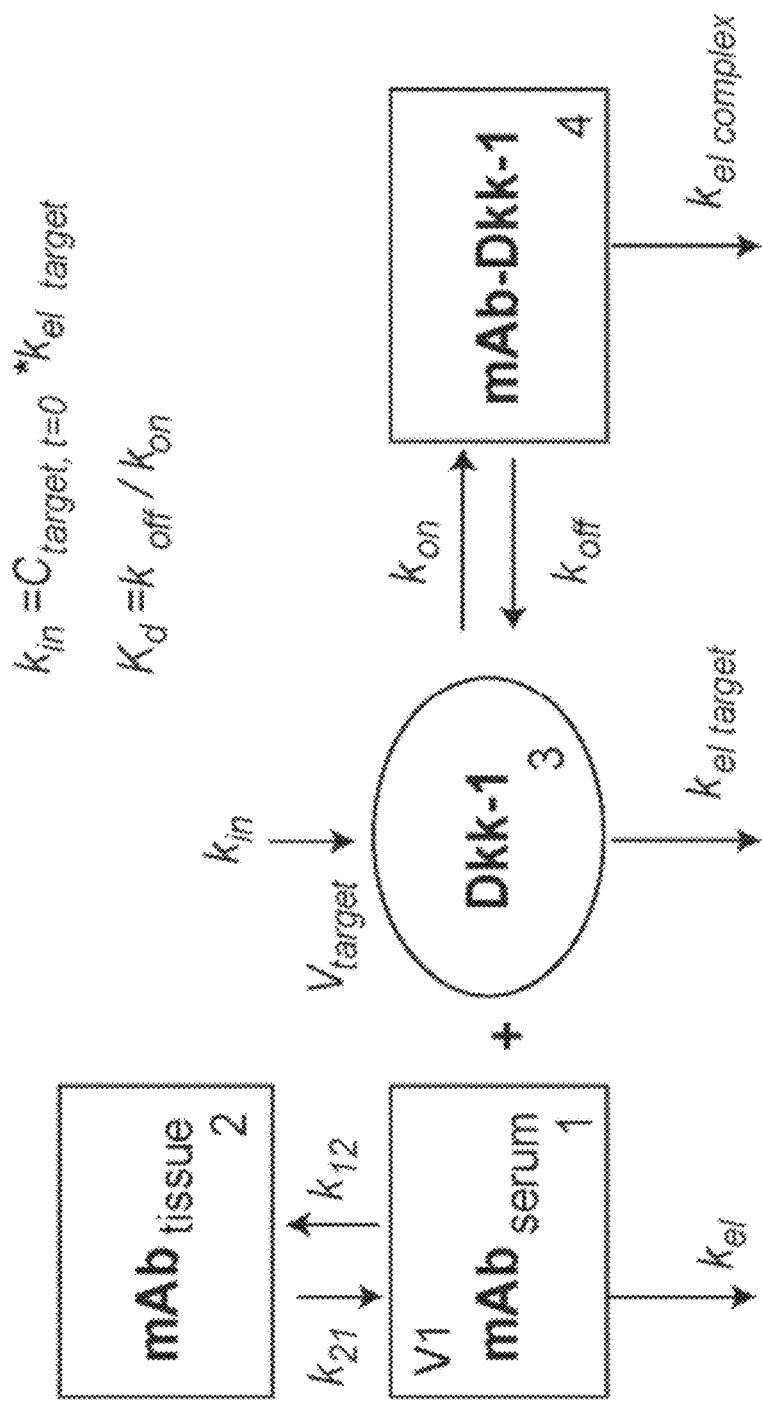

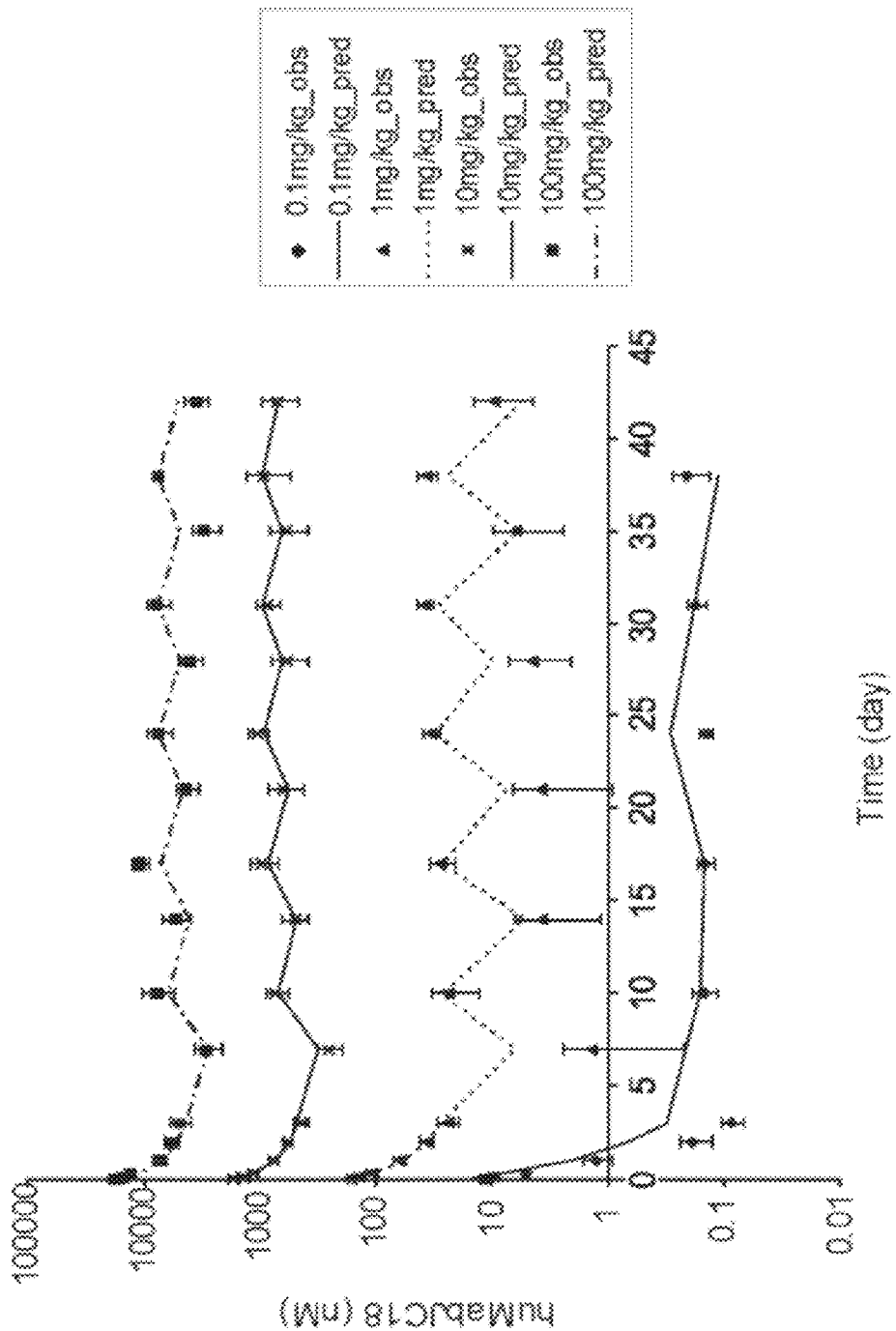

Vehicle

1mg/kg huMabJC18

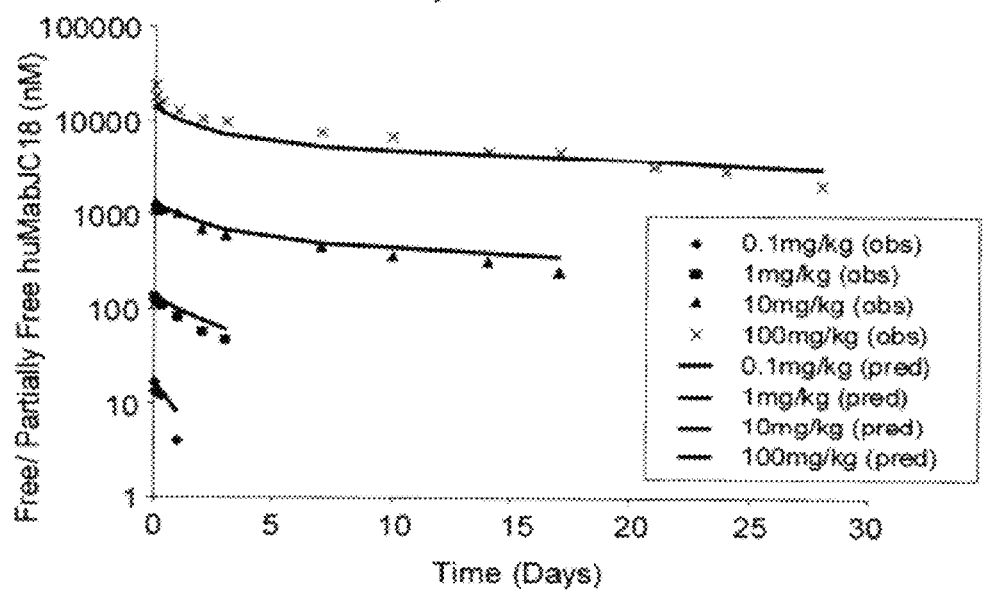
FIG. 9A Male Monkeys
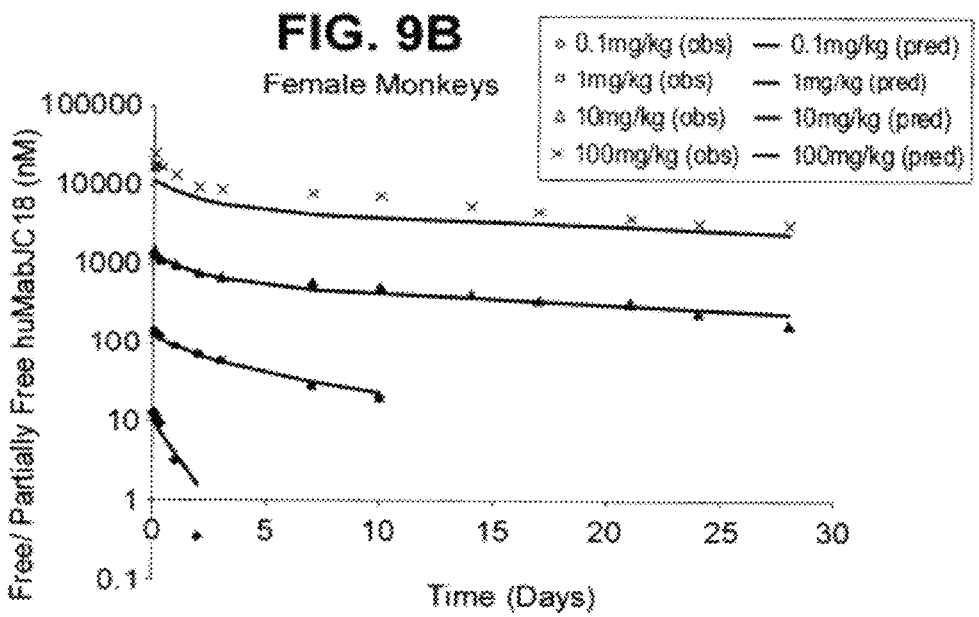
FIG. 9B Female Monkeys

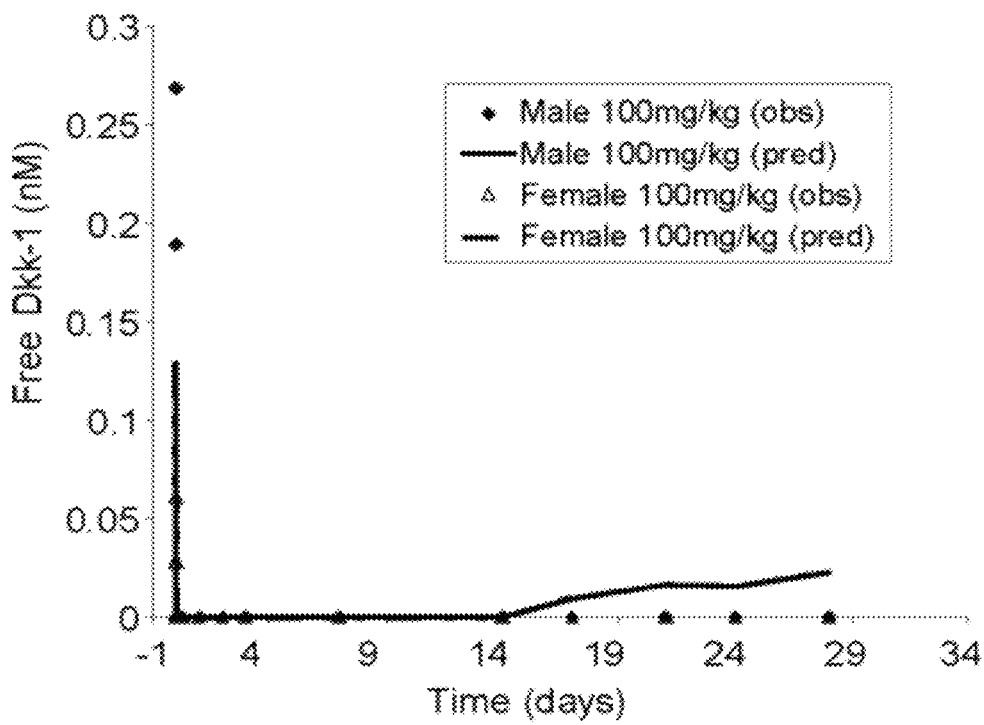
FIG. 10C  100mg/kg huMabJC18
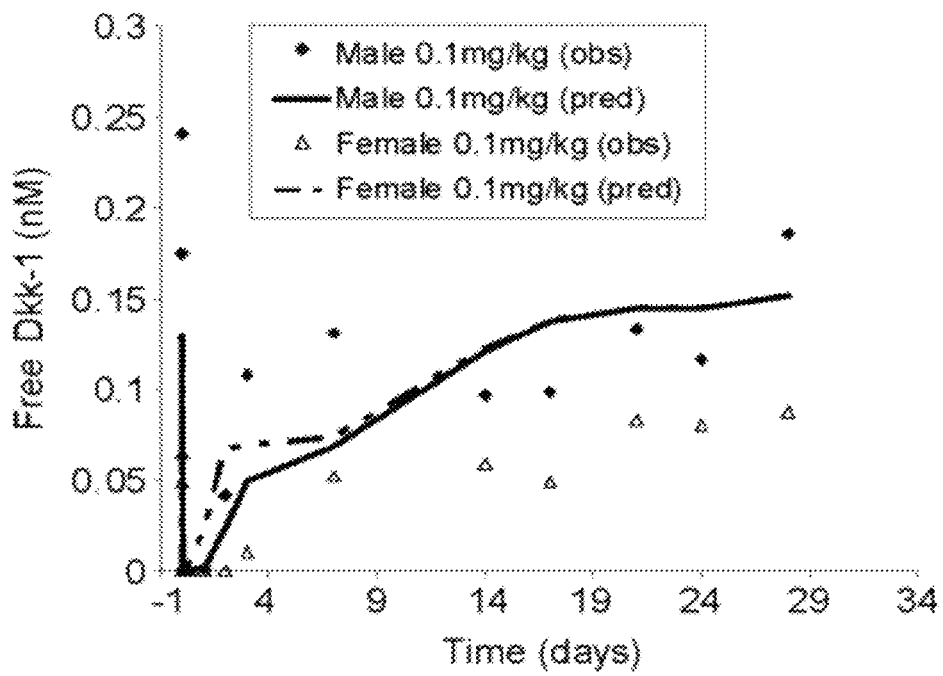
FIG. 10D  0.1mg/kg huMabJC18

ANTIBODIES SPECIFIC FOR DKK-1 AND THEIR USES

RELATED APPLICATIONS

This application claims the benefit of U.S. Provisional Application No. 61/177,650 filed May 12, 2009, and U.S. Provisional Application No. 61/244,638 filed Sep. 22, 2009, which are both hereby incorporated by reference in their entireties.

REFERENCE TO SEQUENCE LISTING

This application is being filed electronically via EFS-Web and includes an electronically submitted sequence listing in .txt format. The .txt file contains a sequence listing entitled "PC33877A_SequenceListing.txt" created on Mar. 9, 2010 and having a size of 42 KB. The sequence listing contained in this .txt file is part of the specification and is incorporated herein by reference in its entirety.

FIELD

The present invention relates to antibodies and fragments thereof that bind to Dkk-1 and, in particular, to humanized antibodies and fragments thereof that bind to Dkk-1 and, even more particularly to fully humanized antibodies and fragments that specifically bind to Dkk-1, in particular human Dkk-1. Nucleic acids encoding anti-Dkk-1 antibodies or fragments thereof, as well as expression vectors and host cells incorporating these nucleic acids for the recombinant expression of anti-Dkk-1 antibodies are provided. Also provided are bone anabolic agents. Pharmaceutical compositions comprising the antibodies or fragments thereof of the invention are also provided. Further provided are methods of treating diseases, conditions and disorders, such as bone disorders, which result in a loss of bone. Methods of treating or preventing a loss of bone mass, methods of inducing increased bone mass, and methods of inducing Wnt activity are also provided.

BACKGROUND

Wnts are secreted glycoproteins that bind to and activate a receptor complex which includes low-density receptor related protein (LRP5/6) and frizzled proteins. Cadigan, K. M. and Y. I. Liu (2005) Journal of Cell Science 119, 395-402; Nusse, R. (2003) Development 130(22):5297-305; and Pinson, K. I. (2000) Nature 2000 407(6803):535-8.

It has been disclosed that Wnt/LRP5 regulates bone mass and, that, activation of the Wnt signaling pathway leads to accrual of bone mass. Boyden, L. M. et al. (2002) N Engl J Med 346:1513-1521; Little, R. D. et al. (2002) Am J Hum Genet 70:11-19; and Gong, Y. et al. (2001) Cell 107:513-523. Wnt signaling is tightly regulated by antagonists, which include secreted molecules such as Dickkopf 1 (Dkk-1). Tian, E. et al. (2003) N Engl J Med 349:2483-2494. The high bone mass (HBM) phenotype observed in humans was found to be due to a single point mutation in LRP5 (G171V) that inhibits the ability of Dkk-1 to bind LRP5. Zhang, Y. et al. (2004) Mol Cell Biol. 24(11):4677-84.

The critical role of Wnt signaling in bone formation and bone growth makes Dkk-1 a useful target for the treatment of diseases or conditions where increased osteoblastic activity (increased bone mass density, increased bone formation without a corresponding increase in bone resorption) would be advantageous to the patient, including, for example, by reducing the number of fractures that occur, e.g., as a result of untreated osteoporosis. WO2006/015373 (US2006/0127393) discloses antibodies to Dkk-1 to treat various diseases, including bone disorders. US2008/0193449 discloses antibodies specific for Dkk-1 which inhibit binding of Dkk-1 to LRP5, compositions comprising such antibodies for stimulating bone growth, and compositions comprising such antibodies for treating bone disorders such as osteoporosis.

There remains a need for new bone anabolic agents that antagonize Dkk-1 activity, thereby increasing osteoblastic activity, to treat diseases, conditions and disorders, such as osteoporosis, where such increased bone formation would be advantageous to the patient.

SUMMARY

The present invention relates to antibodies and fragments (e.g., antigen binding portions) thereof that bind to Dkk-1 and, in particular, to humanized antibodies and fragments thereof that bind to Dkk-1 and, even more particularly to fully humanized antibodies and immunologically functional fragments that bind to Dkk-1. The antibodies and fragments thereof antagonize the ability of Dkk-1 to inhibit Wnt activity. The antibodies and immunologically functional fragments thereof antagonize the ability of Dkk-1 to inhibit the Wnt signaling pathway in bone with a corresponding increase in bone mass. The antibodies and immunologically functional fragments thereof include antibodies with a naturally occurring structure, as well as polypeptides that have an antigen binding domain (e.g., domain antibody). The antibodies and immunologically functional fragments thereof can be used to treat a variety of diseases, conditions and disorders, including those relating to a loss of bone mass, such as osteoporosis. The antibodies and immunologically functional fragments thereof can also be used to treat diseases, conditions, or disorders relating to secondary bone loss, such as, bone loss resulting from or attendant to, for example, chronic treatment with corticosteroids, aromatase inhibitors, or thiazolidinethiones (TZDs); anorexia; or bone loss related to hypogonadism or renal osteodystrophy.

Some of the antibodies and functional fragments thereof that are provided include:

(a) one or more light chain (LC) complementarity determining regions (CDRs) selected from the group consisting of:
  (i) a CDR1 with at least 80% sequence identity to SEQ ID NO: 22;
  (ii) a CDR2 with at least 80% sequence identity to SEQ ID NO: 24; and
  (iii) a CDR3 with at least 80% sequence identity to SEQ ID NO: 26;

(b) one or more heavy chain (HC) complementarity determining regions (CDRs) selected from the group consisting of:
  (i) a CDR1 with at least 80% sequence identity to SEQ ID NO: 30, 49 or 50;
  (ii) a CDR2 with at least 80% sequence identity to SEQ ID NO: 32 or 51; and
  (iii) a CDR3 with at least 80% sequence identity to SEQ ID NO: 34 or 52; or (c) one or more CDRs of (a) and one or more CDRs of (b). Such antibodies and immunologically functional fragments thereof can specifically bind a Dkk-1 polypeptide. Some of these antibodies and immunologically functional fragments thereof include one, two, three, four, five or all six of the foregoing CDRs.

Conservative modifications of the provided sequences are also provided.

The LCs and HCs of further provided antibodies and immunologically functional fragments thereof have at least 90% sequence identity to the foregoing sequences.

Further provided are antibodies and immunologically functional fragments thereof that have a LC in which CDR1 has the amino acid sequence as set forth in SEQ ID NO: 22, CDR2 has the amino acid sequence as set forth in SEQ ID NO: 24 and/or CDR3 has the amino acid sequence as set forth in SEQ ID NO: 26.

Further provided are antibodies and immunologically functional fragments thereof that have a HC in which CDR1 has the amino acid sequence as set forth in SEQ ID NO: 30, 49 or 50, CDR2 has the amino acid sequence as set forth in SEQ ID NO: 32 or 51 and/or CDR3 has the amino acid sequence as set forth in SEQ ID NO: 34 or 52.

Further provided are antibodies and immunologically functional fragments thereof that have a LC in which CDR1 has the amino acid sequence as set forth in SEQ ID NO: 22, CDR2 has the amino acid sequence as set forth in SEQ ID NO: 24 and/or CDR3 has the amino acid sequence as set forth in SEQ ID NO: 26, and a HC in which CDR1 has the amino acid sequence as set forth in SEQ ID NO: 30, 49 or 50, CDR2 has the amino acid sequence as set forth in SEQ ID NO: 32 or 51 and/or CDR3 has the amino acid sequence as set forth in SEQ ID NO: 34 or 52.

Further provided are antibodies and immunologically functional fragments thereof that have a LC in which CDR1 has the amino acid sequence as set forth in SEQ ID NO: 22, CDR2 has the amino acid sequence as set forth in SEQ ID NO: 24 and CDR3 has the amino acid sequence as set forth in SEQ ID NO: 26, and a HC in which CDR1 has the amino acid sequence as set forth in SEQ ID NO: 30, 49 or 50, CDR2 has the amino acid sequence as set forth in SEQ ID NO: 32 or 51 and CDR3 has the amino acid sequence as set forth in SEQ ID NO: 34 or 52.

Also provided are antibodies and immunologically functional fragments thereof which include: (a) a LC variable region (VL) having at least 80% sequence identity with the sequence as set forth in SEQ ID NO: 20; (b) a HC variable region (VH) having at least 80% sequence identity with the sequence as set forth in SEQ ID NO: 28; or (c) a VL of (a) and VH of (b).

Also provided are antibodies and immunologically functional fragments thereof that are similar in structure but the VL has at least 90% sequence identity with the sequence as set forth in SEQ ID NO: 20 and the VH has at least 90% sequence identity with the sequence as set forth in SEQ ID NO: 28.

Also provided are antibodies and immunologically functional fragments thereof that are similar in structure but the VL has at least 95% sequence identity with the sequence as set forth in SEQ ID NO: 20 and the VH has at least 95% sequence identity with the sequence as set forth in SEQ ID NO: 28.

Also provided are antibodies and immunologically functional fragments thereof which include a VL that has the sequence as set forth in SEQ ID NO: 20 and the VH has the sequence as set forth in SEQ ID NO: 28.

Some of the antibodies and functional fragments thereof that are provided have a LC that comprises or consists of the amino acid sequence as set forth in SEQ ID NO: 38 or SEQ ID NO: 42, and/or a HC that comprises or consists of the amino acid sequence as set forth in SEQ ID NO: 36 or SEQ ID NO: 40.

Some of the antibodies and functional fragments thereof that are provided have a LC that consists of the amino acid sequence as set forth in SEQ ID NO: 38 or SEQ ID NO: 42, and a HC that consists of the amino acid sequence as set forth in SEQ ID NO: 36 or SEQ ID NO: 40.

Further provided are antibodies and immunologically functional fragments thereof that can compete with mouse MabJC18 for binding to Dkk-1$^+$ cells. In an embodiment the invention provides a humanized antibody or a fragment thereof, wherein said antibody or fragment specifically binds to human Dkk-1 antigen, wherein the CDRs of the LC variable region (CDR1, CDR2 and CDR3) and the CDRs of the HC variable region (CDR1, CDR2 and CDR3) have the following amino acid sequences and wherein the antibody or fragment can compete with mouse MabJC18 for binding to Dkk-1$^+$ cells: LC: (i) CDR1 (SEQ ID NO: 22), (ii) CDR2 (SEQ ID NO: 24) and (iii) CDR3 (SEQ ID NO: 26); and HC: (i) CDR1 (SEQ ID NO: 30, 49 or 50), (ii) CDR2 (SEQ ID NO: 32 or 51), and (iii) CDR3 (SEQ ID NO: 34 or 52).

The invention also provides a humanized antibody or a fragment thereof, wherein said antibody or fragment specifically binds to human DKK-1 antigen, wherein the complementarity determining regions (CDR1, CDR2 and CDR3) of the LC variable region and the complementarity determining regions (CDR1, CDR2 and CDR3) of the HC variable region have the following amino acid sequences: LC: (i) CDR1 (SEQ ID NO: 22), (ii) CDR2 (SEQ ID NO: 24) and (iii) CDR3 (SEQ ID NO: 26); and HC: (i) CDR1 (SEQ ID NO: 30, 49 or 50), (ii) CDR2 (SEQ ID NO: 32 or 51), and (iii) CDR3 (SEQ ID NO: 34 or 52), in which the variable domain framework of the LC contains the human IGKV3-11 germline framework and IGKJ4 region.

The invention also provides a humanized antibody or a fragment thereof, wherein said antibody or fragment specifically binds to human DKK-1 antigen, wherein the complementarity determining regions (CDR1, CDR2 and CDR3) of the LC variable region and the complementarity determining regions (CDR1, CDR2 and CDR3) of the HC variable region have the following amino acid sequences: LC: (i) CDR1 (SEQ ID NO: 22), (ii) CDR2 (SEQ ID NO: 24) and (iii) CDR3 (SEQ ID NO: 26); and HC: (i) CDR1 (SEQ ID NO: 30, 49 or 50), (ii) CDR2 (SEQ ID NO: 32 or 51), and (iii) CDR3 (SEQ ID NO: 34 or 52), in which the variable domain framework of the HC contains the human IGHV3-07 germline framework (with single back mutation: R100 to T) and IGHJ6 region.

The invention also provides a humanized antibody or a fragment thereof, wherein said antibody or fragment specifically binds to human DKK-1 antigen, wherein the complementarity determining regions (CDR1, CDR2 and CDR3) of the LC variable region and the complementarity determining regions (CDR1, CDR2 and CDR3) of the HC variable region have the following amino acid sequences: LC: (i) CDR1 (SEQ ID NO: 22), (ii) CDR2 (SEQ ID NO: 24) and (iii) CDR3 (SEQ ID NO: 26); and HC: (i) CDR1 (SEQ ID NO: 30, 49 or 50), (ii) CDR2 (SEQ ID NO: 32 or 51), and (iii) CDR3 (SEQ ID NO: 34 or 52), in which the variable domain framework of the LC contains the human IGKV3-11 germline framework and IGKJ4 region and the variable domain framework of the HC contains the human IGHV3-07 germline framework (with single back mutation: R100 to T) and IGHJ6 region.

Further provided are fusion proteins comprising one or more fragments or regions of the antibodies of the invention. In an embodiment a fusion polypeptide is provided that comprises at least 10 contiguous amino acids of the LC variable region as set forth in SEQ ID NO: 20 and/or at least 10 amino acids of the HC variable region as set forth in SEQ ID NO: 28.

In another embodiment, the fusion protein comprises a LC variable region as set forth in SEQ ID NO: 20 and/or a HC variable region as set forth in SEQ ID NO: 28.

In another embodiment the fusion polypeptide comprises one or more of:
(a) light chain (LC) complementarity determining regions (CDRs) selected from the group consisting of:
   (i) a CDR1 with at least 80% sequence identity to SEQ ID NO: 22;
   (ii) a CDR2 with at least 80% sequence identity to SEQ ID NO: 24; and
   (iii) a CDR3 with at least 80% sequence identity to SEQ ID NO: 26; or
(b) one or more heavy chain (HC) complementarity determining regions (CDRs) selected from the group consisting of:
   (i) a CDR1 with at least 80% sequence identity to SEQ ID NO: 30, 49 or 50;
   (ii) a CDR2 with at least 80% sequence identity to SEQ ID NO: 32 or 51; and
   (iii) a CDR3 with at least 80% sequence identity to SEQ ID NO: 34 or 52.

In another embodiment the fusion protein comprises HC CDR3 (SEQ ID NO: 34 or 52) and LC CDR3 (SEQ ID NO: 26).

In another embodiment, the fusion protein comprises one or more antibodies of the invention and an amino acid sequence to which it is not attached in the native molecule, such as, for example, a heterologous sequence or homologous sequence from another region. In an embodiment the heterologous sequence is a tag selected from FLAGtag or 6His Tag.

Also provided are antibodies and immunologically functional fragments thereof conjugated to an agent that facilitates coupling to a solid support. In an embodiment the antibodies and fragments thereof are linked to an agent that facilitates coupling to a solid support. In an embodiment the solid support is biotin or avidin.

Also provided are antibodies and immunologically functional fragments thereof linked to a labeling agent. In an embodiment the labeling agent is a fluorescent molecule or a radioactive molecule.

The various antibodies and immunologically functional fragments thereof that are provided can include a single LC or HC, or a single variable light domain and/or a single variable heavy domain. Other antibodies and fragments that are provided can include two LCs and/or two HCs wherein, in some embodiments, the two LCs are identical to one another; and/or wherein, in some embodiments, the two HCs are identical to one another. The antibodies that are provided may include, e.g., monoclonal antibodies, a human antibody, a chimeric antibody, or a humanized antibody. The immunologically functional fragments of the provided antibodies may include, but are not limited to a scFv, a Fab, a Fab', a (FAB')$_2$, or a domain antibody. In an embodiment the antibody dissociates from a Dkk-1 polypeptide with a Kd of about 100 µM or less.

A variety of nucleic acids encoding the antibodies and fragments thereof are also provided. Some nucleic acids, for example, encode a LC CDR with the amino acid sequence as set forth in SEQ ID NO: 22, SEQ ID NO: 24 or SEQ ID NO: 26, such that the encoded CDR encodes an antibody or an immunologically functional fragment thereof that can specifically bind a Dkk-1 polypeptide. Some nucleic acids, for example, encode a HC CDR with the amino acid sequence as set forth in SEQ ID NO: 30, SEQ ID NO: 32 or SEQ ID NO: 34, such that the encoded CDR encodes an antibody or an immunologically functional fragment thereof that can specifically bind a Dkk-1 polypeptide. In some embodiments the nucleic acids comprise or consist of a sequence that encodes a VL and/or a VH region of an antibody or immunologically functional fragment thereof wherein the VL has at least 70%, 80%, 90% or 95% sequence identity with the sequence set forth in SEQ ID NO: 20 and the VH has at least 70%, 80%, 90% or 95% sequence identity with the sequence set forth in SEQ ID NO: 28. In some embodiments the nucleic acids include a sequence that encodes a VL that comprises or consists of the sequence as set forth in SEQ ID NO: 20 and/or a sequence that encodes a VH that comprises or consists of a sequence as set forth in SEQ ID NO: 28. In other embodiments the nucleic acids include sequences that encode both a VL and a VH with the foregoing sequence characteristics.

Further provided are polynucleotides encoding any of the following: (a) huMabJC18 or its variants shown in Table 4; (b) a fragment or a region of antibody huMabJC18 or its variants shown in Table 4; (c) a light chain of antibody huMabJC18 or its variants shown in Table 4; (c) a heavy chain of antibody huMabJC18 or its variants shown in Table 4; (d) one or more variable region(s) from a LC and/or a HC of antibody huMabJC18 or its variants shown in Table 4; (e) one or more CDR(s) (one, two, three, four, five or six CDRs) of antibody huMabJC18 or its variants shown in Table 4; (f) CDR H3 from the HC of antibody huMabJC18; (g) CDR H1 from the HC of antibody huMabJC18; (h) CDR H2 from the HC of antibody huMabJC18, wherein amino acid G57 is G or W, and/or F58 is F, L, G, Y, M, or V, and/or Q59 is Q, D, H, G, R, or W: (i) CDR H3 from the HC of antibody huMabJC18, wherein amino acid T100 is T or S, and/or amino acid L102 is L or Y, and/or amino acid E103 is E, R, Q, D, or K; (j) CDR L1 from the LC of antibody huMabJC18, wherein amino acid E27 is E, Q, and/or amino acid D30 is D or S, and/or amino acid D31 is D or S, and/or amino acid F32 is F or S, and/or amino acid G33 is G or Y, and/or amino acid I34 is I or L, and/or amino acid S35 is S or A, and/or amino acid F36 is F or W, and/or amino acid I37 is I or M; (k) CDR L2 from the LC of antibody huMabJC18, wherein amino acid G55 is G or A, and/or amino acid S56 is S or T; (l) CDR L3 from the LC of antibody huMabJC18, wherein amino acid Q94 is Q or H, and/or amino acid L95 is L, S, A, or G, and/or amino acid K96 is K, I, L, W, M or S, and/or amino acid E97 is E or D, and/or amino acid V98 is V or L, and/or amino acid P99 is P or W, and/or amino acid P100 is P, S or G, and/or amino acid T101 is T, Y or L; (m) three CDRs from the LC of antibody huMabJC18 or its variants shown in Table 4; (n) three CDRs from the HC of antibody huMabJC18 or its variants shown in Table 4; (o) three CDRs from the LC and three CDRs from the HC, of antibody huMabJC18 or its variants shown in Table 4; and (p) an antibody comprising any one of (b) through (p).

Polynucleotides complementary to any such nucleic acid sequences are also provided. Polynucleotides can be single-stranded (coding or antisense) or double-stranded, and may be DNA (genomic, cDNA or synthetic) or RNA molecules. RNA molecules include, e.g., HnRNA molecules, which contain introns and correspond to a DNA molecule in a one-to-one manner, and mRNA molecules, which do not contain introns. Additional coding or non-coding sequences may, but need not, be present within a provided polynucleotide, and a polynucleotide may, but need not, be linked to other molecules and/or support materials.

Polynucleotides are provided which can comprise a native sequence (i.e., an endogenous sequence that encodes an antibody or a portion thereof), or may comprise a variant of such a sequence. Polynucleotide variants can contain one or more substitutions, additions, deletions and/or insertions such that the immunoreactivity of the encoded polypeptide is not diminished, relative to a native immunoreactive molecule. Variants preferably exhibit at least about 70% identity, more preferably at least about 80% identity, more preferably at least about 90%, and most preferably about 95% identity to a polynucleotide sequence that encodes a native antibody or a portion thereof.

The invention also provides a DNA molecule encoding the amino acid sequence of a humanized antibody or a fragment thereof, comprising:

(a) one or more LC CDRs selected from the group consisting of:
  (i) a CDR1 with at least 80% sequence identity to SEQ ID NO: 22;
  (ii) a CDR2 with at least 80% sequence identity to SEQ ID NO: 24; and
  (iii) a CDR3 with at least 80% sequence identity to SEQ ID NO: 26;
(b) one or more HC CDRs selected from the group consisting of:
  (i) a CDR1 with at least 80% sequence identity to SEQ ID NO: 30, 49 or 50;
  (ii) a CDR2 with at least 80% sequence identity to SEQ ID NO: 32 or 51; and
  (iii) a CDR3 with at least 80% sequence identity to SEQ ID NO: 34 or 52; or
(c) one or more CDRs of (a) and one or more CDRs of (b), in which the variable domain framework of the LC contains the human IGKV3-11 germline framework and IGKJ4 region.

The invention also provides a DNA molecule encoding the amino acid sequence of a humanized antibody or a fragment thereof, comprising:

(a) one or more LC CDRs selected from the group consisting of:
  (i) a CDR1 with at least 80% sequence identity to SEQ ID NO: 22;
  (ii) a CDR2 with at least 80% sequence identity to SEQ ID NO: 24; and
  (iii) a CDR3 with at least 80% sequence identity to SEQ ID NO: 26;
(b) one or more HC CDRs selected from the group consisting of:
  (i) a CDR1 with at least 80% sequence identity to SEQ ID NO: 30, 49 or 50;
  (ii) a CDR2 with at least 80% sequence identity to SEQ ID NO: 32 or 51; and
  (iii) a CDR3 with at least 80% sequence identity to SEQ ID NO: 34 or 52; or
(c) one or more CDRs of (a) and one or more CDRs of (b), in which the variable domain framework of the HC contains the human IGHV3-07 germline framework (with single back mutation: R100 to T) and IGHJ6 region.

The invention also provides a DNA molecule encoding the amino acid sequence of a humanized antibody or a fragment thereof, comprising:

(a) one or more LC CDRs selected from the group consisting of:
  (i) a CDR1 with at least 80% sequence identity to SEQ ID NO: 22;
  (ii) a CDR2 with at least 80% sequence identity to SEQ ID NO: 24; and
  (iii) a CDR3 with at least 80% sequence identity to SEQ ID NO: 26;
(b) one or more HC CDRs selected from the group consisting of:
  (i) a CDR1 with at least 80% sequence identity to SEQ ID NO: 30, 49 or 50;
  (ii) a CDR2 with at least 80% sequence identity to SEQ ID NO: 32 or 51; and
  (iii) a CDR3 with at least 80% sequence identity to SEQ ID NO: 34 or 52; or
(c) one or more CDRs of (a) and one or more CDRs of (b), in which the variable domain framework of the LC contains the human IGKV3-11 germline framework and IGKJ4 region and the variable domain framework of the HC contains the human IGHV3-07 germline framework (with single back mutation: R100 to T) and IGHJ6 region.

The invention also provides a DNA molecule encoding the amino acid sequence of a humanized antibody or a fragment thereof, comprising:

(a) one or more LC CDRs selected from the group consisting of:
  (i) a CDR1 (SEQ ID NO: 22);
  (ii) a CDR2 (SEQ ID NO: 24); and
  (iii) a CDR3 (SEQ ID NO: 26);
(b) one or more HC CDRs selected from the group consisting of:
  (i) a CDR1 (SEQ ID NO: 30, 49 or 50);
  (ii) a CDR2 (SEQ ID NO: 32 or 51); and
  (iii) a CDR3 (SEQ ID NO: 34 or 52); or
(c) one or more CDRs of (a) and one or more CDRs of (b), in which the variable domain framework of the LC contains the human IGKV3-11 germline framework and IGKJ4 region and the variable domain framework of the HC contains the human IGHV3-07 germline framework (with single back mutation: R100 to T) and IGHJ6 region.

In some embodiments of the DNA molecules the nucleotide sequences of the LC CDRs are as follows:
CDR1: as set forth in SEQ ID NO: 21
CDR2: as set forth in SEQ ID NO: 23
CDR3: as set forth in SEQ ID NO: 25.

In some embodiments of the DNA molecules the nucleotide sequences of the HC CDRs are as follows:
CDR1: as set forth in SEQ ID NO: 29
CDR2: as set forth in SEQ ID NO: 31
CDR3: as set forth in SEQ ID NO: 33.

In some embodiments of the DNA molecules the nucleotide sequence of the LC variable region is as set forth in SEQ ID NO: 19.

In some embodiments of the DNA molecules the nucleotide sequence of the HC variable region is as set forth in SEQ ID NO: 27.

In some embodiments of the DNA molecules the nucleotide sequence of the LC is as set forth in SEQ ID NO: 37 or SEQ ID NO: 41.

In some embodiments of the DNA molecules the nucleotide sequence of the HC is as set forth in SEQ ID NO: 35 or SEQ ID NO: 39.

Further provided are vectors, e.g., expression vectors, comprising any of the polynucleotide sequences or DNA molecules encoding the antibodies or fragments thereof.

In an embodiment provided is a DNA molecule encoding the amino acid sequence of a humanized antibody or a fragment thereof, comprising:

(a) one or more LC CDRs selected from the group consisting of:
  (i) a CDR1 with at least 80% sequence identity to SEQ ID NO: 22;
  (ii) a CDR2 with at least 80% sequence identity to SEQ ID NO: 24; and
  (iii) a CDR3 with at least 80% sequence identity to SEQ ID NO: 26;
(b) one or more HC CDRs selected from the group consisting of:
  (i) a CDR1 with at least 80% sequence identity to SEQ ID NO: 30, 49 or 50;

(ii) a CDR2 with at least 80% sequence identity to SEQ ID NO: 32 or 51; and (iii) a CDR3 with at least 80% sequence identity to SEQ ID NO: 34 or 52; or (c) one or more CDRs of (a) and one or more CDRs of (b), in which the variable domain framework of the LC contains the human IGKV3-11 germline framework and IGKJ4 region, in the form of an expression vector.

In an embodiment provided is a DNA molecule encoding the amino acid sequence of a humanized antibody or a fragment thereof, comprising:

(a) one or more LC CDRs selected from the group consisting of:
(i) a CDR1 with at least 80% sequence identity to SEQ ID NO: 22;
(ii) a CDR2 with at least 80% sequence identity to SEQ ID NO: 24; and
(iii) a CDR3 with at least 80% sequence identity to SEQ ID NO: 26;

(b) one or more HC CDRs selected from the group consisting of:
(i) a CDR1 with at least 80% sequence identity to SEQ ID NO: 30, 49 or 50;
(ii) a CDR2 with at least 80% sequence identity to SEQ ID NO: 32 or 51; and
(iii) a CDR3 with at least 80% sequence identity to SEQ ID NO: 34 or 52; or (c) one or more CDRs of (a) and one or more CDRs of (b), in which the variable domain framework of the HC contains the human IGHV3-07 germline framework (with single back mutation: R100 to T) and IGHJ6 region, in the form of an expression vector.

In an embodiment provided is a DNA molecule encoding the amino acid sequence of a humanized antibody or a fragment thereof, comprising:

(a) one or more LC CDRs selected from the group consisting of:
(i) a CDR1 with at least 80% sequence identity to SEQ ID NO: 22;
(ii) a CDR2 with at least 80% sequence identity to SEQ ID NO: 24; and
(iii) a CDR3 with at least 80% sequence identity to SEQ ID NO: 26;

(b) one or more HC CDRs selected from the group consisting of:
(i) a CDR1 with at least 80% sequence identity to SEQ ID NO: 30, 49 or 50;
(ii) a CDR2 with at least 80% sequence identity to SEQ ID NO: 32 or 51; and
(iii) a CDR3 with at least 80% sequence identity to SEQ ID NO: 34 or 52; or (c) one or more CDRs of (a) and one or more CDRs of (b), in which the variable domain framework of the LC contains the human IGKV3-11 germline framework and IGKJ4 region and the variable domain framework of the HC contains the human IGHV3-07 germline framework (with single back mutation: R100 to T) and IGHJ6 region, in the form of an expression vector.

In an embodiment provided is a DNA molecule encoding the amino acid sequence of a humanized antibody or a fragment thereof, comprising:

(a) one or more LC CDRs selected from the group consisting of:
(i) a CDR1 (SEQ ID NO: 22);
(ii) a CDR2 (SEQ ID NO: 24); and
(iii) a CDR3 (SEQ ID NO: 26);

(b) one or more HC CDRs selected from the group consisting of:
(i) a CDR1 (SEQ ID NO: 30, 49 or 50);
(ii) a CDR2 (SEQ ID NO: 32 or 51); and
(iii) a CDR3 (SEQ ID NO: 34 or 52); or (c) one or more CDRs of (a) and one or more CDRs of (b), in which the variable domain framework of the LC contains the human IGKV3-11 germline framework and IGKJ4 region and the variable domain framework of the HC contains the human IGHV3-07 germline framework (with single back mutation: R100 to T) and IGHJ6 region, in the form of an expression vector.

Also provided is a host transformed with an expression vector of the invention. In an embodiment provided is a host transformed with an expression vector comprising a DNA molecule encoding the amino acid sequence of a humanized antibody or a fragment thereof, comprising:

(a) one or more LC CDRs selected from the group consisting of:
(i) a CDR1 (SEQ ID NO: 22);
(ii) a CDR2 (SEQ ID NO: 24); and
(iii) a CDR3 (SEQ ID NO: 26);

(b) one or more HC CDRs selected from the group consisting of:
(i) a CDR1 (SEQ ID NO: 30, 49 or 50);
(ii) a CDR2 (SEQ ID NO: 32 or 51); and
(iii) a CDR3 (SEQ ID NO: 34 or 52); or (c) one or more CDRs of (a) and one or more CDRs of (b), in which the variable domain framework of the LC contains the human IGKV3-11 germline framework and IGKJ4 region and the variable domain framework of the HC contains the human IGHV3-07 germline framework (with single back mutation: R100 to T) and IGHJ6 region.

Also provided is a host cell comprising a recombinant expression system encoding the light and heavy chains of a humanized antibody or fragment thereof, wherein said antibody or fragment specifically binds to human DKK-1 antigen, and wherein the CDRs of the LC and the HC have the following amino acid sequences:

(a) one or more LC CDRs selected from the group consisting of:
(i) a CDR1 (SEQ ID NO: 22);
(ii) a CDR2 (SEQ ID NO: 24); and
(iii) a CDR3 (SEQ ID NO: 26);

(b) one or more HC CDRs selected from the group consisting of:
(i) a CDR1 (SEQ ID NO: 30, 49 or 50);
(ii) a CDR2 (SEQ ID NO: 32 or 51); and
(iii) a CDR3 (SEQ ID NO: 34 or 52); or (c) one or more CDRs of (a) and one or more CDRs of (b).

Further provided is a process for the preparation of a humanized antibody or fragment thereof, wherein said antibody or fragment specifically binds to human Dkk-1 antigen, and wherein the CDRs of the LC and the HC have the following amino acid sequences:

(a) one or more LC CDRs selected from the group consisting of:
(i) a CDR1 (SEQ ID NO: 22);
(ii) a CDR2 (SEQ ID NO: 24); and
(iii) a CDR3 (SEQ ID NO: 26);

(b) one or more HC CDRs selected from the group consisting of:
(i) a CDR1 (SEQ ID NO: 30, 49 or 50);
(ii) a CDR2 (SEQ ID NO: 32 or 51); and
(iii) a CDR3 (SEQ ID NO: 34 or 52); or (c) one or more CDRs of (a) and one or more CDRs of (b), which process comprises providing a host transformed with either (i) a first expression vector which encodes the light chain of the humanized antibody or fragment thereof and a second expression vector which encodes the heavy chain of the humanized antibody or fragment thereof; or (ii) a single expression vector which encodes both the light chain and the heavy chain of the humanized antibody or fragment thereof; and maintaining said host under such conditions that each chain is expressed and isolating the humanized antibody or fragment thereof formed by assembly of the thus-expressed chains.

Further provided is a method for producing a humanized antibody or fragment thereof, which specifically binds to human DKK-1 antigen, and wherein the CDRs of the LC and the HC have the following amino acid sequences:

(a) one or more LC CDRs selected from the group consisting of:
  (i) a CDR1 (SEQ ID NO: 22);
  (ii) a CDR2 (SEQ ID NO: 24); and
  (iii) a CDR3 (SEQ ID NO: 26);
(b) one or more HC CDRs selected from the group consisting of:
  (i) a CDR1 (SEQ ID NO: 30, 49 or 50);
  (ii) a CDR2 (SEQ ID NO: 32 or 51); and
  (iii) a CDR3 (SEQ ID NO: 34 or 52); or
(c) one or more CDRs of (a) and one or more CDRs of (b), said method comprising culturing a host cell, wherein said host cell comprises a recombinant expression system encoding the LC and HC of said antibody or fragment thereof, and recovering said antibody or fragment thereof.

The invention provides a humanized antibody or fragment thereof, comprising culturing a host cell comprising a recombinant expression system encoding the light and heavy chains of a humanized antibody or fragment thereof, wherein said antibody or fragment specifically binds to human DKK-1 antigen, and wherein the CDRs of the LC and the HC have the following amino acid sequences:

(a) one or more LC CDRs selected from the group consisting of:
  (i) a CDR1 (SEQ ID NO: 22);
  (ii) a CDR2 (SEQ ID NO: 24); and
  (iii) a CDR3 (SEQ ID NO: 26);
(b) one or more HC CDRs selected from the group consisting of:
  (i) a CDR1 (SEQ ID NO: 30, 49 or 50);
  (ii) a CDR2 (SEQ ID NO: 32 or 51); and
  (iii) a CDR3 (SEQ ID NO: 34 or 52); or
(c) one or more CDRs of (a) and one or more CDRs of (b), and wherein said humanized antibody or fragment thereof can compete with muMabJC18 for binding to human Dkk-1 antigen.

Also provided is a pharmaceutical composition comprising a humanized antibody or a fragment thereof, wherein said antibody or fragment specifically binds to human Dkk-1 antigen, and wherein the CDRs of the LC and the HC have the following amino acid sequences:

(a) one or more LC CDRs selected from the group consisting of:
  (i) a CDR1 (SEQ ID NO: 22);
  (ii) a CDR2 (SEQ ID NO: 24); and
  (iii) a CDR3 (SEQ ID NO: 26);
(b) one or more HC CDRs selected from the group consisting of:
  (i) a CDR1 (SEQ ID NO: 30, 49 or 50);
  (ii) a CDR2 (SEQ ID NO: 32 or 51); and
  (iii) a CDR3 (SEQ ID NO: 34 or 52); or
(c) one or more CDRs of (a) and one or more CDRs of (b), and pharmaceutically acceptable excipient, diluent or carrier.

Also provided is a pharmaceutical composition comprising a humanized antibody or a fragment thereof, wherein said antibody or fragment specifically binds to human Dkk-1 antigen, and wherein the CDRs of the LC and the HC have the following amino acid sequences:

(a) one or more LC CDRs selected from the group consisting of:
  (i) a CDR1 (SEQ ID NO: 22);
  (ii) a CDR2 (SEQ ID NO: 24); and
  (iii) a CDR3 (SEQ ID NO: 26);
(b) one or more HC CDRs selected from the group consisting of:
  (i) a CDR1 (SEQ ID NO: 30, 49 or 50);
  (ii) a CDR2 (SEQ ID NO: 32 or 51); and
  (iii) a CDR3 (SEQ ID NO: 34 or 52); or
(c) one or more CDRs of (a) and one or more CDRs of (b), wherein said humanized antibody or fragment thereof can compete with muMabJC18 for binding to human DKK-1 antigen, and a pharmaceutically acceptable excipient, diluent or carrier.

Further provided is a method for producing a humanized antibody or fragment thereof, comprising culturing a host cell comprising a recombinant expression system encoding the LC and HC of a humanized antibody or a fragment thereof, wherein said antibody or fragment specifically binds to human Dkk-1 antigen, and wherein the CDRs of the LC and the HC have the following amino acid sequences:

(a) one or more LC CDRs selected from the group consisting of:
  (i) a CDR1 (SEQ ID NO: 22);
  (ii) a CDR2 (SEQ ID NO: 24); and
  (iii) a CDR3 (SEQ ID NO: 26);
(b) one or more HC CDRs selected from the group consisting of:
  (i) a CDR1 (SEQ ID NO: 30, 49 or 50);
  (ii) a CDR2 (SEQ ID NO: 32 or 51); and
  (iii) a CDR3 (SEQ ID NO: 34 or 52); or
(c) one or more CDRs of (a) and one or more CDRs of (b), wherein said humanized antibody or fragment thereof can compete with muMabJC18 for binding to human Dkk-1 antigen, and recovering said humanized antibody or fragment thereof.

The invention also provides a method of treating or preventing a loss of bone mass comprising administering to a patient in need thereof an effective amount of the humanized antibodies and fragments thereof of the invention. In an embodiment the patient is one who suffers from cancer that metastasizes to bone. In an embodiment the patient is one who suffers from multiple myeloma. In an embodiment the patient is selected from patients who suffer from osteoporosis, osteopenia, Paget's Disease, periodontitis, rheumatoid arthritis, and bone loss due to immobilization. In an embodiment the patient suffers from osteoporosis. In an embodiment the patient suffers from an estrogen deficiency.

The invention also provides a method of inducing increased bone mass comprising administering to a patient in need thereof an effective amount of the humanized antibodies and fragments thereof of the invention. In an embodiment the patient is one who suffers from cancer that metastasizes to bone. In an embodiment the patient is one who suffers from multiple myeloma. In an embodiment the patient is selected from patients who suffer from osteoporosis, osteopenia, Paget's Disease, periodontitis, rheumatoid arthritis, and bone loss due to immobilization. In an embodiment the patient suffers from osteoporosis. In an embodiment the patient is a bone graft recipient or one who suffers from a bone fracture. In an embodiment the patient has secondary bone loss due to:

chronic treatment with corticosteroids, aromatase inhibitors, or TZDs; anorexia; or caused by hypogonadism or renal osteodystrophy.

The invention also provides a method of inducing Wnt activity comprising administering to a patient in need thereof an effective amount of a humanized antibody or a fragment thereof of the invention.

The invention also provides anti-Dkk-1 neutralizing monoclonal antibodies and immunologically functional fragments thereof. In an embodiment the antibody or fragment thereof binds to human Dkk-1 with a Kd of <100 pM. In an embodiment the antibody or fragment thereof antagonizes the action of Dkk-1 with an $IC_{50}$<100 nM in functional cell-based assays. In an embodiment the antibody or fragment thereof has a predicted human exposure profile expected to increase Bone Mineral Density (BMD) measurements after once-a-month dosing of ≦250 mg.

Also provided are bone anabolic agents which antagonize the ability of Dkk-1 to inhibit Wnt activity and, as such, result in increased bone mass, useful in treating diseases, conditions and disorders, such as osteoporosis, and those resulting in secondary bone loss (e.g., due to: chronic treatment with corticosteroids, aromatase inhibitors, or TZDs; anorexia; or caused by hypogonadism or renal osteodystrophy), where such increased bone formation would be advantageous to the patient.

The antibodies and fragments thereof of the invention may be administered in combination with other pharmaceutical agents (in particular, agents used to treat or prevent primary and secondary bone loss, decreases in bone mass, and those that weaken bone strength as described herein below). The combination therapy may be administered in any suitable way, such as, for example: (a) as a single pharmaceutical composition which comprises a humanized antibody or fragment thereof of the present invention, at least one additional pharmaceutical agent described herein and a pharmaceutically acceptable excipient, diluent, or carrier; or (b) as two separate pharmaceutical compositions comprising (i) a first composition comprising a humanized antibody or fragment thereof of the present invention and a pharmaceutically acceptable excipient, diluent, or carrier, and (ii) a second composition comprising at least one additional pharmaceutical agent described herein and a pharmaceutically acceptable excipient, diluent, or carrier. The pharmaceutical compositions may be administered simultaneously or sequentially and in any suitable order.

Further provided are kits comprising the antibodies and/or fragments thereof provided by the invention, or comprising the pharmaceutical compositions provided by the invention. In an embodiment the kit further includes instructions for how to prepare the antibody or fragment and/or how to administer the antibody or fragment. In another embodiment the kit is used as a diagnostic to determine whether a patient has the ability to increase bone mass by inhibiting the Wnt signaling pathway.

Also provided are two deposits made with the ATCC (under the terms of the Budapest Treaty) on Feb. 18, 2009. *E. coli* DH5a carrying plasmid that has the HC variable region of huMabJC18 was deposited: pCR2.1 TOPO from *E. coli* in host *E. coli* DH5a, UC 25553, ATCC Patent Deposit Designation PTA-9835. *E. coli* DH5a carrying plasmid that has the LC variable region of huMabJC18 was deposited: pCR2.1 TOPO from *E. coli* in host *E. coli* DH5a, UC 25554, ATCC Patent Deposit Designation PTA-9836. All restrictions on the availability to the public of the plasmids so deposited will be irrevocably removed upon the issuance of a patent from the specification of the present invention.

Other features and advantages of the present disclosure will be apparent from the following detailed description and Examples which should not be construed as limiting. The contents of all references, Genbank entries, patents and published patent applications cited throughout this specification are expressly incorporated herein by reference in their entireties.

BRIEF DESCRIPTION OF THE DRAWINGS

FIG. 2 shows the effect of a mouse chimera of Dkk-1 monoclonal antibody (mouse chimera—chimeric human-mouse antibody) in an intact mouse model. The mouse chimera increased total BMD at doses from 1 to 30 mg/kg compared with vehicle.

FIG. 3 shows that JC18 prevented bone loss induced by estrogen deficiency in OVX mouse model. As expected, the mice treated with vehicle exhibited osteopenia at 8 weeks post-OVX as demonstrated by a significant decrease in total BMD. JC18 dose-responsively increased total BMD as measured by pQCT at distal femurs by 7 to 20% compared with vehicle treatment of OVX mice. In the mice treated with JC18 at 15 mg/kg twice weekly the total BMD was not only higher than vehicle-treated OVX mice but also maintained at the sham control level, indicating that at this dose and dosing regimen JC18 completely prevented the development of osteopenia in OVX mice.

FIG. 4 shows the specificity of binding of JC18 to human homologues Dkk-1, Dkk-3 and Dkk-4. JC18 showed weak binding to human Dkk-4 and no binding to human Dkk-3 up to 5 ug/ml.

FIG. 5 shows a Target Mediated Drug Disposition (TMDD) Model.

FIG. 7 shows a graph of observed and model predicted free/partially free huMabJC18 concentrations versus time following weekly intravenous administration of huMabJC18 to Sprague-Dawley rats. Symbols represent the mean observed data (±SD) and lines represent the predicted profiles from the model.

FIGS. 9A-B show graphs of observed and model predicted free/partially free huMabJC18 concentrations versus time following single intravenous administration of huMabJC18 to Cynomolgous monkeys. (A) Male monkeys. (B) Female monkeys. Symbols represent the observed individual monkey data and lines represent the predicted profiles from the model.

FIGS. 10A-E show graphs of observed and model predicted free Dkk-1 concentrations versus time following single intravenous administration of huMabJC18 to Cynomolgous monkeys. Symbols represent the observed data and lines represent the predicted profiles from the model.

DETAILED DESCRIPTION

Figure 1A:
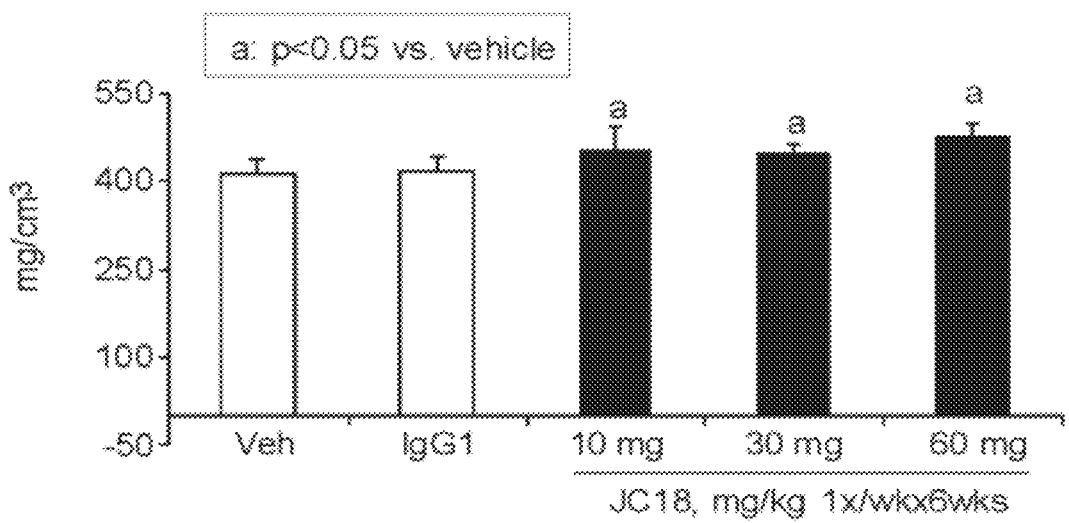
FIGS. 1A and 1B show the effect of anti-mouse Dkk-1 monoclonal antibody (JC18) in an intact mouse model. Total BMD of distal femurs was significantly increased by JC18 treatment at all dose levels (FIG. 1A). JC18 also increased bone formation rates significantly at 60 mg/kg dose level in mice (FIG. 1B).

The present disclosure relates to isolated antibodies and fragments (e.g., antigen binding portions) thereof, particularly humanized monoclonal antibodies and fragments thereof, that specifically bind to Dkk-1. In some embodiments the antibodies and fragments thereof of the disclosure are derived from particular heavy and light chain germline sequences and/or comprise particular structural features such as CDR regions comprising particular amino acid sequences. The disclosure provides, e.g., isolated antibodies and fragments thereof, methods of making such antibodies or fragments thereof, and pharmaceutical compositions containing the antibodies or fragments thereof. The disclosure also relates to methods of using the antibodies and fragments thereof, such as to detect Dkk-1, as well as to treat various diseases, conditions or disorders, such as bone disorders, which result in a loss of bone. Methods of treating or preventing a loss of bone mass, methods of inducing increased bone mass, and methods of inducing Wnt activity are also provided.

DEFINITIONS

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, e.g., Sambrook et al. Molecular Cloning: A Laboratory Manual, 2d ed., Cold Spring Harbor Laboratory Press, Cold Spring Harbor, N.Y. (1989) and Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990), which are incorporated herein by reference. Enzymatic reactions and purification techniques are performed according to manufacturer's specifications, as commonly accomplished in the art or as described herein. The terminology used in connection with, and the laboratory procedures and techniques of, analytical chemistry, synthetic organic chemistry, and medicinal and pharmaceutical chemistry described herein are those well known and commonly used in the art. Standard techniques can be used for chemical syntheses, chemical analyses, pharmaceutical preparation, formulation, and delivery, and treatment of patients.

The following terms utilized in this disclosure, unless otherwise indicated, will be understood to have the following meanings:

"Dkk-1" as used herein includes, for example, murine and human native forms of Dkk-1. Exemplary Dkk-1 protein and nucleotide sequences are disclosed, e.g., in US2006/0127393 (WO2006/015373) and US2008/0193449. The term also includes variants of such native sequences that are immunologically cross-reactive with these native proteins. These proteins can inhibit the interaction between LRP5 or LRP6 with Wnt. The term can also refer to a fragment of a native or variant form of Dkk-1 that contains an epitope to which an antibody can specifically bind.

The term "polynucleotide" or "nucleic acid" means single-stranded or double-stranded polymers. The nucleotides comprising the polynucleotide can be ribonucleotides or deoxyribonucleotides or a modified form of either type of nucleotide. Said modifications include base modifications such as bromouridine and inosine derivatives, ribose modifications such as 2',3'-dideoxyribose, and internucleotide linkage modifications such as phosphorothioate, phosphorodithioate, phosphoroselenoate, phosphorodiselenoate, phosphoroanilothioate, phoshoranil-adate and phosphoroamidate. The term includes both single and double stranded forms.

The term "oligonucleotide" means a polynucleotide comprising 200 or fewer nucleotides. In some embodiments, oligonucleotides are 10 to 60 bases in length. In other embodiments, oligonucleotides are 12, 13, 14, 15, 16, 17, 18, 19, or 20 to 40 nucleotides in length. Oligonucleotides may be single stranded or double stranded, e.g., for use in the construction of a mutant gene. Oligonucleotides of the invention may be sense or antisense oligonucleotides. An oligonucleotide of the invention can include a label, including a radiolabel, a fluorescent label, a hapten or an antigenic label, for detection assays. Oligonucleotides of the invention may be used, for example, as PCR primers, cloning primers or hybridization probes.

An "isolated nucleic acid molecule" means a DNA or RNA of genomic, mRNA, cDNA, or synthetic origin or some combination thereof which is not associated with all or a portion of a polynucleotide in which the isolated polynucleotide is found in nature, or is linked to a polynucleotide to which it is not linked in nature. For purposes of this disclosure, it should be understood that "a nucleic acid molecule comprising" a particular nucleotide sequence does not encompass intact chromosomes. Isolated nucleic acid molecules "comprising" specified nucleic acid sequences may include, in addition to the specified sequences, coding sequences for up to ten or even up to twenty other proteins or portions thereof, or may include operably linked regulatory sequences that control expression of the coding region of the recited nucleic acid sequences, and/or may include vector sequences.

Unless specified otherwise, the left-hand end of any single-stranded polynucleotide sequence discussed herein is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA transcript that are 5' to the 5' end of the RNA transcript are referred to as "upstream sequences"; sequence regions on the DNA strand having the same sequence as the RNA transcript that are 3' to the 3' end of the RNA transcript are referred to as "downstream sequences".

The term "control sequence" refers to a polynucleotide sequence that can affect the expression and processing of coding sequences to which it is ligated. The nature of such control sequences may depend upon the host organism. In particular embodiments, control sequences for prokaryotes may include a promoter, a ribosomal binding site, and a transcription termination sequence. For example, control sequences for eukaryotes may include promoters comprising one or a plurality of recognition sites for transcription factors, transcription enhancer sequences, and transcription termination sequence. "Control sequences" according to the invention can include leader sequences and/or fusion partner sequences.

The term "vector" means any molecule or entity (e.g., nucleic acid, plasmid, bacteriophage or virus) used to transfer protein coding information into a host cell.

The term "expression vector" or "expression construct" refers to a vector that is suitable for transformation of a host cell and contains nucleic acid sequences that direct and/or control (in conjunction with the host cell) expression of one or more heterologous coding regions operatively linked thereto. An expression construct may include, but is not limited to, sequences that affect or control transcription, translation, and, if introns are present, affect RNA splicing of a coding region operably linked thereto.

As used herein, "operably linked" means that the components to which the term is applied are in a relationship that allows them to carry out their inherent functions under suitable conditions. For example, a control sequence in a vector that is "operably linked" to a protein coding sequence is ligated thereto so that expression of the protein coding sequence is achieved under conditions compatible with the transcriptional activity of the control sequences.

The term "host cell" means a cell that has been transformed, or is capable of being transformed, with a nucleic acid sequence and thereby expresses a gene of interest. The term includes the progeny of the parent cell, whether or not the progeny is identical in morphology or in genetic make-up to the original parent cell, so long as the gene of interest is present.

The term "transduction" means the transfer of genes from one bacterium to another, usually by bacteriophage. "Transduction" also refers to the acquisition and transfer of eukaryotic cellular sequences by retroviruses.

The term "transfection" means the uptake of foreign or exogenous DNA by a cell, and a cell has been "transfected" when the exogenous DNA has been introduced inside the cell membrane. A number of transfection techniques are well known in the art and are disclosed herein. See, e.g., Graham et al., 1973, Virology 52:456; Sambrook et al., 2001, Molecular Cloning: A Laboratory Manual, Id.; Davis et al., 1986, Basic Methods in Molecular Biology, Elsevier; and Chu et al., 1981, Gene 13:197. Such techniques can be used to introduce one or more exogenous DNA moieties into suitable host cells.

The term "transformation" refers to a change in a cell's genetic characteristics, and a cell has been transformed when it has been modified to contain new DNA or RNA. For example, a cell is transformed where it is genetically modified from its native state by introducing new genetic material via transfection, transduction, or other techniques. Following transfection or transduction, the transforming DNA may recombine with that of the cell by physically integrating into a chromosome of the cell, or may be maintained transiently as an episomal element without being replicated, or may replicate independently as a plasmid. A cell is considered to have been "stably transformed" when the transforming DNA is replicated with the division of the cell.

The terms "polypeptide" or "protein" mean a macromolecule having the amino acid sequence of a native protein, that is, a protein produced by a naturally-occurring and non-recombinant cell, or produced by a genetically-engineered or recombinant cell, and comprise molecules having the amino acid sequence of the native protein, or molecules having deletions from, additions to, and/or substitutions of one or more amino acids of the native sequence. The terms "polypeptide" and "protein" specifically encompass anti-Dkk-1 antibodies, or sequences that have deletions from, additions to, and/or substitutions of one or more amino acid of anti-Dkk-1 antibody. The term "polypeptide fragment" refers to a polypeptide that has an amino-terminal deletion, a carboxyl-terminal deletion, and/or an internal deletion as compared with the full-length native protein. Such fragments may also contain modified amino acids as compared with the native protein. In certain embodiments, fragments are about 5 to 500 amino acids long. For example, fragments may be at least 5, 6, 8, 10, 14, 20, 50, 70, 100, 110, 150, 200, 250, 300, 350, 400, or 450 amino acids long. Useful polypeptide fragments for this invention include immunologically functional fragments of antibodies, including binding domains. In the case of anti-Dkk-1 antibody, useful fragments include but are not limited to a CDR region, a variable domain of a heavy or light chain, a portion of an antibody chain or just its variable region including two CDRs, and the like.

The term "isolated protein" referred to herein means that a subject protein (1) is free of at least some other proteins with which it would normally be found, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is operably associated (by covalent or noncovalent interaction) with a polypeptide with which it is not associated in nature, or (6) does not occur in nature. Genomic DNA, cDNA, mRNA or other RNA, of synthetic origin, or any combination thereof may encode such an isolated protein. Preferably, the isolated protein is substantially free from proteins or polypeptides or other contaminants that are found in its natural environment that would interfere with its therapeutic, diagnostic, prophylactic, research or other use.

A "variant" of a polypeptide (e.g., an antibody) comprises an amino acid sequence wherein one or more amino acid residues are inserted into, deleted from and/or substituted into the amino acid sequence relative to another polypeptide sequence. Variants of the invention include fusion proteins.

A "derivative" of a polypeptide is a polypeptide (e.g., an antibody) that has been chemically modified in some manner distinct from insertion, deletion, or substitution variants, e.g., via conjugation to another chemical moiety.

An "immune response", as would be understood by the skilled artisan, includes, but is not limited to, any detectable antigen-specific or allogenic activation of a helper T cell or cytotoxic T cell response, production of antibodies, T cell-mediated activation of allergic reactions, and the like. The term encompasses the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

A "signal transduction pathway" refers to the biochemical relationship between a variety of signal transduction molecules that play a role in the transmission of a signal from one portion of a cell to another portion of a cell. As used herein, the phrase "cell surface receptor" includes, for example, molecules and complexes of molecules capable of receiving a signal and the transmission of such a signal across the plasma membrane of a cell.

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also fragments thereof (such as Fab, Fab', $F(ab')_2$, Fv), single chain (ScFv) and domain antibodies, including shark and camelid antibodies), and fusion proteins comprising an antibody portion, and any other modified configuration of the immunoglobulin molecule that comprises an antigen recognition site. An antibody includes an antibody of any class, such as IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

Antibodies according to the invention may be derived solely from a single source, or may be "chimeric," that is, different portions of the antibody may be derived from two different antibodies. For example, the CDR regions may be derived from a rat or murine source, while the framework regions of the V region are derived from a different animal source, such as a human. The antibodies or binding fragments of the invention may be produced in hybridomas, by recombinant DNA techniques, or by enzymatic or chemical cleavage of intact antibodies. Unless otherwise indicated, the term "antibody" includes, in addition to antibodies comprising two full-length heavy chains and two full-length light chains, derivatives, variants, fragments, and muteins thereof, examples of which are described below.

The term "light chain" includes a full-length light chain and fragments thereof having sufficient variable region sequence to confer binding specificity. A full-length light chain includes a variable region domain, VL, and a constant region domain, CL. The variable region domain of the light chain is at the amino-terminus of the polypeptide. Light chains according to the invention include kappa chains and lambda chains.

The term "heavy chain" includes a full-length heavy chain and fragments thereof having sufficient variable region sequence to confer binding specificity. A full-length heavy chain includes a variable region domain, VH, and three constant region domains, CH1, CH2, and CH3. The VH domain is at the amino-terminus of the polypeptide, and the CH domains are at the carboxyl-terminus, with the CH3 being closest to the —COON end. Heavy chains according to the invention may be of any isotype, including IgG (including IgG1, IgG2, IgG3 and IgG4 subtypes), IgA (including IgA1 and IgA2 subtypes), IgM an The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system. Within light and heavy chains, the variable and constant regions are joined by a "J" region of about 12 or more amino acids, with the heavy chain also including a "D" region of about 10 or more amino acids. See generally, Fundamental Immunology Ch. 7 (Paul, W., ed., $2^{nd}$ ed. Raven Press, N.Y. (1989)).

The term "antigen-binding portion" of an antibody (or simply "antibody portion"), as used herein, refers to one or more fragments of an antibody that retain the ability to specifically bind to an antigen (e.g., $\alpha 5\beta 1$). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a $F(ab')_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. These antibody fragments may be obtained using any suitable technique, including conventional techniques known to those with skill in the art, and the fragments may be screened for utility in the same manner as are intact antibodies.

An "isolated antibody", as used herein, is intended to refer to an antibody that is substantially free of other antibodies having different antigenic specificities (e.g., an isolated antibody that specifically binds Dkk-1 is substantially free of antibodies that specifically bind antigens other than Dkk-1).

An isolated antibody that specifically binds Dkk-1 may, however, have cross-reactivity to other antigens, such as Dkk-1 molecules from other species. Moreover, an isolated antibody may be substantially free of other cellular material and/or chemicals.

The term "immunologically functional fragment" (or simply "fragment") of an immunoglobulin chain, as used herein, refers to a portion of an antibody light chain or heavy chain that lacks at least some of the amino acids present in a full-length chain but which is capable of binding specifically to an antigen. Such fragments are biologically active in that they bind specifically to the target antigen and can compete with intact antibodies for specific binding to a given epitope. In one aspect of the invention, such a fragment will retain at least one CDR present in the full-length light or heavy chain, and in some embodiments will comprise a single heavy chain and/or light chain or portion thereof. These biologically active fragments may be produced by recombinant DNA techniques, or may be produced by enzymatic or chemical cleavage of intact antibodies. Immunologically functional immunoglobulin fragments of the invention include, but are not limited to, Fab, Fab', $F(ab')_2$, Fv, domain antibodies and single-chain antibodies, and may be derived from any mammalian source, including but not limited to human, mouse, rat, camelid or rabbit. It is contemplated further that a functional portion of the inventive antibodies, for example, one or more CDRs, could be covalently bound to a second protein or to a small molecule to create a therapeutic agent directed to a particular target in the body, possessing bifunctional therapeutic properties, or having a prolonged serum half-life.

A "Fab fragment" is comprised of one light chain and the CH1 and variable regions of one heavy chain. The heavy chain of a Fab molecule cannot form a disulfide bond with another heavy chain molecule.

An "Fc" region contains two heavy chain fragments comprising the CH1 and CH2 domains of an antibody. The two heavy chain fragments are held together by two or more disulfide bonds and by hydrophobic interactions of the CH3 domains.

A "Fab' fragment" contains one light chain and a portion of one heavy chain that contains the VH domain and the CH1 domain and also the region between the CH1 and CH2 domains, such that an interchain disulfide bond can be formed between the two heavy chains of two Fab' fragments to form a $F(ab')_2$ molecule.

A "$F(ab')_2$ fragment" contains two light chains and two heavy chains containing a portion of the constant region between the CH1 and CH.sup.2 domains, such that an interchain disulfide bond is formed between the two heavy chains. A $F(ab')_2$ fragment thus is composed of two Fab' fragments that are held together by a disulfide bond between the two heavy chains.

The "Fv region" comprises the variable regions from both the heavy and light chains, but lacks the constant regions.

"Single-chain antibodies" are Fv molecules in which the heavy and light chain variable regions have been connected by a flexible linker to form a single polypeptide chain, which forms an antigen-binding region. Single chain antibodies are discussed in detail, for example, in WO 88/01649 and U.S. Pat. Nos. 4,946,778 and 5,260,203.

A "domain antibody" is an immunologically functional immunoglobulin fragment containing only the variable region of a heavy chain or the variable region of a light chain. In some instances, two or more VH regions are covalently joined with a peptide linker to create a bivalent domain antibody. The two VH regions of a bivalent domain antibody may target the same or different antigens.

A "bivalent antibody" comprises two antigen binding sites. In some instances, the two binding sites have the same antigen specificities. However, bivalent antibodies may be bispecific (see below).

A "multispecific antibody" is one that targets more than one antigen or epitope.

A "bispecific," "dual-specific" or "bifunctional" antibody is a hybrid antibody having two different antigen binding sites. Bispecific antibodies are a species of multispecific antibody and may be produced by a variety of methods including, but not limited to, fusion of hybridomas or linking of Fab' fragments. See, e.g., Songsivilai & Lachmann (1990), Clin. Exp. Immunol. 79:315-321; and Kostelny et al. (1992), J. Immunol. 148:1547-1553. The two binding sites of a bispecific antibody will bind to two different epitopes, which may reside on the same or different protein targets.

As used herein, "monoclonal antibody" refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein (1975) Nature 256:495, or may be made by recombinant DNA methods such as described in U.S. Pat. No. 4,816,567. The monoclonal antibodies may also be isolated from phage libraries generated using the techniques described in McCafferty et al. (1990) Nature 348:552-554, for example.

The term "human antibody derivatives" refers to any modified form of the human antibody, e.g., a conjugate of the antibody and another agent or antibody.

The term "humanized antibody" is intended to refer to antibodies in which CDR sequences derived from the germ-line of another mammalian species, such as a mouse, have been grafted onto human framework sequences. Additional framework region modifications may be made within the human framework sequences.

As used herein, "humanized" antibody refers to forms of non-human (e.g., murine) antibodies that are chimeric immunoglobulins, immunoglobulin chains, or fragments thereof (such as Fv, Fab, Fab', $F(ab')_2$ or other antigen-binding subsequences of antibodies) that contain minimal sequence derived from non-human immunoglobulin. Preferably, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Preferred are antibodies having Fc regions modified as described in WO 99/58572. Other forms of humanized antibodies have one or more CDRs (CDR L1, CDR L2, CDR L3, CDR H1, CDR H2, and/or CDR H3) which are altered with respect to the original antibody, which are also.

The terms "human antibody", or "fully human antibody", as used herein, are intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the disclosure or antigen binding portions thereof may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The terms "human monoclonal antibody" or "fully human monoclonal antibody" refer to antibodies displaying a single binding specificity which have variable regions in which both the framework and CDR regions are derived from human germline immunoglobulin sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene, where the B cell is fused to an immortalized cell.

The term "recombinant human antibody", as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

As used herein, "isotype" or "class" refers to the antibody class (e.g., IgM or IgG) that is encoded by the heavy chain constant region genes. The constant domains of antibodies are not involved in binding to antigen, but exhibit various effector functions. Depending on the amino acid sequence of the heavy chain constant region, a given human antibody or immunoglobulin can be assigned to one of five major classes of immunoglobulins: IgA, IgD, IgE, IgG, and IgM. The structures and three-dimensional configurations of different classes of immunoglobulins are well-known. Of the various human immunoglobulin classes, only human IgG1, IgG2, IgG3, IgG4, and IgM are known to activate complement. Human IgG1 and IgG3 are known to mediate ADCC in humans.

As used herein, "subclass" refers to the further specification within an isotype of the heavy chain constant region gene, such as, for example, the IgG1, IgG2, IgG3, or IgG4 subclasses within the IgG isotype.

As used herein, the term "compound" or "pharmaceutical compound" includes antibodies, antigen-binding portions thereof, immunoconjugates, and bispecific molecules.

The phrases "an antibody recognizing an antigen" and "an antibody specific for an antigen" are used interchangeably herein with the term "an antibody which binds specifically to an antigen."

The term "antibody dependent cellular cytotoxicity" or "ADCC" refers to a cell-mediated reaction in which non-specific cytotoxic cells (e.g. NK cells, neutrophils, macrophages, etc.) recognize antibody bound on a target cell and subsequently cause lysis of the target cell. Such cytotoxic cells that mediate ADCC generally express Fc receptors (FcR). The primary cells for mediating ADCC (NK cells) express FcγRIII, whereas monocytes express FcγRI, FcγRII, FcγRIII, and/or FcγRIV. FcR expression on hematopoietic cells is summarized in Ravetch and Kinet, *Annu. Rev. Immunol.*, 9:457-92 (1991). To assess ADCC activity of a molecule, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecules of interest may be assessed in vivo, e.g., in an animal model such as that disclosed in Clynes et al., *Proc. Natl. Acad. Sci.* (USA), 95:652-656 (1998).

The terms "Fc receptor" or "FcR" are used to describe a receptor that binds to the Fc region of an antibody where the Fc region comprises a hinge region and the $C_H2$ and $C_H3$ domains of the heavy chain. For example, the FcR can be a native sequence human FcR. The FcR can be one that binds an IgG antibody (a gamma receptor) and includes receptors of the FcγRI, FcγRII, FcγRIII, and FcγRIV subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see, Daeron, Annu. Rev. Immunol., 15:203-234 (1997)). FcRs are reviewed in Ravetch and Kinet, Annu. Rev. Immunol., 9:457-92 (1991); Capel et al., Immunomethods, 4:25-34 (1994); and de Haas et al., J. Lab. Clin. Med., 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., Immunol., 117:587 (1976) and Kim et al., J. Immunol., 24:249 (1994)). The primary FcR binding site on immunoglobulin Fc fragments resides in the hinge region between the $C_H1$ and $C_H2$ domains. This hinge region interacts with the FcR1-3 on various leukocytes and triggers these cells to attack the target (Wines et al., J. Immunol., 164:5313-5318 (2000)). The hinge region encompasses, but is no limited to, the sequences described in U.S. Pat. No. 6,165,476.

The term "capable of inducing antibody dependent cellular cytotoxicity" refers to the ability of an agent, such as an antibody, to demonstrate ADCC as measured by assay(s) known to those of skill in the art. Such activity is typically characterized by the binding of the Fc region with various FcRs. Without being limited by any particular mechanism, those of skill in the art will recognize that the ability of an antibody to demonstrate ADCC can be, for example, by virtue of it subclass (such as IgG1 or IgG3), by mutations introduced into the Fc region, or by virtue of modifications to the carbohydrate patterns in the Fc region of the antibody. Such modifications are described, for example, in U.S. Patent Application Publication No. 2007/0092521.

The term "neutralizing antibody" refers to an antibody that binds to a ligand, prevents binding of the ligand to its binding partner and interrupts the biological response that otherwise would result from the ligand binding to its binding partner. In assessing the binding and specificity of an antibody or immunologically functional fragment thereof, an antibody or fragment will substantially inhibit binding of a ligand to its binding partner when an excess of antibody reduces the quantity of binding partner bound to the ligand by at least about 20%, 30%, 40%, 50%, 60%, 70%, 80%, 85%, 90%, 95%, 97%, 99% or more (as measured in an in vitro competitive binding assay). In the case of antibodies to Dkk-1, a neutralizing antibody will diminish the ability of Dkk-1 to bind LRP5 or LRP6, thereby inducing a measurable increase in Wnt activity.

The term "compete" when used in the context of antibodies that compete for the same epitope means competition between antibodies is determined by an assay in which the antibody or immunologically functional fragment under test prevents or inhibits specific binding of a reference antibody to a common antigen (e.g., Dkk-1 or a fragment thereof). Numerous types of competitive binding assays can be used, for example: solid phase direct or indirect radioimmunoassay (RIA), solid phase direct or indirect enzyme immunoassay (EIA), sandwich competition assay (see, e.g., Stahli et al. (1983) Methods in Enzymology 9:242-253); solid phase direct biotin-avidin EIA (see, e.g., Kirkland et al., (1986) J. Immunol. 137:3614-3619) solid phase direct labeled assay, solid phase direct labeled sandwich assay (see, e.g., Harlow and Lane (1988) Antibodies, A Laboratory Manual, Cold Spring Harbor Press); solid phase direct label RIA using 1-125 label (see, e.g., Morel et al. (1988) Molec. Immunol. 25:7-15); solid phase direct biotin-avidin EIA (see, e.g., Cheung, et al. (1990) Virology 176:546-552); and direct labeled RIA (Moldenhauer et al. (1990) Scand. J. Immunol. 32:77-82). Typically, such an assay involves the use of purified antigen bound to a solid surface or cells bearing either of these, an unlabelled test immunoglobulin and a labeled reference immunoglobulin. Competitive inhibition is measured by determining the amount of label bound to the solid surface or cells in the presence of the test immunoglobulin. Usually the test immunoglobulin is present in excess. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Additional details regarding methods for determining competitive binding are provided in the examples herein. Usually, when a competing antibody is present in excess, it will inhibit specific binding of a reference antibody to a common antigen by at least 40%, 45%, 50%, 55%, 60%, 65%, 70% or 75%. In some instance, binding is inhibited by at least 80%, 85%, 90%, 95%, or 97% or more.

The term "antigen" refers to a molecule or a portion of a molecule capable of being bound by a selective binding agent, such as an antibody, and additionally capable of being used in an animal to produce antibodies capable of binding to that antigen. An antigen may possess one or more epitopes that are capable of interacting with different antibodies.

The term "epitope" includes any determinant capable of specifically binding to an immunoglobulin or to a T-cell receptor. An epitope is a region of an antigen that is bound by an antibody that specifically targets that antigen, and when the antigen is a protein, includes specific amino acids that directly contact the antibody. Most often, epitopes reside on proteins, but in some instances may reside on other kinds of molecules, such as nucleic acids. Epitope determinants may include chemically active surface groupings of molecules such as amino acids, sugar side chains, phosphoryl or sulfonyl groups, and may have specific three dimensional structural characteristics, and/or specific charge characteristics. Generally, antibodies specific for a particular target antigen will preferentially recognize an epitope on the target antigen in a complex mixture of proteins and/or macromolecules.

By the phrase "specifically binds," as used herein, is meant a compound, e.g., a protein, a nucleic acid, an antibody, and the like, which recognizes and binds a specific molecule, but does not substantially recognize or bind other molecules in a sample. For instance, an antibody or a peptide inhibitor which recognizes and binds a cognate ligand (e.g., an anti-Dkk-1 antibody that binds with its cognate antigen, Dkk-1) in a sample, but does not substantially recognize or bind other molecules in the sample. Thus, under designated assay conditions, the specified binding moiety (e.g., an antibody or a fragment thereof (e.g., antigen-binding portion thereof)) binds preferentially to a particular target molecule, e.g., Dkk-1, and does not bind in a significant amount to other components present in a test sample. A variety of assay formats may be used to select an antibody that specifically binds a molecule of interest. For example, solid-phase ELISA immunoassay, immunoprecipitation, BIAcore, FACS, and Western blot analysis are among many assays that may be used to identify an antibody that specifically reacts with Dkk-1. Typically, a specific or selective reaction will be at least twice the background signal or noise and more typically more than 10 times the background, even more specifically, an antibody is said to "specifically bind" an antigen when the equilibrium dissociation constant ($K_D$) is $\leq 1$ μM, for example $\leq 100$ nM and, further for example, $\leq 10$ nM.

An antibody of the invention is said to "specifically bind" its target antigen when the dissociation constant (Kd) is preferably about 100 pM or less, about $1 \times 10^{-9}$ or less, or $1 \times 10^{-8}$ or less.

The term "$k_{on}$", as used herein, is intended to refer to the on-rate, or association rate of a particular antibody-antigen interaction, whereas the term "$k_{off}$" as used herein, is intended to refer to the off-rate, or dissociation rate of a particular antibody-antigen interaction. The term "$K_D$", as used herein, is intended to refer to the dissociation constant, which is obtained from the ratio of $k_{off}$ to $k_{on}$ (i.e., $k_{off}/k_{on}$) and is expressed as a molar concentration (M). $K_D$ values for antibodies can be determined using methods well established in the art. One method for determining the $K_D$ of an antibody is by using surface plasmon resonance, typically using a biosensor system such as a BIAcore® system.

The term "high affinity" for an IgG antibody generally refers to an antibody having a $K_D$ of $1 \times 10^{-7}$ M or less, $5 \times 10^{-8}$ M or less, or 5×10$^{-9}$ M or less for a target antigen. However, "high affinity" binding can vary for other antibody isotypes. For example, "high affinity" binding for an IgM isotype refers to an antibody having a K$_D$ of 10$^{-8}$ M or less, 10$^{-7}$ M or less, or 10$^{-8}$ M or less.

The term "identity" refers to a relationship between the sequences of two or more polypeptide molecules or two or more nucleic acid molecules, as determined by aligning and comparing the sequences. "Percent identity" means the percent of identical residues between the amino acids or nucleotides in the compared molecules and is calculated based on the size of the smallest of the molecules being compared. For these calculations, gaps in alignments (if any) must be addressed by a particular mathematical model or computer program (i.e., an "algorithm"). Methods that can be used to calculate the identity of the aligned nucleic acids or polypeptides include those described in Computational Molecular Biology, (Lesk, A. M., ed.) (1988) New York: Oxford University Press; Biocomputing Informatics and Genome Projects, (Smith, D. W., ed.) (1993) New York: Academic Press; Computer Analysis of Sequence Data, Part I, (Griffin, A. M., and Griffin, H. G., eds.) (1994) New Jersey: Humana Press; von Heinje, G. (1987) Sequence Analysis in Molecular Biology, New York: Academic Press; Sequence Analysis Primer, (Gribskov, M. and Devereux, J., eds.) (1991) New York: M. Stockton Press; and Carillo et al. (1988) SIAM J. Applied Math. 48: 1073.

In calculating percent identity, the sequences being compared are aligned in a way that gives the largest match between the sequences. The computer program used to determine percent identity is the GCG program package, which includes GAP (Devereux et al. (1984) Nucl Acid Res 12:387; Genetics Computer Group, University of Wisconsin, Madison, Wis.). The computer algorithm GAP is used to align the two polypeptides or polynucleotides for which the percent sequence identity is to be determined. The sequences are aligned for optimal matching of their respective amino acid or nucleotide (the "matched span", as determined by the algorithm). A gap opening penalty (which is calculated as 3.times. the average diagonal, wherein the "average diagonal" is the average of the diagonal of the comparison matrix being used; the "diagonal" is the score or number assigned to each perfect amino acid match by the particular comparison matrix) and a gap extension penalty (which is usually ⅒ times the gap opening penalty), as well as a comparison matrix such as PAM 250 or BLOSUM 62 are used in conjunction with the algorithm. In certain embodiments, a standard comparison matrix (see Dayhoff et al. (1978) Atlas of Protein Sequence and Structure 5:345-352 for the PAM 250 comparison matrix; Henikoff et al. (1992) Proc. Natl. Acad. Sci. USA 89: 10915-10919 for the BLOSUM 62 comparison matrix) is also used by the algorithm.

Recommended parameters for determining percent identity for polypeptides or nucleotide sequences using the GAP program are the following:

Algorithm: Needleman et al. (1970) J. Mol. Biol. 48:443-453;

Comparison matrix: BLOSUM 62 from Henikoff et al. (1992) supra;

Gap Penalty: 12 (but with no penalty for end gaps)

Gap Length Penalty: 4

Threshold of Similarity: 0

Certain alignment schemes for aligning two amino acid sequences may result in matching of only a short region of the two sequences, and this small aligned region may have very high sequence identity even though there is no significant relationship between the two full-length sequences. Accordingly, the selected alignment method (GAP program) can be adjusted if so desired to result in an alignment that spans at least 50 contiguous amino acids of the target polypeptide.

As used herein, "substantially pure" means that the described species of molecule is the predominant species present, that is, on a molar basis it is more abundant than any other individual species in the same mixture. In certain embodiments, a substantially pure molecule is a composition wherein the object species comprises at least 50% (on a molar basis) of all macromolecular species present. In other embodiments, a substantially pure composition will comprise at least 80%, 85%, 90%, 95%, or 99% of all macromolecular species present in the composition. In other embodiments, the object species is purified to essential homogeneity wherein contaminating species cannot be detected in the composition by conventional detection methods and thus the composition consists of a single detectable macromolecular species.

"Amino acid" includes its normal meaning in the art. The twenty naturally-occurring amino acids and their abbreviations follow conventional usage. See Immunology—A Synthesis, 2nd Edition, (E. S. Golub and D. R. Gren, eds.), Sinauer Associates: Sunderland, Mass. (1991), incorporated herein by reference for any purpose. Stereoisomers (e.g., D-amino acids) of the twenty conventional amino acids, unnatural amino acids such as α-, α-disubstituted amino acids, N-alkyl amino acids, and other unconventional amino acids may also be suitable components for polypeptides of the invention. Examples of unconventional amino acids include: 4-hydroxyproline, .gamma.-carboxyglutamate, .epsilon.-N, N,N-trimethyllysine, .epsilon.-N-acetyllysine, O-phosphoserine, N-acetylserine, N-formylmethionine, 3-methylhistidine, 5-hydroxylysine, .sigma.-N-methylarginine, and other similar amino acids and imino acids (e.g., 4-hydroxyproline). In the polypeptide notation used herein, the left-hand direction is the amino terminal direction and the right-hand direction is the carboxyl-terminal direction, in accordance with standard usage and convention.

The term "osteopenia" refers to a patient with bone loss of at least one standard deviation compared with a standard patient considered to have normal bone mineral density (BMD). For example, the measurement can be determined by Dual Energy X-ray Absorptiometry (DEXA) and the patient's BMD is compared with an age and gender-matched standard (Z score). In determining osteopenia, BMD measurements may be taken of one or more bones.

The term "therapeutically effective amount" refers to the amount of an anti-Dkk-1 antibody determined to produce a therapeutic response in a mammal. Such therapeutically effective amounts are readily ascertained by one of ordinary skill in the art.

"Glycoform" refers to a complex oligosaccharide structure comprising linkages of various carbohydrate units. Such structures are described in, e.g., *Essentials of Glycobiology* Varki et al., eds., Cold Spring Harbor Laboratory Press, Cold Spring Harbor, N.Y. (1999), which also provides a review of standard glycobiology nomenclature. Such glycoforms include, but are not limited to, G2, G1, G0, G-1, and G-2 (see, e.g., WO 99/22764).

"Glycosylation pattern" is defined as the pattern of carbohydrate units that are covalently attached to a protein (e.g., the glycoform) as well as to the site(s) to which the glycoform(s) are covalently attached to the peptide backbone of a protein, more specifically to an immunoglobulin protein.

It is likely that antibodies expressed by different cell lines or in transgenic animals will have different glycoforms and/or glycosylation patterns compared with each other. However, all antibodies encoded by the nucleic acid molecules provided herein, or comprising the amino acid sequences provided herein are part of the present disclosure, regardless of the glycosylation of such antibodies.

As used herein, the term "subject" includes any human or nonhuman animal. The term "nonhuman animal" includes all vertebrates, e.g., mammals and non-mammals, such as non-human primates, sheep, dogs, cats, horses, cows, chickens, amphibians, reptiles, etc.

As used herein, to "treat" means reducing the frequency with which symptoms of a disease are experienced by a patient. The term includes the administration of the compounds or agents of the present disclosure to prevent or delay the onset of the symptoms, complications, or biochemical indicia of a disease, alleviating the symptoms or arresting or inhibiting further development of the disease, condition, or disorder. Treatment may be prophylactic (to prevent or delay the onset of the disease, or to prevent the manifestation of clinical or subclinical symptoms thereof) or therapeutic suppression or alleviation of symptoms after the manifestation of the disease.

Various general aspects of the disclosure are described in further detail in the following subsections.

Overview

The present invention provides novel compositions comprising antibodies and antigen-binding sites of immunoglobulins specific for Dkk-1. Some of these antibodies and antibody fragments can cross-react with Dkk-1 from several mammalian sources, including rat, mouse and human Dkk-1. Some of the antibodies and fragments have higher affinity for Dkk-1 from one species than another. The invention also provides novel neutralizing antibodies, including chimeric, humanized and human antibodies, as well as antibodies and immunologically functional fragments thereof. Nucleic acids encoding the antibodies and fragments are also disclosed, as well as methods for expressing the antibodies using these nucleic acids. In another aspect, the invention relates to molecules (e.g., immunologically functional fragments and polypeptides) that are capable of exhibiting immunological binding properties of antibody antigen-binding sites.

The antibodies and immunologically functional fragments that are disclosed herein have a variety of utilities. Some of the antibodies and fragments, are useful in specific binding assays, affinity purification of Dkk-1 or its ligands and in screening assays to identify other antagonists of Dkk-1 activity. Certain of the antibodies can be used to treat various diseases that are associated with the activity of Dkk-1. Some antibodies and fragments can thus be used in a variety of treatments related to bone such as increasing BMD, synthesis of new bone, treatment of systemic bone loss (e.g., bone erosions), bone repair, and treatments for various forms of arthritis. Certain of the antibodies and fragments that are disclosed, however, can be used to treat a variety of diverse diseases that are unrelated to bone diseases.

Antibodies and Fragments

A variety of selective binding agents useful for regulating the activity of Dkk-1 are provided. These agents include, for instance, antibodies and immunologically functional fragments thereof that contain an antigen binding domain (e.g., single chain antibodies, domain antibodies, immunoadhesions, and polypeptides with an antigen binding region) and specifically bind to a Dkk-1 polypeptide (e.g., a human, rat and/or murine Dkk-1 polypeptide). Some of the agents, for example, are useful in inhibiting the binding of Dkk-1 to LRP5 and/or LRP6, and can thus be used to stimulate one or more activities associated with Wnt signaling.

Naturally Occurring Antibody Structure

Some of the binding agents that are provided have the structure typically associated with naturally occurring antibodies. The structural units of these antibodies typically comprise one or more tetramers, each composed of two identical couplets of polypeptide chains, though some species of mammals also produce antibodies having only a single heavy chain. In a typical antibody, each pair or couplet includes one full-length "light" chain (in certain embodiments, about 25 kDa) and one full-length "heavy" chain (in certain embodiments, about 50-70 kDa). Each individual immunoglobulin chain is composed of several "immunoglobulin domains," each consisting of roughly 90 to 110 amino acids and expressing a characteristic folding pattern. These domains are the basic units of which antibody polypeptides are composed. The amino-terminal portion of each chain typically includes a variable domain that is responsible for antigen recognition. The carboxy-terminal portion is more conserved evolutionarily than the other end of the chain and is referred to as the "constant region" or "C region." Human light chains generally are classified as kappa and lambda light chains, and each of these contains one variable domain and one constant domain. Heavy chains are typically classified as mu, delta, gamma, alpha, or epsilon chains, and these define the antibody's isotype as IgM, IgD, IgG, IgA, and IgE, respectively. IgG has several subtypes, including, but not limited to, IgG1, IgG2, IgG3, and IgG4. IgM subtypes include IgM, and IgM2. IgA subtypes include IgA1 and IgA2. In humans, the IgA and IgD isotypes contain four heavy chains and four light chains; the IgG and IgE isotypes contain two heavy chains and two light chains; and the IgM isotype contains five heavy chains and five light chains. The heavy chain C region typically comprises one or more domains that may be responsible for effector function. The number of heavy chain constant region domains will depend on the isotype. IgG heavy chains, for example, each contains three C region domains known as CH1, CH2 and CH3. The antibodies that are provided can have any of these isotypes and subtypes.

In full-length light and heavy chains, the variable and constant regions are joined by a "J" region of about 12 or more amino acids, with the heavy chain also including a "D" region of about 10 more amino acids. See, e.g., Fundamental Immunology, 2nd ed., Ch. 7 (Paul, W., ed.) (1989) New York: Raven Press (hereby incorporated by reference in its entirety for all purposes). The variable regions of each light/heavy chain pair typically form the antigen binding site.

Variable regions of immunoglobulin chains generally exhibit the same overall structure, comprising relatively conserved framework regions (FR) joined by three hypervariable regions, more often called "complementarity determining regions" or CDRs. The CDRs from the two chains of each heavy chain/light chain pair mentioned above typically are aligned by the framework regions to form a structure that binds specifically with a specific epitope on the target protein (e.g., Dkk-1). From N-terminal to C-terminal, naturally-occurring light and heavy chain variable regions both typically conform with the following order of these elements: FR1, CDR1, FR2, CDR2, FR3, CDR3 and FR4. A numbering system has been devised for assigning numbers to amino acids that occupy positions in each of these domains. This numbering system is defined in Kabat Sequences of Proteins of Immunological Interest ((1987 and 1991) National Institutes of Health, Bethesda, Md.), or Chothia & Lesk (1987) J. Mol. Biol. 196: 901-917; Chothia et al. (1989) Nature 342: 878-883. Each of the light chains provided by the present disclosure can be combined with any of the heavy chains provided by the present disclosure to form an antibody. In some embodiments, the antibodies contain two identical light chains and two identical heavy chains. Other antibodies that are provided are variants of antibodies formed by combination of the provided heavy and light chains and comprise light and/or heavy chains that each has at least 70%, 75%, 80%, 85%, 90%, 95%, 97% or 99% identity to the amino acid sequences of these chains. In some instances, such antibodies include at least one heavy chain and one light chain, whereas in other instances such variant forms contain two identical light chains and two identical heavy chains.

CDRs of Antibodies

Complementarity determining regions (CDRs) and framework regions (FR) of a given antibody may be identified using the system described by Kabat et al. in Sequences of Proteins of Immunological Interest, 5th Ed., US Dept. of Health and Human Services, PHS, NIH, NIH Publication no. 91-3242 (1991). Certain antibodies that are disclosed herein comprise one or more amino acid sequences that are identical or have substantial sequence identity to the amino acid sequences of one or more of the CDRs as provided.

The antibodies and fragments that are provided can include one, two, three, four, five or all six of the CDRs listed above. Some antibodies have variant forms of the CDRs listed in Table 4, with one or more (i.e., 2, 3, 4, 5 or 6) of the CDRs each having at least 80%, 85%, 90% or 95% sequence identity to a specific CDR sequence provided.

Competing Antibodies and Fragments

Antibodies and immunologically functional fragments thereof that compete with one the exemplified antibodies or functional fragments for specific binding to Dkk-1 are also provided. Such antibodies and fragments may also bind to the same epitope as one of the exemplified antibodies. Antibodies and fragments that compete with or bind to the same epitope as the exemplified antibody or fragment are expected to show similar functional properties.

Monoclonal Antibodies

The antibodies that are provided include monoclonal antibodies that bind to Dkk-1. Monoclonal antibodies may be produced using any technique known in the art, e.g., by immortalizing spleen cells harvested from the transgenic animal after completion of the immunization schedule. The spleen cells can be immortalized using any technique known in the art, e.g., by fusing them with myeloma cells to produce hybridomas. Myeloma cells for use in hybridoma-producing fusion procedures preferably are non-antibody-producing, have high fusion efficiency, and enzyme deficiencies that render them incapable of growing in certain selective media which support the growth of only the desired fused cells (hybridomas). Examples of suitable cell lines for use in mouse fusions include Sp-20, P3-X63/Ag8, P3-X63-Ag8.653, NS1/1.Ag 4 1, Sp210-Ag14, FO, NSO/U, MPC-11, MPC11-X45-GTG 1.7 and S19415XXO Bul; examples of cell lines used in rat fusions include R210.RCY3, Y3-Ag 1.2.3, IR983F and 4B210. Other cell lines useful for cell fusions are U-266, GM1500-GRG2, LICR-LON-HMy2 and UC729-6.

In some instances, a hybridoma cell line is produced by immunizing an animal (e.g., a transgenic animal having human immunoglobulin sequences) with a Dkk-1 immunogen; harvesting spleen cells from the immunized animal; fusing the harvested spleen cells to a myeloma cell line, thereby generating hybridoma cells; establishing hybridoma cell lines from the hybridoma cells, and identifying a hybridoma cell line that produces an antibody that binds a Dkk-1 polypeptide. Such hybridoma cell lines, and anti-Dkk-1 monoclonal antibodies produced by them, are encompassed by the present invention.

Monoclonal antibodies secreted by a hybridoma cell line can be purified using any technique known in the art. Hybridomas or Mabs may be further screened to identify Mabs with particular properties, such as the ability to block a Wnt induced activity. Examples of such screens are provided in the examples below.

Chimeric and Humanized Antibodies

Chimeric and humanized antibodies based upon the foregoing sequences are also provided. Monoclonal antibodies for use as therapeutic agents may be modified in various ways prior to use. One example is a "chimeric" antibody, which is an antibody composed of protein segments from different antibodies that are covalently joined to produce functional immunoglobulin light or heavy chains or immunologically functional portions thereof. Generally, a portion of the heavy chain and/or light chain is identical with or homologous to a corresponding sequence in antibodies derived from a particular species or belonging to a particular antibody class or subclass, while the remainder of the chain(s) is/are identical with or homologous to a corresponding sequence in antibodies derived from another species or belonging to another antibody class or subclass. For methods relating to chimeric antibodies, see, for example, U.S. Pat. No. 4,816,567; and Morrison et al., Proc. Natl. Acad. Sci. USA 81:6851-6855 (1985). CDR grafting is described, for example, in U.S. Pat. Nos. 6,180,370; 5,693,762; 5,693,761; 5,585,089; and 5,530, 101.

Generally, the goal of making a chimeric antibody is to create a chimera in which the number of amino acids from the intended patient species is maximized. One example is the "CDR-grafted" antibody, in which the antibody comprises one or more complementarity determining regions (CDRs) from a particular species or belonging to a particular antibody class or subclass, while the remainder of the antibody chain(s) is/are identical with or homologous to a corresponding sequence in antibodies derived from another species or belonging to another antibody class or subclass. For use in humans, the V region or selected CDRs from a rodent antibody often are grafted into a human antibody, replacing the naturally-occurring V regions or CDRs of the human antibody.

One useful type of chimeric antibody is a "humanized" antibody. Generally, a humanized antibody is produced from a monoclonal antibody raised initially in a non-human animal. Certain amino acid residues in this monoclonal antibody, typically from non-antigen recognizing portions of the antibody, are modified to be homologous to corresponding residues in a human antibody of corresponding isotype. Humanization can be performed, for example, using various methods by substituting at least a portion of a rodent variable region for the corresponding regions of a human antibody (see, e.g., U.S. Pat. Nos. 5,585,089 and 5,693,762; Jones et al. (1986) Nature 321:522-25; Riechmann et al. (1988) Nature 332:323-27; Verhoeyen et al. (1988) Science 239:1534-36). In some embodiments constant regions from species other than human can be used along with the human variable region(s) to produce hybrid antibodies.

Fully Human Antibodies

Fully human antibodies are also provided. Methods are available for making fully human antibodies specific for a given antigen without exposing human beings to the antigen ("fully human antibodies"). One means for implementing the production of fully human antibodies is the "humanization" of the mouse humoral immune system. Introduction of human immunoglobulin (Ig) loci into mice in which the endogenous Ig genes have been inactivated is one means of producing fully human monoclonal antibodies (Mabs) in mouse, an animal that can be immunized with any desirable antigen. Using fully human antibodies can minimize the immunogenic and allergic responses that can sometimes be caused by administering mouse or mouse-derivatized Mabs to humans as therapeutic agents.

Fully human antibodies can be produced by immunizing transgenic animals (usually mice) that are capable of producing a repertoire of human antibodies in the absence of endogenous immunoglobulin production. Antigens for this purpose typically have six or more contiguous amino acids, and optionally are conjugated to a carrier, such as a hapten. See, for example, Jakobovits et al. (1993) Proc. Natl. Acad. Sci. USA 90:2551-2555; Jakobovits et al. (1993) Nature 362:255-258; and Bruggermann et al. (1993) Year in Immunol. 7:33. In one example of such a method, transgenic animals are produced by incapacitating the endogenous mouse immunoglobulin loci encoding the mouse heavy and light immunoglobulin chains therein, and inserting into the mouse genome large fragments of human genome DNA containing loci that encode human heavy and light chain proteins. Partially modified animals, which have less than the full complement of human immunoglobulin loci, are then cross-bred to obtain an animal having all of the desired immune system modifications. When administered an immunogen, these transgenic animals produce antibodies that are immunospecific for the immunogen but have human rather than murine amino acid sequences, including the variable regions. For further details of such methods, see, for example, WO96/33735 and WO94/02602, which are hereby incorporated by reference. Additional methods relating to transgenic mice for making human antibodies are described in U.S. Pat. Nos. 5,545,807; 6,713,610; 6,673,986; 6,162,963; 5,545,807; 6,300,129; 6,255,458; 5,877,397; 5,874,299 and 5,545,806; in WO91/10741 and WO90/04036, and in EP 546073B1 and EP 546073A1.

The transgenic mice described above, referred to herein as "HuMab" mice, contain a human immunoglobulin gene minilocus that encodes unrearranged human heavy (μ and γ) and κ light chain immunoglobulin sequences, together with targeted mutations that inactivate the endogenous μ and k chain loci (Lonberg et al. (1994) Nature 368: 856-859). Accordingly, the mice exhibit reduced expression of mouse IgM and k in response to immunization, and the introduced human heavy and light chain transgenes undergo class switching and somatic mutation to generate high affinity human IgG κ monoclonal antibodies (Lonberg et al., supra.; Lonberg and Huszar (1995) Intern. Rev. Immunol., 13: 65-93; Harding and Lonberg (1995) Ann. N.Y. Acad. Sci. 764: 536-546). The preparation of HuMab mice is described in detail in Taylor et al. (1992) Nucleic Acids Research, 20: 6287-6295; Chen et al. (1993) International Immunology 5: 647-656; Tuaillon et al. (1994) J. Immunol. 152: 2912-2920; Lonberg et al. (1994) Nature 368: 856-859; Lonberg (1994) Handbook of Exp. Pharmacology 113: 49-101; Taylor et al. (1994) International Immunology 6: 579-591; Lonberg and Huszar (1995) Intern. Rev. Immunol. 13: 65-93; Harding and Lonberg, 1995, Ann. N.Y. Acad. Sci. 764: 536-546; Fishwild et al. (1996) Nature Biotechnology 14: 845-851; the foregoing references are hereby incorporated by reference in their entirety for all purposes. See further U.S. Pat. Nos. 5,545,806; 5,569,825; 5,625,126; 5,633,425; 5,789,650; 5,877,397; 5,661,016; 5,814,318; 5,874,299; and 5,770,429; as well as U.S. Pat. No. 5,545,807; and WO 93/1227; WO 92/22646; and WO 92/03918 Technologies utilized for producing human antibodies in these transgenic mice are disclosed also in WO 98/24893, and Mendez et al. (1997) Nature Genetics 15: 146-156, which are hereby incorporated by reference. For example, the HCo7 and HCo12 transgenic mice strains can be used to generate human anti-Dkk-1 antibodies.

Using hybridoma technology, antigen-specific human MAbs with the desired specificity can be produced and selected from the transgenic mice such as those described above. Such antibodies may be cloned and expressed using a suitable vector and host cell, or the antibodies can be harvested from cultured hybridoma cells.

Fully human antibodies can also be derived from phage-display libraries (as disclosed in Hoogenboom et al. (1991) J. Mol. Biol. 227:381; and Marks et al. (1991) J. Mol. Biol. 222:581). Phage display techniques mimic immune selection through the display of antibody repertoires on the surface of filamentous bacteriophage, and subsequent selection of phage by their binding to an antigen of choice. One such technique is described in WO99/10494 (hereby incorporated by reference), which describes the isolation of high affinity and functional agonistic antibodies for MPL- and msk-receptors using such an approach.

Bispecific or Bifunctional Antibodies

The antibodies that are provided also include bispecific and bifunctional antibodies that include one or more CDRs or one or more variable regions as described above. A bispecific or bifunctional antibody in some instances is an artificial hybrid antibody having two different heavy/light chain pairs and two different binding sites. Bispecific antibodies may be produced by a variety of methods including, but not limited to, fusion of hybridomas or linking of Fab' fragments. See, e.g., Songsivilai & Lachmann (1990) Clin. Exp. Immunol. 79: 315-321; Kostelny et al. (1992) J. Immunol. 148: 1547-1553.

Various Other Forms

Some of the antibodies or immunologically functional fragments that are provided are variant forms of the antibodies and fragments disclosed above. Naturally-occurring amino acids may be divided into classes based on common side chain properties: [0149] 1) hydrophobic: norleucine, Met, Ala, Val, Leu, Ile; [0150] 2) neutral hydrophilic: Cys, Ser, Thr, Asn, Gln; [0151] 3) acidic: Asp, Glu; [0152] 4) basic: His, Lys, Arg; [0153] 5) residues that influence chain orientation: Gly, Pro; and [0154] 6) aromatic: Trp, Tyr, Phe. Conservative amino acid substitutions may involve exchange of a member of one of these classes with another member of the same class. Conservative amino acid substitutions may encompass non-naturally occurring amino acid residues, which are typically incorporated by chemical peptide synthesis rather than by synthesis in biological systems. These include peptidomimetics and other reversed or inverted forms of amino acid moieties. Non-conservative substitutions may involve the exchange of a member of one of the above classes for a member from another class. Such substituted residues may be introduced into regions of the antibody that are homologous with human antibodies, or into the non-homologous regions of the molecule.

In making such changes, according to certain embodiments, the hydropathic index of amino acids may be considered. The hydropathic profile of a protein is calculated by assigning each amino acid a numerical value ("hydropathy index") and then repetitively averaging these values along the peptide chain. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic profile in conferring interactive biological function on a protein is understood in the art (see, for example, Kyte et al., 1982, J. Mol. Biol. 157:105-131). It is known that certain amino acids may be substituted for other amino acids having a similar hydropathic index or score and still retain a similar biological activity. In making changes based upon the hydropathic index, in certain embodiments, the substitution of amino acids whose hydropathic indices are within .+−.2 is included. In some aspects of the invention, those which are within .+−.1 are included, and in other aspects of the invention, those within .+−.0.5 are included.

It is also understood in the art that the substitution of like amino acids can be made effectively on the basis of hydrophilicity, particularly where the biologically functional protein or peptide thereby created is intended for use in immunological embodiments, as in the present case. In some embodiments, the greatest local average hydrophilicity of a protein, as governed by the hydrophilicity of its adjacent amino acids, correlates with its immunogenicity and antigen-binding or immunogenicity, that is, with a biological property of the protein.

The following hydrophilicity values have been assigned to these amino acid residues: arginine (+3.0); lysine (+3.0); aspartate (+3.0.+−.1); glutamate (+3.0.+−0.1); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in some embodiments, the substitution of amino acids whose hydrophilicity values are within .+−.2 is included, in other embodiments, those which are within .+−.1 are included, and in still other embodiments, those within .+−.0.5 are included. In some instances, one may also identify epitopes from primary amino acid sequences on the basis of hydrophilicity. These regions are also referred to as "epitopic core regions."

A skilled artisan will be able to determine suitable variants of polypeptides as set forth herein using well-known techniques. One skilled in the art may identify suitable areas of the molecule that may be changed without destroying activity by targeting regions not believed to be important for activity. The skilled artisan also will be able to identify residues and portions of the molecules that are conserved among similar polypeptides. In further embodiments, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a protein that correspond to amino acid residues important for activity or structure in similar proteins. One skilled in the art may opt for chemically similar amino acid substitutions for such predicted important amino acid residues.

One skilled in the art can also analyze the three-dimensional structure and amino acid sequence in relation to that structure in similar polypeptides. In view of such information, one skilled in the art may predict the alignment of amino acid residues of an antibody with respect to its three dimensional structure. One skilled in the art may choose not to make radical changes to amino acid residues predicted to be on the surface of the protein, since such residues may be involved in important interactions with other molecules. Moreover, one skilled in the art may generate test variants containing a single amino acid substitution at each desired amino acid residue. These variants can then be screened using assays for Dkk-1 neutralizing activity, (see examples below) thus yielding information regarding which amino acids can be changed and which must not be changed. In other words, based on information gathered from such routine experiments, one skilled in the art can readily determine the amino acid positions where further substitutions should be avoided either alone or in combination with other mutations.

A number of scientific publications have been devoted to the prediction of secondary structure. See Moult (1996) Curr. Op. in Biotech. 7:422-427; Chou et al. (1974) Biochemistry 13:222-245; Chou et al. (1974) Biochemistry 113:211-222; Chou et al. (1978) Adv. Enzymol. Relat. Areas Mol. Biol. 47:45-148; Chou et al. (1979) Ann. Rev. Biochem. 47:251-276; and Chou et al. (1979) Biophys. J. 26:367-384. Moreover, computer programs are currently available to assist with predicting secondary structure. One method of predicting secondary structure is based upon homology modeling. For example, two polypeptides or proteins that have a sequence identity of greater than 30%, or similarity greater than 40% often have similar structural topologies. The recent growth of the protein structural database (PDB) has provided enhanced predictability of secondary structure, including the potential number of folds within a polypeptide's or protein's structure. See Holm et al. (1999) Nucl. Acid. Res. 27:244-247. It has been suggested (Brenner et al. (1997) Curr. Op. Struct. Biol. 7:369-376) that there are a limited number of folds in a given polypeptide or protein and that once a critical number of structures have been resolved, structural prediction will become dramatically more accurate.

Additional methods of predicting secondary structure include "threading" (Jones (1997) Curr. Opin. Struct. Biol. 7:377-87; Sippl et al. (1996) Structure 4:15-19), "profile analysis" (Bowie et al. (1991) Science 253:164-170; Gribskov et al. (1990) Meth. Enzym. 183:146-159; Gribskov et al. (1987) Proc. Nat. Acad. Sci. 84:4355-4358), and "evolutionary linkage" (See Holm (1999), supra; and Brenner (1997), supra).

In some embodiments of the invention, amino acid substitutions are made that: (1) reduce susceptibility to proteolysis, (2) reduce susceptibility to oxidation, (3) alter binding affinity for forming protein complexes, (4) alter ligand or antigen binding affinities, and/or (4) confer or modify other physicochemical or functional properties on such polypeptides. For example, single or multiple amino acid substitutions (in certain embodiments, conservative amino acid substitutions) may be made in the naturally-occurring sequence. Substitutions can be made in that portion of the antibody that lies outside the domain(s) forming intermolecular contacts). In such embodiments, conservative amino acid substitutions can be used that do not substantially change the structural characteristics of the parent sequence (e.g., one or more replacement amino acids that do not disrupt the secondary structure that characterizes the parent or native antibody). Examples of art-recognized polypeptide secondary and tertiary structures are described in Proteins, Structures and Molecular Principles (Creighton, Ed.) (1984) W. H. New York: Freeman and Company; Introduction to Protein Structure (Branden and Tooze, eds.) (1991) New York: Garland Publishing; and Thornton et al. (1991) Nature 354: 105.

The invention also encompasses glycosylation variants of the inventive antibodies wherein the number and/or type of glycosylation site(s) has been altered compared to the amino acid sequences of the parent polypeptide. In certain embodiments, antibody protein variants comprise a greater or a lesser number of N-linked glycosylation sites than the native antibody. An N-linked glycosylation site is characterized by the sequence: Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions that eliminate or alter this sequence will prevent addition of an N-linked carbohydrate chain present in the native polypeptide. For example, the glycosylation can be reduced by the deletion of an Asn or by substituting the Asn with a different amino acid. In other embodiments, one or more new N-linked sites are created. Antibodies typically have a N-linked glycosylation site in the Fc region.

Additional preferred antibody variants include cysteine variants wherein one or more cysteine residues in the parent or native amino acid sequence are deleted from or substituted with another amino acid (e.g., serine). Cysteine variants are useful, inter alia when antibodies must be refolded into a biologically active conformation. Cysteine variants may have fewer cysteine residues than the native antibody, and typically have an even number to minimize interactions resulting from unpaired cysteines.

The heavy and light chains, variable regions domains and CDRs that are disclosed can be used to prepare polypeptides that contain an antigen binding region that can specifically bind to a Dkk-1 polypeptide. For example, one or more of the CDRs listed in Table 4 can be incorporated into a molecule (e.g., a polypeptide) covalently or noncovalently to make an immunoadhesion. An immunoadhesion may incorporate the CDR(s) as part of a larger polypeptide chain, may covalently link the CDR(s) to another polypeptide chain, or may incorporate the CDR(s) noncovalently. The CDR(s) enable the immunoadhesion to bind specifically to a particular antigen of interest (e.g., a Dkk-1 polypeptide or epitope thereof).

Mimetics (e.g., peptide mimetics" or "peptidomimetics") based upon the variable region domains and CDRs that are described herein are also provided. These analogs can be peptides, non-peptides or combinations of peptide and non-peptide regions. Fauchere (1986) Adv. Drug Res. 15: 29; Veber and Freidinger (1985) TINS p. 392; and Evans et al. (1987) J. Med. Chem. 30: 1229, which are incorporated herein by reference for any purpose. Peptide mimetics that are structurally similar to therapeutically useful peptides may be used to produce a similar therapeutic or prophylactic effect. Such compounds are often developed with the aid of computerized molecular modeling. Generally, peptidomimetics of the invention are proteins that are structurally similar to an antibody displaying a desired biological activity, such as here the ability to specifically bind Dkk-1, but have one or more peptide linkages optionally replaced by a linkage selected from: —$CH_2NH$—, —$CH_2S$—, —$CH_2$—$CH_2$—, —CH=CH-(cis and trans), —$COCH_2$—, —CH(OH) $CH_2$—, and —$CH_2SO$—, by methods well known in the art. Systematic substitution of one or more amino acids of a consensus sequence with a D-amino acid of the same type (e.g., D-lysine in place of L-lysine) may be used in certain embodiments of the invention to generate more stable proteins. In addition, constrained peptides comprising a consensus sequence or a substantially identical consensus sequence variation may be generated by methods known in the art (Rizo and Gierasch (1992) Ann. Rev. Biochem. 61: 387), incorporated herein by reference), for example, by adding internal cysteine residues capable of forming intramolecular disulfide bridges which cyclize the peptide.

Derivatives of the antibodies and immunologically functional fragments that are described herein are also provided. The derivatized antibody or fragment may comprise any molecule or substance that imparts a desired property to the antibody or fragment, such as increased half-life in a particular use. The derivatized antibody can comprise, for example, a detectable (or labeling) moiety (e.g., a radioactive, colorimetric, antigenic or enzymatic molecule, a detectable bead (such as a magnetic or electrodense (e.g., gold) bead), or a molecule that binds to another molecule (e.g., biotin or streptavidin)), a therapeutic or diagnostic moiety (e.g., a radioactive, cytotoxic, or pharmaceutically active moiety), or a molecule that increases the suitability of the antibody for a particular use (e.g., administration to a subject, such as a human subject, or other in vivo or in vitro uses). Examples of molecules that can be used to derivatize an antibody include albumin (e.g., human serum albumin) and polyethylene glycol (PEG). Albumin-linked and PEGylated derivatives of antibodies can be prepared using techniques well known in the art. In one embodiment, the antibody is conjugated or otherwise linked to transthyretin (TTR) or a TTR variant. The TTR or TTR variant can be chemically modified with, for example, a chemical selected from the group consisting of dextran, poly(n-vinyl pyrrolidone), polyethylene glycols, propropylene glycol homopolymers, polypropylene oxide/ethylene oxide co-polymers, polyoxyethylated polyols and polyvinyl alcohols.

Other derivatives include covalent or aggregative conjugates of anti-Dkk-1 antibodies, or fragments thereof, with other proteins or polypeptides, such as by expression of recombinant fusion proteins comprising heterologous polypeptides fused to the N-terminus or C-terminus of an anti-Dkk-1 antibody polypeptide. For example, the conjugated peptide may be a heterologous signal (or leader) polypeptide, e.g., the yeast alpha-factor leader, or a peptide such as an epitope tag. Anti-Dkk-1 antibody-containing fusion proteins can comprise peptides added to facilitate purification or identification of the anti-Dkk-1 antibody (e.g., poly-His). An anti-Dkk-1 antibody polypeptide also can be linked to the FLAG peptide as described in Hopp et al., Bio/Technology 6:1204 (1988) and U.S. Pat. No. 5,011,912. The FLAG peptide is highly antigenic and provides an epitope reversibly bound by a specific monoclonal antibody (Mab), enabling rapid assay and facile purification of expressed recombinant protein. Reagents useful for preparing fusion proteins in which the FLAG peptide is fused to a given polypeptide are commercially available (Sigma, St. Louis, Mo.).

Oligomers that contain one or more anti-Dkk-1 antibody polypeptides may be employed as Dkk-1 antagonists. Oligomers may be in the form of covalently-linked or non-covalently-linked dimers, trimers, or higher oligomers. Oligomers comprising two or more anti-Dkk-1 antibody polypeptides are contemplated for use, with one example being a homodimer. Other oligomers include heterodimers, homotrimers, heterotrimers, homotetramers, heterotetramers, etc.

One embodiment is directed to oligomers comprising multiple anti-Dkk-1 antibody polypeptides joined via covalent or non-covalent interactions between peptide moieties fused to the anti-Dkk-1 antibody polypeptides. Such peptides may be peptide linkers (spacers), or peptides that have the property of promoting oligomerization. Leucine zippers and certain polypeptides derived from antibodies are among the peptides that can promote oligomerization of anti-Dkk-1 antibody polypeptides attached thereto, as described in more detail below.

In particular embodiments, the oligomers comprise from two to four anti-Dkk-1 antibody polypeptides. The anti-Dkk-1 antibody moieties of the oligomer may be in any of the forms described above, e.g., variants or fragments. Preferably, the oligomers comprise anti-Dkk-1 antibody polypeptides that have Dkk-1 binding activity.

In one embodiment, an oligomer is prepared using polypeptides derived from immunoglobulins. Preparation of fusion proteins comprising certain heterologous polypeptides fused to various portions of antibody-derived polypeptides (including the Fc domain) has been described, e.g., by Ashkenazi et al., (1991) PNAS USA 88:10535; Byrn et al., (1990) Nature 344:677; and Hollenbaugh et al., (1992) "Construction of Immunoglobulin Fusion Proteins", in Current Protocols in Immunology, Suppl. 4, pages 10.19.1-10.19.11.

One embodiment of the present invention is directed to a dimer comprising two fusion proteins created by fusing a Dkk-1 binding fragment of an anti-Dkk-1 antibody to the Fc region of an antibody. The dimer can be made by, for example, inserting a gene fusion encoding the fusion protein into an appropriate expression vector, expressing the gene fusion in host cells transformed with the recombinant expression vector, and allowing the expressed fusion protein to assemble much like antibody molecules, whereupon interchain disulfide bonds form between the Fc moieties to yield the dimer.

The term "Fc polypeptide" as used herein includes native and mutein forms of polypeptides derived from the Fc region of an antibody. Truncated forms of such polypeptides containing the hinge region that promotes dimerization also are included. Fusion proteins comprising Fc moieties (and oligomers formed therefrom) offer the advantage of facile purification by affinity chromatography over Protein A or Protein G columns.

One suitable Fc polypeptide, described in PCT application WO 93/10151 and U.S. Pat. Nos. 5,426,048 and 5,262,522, is a single chain polypeptide extending from the N-terminal hinge region to the native C-terminus of the Fc region of a human IgG1 antibody. Another useful Fc polypeptide is the Fc mutein described in U.S. Pat. No. 5,457,035 and in Baum et al. (1994) EMBO J. 13:3992-4001. The amino acid sequence of this mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors.

In other embodiments, the variable portion of the heavy and/or light chains of an anti-Dkk-1 antibody such as disclosed herein may be substituted for the variable portion of an antibody heavy and/or light chain.

Alternatively, the oligomer is a fusion protein comprising multiple anti-Dkk-1 antibody polypeptides, with or without peptide linkers (spacer peptides). Among the suitable peptide linkers are those described in U.S. Pat. Nos. 4,751,180 and 4,935,233.

Another method for preparing oligomeric anti-Dkk-1 antibody derivatives involves use of a leucine zipper. Leucine zipper domains are peptides that promote oligomerization of the proteins in which they are found. Leucine zippers were originally identified in several DNA-binding proteins (Landschulz et al. (1988) Science 240:1759), and have since been found in a variety of different proteins. Among the known leucine zippers are naturally occurring peptides and derivatives thereof that dimerize or trimerize. Examples of leucine zipper domains suitable for producing soluble oligomeric proteins are described in WO 94/10308, and the leucine zipper derived from lung surfactant protein D (SPD) described in Hoppe et al. (1994) FEBS Letters 344:191, hereby incorporated by reference. The use of a modified leucine zipper that allows for stable trimerization of a heterologous protein fused thereto is described in Fanslow et al. (1994) Semin. Immunol. 6:267-78. In one approach, recombinant fusion proteins comprising an anti-Dkk-1 antibody fragment or derivative fused to a leucine zipper peptide are expressed in suitable host cells, and the soluble oligomeric anti-Dkk-1 antibody fragments or derivatives that form are recovered from the culture supernatant.

Nucleic Acids

Nucleic acids that encode one or both chains of an antibody of the invention, or a fragment, derivative, mutein, or variant thereof, polynucleotides sufficient for use as hybridization probes, PCR primers or sequencing primers for identifying, analyzing, mutating or amplifying a polynucleotide encoding a polypeptide, anti-sense nucleic acids for inhibiting expression of a polynucleotide, and complementary sequences of the foregoing are also provided. The nucleic acids can be any length. They can be, for example, 5, 10, 15, 20, 25, 30, 35, 40, 45, 50, 75, 100, 125, 150, 175, 200, 250, 300, 350, 400, 450, 500, 750, 1,000, 1,500, 3,000, 5,000 or more nucleotides in length, and/or can comprise one or more additional sequences, for example, regulatory sequences, and/or be part of a larger nucleic acid, for example, a vector. The nucleic acids can be single-stranded or double-stranded and can comprise RNA and/or DNA nucleotides, and artificial variants thereof (e.g., peptide nucleic acids). Nucleic acids encoding fusion proteins that include these peptides are also provided.

DNA encoding antibody polypeptides (e.g., heavy or light chain, variable domain only, or full length) may be isolated from B-cells of mice that have been immunized with Dkk-1 or an immunogenic fragment thereof. The DNA may be isolated by conventional procedures such as polymerase chain reaction (PCR). Phage display is another example of a known technique whereby derivatives of antibodies may be prepared. In one approach, polypeptides that are components of an antibody of interest are expressed in any suitable recombinant expression system, and the expressed polypeptides are allowed to assemble to form antibody molecules.

Exemplary nucleic acids that encode the light and heavy chains, variable regions and CDRs of the antibodies and immunologically functional fragments are provided. Due to the degeneracy of the genetic code, each of the polypeptide sequences is also encoded by a large number of other nucleic acid sequences besides those listed. The present invention provides each degenerate nucleotide sequence encoding each antibody of the invention.

The invention further provides nucleic acids that hybridize to other nucleic acids under particular hybridization conditions. Methods for hybridizing nucleic acids are well-known in the art. See, e.g., Current Protocols in Molecular Biology, John Wiley & Sons, N.Y. (1989), 6.3.1-6.3.6. Examples of known moderately stringent hybridization condition use a prewashing solution containing 5.times. sodium chloride/sodium citrate (SSC), 0.5% SDS, 1.0 mM EDTA (pH 8.0), hybridization buffer of about 50% formamide, 6.times.SSC, and a hybridization temperature of 55° C. (or other similar hybridization solutions, such as one containing about 50% formamide, with a hybridization temperature of 42° C.), and washing conditions of 60° C., in 0.5.times.SSC, 0.1% SDS. Examples of known stringent hybridization conditions hybridize in 6.times.SSC at 45° C., followed by one or more washes in 0.1.times.SSC, 0.2% SDS at 68° C. Furthermore, one of skill in the art can manipulate the hybridization and/or washing conditions to increase or decrease the stringency of hybridization such that nucleic acids comprising nucleotide sequences that are at least 65, 70, 75, 80, 85, 90, 95, 98 or 99% identical to each other typically remain hybridized to each other.

The basic parameters affecting the choice of hybridization conditions and guidance for devising suitable conditions are set forth by, for example, Sambrook, Fritsch, and Maniatis (1989) Molecular Cloning: A Laboratory Manual, Cold Spring Harbor Laboratory Press, Cold Spring Harbor, N.Y., chapters 9 and 11; and Current Protocols in Molecular Biology (1995) Ausubel et al., eds., John Wiley & Sons, Inc., sections 2.10 and 6.3-6.4), and can be readily determined by those having ordinary skill in the art based on, for example, the length and/or base composition of the DNA.

Changes can be introduced by mutation into a nucleic acid, thereby leading to changes in the amino acid sequence of a polypeptide (e.g., an antibody or antibody derivative of the invention) that it encodes. Mutations can be introduced using any technique known in the art. In one embodiment, one or more particular amino acid residues are changed using, for example, a site-directed mutagenesis protocol. In another embodiment, one or more randomly selected residues is changed using, for example, a random mutagenesis protocol. However it is made, a mutant polypeptide can be expressed and screened for a desired property.

Mutations can be introduced into a nucleic acid without significantly altering the biological activity of a polypeptide that it encodes. For example, one can make nucleotide substitutions leading to amino acid substitutions at non-essential amino acid residues. Alternatively, one or more mutations can be introduced into a nucleic acid that selectively changes the biological activity of a polypeptide that it encodes. For example, the mutation can quantitatively or qualitatively change the biological activity. Examples of quantitative changes include increasing, reducing or eliminating the activity. Examples of qualitative changes include changing the antigen specificity of an antibody.

In another aspect, the present invention provides nucleic acid molecules that are suitable for use as primers or hybridization probes for the detection of nucleic acid sequences of the invention. A nucleic acid molecule of the invention can comprise only a portion of a nucleic acid sequence encoding a full-length polypeptide of the invention, for example, a fragment that can be used as a probe or primer or a fragment encoding an active portion (e.g., a Dkk-1 binding portion) of a polypeptide of the invention.

Probes based on the sequence of a nucleic acid of the invention can be used to detect the nucleic acid or similar nucleic acids, for example, transcripts encoding a polypeptide of the invention. The probe can comprise a label group, e.g., a radioisotope, a fluorescent compound, an enzyme, or an enzyme co-factor. Such probes can be used to identify a cell that expresses the polypeptide.

In another aspect, the present invention provides vectors comprising a nucleic acid encoding a polypeptide of the invention or a portion thereof (e.g., a fragment containing one or more CDRs or one or more variable region domains). Examples of vectors include, but are not limited to, plasmids, viral vectors, non-episomal mammalian vectors and expression vectors, for example, recombinant expression vectors. The recombinant expression vectors of the invention can comprise a nucleic acid of the invention in a form suitable for expression of the nucleic acid in a host cell. The recombinant expression vectors include one or more regulatory sequences, selected on the basis of the host cells to be used for expression, which is operably linked to the nucleic acid sequence to be expressed. Regulatory sequences include those that direct constitutive expression of a nucleotide sequence in many types of host cells (e.g., SV40 early gene enhancer, Rous sarcoma virus promoter and cytomegalovirus promoter), those that direct expression of the nucleotide sequence only in certain host cells (e.g., tissue-specific regulatory sequences, see Voss et al. (1986) Trends Biochem. Sci. 11:287, Maniatis et al. (1987) Science 236:1237, incorporated by reference herein in their entireties), and those that direct inducible expression of a nucleotide sequence in response to particular treatment or condition (e.g., the metallothionine promoter in mammalian cells and the tet-responsive and/or streptomycin responsive promoter in both prokaryotic and eukaryotic systems (see id.). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

In another aspect, the present invention provides host cells into which a recombinant expression vector of the invention has been introduced. A host cell can be any prokaryotic cell (for example, E. coli) or eukaryotic cell (for example, yeast, insect, or mammalian cells (e.g., CHO cells)). Vector DNA can be introduced into prokaryotic or eukaryotic cells via conventional transformation or transfection techniques. For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die), among other methods.

Preparation of Antibodies

The non-human antibodies that are provided can be, for example, derived from any antibody-producing animal, such as mouse, rat, rabbit, goat, donkey, or non-human primate (such as monkey (e.g., cynomologous or rhesus monkey) or ape (e.g., chimpanzee)). Non-human antibodies can be used, for instance, in in vitro cell culture and cell-culture based applications, or any other application where an immune response to the antibody does not occur or is insignificant, can be prevented, is not a concern, or is desired. In certain embodiments of the invention, the antibodies may be produced by immunizing with full-length Dkk-1 or with the carboxy-terminal half of Dkk-1. The antibodies may be polyclonal, monoclonal, or may be synthesized in host cells by expressing recombinant DNA.

Fully human antibodies may be prepared as described above by immunizing transgenic animals containing human immunoglobulin loci or by selecting a phage display library that is expressing a repertoire of human antibodies.

The monoclonal antibodies (Mabs) of the invention can be produced by a variety of techniques, including conventional monoclonal antibody methodology, e.g., the standard somatic cell hybridization technique of Kohler and Milstein (1975) Nature 256: 495. Alternatively, other techniques for producing monoclonal antibodies can be employed, for example, the viral or oncogenic transformation of B-lymphocytes. One suitable animal system for preparing hybridomas is the murine system, which is a very well established procedure.

Immunization protocols and techniques for isolation of immunized splenocytes for fusion are known in the art. For such procedures, B cells from immunized mice are fused with a suitable immortalized fusion partner, such as a murine myeloma cell line. If desired, rats or other mammals besides can be immunized instead of mice and B cells from such animals can be fused with the murine myeloma cell line to form hybridomas. Alternatively, a myeloma cell line from a source other than mouse may be used. Fusion procedures for making hybridomas also are well known.

The single chain antibodies that are provided may be formed by linking heavy and light chain variable domain (Fv region) fragments via an amino acid bridge (short peptide linker), resulting in a single polypeptide chain. Such single-chain Fvs (scFvs) may be prepared by fusing DNA encoding a peptide linker between DNAs encoding the two variable domain polypeptides (VL and VH). The resulting polypeptides can fold back on themselves to form antigen-binding monomers, or they can form multimers (e.g., dimers, trimers, or tetramers), depending on the length of a flexible linker between the two variable domains (Kortt et al. (1997) Prot. Eng. 10:423; Kortt et al. (2001) Biomol. Eng. 18:95-108). By combining different VL and VH-comprising polypeptides, one can form multimeric scFvs that bind to different epitopes (Kriangkum et al. (2001) Biomol. Eng. 18:31-40). Techniques developed for the production of single chain antibodies include those described in U.S. Pat. No. 4,946,778; Bird (1988) Science 242:423; Huston et al. (1988) Proc. Natl. Acad. Sci. USA 85:5879; Ward et al. (1989) Nature 334:544, de Graaf et al. (2002) Methods Mol. Biol. 178:379-87.

Antibodies provided herein that are of one subclass can be changed to antibodies from a different subclass using subclass switching methods. Thus, IgG antibodies may be derived from an IgM antibody, for example, and vice versa. Such techniques allow the preparation of new antibodies that possess the antigen-binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g., DNA encoding the constant domain of an antibody of the desired isotype. See, e.g., Lantto et al. (2002) Methods Mol. Biol. 178:303-16.

Moreover, techniques for deriving antibodies having different properties (i.e., varying affinities for the antigen to which they bind) are also known. One such technique, referred to as chain shuffling, involves displaying immunoglobulin variable domain gene repertoires on the surface of filamentous bacteriophage, often referred to as phage display. Chain shuffling has been used to prepare high affinity antibodies to the hapten 2-phenyloxazol-5-one, as described by Marks et al. (1992) BioTechnology, 10:779.

Conservative modifications may be made to the heavy and light chains described in Table 1 (and corresponding modifications to the encoding nucleic acids) to produce an anti-Dkk-1 antibody having functional and biochemical characteristics. Methods for achieving such modifications are described above.

Antibodies and functional fragments thereof according to the invention may be further modified in various ways. For example, if they are to be used for therapeutic purposes, they may be conjugated with polyethylene glycol (pegylated) to prolong the serum half-life or to enhance protein delivery. Alternatively, the V region of the subject antibodies or fragments thereof may be fused with the Fc region of a different antibody molecule. The Fc region used for this purpose may be modified so that it does not bind complement, thus reducing the likelihood of inducing cell lysis in the patient when the fusion protein is used as a therapeutic agent. In addition, the subject antibodies or functional fragments thereof may be conjugated with human serum albumin to enhance the serum half-life of the antibody or fragment thereof. Another useful fusion partner for the inventive antibodies or fragments thereof is transthyretin (TTR). TTR has the capacity to form a tetramer, thus an antibody-TTR fusion protein can form a multivalent antibody which may increase its binding avidity.

Alternatively, substantial modifications in the functional and/or biochemical characteristics of the antibodies and fragments described herein may be achieved by creating substitutions in the amino acid sequence of the heavy and light chains that differ significantly in their effect on maintaining (a) the structure of the molecular backbone in the area of the substitution, for example, as a sheet or helical conformation, (b) the charge or hydrophobicity of the molecule at the target site, or (c) the bulkiness of the side chain. A "conservative amino acid substitution" may involve a substitution of a native amino acid residue with a normative residue that has little or no effect on the polarity or charge of the amino acid residue at that position. Furthermore, any native residue in the polypeptide may also be substituted with alanine, as has been previously described for alanine scanning mutagenesis.

Amino acid substitutions (whether conservative or non-conservative) of the subject antibodies can be implemented by those skilled in the art by applying routine techniques. Amino acid substitutions can be used to identify important residues of the antibodies provided herein, or to increase or decrease the affinity of these antibodies for human Dkk-1 or for modifying the binding affinity of other anti-Dkk-1 antibodies described herein.

Expression of Anti-Dkk-1 Antibodies

The anti-Dkk-1 antibodies and immunological functional fragments can be prepared by any of a number of conventional techniques. For example, anti-Dkk-1 antibodies may be produced by recombinant expression systems, using any technique known in the art. See, for example, Monoclonal Antibodies, Hybridomas: A New Dimension in Biological Analyses, Kennet et al. (eds.) Plenum Press, New York (1980): and Antibodies: A Laboratory Manual, Harlow and Lane (eds.), Cold Spring Harbor Laboratory Press, Cold Spring Harbor, N.Y. (1988).

Antibodies of the present invention can be expressed in hybridoma cell lines or in cell lines other than hybridomas. Expression constructs encoding the antibodies can be used to transform a mammalian, insect or microbial host cell. Transformation can be performed using any known method for introducing polynucleotides into a host cell, including, for example packaging the polynucleotide in a virus or bacteriophage and transducing a host cell with the construct by transfection procedures known in the art, as exemplified by U.S. Pat. Nos. 4,399,216, 4,912,040, 4,740,461, and 4,959, 455. The optimal transformation procedure used will depend upon which type of host cell is being transformed. Methods for introduction of heterologous polynucleotides into mammalian cells are well known in the art and include, but are not limited to, dextran-mediated transfection, calcium phosphate precipitation, polybrene mediated transfection, protoplast fusion, electroporation, encapsulation of the polynucleotide(s) in liposomes, mixing nucleic acid with positively-charged lipids, and direct microinjection of the DNA into nuclei.

Recombinant expression constructs of the invention typically comprise a nucleic acid molecule encoding a polypeptide comprising one or more of the following: a heavy chain constant region; a heavy chain variable region; a light chain constant region; a light chain variable region; one or more CDRs of the light or heavy chain of the anti-Dkk-1 antibody. These nucleic acid sequences are inserted into an appropriate expression vector using standard ligation techniques. The vector is typically selected to be functional in the particular host cell employed (i.e., the vector is compatible with the host cell machinery, permitting amplification and/or expression of the gene can occur). In some embodiments, vectors are used that employ protein-fragment complementation assays using protein reporters, such as dihydrofolate reductase (see, for example, U.S. Pat. No. 6,270,964, which is hereby incorporated by reference). Suitable expression vectors can be purchased, for example, from Invitrogen Life Technologies or BD Biosciences (formerly "Clontech"). Other useful vectors for cloning and expressing the antibodies and fragments of the invention include those described in Bianchi and McGrew, Biotech Biotechnol Bioeng 84(4):439-44 (2003), which is hereby incorporated by reference. Additional suitable expression vectors are discussed, for example, in Methods Enzymol, vol. 185 (D. V. Goeddel, ed.) (1990) New York: Academic Press.

Typically, expression vectors used in any of the host cells contain sequences for plasmid or virus maintenance and for cloning and expression of exogenous nucleotide sequences. Such sequences, collectively referred to as "flanking sequences" typically include one or more of the following operatively linked nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element.

Optionally, the vector may contain a "tag"-encoding sequence, that is, an oligonucleotide molecule located at the 5' or 3' end of the coding sequence, the oligonucleotide sequence encoding polyHis (such as hexaHis), or another "tag" for which commercially available antibodies exist, such as FLAG®, HA (hemaglutinin from influenza virus), or myc. The tag is typically fused to the antibody protein upon expression, and can serve as a means for affinity purification of the antibody from the host cell. Affinity purification can be accomplished, for example, by column chromatography using antibodies against the tag as an affinity matrix. Optionally, the tag can subsequently be removed from the purified antibody polypeptide by various means such as using certain peptidases for cleavage.

Flanking sequences in the expression vector may be homologous (i.e., from the same species and/or strain as the host cell), heterologous (i.e., from a species other than the host cell species or strain), hybrid (i.e., a combination of flanking sequences from more than one source), synthetic or native. As such, the source of a flanking sequence may be any prokaryotic or eukaryotic organism, any vertebrate or invertebrate organism, or any plant, provided that the flanking sequence is functional in, and can be activated by, the host cell machinery.

Flanking sequences useful in the vectors of this invention may be obtained by any of several methods well known in the art. Typically, flanking sequences useful herein will have been previously identified by mapping and/or by restriction endonuclease digestion and can thus be isolated from the proper tissue source using the appropriate restriction endonucleases. In some cases, the full nucleotide sequence of a flanking sequence may be known. Here, the flanking sequence may be synthesized using the methods described herein for nucleic acid synthesis or cloning.

Where all or only a portion of the flanking sequence is known, it may be obtained using PCR and/or by screening a genomic library with a suitable oligonucleotide and/or flanking sequence fragment from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagen® column chromatography (Chatsworth, Calif.), or other methods known to the skilled artisan. The selection of suitable enzymes to accomplish this purpose will be readily apparent to those skilled in the art.

An origin of replication is typically a part of prokaryotic expression vectors, particularly those purchased commercially, and the origin aids in the amplification of the vector in a host cell. If the vector of choice does not contain an origin of replication site, one may be chemically synthesized based on a known sequence, and ligated into the vector. For example, the origin of replication from the plasmid pBR322 (New England Biolabs, Beverly, Mass.) is suitable for most gram-negative bacteria and various origins (e.g., SV40, polyoma, adenovirus, vesicular stomatitis virus (VSV), or papillomaviruses such as HPV or BPV) are useful for cloning vectors in mammalian cells. Generally, a mammalian origin of replication is not needed for mammalian expression vectors (for example, the SV40 origin is often used only because it contains the early promoter).

The expression and cloning vectors of the present invention will typically contain a promoter that is recognized by the host organism and operably linked to nucleic acid encoding the anti-Dkk-1 antibody or immunologically functional fragment thereof. Promoters are untranscribed sequences located upstream (i.e., 5') to the start codon of a structural gene (generally within about 100 to 1000 bp) that control transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, initiate continuous gene product production; that is, there is little or no experimental control over gene expression. A large number of promoters, recognized by a variety of potential host cells, are well known. A suitable promoter is operably linked to the DNA encoding anti-Dkk-1 antibody by removing the promoter from the source DNA by restriction enzyme digestion or amplifying the promoter by polymerase chain reaction and inserting the desired promoter sequence into the vector.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus and—most preferably Simian Virus 40 (SV40). Other suitable mammalian promoters include heterologous mammalian promoters, for example, heat-shock promoters and the actin promoter.

Particular promoters useful in the practice of the recombinant expression vectors of the invention include, but are not limited to: the SV40 early promoter region (Bemoist and Chambon (1981) Nature 290: 304-10); the CMV promoter; the promoter contained in the 3' long terminal repeat of Rous sarcoma virus (Yamamoto, et al. (1980) Cell 22: 787-97); the herpes thymidine kinase promoter (Wagner et al. (1981) Proc. Natl. Acad. Sci. U.S.A. 78: 1444-45); the regulatory sequences of the metallothionine gene (Brinster et al. (1982) Nature 296: 39-42); prokaryotic expression vectors such as the beta-lactamase promoter (Villa-Kamaroff et al. (1978) Proc. Natl. Acad. Sci. U.S.A., 75: 3727-31); or the tac promoter (DeBoer et al. (1983) Proc. Natl. Acad. Sci. U.S.A. 80: 21-25). Also available for use are the following animal transcriptional control regions, which exhibit tissue specificity and have been utilized in transgenic animals: the elastase I gene control region that is active in pancreatic acinar cells (Swift et al. (1984) Cell 38: 63946; Ornitz et al. (1986) Cold Spring Harbor Symp. Quant. Biol. 50: 399409; MacDonald, 1987, Hepatology 7: 425-515); the insulin gene control region that is active in pancreatic beta cells (Hanahan (1985) Nature 315: 115-22); the mouse mammary tumor virus control region that is active in testicular, breast, lymphoid and mast cells (Leder et al. (1986) Cell 45: 485-95); the albumin gene control region that is active in liver (Pinkert et al. (1987) Genes and Devel. 1: 268-76); the alpha-feto-protein gene control region that is active in liver (Krumlauf et al. (1985) Mol. Cell. Biol. 5: 1639-48; Hammer et al. (1987) Science 235: 53-58); the alpha 1-antitrypsin gene control region that is active in the liver (Kelsey et al. (1987) Genes and Devel. 1: 161-71); the beta-globin gene control region that is active in myeloid cells (Mogram et al., 1985, Nature 315: 338-40; Kollias et al. (1986) Cell 46: 89-94); the myelin basic protein gene control region that is active in oligodendrocyte cells in the brain (Readhead et al. (1987) Cell 48: 703-12); the myosin light chain-2 gene control region that is active in skeletal muscle (Sani (1985) Nature 314: 283-86); the gonadotropic releasing hormone gene control region that is active in the hypothalamus (Mason et al. (1986) Science 234: 1372-78); and most particularly the immunoglobulin gene control region that is active in lymphoid cells (Grosschedl et al. (1984) Cell 38: 647-58; Adames et al. (1985) Nature 318: 533-38; Alexander et al. (1987) Mol. Cell Biol. 7: 1436-44).

An enhancer sequence may be inserted into the vector to increase the transcription in higher eukaryotes of a nucleic acid encoding an anti-Dkk-1 antibody or immunologically functional fragment thereof of the present invention. Enhancers are cis-acting elements of DNA, usually about 10-300 bp in length, that act on promoters to increase transcription. Enhancers are relatively orientation and position independent. They have been found 5' and 3' to the transcription unit. Several enhancer sequences available from mammalian genes are known (e.g., globin, elastase, albumin, alpha-fetoprotein and insulin). An enhancer sequence from a virus also can be used. The SV40 enhancer, the cytomegalovirus early promoter enhancer, the polyoma enhancer, and adenovirus enhancers are exemplary enhancing elements for the activation of eukaryotic promoters. While an enhancer may be spliced into the vector at a position 5' or 3' to a nucleic acid molecule, it is typically placed at a site 5' to the promoter.

In expression vectors, a transcription termination sequence is typically located 3' of the end of a polypeptide-coding region and serves to terminate transcription. A transcription termination sequence used for expression in prokaryotic cells typically is a G-C rich fragment followed by a poly-T sequence. While the sequence is easily cloned from a library or even purchased commercially as part of a vector, it can also be readily synthesized using methods for nucleic acid synthesis such as those described herein.

A selectable marker gene element encodes a protein necessary for the survival and growth of a host cell grown in a selective culture medium. Typical selection marker genes used in expression vectors encode proteins that (a) confer resistance to antibiotics or other toxins, e.g., ampicillin, tetracycline, or kanamycin for prokaryotic host cells; (b) complement auxotrophic deficiencies of the cell; or (c) supply critical nutrients not available from complex media. Examples of selectable markers include the kanamycin resistance gene, the ampicillin resistance gene and the tetracycline resistance gene. A bacterial neomycin resistance gene can also be used for selection in both prokaryotic and eukaryotic host cells.

Other selection genes can be used to amplify the gene that will be expressed. Amplification is a process whereby genes that cannot in single copy be expressed at high enough levels to permit survival and growth of cells under certain selection conditions are reiterated in tandem within the chromosomes of successive generations of recombinant cells. Examples of suitable amplifiable selectable markers for mammalian cells include dihydrofolate reductase (DHFR) and promoterless thymidine kinase. In the use of these markers mammalian cell transformants are placed under selection pressure wherein only the transformants are uniquely adapted to survive by virtue of the selection gene present in the vector. Selection pressure is imposed by culturing the transformed cells under conditions in which the concentration of selection agent in the medium is successively increased, thereby permitting survival of only those cells in which the selection gene has been amplified. Under these circumstances, DNA adjacent to the selection gene, such as DNA encoding an antibody of the invention, is co-amplified with the selection gene. As a result, increased quantities of anti-Dkk-1 polypeptide are synthesized from the amplified DNA.

A ribosome-binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of the polypeptide to be expressed.

In some cases, for example where glycosylation is desired in a eukaryotic host cell expression system, various presequences can be manipulated to improve glycosylation or yield. For example, the peptidase cleavage site of a particular signal peptide can be altered, or pro-sequences added, which also may affect glycosylation. The final protein product may have, in the −1 position (relative to the first amino acid of the mature protein) one or more additional amino acids incident to expression, which may not have been totally removed. For example, the final protein product may have one or two amino acid residues found in the peptidase cleavage site, attached to the amino-terminus. Alternatively, use of some enzyme cleavage sites may result in a slightly truncated yet active form of the desired polypeptide, if the enzyme cuts at such area within the mature polypeptide.

Where a commercially available expression vector lacks some of the desired flanking sequences as described above, the vector can be modified by individually ligating these sequences into the vector. After the vector has been chosen and modified as desired, a nucleic acid molecule encoding an anti-Dkk-1 antibody or immunologically functional fragment thereof is inserted into the proper site of the vector.

The completed vector containing sequences encoding the inventive antibody or immunologically functional fragment thereof is inserted into a suitable host cell for amplification and/or polypeptide expression. The transformation of an expression vector for an anti-Dkk-1 antibody immunologically functional fragment thereof into a selected host cell may be accomplished by well-known methods including methods such as transfection, infection, calcium chloride, electroporation, microinjection, lipofection, DEAE-dextran method, or other known techniques. The method selected will in part be a function of the type of host cell to be used. These methods and other suitable methods are well known to the skilled artisan.

The transformed host cell, when cultured under appropriate conditions, synthesizes an anti-Dkk-1 antibody or functional fragment thereof that can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule.

Mammalian cell lines available as hosts for expression are well known in the art and include, but are not limited to, many immortalized cell lines available from the American Type Culture Collection (ATCC), such as Chinese hamster ovary (CHO) cells, HeLa cells, baby hamster kidney (BHK) cells, monkey kidney cells (COS), human hepatocellular carcinoma cells (e.g., Hep G2), and a number of other cell lines. In certain embodiments, the best cell line for expressing a particular DNA construct may be selected by testing various cell lines to determine which ones have the highest levels of expression levels and produce antibodies with constitutive Dkk-1 binding properties.

Pharmaceutical Compositions

In another aspect, the present disclosure provides a composition, e.g., a pharmaceutical composition, containing one or a combination of monoclonal antibodies, or antigen-binding portion(s) thereof, of the present disclosure, formulated together with a pharmaceutically acceptable carrier. Such compositions may include one or a combination of (e.g., two or more different) antibodies, or immunoconjugates or bispecific molecules of the disclosure. For example, a pharmaceutical composition of the disclosure can comprise a combination of antibodies (or immunoconjugates or bispecifics) that bind to different epitopes on the target antigen or that have complementary activities.

Pharmaceutical compositions of the disclosure also can be administered in combination therapy, i.e., combined with other agents. For example, the combination therapy can include a anti-Dkk-1 antibody of the present disclosure combined with at least one other anti-inflammatory or immunosuppressant agent. Examples of therapeutic agents that can be used in combination therapy are described in greater detail below in the section on uses of the antibodies of the disclosure.

As used herein, "pharmaceutically acceptable carrier" includes any and all solvents, dispersion media, coatings, antibacterial and antifungal agents, isotonic and absorption delaying agents, and the like that are physiologically compatible. Typically, the carrier is suitable for intravenous, intramuscular, subcutaneous, parenteral, spinal or epidermal administration (e.g., by injection or infusion). Depending on the route of administration, the active compound, i.e., antibody, antigen-binding portion thereof, immunoconjugate, or bispecific molecule, may be coated in a material to protect the compound from the action of acids and other natural conditions that may inactivate the compound.

In some embodiments, the antibodies of the present disclosure may be present in a neutral form (including zwitter ionic forms) or as a positively or negatively-charged species. In some cases, the antibodies may be complexed with a counterion to form a pharmaceutically acceptable salt. Thus, the pharmaceutical compounds of the disclosure may include one or more pharmaceutically acceptable salts.

A "pharmaceutically acceptable salt" refers to a salt that retains the desired biological activity of the parent compound (e.g., antibody) and does not impart undesired toxicological effects (see e.g., Berge, S. M., et al. (1977) J. Pharm. Sci. 66:1-19). For example, the term "pharmaceutically acceptable salt" includes a complex comprising one or more antibodies and one or more counterions, where the counterions are derived from pharmaceutically acceptable inorganic and organic acids and bases.

Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

Furthermore, pharmaceutically acceptable inorganic bases include metallic ions. Metallic ions include, but are not limited to, appropriate alkali metal salts, alkaline earth metal salts and other physiological acceptable metal ions. Salts derived from inorganic bases include aluminum, ammonium, calcium, cobalt, nickel, molybdenum, vanadium, manganese, chromium, selenium, tin, copper, ferric, ferrous, lithium, magnesium, manganic salts, manganous, potassium, rubidium, sodium, and zinc, and in their usual valences.

Pharmaceutically acceptable acid addition salts of the antibodies of the present disclosure can be prepared from the following acids, including, without limitation formic, acetic, acetamidobenzoic, adipic, ascorbic, boric, propionic, benzoic, camphoric, carbonic, cyclamic, dehydrocholic, malonic, edetic, ethylsulfuric, fendizoic, metaphosphoric, succinic, glycolic, gluconic, lactic, malic, tartaric, tannic, citric, nitric, ascorbic, glucuronic, maleic, folic, fumaric, propionic, pyruvic, aspartic, glutamic, benzoic, hydrochloric, hydrobromic, hydroiodic, lysine, isocitric, trifluoroacetic, pamoic, propionic, anthranilic, mesylic, orotic, oxalic, oxalacetic, oleic, stearic, salicylic, aminosalicylic, silicate, p-hydroxybenzoic, nicotinic, phenylacetic, mandelic, embonic, sulfonic, methanesulfonic, phosphoric, phosphonic, ethanesulfonic, ethanedisulfonic, ammonium, benzenesulfonic, pantothenic, naphthalenesulfonic, toluenesulfonic, 2-hydroxyethanesulfonic, sulfanilic, sulfuric, nitric, nitrous, sulfuric acid monomethyl ester, cyclohexylaminosulfonic, β-hydroxybutyric, glycine, glycylglycine, glutamic, cacodylate, diaminohexanoic, camphorsulfonic, gluconic, thiocyanic, oxoglutaric, pyridoxal 5-phosphate, chlorophenoxyacetic, undecanoic, N-acetyl-L-aspartic, galactaric and galacturonic acids.

Pharmaceutically acceptable organic bases include trimethylamine, diethylamine, N,N'-dibenzylethylenediamine, chloroprocaine, choline, dibenzylamine, diethanolamine, ethylenediamine, meglumine (N-methylglucamine), procaine, cyclic amines, quaternary ammonium cations, arginine, betaine, caffeine, clemizole, 2-ethylaminoethanol, 2-diethylaminoethanol, 2-dimethylaminoethanol, ethanediamine, butylamine, ethanolamine, ethylenediamine, N-ethylmorpholine, N-ethylpiperidine, ethylglucamine, glucamine, glucosamine, histidine, hydrabamine, imidazole, isopropylamine, methylglucamine, morpholine, piperazine, pyridine, pyridoxine, neodymium, piperidine, polyamine resins, procaine, purines, theobromine, triethylamine, tripropylamine, triethanolamine, tromethamine, methylamine, taurine, cholate, 6-amino-2-methyl-2-heptanol, 2-amino-2-methyl-1,3-propanediol, 2-amino-2-methyl-1-propanol, aliphatic mono- and dicarboxylic acids, phenyl-substituted alkanoic acids, hydroxy alkanoic acids, aromatic acids, aliphatic and aromatic sulfonic acids, strontium, tricine, hydrazine, phenylcyclohexylamine, 2-(N-morpholino)ethanesulfonic acid, bis(2-hydroxyethyl)amino-tris(hydroxymethyl)methane, N-(2-acetamido)-2-aminoethanesulfonic acid, 1,4-piperazinediethanesulfonic acid, 3-morpholino-2-hydroxypropanesulfonic acid, 1,3-bis[tris(hydroxymethyl)methylamino]propane, 4-morpholinepropanesulfonic acid, 4-(2-hydroxyethyl)piperazine-1-ethanesulfonic acid, 2-[(2-hydroxy-1,1-bis(hydroxymethyl)ethyl)amino]ethanesulfonic acid, N,N-bis(2-hydroxyethyl)-2-aminoethanesulfonic acid, 4-(N-morpholino)butanesulfonic acid, 3-(N,N-bis[2-hydroxyethyl]amino)-2-hydroxypropanesulfonic acid, 2-hydroxy-3-[tris(hydroxymethyl)methylamino]-1-propanesulfonic acid, 4-(2-hydroxyethyl)piperazine-1-(2-hydroxypropanesulfonic acid), piperazine-1,4-bis(2-hydroxypropanesulfonic acid) dihydrate, 4-(2-hydroxyethyl)-1-piperazinepropanesulfonic acid, N,N-bis(2-hydroxyethyl)glycine, N-(2-hydroxyethyl)piperazine-N'-(4-butanesulfonic acid), N-[tris(hydroxymethyl)methyl]-3-aminopropanesulfonic acid, N-tris(Hydroxymethyl)methyl-4-aminobutanesulfonic acid, N-(1,1-dimethyl-2-hydroxyethyl)-3-amino-2-hydroxypropanesulfonic acid, 2-(cyclohexylamino)ethanesulfonic acid, 3-(cyclohexylamino)-2-hydroxy-1-propanesulfonic acid, 3-(cyclohexylamino)-1-propanesulfonic acid, N-(2-acetamido)iminodiacetic acid, 4-(cyclohexylamino)-1-butanesulfonic acid, N-[tris(hydroxymethyl)methyl]glycine, 2-amino-2-(hydroxymethyl)-1,3-propanediol, and trometamol.

A pharmaceutical composition of the disclosure also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the disclosure is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation include, but are not limited to, vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the disclosure are dictated by and directly dependent on (a) the unique characteristics of the active compound and the particular therapeutic effect to be achieved, and (b) the limitations inherent in the art of compounding such an active compound for the treatment of sensitivity in individuals.

For administration of the antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1 to 10 mg/kg. An exemplary treatment regime entails administration once per week, once every two weeks, once every three weeks, once every four weeks, once per month, once every 3 months or once every three to 6 months. Dosage regimens for an anti-Dkk-1 antibody or antigen binding portion thereof of the disclosure include, for example, 1 mg/kg body weight or 3 mg/kg body weight via subcutaneous administration, with the antibody being given using one of the following dosing schedules: (i) every four weeks for six dosages, then every three months; (ii) every three weeks; (iii) 3 mg/kg body weight once followed by 1 mg/kg body weight every three weeks.

In some embodiments, two or more antibodies or fragments thereof with different binding specificities are administered simultaneously, in which case the dosage of each antibody administered falls within the ranges indicated. Antibodies are usually administered on multiple occasions. Intervals between single dosages can be, for example, weekly, monthly, every three months or yearly. Intervals can also be irregular as indicated by measuring blood levels of the antibody to the target antigen in the patient. In some methods, dosage is adjusted to achieve a plasma antibody concentration of about 1 to 1000 µg/ml and in some methods about 25 to 300 µg/ml.

Alternatively, the antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present disclosure may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present disclosure employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an anti-Dkk-1 antibody of the disclosure preferably results in a decrease in severity of disease symptoms, an increase in frequency and duration of disease symptom-free periods, or a prevention of impairment or disability due to the disease affliction. One of ordinary skill in the art would be able to determine such amounts based on such factors as the subject's size, the severity of the subject's symptoms, and the particular composition or route of administration selected.

Dosage of an anti-DKK-1 antibody can be calculated using such methods as target mediated drug disposition (TMDD) PK/PD models. Such models can be used to calculate an antibody concentration response relationship. A PK/PD model can be used to estimate antibody non-target mediated elimination, antibody turnover and complex formation and elimination. The TMDD model can be used to translate data determined using an animal model (for example rat or monkey) to human data to predict efficacious dose. The MABEL model can be used to determine expression and turnover rates. The PK/PD model can be used to calculate receptor occupancy based on Kd values. To determine receptor occupancy rate of turnover of the target and/or antibody-target complex kinetics are considered. The PK/PD model may be used to predict safety and efficiency of clinical studies.

A composition of the present disclosure can be administered via one or more routes of administration using one or more of a variety of methods known in the art. As will be appreciated by the skilled artisan, the route and/or mode of administration will vary depending upon the desired results. Routes of administration for antibodies or antigen binding portions thereof of the disclosure include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an antibody or antigen biding portion thereof of the disclosure can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York (1978).

Therapeutic compositions can be administered with medical devices known in the art. For example, a therapeutic composition of the disclosure can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present disclosure include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known to those skilled in the art.

In some embodiments the antibodies or fragments thereof of the disclosure can be formulated to ensure proper distribution in vivo. For example, the blood-brain barrier (BBB) excludes many highly hydrophilic compounds. To ensure that the therapeutic compounds of the disclosure cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) J. Clin. Pharmacol. 29:685). Exemplary targeting moieties include folate or biotin (see, e.g., U.S. Pat. No. 5,416,016 to Low et al.); mannosides (Umezawa et al., (1988) Biochem. Biophys. Res. Commun. 153:1038); antibodies (P. G. Bloeman et al. (1995) FEBS Lett. 357:140; M. Owais et al. (1995) Antimicrob. Agents Chemother. 39:180); surfactant protein A receptor (Briscoe et al. (1995) Am. J. Physiol. 1233:134); p 120 (Schreier et al. (1994) J. Biol. Chem. 269:9090); see also K. Keinanen; M. L. Laukkanen (1994) FEBS Lett. 346:123; J. J. Killion; I. J. Fidler (1994) Immunomethods 4:273.

As provided herein, the pharmaceutical compositions that are provided can be administered for prophylactic and/or therapeutic treatments. An "effective amount" refers generally to an amount that is a sufficient, but non-toxic, amount of the active ingredient (i.e., an anti-Dkk-1 antibody or immunologically functional fragment thereof) to achieve the desired effect, which is a reduction or elimination in the severity and/or frequency of symptoms and/or improvement or remediation of damage. A "therapeutically effective amount" refers to an amount that is sufficient to remedy a disease state or symptoms, or otherwise prevent, hinder, retard or reverse the progression of a disease or any other undesirable symptom. A "prophylactically effective amount" refers to an amount that is effective to prevent, hinder or retard the onset of a disease state or symptom.

In general, toxicity and therapeutic efficacy of the antibody or fragment can be determined according to standard pharmaceutical procedures in cell cultures and/or experimental animals, including, for example, determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions that exhibit large therapeutic indices are preferred.

The data obtained from cell culture and/or animal studies can be used in formulating a range of dosages for humans. The dosage of the active ingredient typically lines within a range of circulating concentrations that include the ED50 with little or no toxicity. The dosage can vary within this range depending upon the dosage form employed and the route of administration utilized.

As mentioned herein, the effective amount of a pharmaceutical composition comprising anti-Dkk-1 antibodies or immunologically functional fragments thereof to be employed therapeutically or prophylactically will depend, for example, upon the therapeutic context and objectives. One skilled in the art will appreciate that the appropriate dosage levels for treatment, according to certain embodiments, will thus vary depending, in part, upon the molecule delivered, the indication for which the anti-Dkk-1 antibody is being used, the route of administration, and the size (body weight, body surface or organ size) and/or condition (the age and general health) of the patient. A clinician may titer the dosage and modify the route of administration to obtain the optimal therapeutic effect.

The dosing frequency will depend upon the pharmacokinetic parameters of the anti-Dkk-1 antibody or immunologically functional fragment thereof in the formulation. For example, a clinician will administer the composition until a dosage is reached that achieves the desired effect. The composition may therefore be administered as a single dose, or as two or more doses (which may or may not contain the same amount of the desired molecule) over time, or as a continuous infusion via an implantation device or catheter. Treatment may be continuous over time or intermittent. Further refinement of the appropriate dosage is routinely made by those of ordinary skill in the art and is within the ambit of tasks routinely performed by them. Appropriate dosages may be ascertained through use of appropriate dose-response data.

To treat a medical disorder characterized by abnormal or excess expression of Dkk-1, a composition comprising the subject anti-Dkk-1 antibodies or immunologically functional fragments thereof may be administered to the patient in an amount and for a time sufficient to induce a sustained improvement in at least one indicator that reflects the severity of the disorder. An improvement is considered "sustained" if the patient exhibits the improvement on at least two occasions separated by at least one to seven days, or in some instances one to six weeks. The appropriate interval will depend to some extent on what disease condition is being treated; it is within the purview of the skilled physician to determine the appropriate interval for determining whether the improvement is sustained. The degree of improvement is determined based on signs or symptoms, and may also employ questionnaires that are administered to the patient, such as quality-of-life questionnaires.

Various indicators that reflect the extent of the patient's illness may be assessed for determining whether the amount and time of the treatment is sufficient. The baseline value for the chosen indicator or indicators is established by examination of the patient prior to administration of the first dose of antibody. Preferably, the baseline examination is done within about 60 days of administering the first dose. If the antibody is being administered to treat acute symptoms, such as for example to treat a broken bone, the first dose is administered as soon as practically possible after the injury has occurred.

Improvement is induced by administering the subject anti-Dkk-1 antibodies or immunologically functional fragments thereof until the patient manifests an improvement over baseline for the chosen indicator or indicators. In treating chronic conditions, this degree of improvement is obtained by repeatedly administering this medicament over a period of at least a month or more, e.g., for one, two, or three months or longer, or indefinitely. A period of one to six weeks, or even a single dose, often is sufficient for treating acute conditions. For injuries or acute conditions, a single dose may be sufficient.

Although the extent of the patient's illness after treatment may appear improved according to one or more indicators, treatment may be continued indefinitely at the same level or at a reduced dose or frequency. Once treatment has been reduced or discontinued, it later may be resumed at the original level if symptoms should reappear.

Exemplary Utilities for Anti-Dkk-1 Antibodies

Detection and Screening

The subject anti-Dkk-1 antibodies and immunologically functional fragments thereof can be used to detect Dkk-1 in biological samples. Such uses allow the identification of cells or tissues that produce the protein or serve as a diagnostic for detecting pathological conditions in which Dkk-1 is overproduced or underproduced.

The antibodies and fragments that are provided can also be used in methods to screen for a molecule that binds to Dkk-1. A variety of competitive screening methods, for example, can be used. In some methods, a Dkk-1 molecule or fragment thereof to which an anti-Dkk-1 antibody binds, is contacted with an antibody or fragment disclosed herein together with another molecule (i.e., a candidate molecule). A reduction in binding between the antibody or fragment and Dkk-1 is an indication that the molecule binds Dkk-1. Binding of the antibody or fragment can be detected using a variety of methods, e.g., an ELISA. Detection of binding between the anti-Dkk-1 antibody or fragment to Dkk-1 can be simplified by detectably labeling the antibody. In some methods, a molecule that exhibits binding in the initial screen is further analyzed to determine whether it inhibits a Dkk-1 activity (e.g., whether the molecule activates Wnt signaling).

Treatment of Bone Related Disorders

In other aspects, certain of the antibodies and immunologically functional fragments that are provided can be used to treat patients with a variety of different diseases including, for example, diseases that are responsive to the inhibition of Dkk-1 activity. These antibodies and fragments can also be used to treat diseases that are responsive to the induction of Wnt signaling. The term "patient" as used herein includes human and animal subjects unless stated otherwise. Examples of such diseases include, but are not limited to, a variety of diseases involving a bone disorder including low bone mass conditions, systemic bone loss, suppressed bone formation and bone erosions. Some of the antibodies and fragments can also be used in bone repair.

In some embodiments the antibodies or fragments have therapeutic use in stimulating osteoblast activity and increasing bone mineral density or bone mass. These antibodies and fragments are thus useful for treating patients suffering from various medical disorders that involve excessive bone loss or patients who require the formation of new bone even where there may not necessarily be excessive osteoclast activity. Blocking Dkk-1 activity results in osteoblast activation via signaling transmitted by Wnt proteins. Excessive osteoclast activity is associated with numerous osteopenic disorders that can be treated with the antibodies and immunologically functional fragments that are provided, including ostopenia, osteoporosis, periodontitis, Paget's disease, bone loss due to immobilization, lytic bone metastases and arthritis, including rheumatoid arthritis, psoriatic arthritis, ankylosing spondylitis and other conditions that involve bone erosion.

Various other low bone mass conditions can also be treated including a variety of forms of osteoporosis, including but not limited to, glucocorticoid induced osteoporosis, osteoporosis induced after transplantation, osteoporosis associated with chemotherapy (i.e., chemotherapy induced osteoporosis), immobilization induced osteoporosis, osteoporosis due to mechanical unloading, and osteoporosis associated with anti-convulsant use. Additional bone diseases that can be treated with some of the antibodies or fragments include bone disease associated with renal failure and nutritional, gastrointestinal and/or hepatic associated bone diseases.

Different forms of arthritis can also be treated, examples including osteoarthritis and rheumatoid arthritis. The antibodies and fragments can also be used to treat systemic bone loss associated with arthritis (e.g., rheumatoid arthritis). In treating arthritis, patients may benefit by perilesional or intralesional injections of the subject antibodies or fragments thereof. For example, the antibody or fragment thereof can be injected adjacent to or directly into an inflamed joint, thus stimulating repair of damaged bone at the site.

Some cancers are known to increase osteoclast activity and induce bone resorption, such as breast and prostate cancer. Multiple myeloma, which arises in bone marrow, also is associated with bone loss, in part likely due to the increased expression of Dkk-1 by plasma cells, which then suppresses the bone building activity of osteoblasts in the vicinity. Reducing Dkk-1 activity by administering the subject antibodies or immunologically functional fragments thereof can result in an increase in osteoblast activity that serves to counteract the excessive osteoclast activity, thereby reducing the severity of the aforementioned disorders, reducing bone erosion and inducing new bone formation in the patient. Treatment with certain of the anti-Dkk-1-specific antibodies or immunologically functional fragments can induce a significant increase in bone mineral density in a patient suffering from an osteopenic disorder.

Inhibiting Dkk-1 with the antibodies or immunologically functional fragments described herein can also be used in various bone repair applications. For example, certain antibodies and fragments can be useful in retarding wear debris osteolysis associated with artificial joints, accelerating the repair of bone fractures, and enhancing the incorporation of bone grafts into the surrounding living bone into which they have been engrafted.

As disclosed herein, anti-Dkk-1 antibodies or immunologically functional fragments thereof can be administered alone or in combination with other therapeutic agents, for example, in combination with cancer therapy agents, with agents that inhibit osteoclast activity or with other agents that enhance osteoblast activity. For example, the inventive antibodies can be administered to cancer patients undergoing radiation therapy or chemotherapy. Chemotherapies used in combination with the inventive antibodies may include anthracyclines, taxol, tamoxifen, doxorubicin, 5-fluorouracil, oxaloplatin, Velcade® ([(1R)-3-methyl-1-[[(2S)-1-oxo-3-phenyl-2-[(pyrazinylcarbonyl)amino]propy-1]amino]butyl] boronic acid) and/or other small molecule drugs that are used in treating cancer. Breast cancer patients will benefit from the administration of an aromatase inhibitor concurrently with combination treatments comprising a chemotherapeutic agent and an anti-Dkk-1 antibody or immunologically functional fragment thereof.

Anti-Dkk-1 antibodies and immunologically functional fragments thereof may be used alone for the treatment of the above referenced conditions resulting in loss of bone mass or in combination with a therapeutically effective amount of a bone growth promoting (anabolic) agent or a bone anti-resorptive agent including but not limited to: bone morphogenic factors designated BMP-1 to BMP-12; transforming growth factor-13 and TGF-β family members; fibroblast growth factors FGF-1 to FGF-10; interleukin-1 inhibitors (including IL-1ra, antibodies to IL-1 and antibodies to IL-1 receptors); TNFα inhibitors (including etanercept, adalibumab and infliximab); RANK ligand inhibitors (including soluble RANK, osteoprotegerin and antagonistic antibodies that specifically bind RANK or RANK ligand), parathyroid hormone, E series prostaglandins, bisphosphonates and bone-enhancing minerals such as fluoride and calcium. Anabolic agents that can be used in combination with the inventive antibodies and functional fragments thereof include parathyroid hormone and insulin-like growth factor (IGF), wherein the latter agent is preferably complexed with an IGF binding protein. An IL-1 receptor antagonist suitable for such combination treatment is described in WO89/11540 and a suitable soluble TNF receptor-1 is described in WO98/01555. Exemplary RANK ligand antagonists are disclosed, for example, in WO 03/086289, WO 03/002713, U.S. Pat. Nos. 6,740,511 and 6,479,635. All of the aforementioned patents and patent applications are hereby incorporated by reference).

In addition, anti-Dkk-1 antibodies can be administered to patients in combination with antibodies that bind to tumor cells and induce a cytotoxic and/or cytostatic effect on tumor growth. Examples of such antibodies include those that bind to cell surface proteins Her2, CDC20, CDC33, mucin-like glycoprotein and epidermal growth factor receptor (EGFR) present on tumor cells and induce a cytostatic and/or cytotoxic effect on tumor cells displaying these proteins. Examples of such antibodies include HERCEPTIN® for treatment of breast cancer and RITUXAN® for the treatment of non-Hodgkin's lymphoma, and include also antibody-based drugs such as ERBITUX® and AVASTIN®. Also, combination therapy can include as cancer therapy agents polypeptides that selectively induce apoptosis in tumor cells, such as the TNF-related polypeptide TRAIL.

The subject antibodies or immunologically functional fragments thereof can be administered concurrently with other treatments and therapeutic agents being administered for the same condition. "Concurrent administration," as used herein, encompasses treatments that are administered simultaneously or sequentially. Anti-Dkk-1 antibodies or immunologically functional fragments thereof can be administered prophylactically to prevent or mitigate the onset of loss of bone mass by early stage cancer (stages I or II), or can be given to ameliorate an existing condition of loss of bone mass due to metastasis to the bone.

Anti-Dkk-1 antibodies of the invention may be used to prevent and/or treat the growth of tumor cells in bone. Cancer that metastasizes to bone can spread readily as tumor cells stimulate osteoclasts to resorb the internal bone matrix. Treatment with an anti-Dkk-1 antibody or immunologically functional fragment thereof will help maintain bone mineral density at the site of such metastases by stimulating increased osteoblast activity. Any cancer that has potential to metastasize to bone may be prevented or treated with an anti-Dkk-1 antibody administered before or after metastasis has occurred.

Multiple myeloma is an example of a type of cancer that may be prevented and/or treated with an anti-Dkk-1 antibody or antigen binding fragment thereof. Affected patients typically exhibit a loss of bone mass due to increased osteoclast activation in localized regions of the bone. Myeloma cells either directly or indirectly produce RANK ligand, a protein that activates osteoclasts resulting in lysis of the bone surrounding the myeloma cells embedded in bone marrow spaces. The normal osteoclasts adjacent to the myeloma cell in turn produce IL-6, leading to growth and proliferation of myeloma cells. In addition multiple myeloma cells produce Dkk-1 thereby inhibiting osteoblast activity and further promoting bone resorptive activity in this disease. Treatment of an animal with an anti-Dkk-1 antibody or immunologically functional fragment thereof will instigate osteoblast activity, thereby resulting in increased bone mass at the site of the tumors. Such treatment may result in reduction of bone pain, and may block further metastisis to bone by preventing the resorptive activity that releases bone nutrients utilized by the tumor cells. In treating this disease, the anti-Dkk-1 antibody or immunologically functional fragment thereof can be administered concurrently with antagonistic antibodies directed against RANK ligand or antibodies against IL-6.

Treatment of Other Disorders

In addition to the foregoing uses related to bone disorders, certain of the antibodies and immunologically functional fragments that are provided can be used to treat other diseases. The role of Dkk-1 in these various diseases is supported in part by its expression in various different tissues. The antibodies and fragments, for example, can be used to treat diseases in which it is desirable to promote stem cell renewal. Such diseases include, but are not limited to, diabetes, chronic heart failure and various diseases of the muscle [e.g., disuse atrophy resulting, for instance, from immobilization or bedrest); aging frailty (sarcopenia of the elderly); muscular dystrophies; cachexia associated with cancer, AIDS or inflammation; protein-energy malnutrition in renal failure/uremia, and muscle wasting in obesity]. Various inflammatory diseases can also be treated, including, for instance, Crohn's disease, colitis, and inflammatory bowel disease. The antibodies and fragments can also be used in the treatment of various neurological diseases (e.g., Alzheimer's disease, Parkinson's disease, and Huntington's disease). Ocular diseases (e.g., macular degeneration and various retinopathies) can also be treated with certain of the antibodies and fragments. Different renal diseases (e.g., end stage renal disease, chronic renal disease, glomerulonephritis, tubulointerstitial nephritis and IgA nephropathy) can also be treated with some antibodies. Additionally, various pulmonary diseases (e.g., chronic obstructive pulmonary disease, idiopathic pulmonary fibrosis and cystic fibrosis) and various skin disorders, including dermal and epidermal diseases, can also be treated. Examples of skin disorders that can be treated include damaged intestinal epithelium (e.g., chemotherapy induced damage), and other diseases in which it is desirable to stimulate growth and survival of the intestinal epithelium.

Kits

Kits that include an antibody or immunologically functional fragment or a pharmaceutical composition as described herein are also provided. Some kits include such an antibody, fragment or composition in a container (e.g., vial or ampule), and may also include instructions for use of the antibody or fragment in the various detection, screening and therapeutic applications disclosed above. The antibody, fragment or composition can be in various forms, including, for instance, as part of a solution or as a solid (e.g., lyophilized powder). The instructions may include a description of how to prepare (e.g., dissolve or resuspend) the antibody or fragment in an appropriate fluid and/or how to administer the antibody or fragment for the treatment of the diseases described above (e.g., bone disorders such as low bone mass, systemic bone loss, suppressed bone formation and bone erosions; stem cell renewal; inflammatory diseases; neurological diseases; ocular diseases; renal diseases and skin disorders).

The kits may also include various other components, such as buffers, salts, complexing metal ions and other agents described above in the section on pharmaceutical compositions. These components may be included with the antibody or fragment or may be in separate containers. The kits may also include other therapeutic agents for administration with the antibody or fragment. Examples of such agents include, but are not limited to, agents to treat cancers, bone promoting agents and antibodies that bind tumor cells, and other agents listed above.

Further Specific Description of Anti-Dkk-1 Antibodies
Modifications to the Fcγ Portion In the recombinant humanized antibodies, the Fcγ portion can be modified to avoid interaction with Fcγ receptor and the complement immune system. This type of modification was designed by Dr. Mike Clark from the Department of Pathology at Cambridge University, and techniques for preparation of such antibodies are described, for example, in WO 99/58572, published Nov. 18, 1999. For example, the constant region may be engineered to more resemble human constant regions to avoid an immune response if the antibody is used for treating human beings. See, for example, U.S. Pat. Nos. 5,997,867 and 5,866,692.

Modifications to huMabJC18 huMabJC18 is a fully humanized anti-Dkk-1 monoclonal antibody. The present disclosure encompasses modifications to huMabJC18, including functionally equivalent antibodies which do not significantly affect their properties and variants which have enhanced or decreased activity and/or affinity. For example, as those skilled in the art will appreciate, the amino acid sequence of huMabJC18 may be mutated to obtain an antibody with a desired binding affinity to Dkk-1. Modification of polypeptides is routine practice in the art and need not be described in detail herein. Modification of polypeptides is exemplified in the Examples. Examples of modified polypeptides include: polypeptides with conservative substitutions of amino acid residues, one or more deletions or additions of amino acids which do not significantly deleteriously change the functional activity, or use of chemical analogs.

Amino acid sequence insertions include: amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to an epitope tag. Other insertional variants of the antibody molecule include the fusion to the N- or C-terminus of the antibody of an enzyme or a polypeptide which increases the serum half-life of the antibody.

Substitution variants have at least one amino acid residue in the antibody molecule removed and a different residue inserted in its place. The sites of greatest interest for substitutional mutagenesis include the hypervariable regions, but framework (FR) alterations are also contemplated. Conservative substitutions are shown in Table 1 under the heading of "conservative substitutions". If such substitutions result in a change in biological activity, then more substantial changes, denominated "exemplary substitutions" in Table 1, or as further described below in reference to amino acid classes, may be introduced and the products screened.

TABLE 1

Amino Acid Substitutions

| Original Residue | Conservative Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |

TABLE 1-continued

Amino Acid Substitutions

| Original Residue | Conservative Substitutions | Exemplary Substitutions |
|---|---|---|
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) Non-polar: Norleucine, Met, Ala, Val, Leu, Ile;
(2) Polar without charge: Cys, Ser, Thr, Asn, Gin;
(3) Acidic (negatively charged): Asp, Glu;
(4) Basic (positively charged): Lys, Arg;
(5) Residues that influence chain orientation: Gly, Pro; and
(6) Aromatic: Trp, Tyr, Phe, His.

Non-conservative substitutions are made by exchanging a member of one of these classes for another class.

Any cysteine residue not involved in maintaining the proper conformation of the antibody also may be substituted, generally with serine, to improve the oxidative stability of the molecule and prevent aberrant cross-linking. Conversely, cysteine bond(s) may be added to the antibody to improve its stability, particularly where the antibody is an antibody fragment such as an Fv fragment.

Amino acid modifications can range from changing or modifying one or more amino acids to complete redesign of a region, such as the variable region. Changes in the variable region can alter binding affinity and/or specificity. In some embodiments, no more than one to five conservative amino acid substitutions are made within a CDR domain. In other embodiments, no more than one to three conservative amino acid substitutions are made within a CDR domain. In still other embodiments, the CDR domain is CDR H3 and/or CDR L3.

Glycosylation of huMabJC18

Modifications also include glycosylated and nonglycosylated polypeptides, as well as polypeptides with other post-translational modifications, such as, for example, glycosylation with different sugars, acetylation, and phosphorylation. Antibodies are glycosylated at conserved positions in their constant regions (see, e.g., Jefferis and Lund (1997) Chem. Immunol. 65:111-128; Wright and Morrison (1997) TibTECH 15:26-32). The oligosaccharide side chains of the immunoglobulins affect the protein's function (see, e.g., Boyd et al. (1996) Mol. Immunol. 32:1311-1318; Wittwe and Howard (1990) Biochem. 29:4175-4180) and the intramolecular interaction between portions of the glycoprotein, which can affect the conformation and presented three-dimensional surface of the glycoprotein (Hefferis and Lund, supra; Wyss and Wagner (1996) Current Opin. Biotech. 7:409-416). Oligosaccharides may also serve to target a given glycoprotein to certain molecules based upon specific recognition structures. Glycosylation of antibodies has also been reported to affect antibody-dependent cellular cytotoxicity (ADCC). In particular, CHO cells with tetracycline-regulated expression of β(1,4)-N-acetylglucosaminyltransferase III (GnTIII), a glycosyltransferase catalyzing formation of bisecting GlcNAc, was reported to have improved ADCC activity (see, e.g., Umana et al. (1999) Nature Biotech. 17:176-180).

Glycosylation of antibodies is typically either N-linked or O-linked. N-linked refers to the attachment of the carbohydrate moiety to the side chain of an asparagine residue. The tripeptide sequences asparagine-X-serine, asparagine-X-threonine, and asparagine-X-cysteine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

The glycosylation pattern of antibodies may also be altered without altering the underlying nucleotide sequence. Glycosylation largely depends on the host cell used to express the antibody. Since the cell type used for expression of recombinant glycoproteins, e.g., antibodies, as potential therapeutics is rarely the native cell, variations in the glycosylation pattern of the antibodies can be expected (see, e.g., Hse et al. (1997) J. Biol. Chem. 272:9062-9070).

In addition to the choice of host cells, factors that affect glycosylation during recombinant production of antibodies include growth mode, media formulation, culture density, oxygenation, pH, purification schemes and the like. Various methods have been proposed to alter the glycosylation pattern achieved in a particular host organism including introducing or overexpressing certain enzymes involved in oligosaccharide production (see, e.g., U.S. Pat. Nos. 5,047,335; 5,510,261; and 5,278,299). Glycosylation, or certain types of glycosylation, can be enzymatically removed from the glycoprotein, for example using endoglycosidase H (Endo H). In addition, the recombinant host cell can be genetically engineered to be defective in processing certain types of polysaccharides. These and similar techniques are well known in the art.

Coupling Techniques

As noted in the foregoing, other methods of modification include using coupling techniques known in the art, including, but not limited to, enzymatic means, oxidative substitution and chelation. Modifications can be used, for example, for attachment of labels for immunoassay. Modified huM-abJC18 polypeptides can be made using established procedures in the art and can be screened using standard assays known in the art, some of which are described below and in the Examples. Those skilled in the art will appreciate that any suitable methods for making and screening such modifications.

Modified Constant Region

In some embodiments of the invention, the antibody comprises a modified constant region, such as a constant region that is immunologically inert or partially inert, e.g., does not trigger complement mediated lysis, does not stimulate antibody-dependent cell mediated cytotoxicity (ADCC), or does not activate microglia; or have reduced activities (compared to the unmodified antibody) in any one or more of the following: triggering complement mediated lysis, stimulating antibody-dependent cell mediated cytotoxicity (ADCC), or activating microglia. Different modifications of the constant region may be used to achieve optimal level and/or combination of effector functions. See, for example, Morgan et al., *Immunology* 86:319-324 (1995); Lund et al., *J. Immunology* 157:4963-9 157:4963-4969 (1996); Idusogie et al., *J. Immunology* 164:4178-4184 (2000); Tao et al., *J. Immunology* 143: 2595-2601 (1989); and Jefferis et al., *Immunological Reviews* 163:59-76 (1998). In an embodiment, the constant region is modified as described in Eur. J. Immunol. (1999) 29:2613-2624; PCT Application No. PCT/GB99/01441; and/or UK Patent Application No. 9809951.8.

In an embodiment, the antibody comprises a human heavy chain IgG2a constant region comprising the following mutations: A330P331 to S330S331 (amino acid numbering with reference to the wildtype IgG2a sequence). Eur. J. Immunol. (1999) 29:2613-2624. In another embodiment, the constant region is aglycosylated. In another embodiment, the constant region is aglycosylated by mutating the glycosylated amino acid residue in the constant region. For example, N-glycosylation site N297 may be mutated to A, Q, K, or H. See, e.g., Tao et al., *J. Immunology* 143: 2595-2601 (1989); and Jefferis et al., *Immunological Reviews* 163:59-76 (1998). In an embodiment, the constant region is aglycosylated enzymatically (such as removing carbohydrate by enzyme PNGase).

Effector Domain

Other antibody modifications include antibodies that have been modified as described, e.g., in WO 99/58572, published Nov. 18, 1999. These antibodies comprise, in addition to a binding domain directed at the target molecule, an effector domain having an amino acid sequence substantially homologous to all or part of a constant domain of a human immunoglobulin heavy chain. These antibodies are capable of binding the target molecule without triggering significant complement dependent lysis, or cell-mediated destruction of the target. In some embodiments, the effector domain is capable of specifically binding FcRn and/or FcγRIIb. These are typically based on chimeric domains derived from two or more human immunoglobulin heavy chain $C_H2$ domains. Antibodies modified in this manner are particularly suitable for use in chronic antibody therapy, to avoid inflammatory and other adverse reactions to conventional antibody therapy.

Affinity Matured

In an embodiment the antibody is an affinity matured antibody. For example, affinity matured antibodies can be produced by procedures known in the art (e.g., Marks et al., 1992, Bio/Technology, 10:779-783; Barbas et al. (1994) Proc Nat. Acad. Sci, USA 91:3809-3813; Schier et al. (1995) Gene, 169:147-155; Yelton et al. (1995) J. Immunol., 155:1994-2004; Jackson et al. (1995) J. Immunol., 154(7):3310-9; Hawkins et al. (1992) J. Mol. Biol., 226:889-896).

Library Scanning Mutagenesis

The following methods may be used for adjusting the affinity of an antibody and for characterizing a CDR. One way of characterizing a CDR of an antibody and/or altering (such as improving) the binding affinity of a polypeptide, such as an antibody, termed "library scanning mutagenesis". Generally, library scanning mutagenesis works as follows. One or more amino acid positions in the CDR are replaced with two or more (such as 3, 4, 5, 6, 7, 8, 9, 10, 11, 12, 13, 14, 15, 16, 17, 18, 19, or 20) amino acids using art recognized methods. This generates small libraries of clones (in some embodiments, one for every amino acid position that is analyzed), each with a complexity of two or more members (if two or more amino acids are substituted at every position). Generally, the library also includes a clone comprising the native (unsubstituted) amino acid. A small number of clones, e.g., about 20-80 clones (depending on the complexity of the library), from each library are screened for binding affinity to the target polypeptide (or other binding target), and candidates with increased, the same, decreased or no binding are identified.

Determining Binding Affinity

Methods for determining binding affinity are well-known in the art. Binding affinity may be determined using BIAcore or ProteOn surface plasmon resonance analysis, which detects differences in binding affinity of about 2-fold or greater. These types of analyses are particularly useful when the starting antibody already binds with a relatively high affinity, for example a $K_D$ of about 10 nM or lower. Screening using BIAcore or ProteOn surface plasmon resonance is described in the Examples, herein.

Binding affinity may be determined using Kinexa Biocensor, scintillation proximity assays, ELISA, ORIGEN immunoassay (IGEN), fluorescence quenching, fluorescence transfer, and/or yeast display. Binding affinity may also be screened using a suitable bioassay.

In some embodiments, every amino acid position in a CDR is replaced (in some embodiments, one at a time) with all 20 natural amino acids using art recognized mutagenesis methods (some of which are described herein). This generates small libraries of clones (in some embodiments, one for every amino acid position that is analyzed), each with a complexity of 20 members (if all 20 amino acids are substituted at every position).

In some embodiments, the library to be screened comprises substitutions in two or more positions, which may be in the same CDR or in two or more CDRs. Thus, the library may comprise substitutions in two or more positions in one CDR. The library may comprise substitution in two or more positions in two or more CDRs. The library may comprise substitution in 3, 4, 5, or more positions, said positions found in two, three, four, five or six CDRs. The substitution may be prepared using low redundancy codons. See, e.g., Table 2 of Balint et al. (1993) Gene 137(1):109-18).

The CDR may be CDRH3 and/or CDRL3. The CDR may be one or more of CDRL1, CDRL2, CDRL3, CDRH1, CDRH2, and/or CDRH3. The CDR may be a Kabat CDR, a Chothia CDR, or an extended CDR.

Candidates with improved binding may be sequenced, thereby identifying a CDR substitution mutant which results in improved affinity (also termed an "improved" substitution). Candidates that bind may also be sequenced, thereby identifying a CDR substitution which retains binding.

Multiple rounds of screening may be conducted. For example, candidates (each comprising an amino acid substitution at one or more position of one or more CDR) with improved binding are also useful for the design of a second library containing at least the original and substituted amino acid at each improved CDR position (i.e., amino acid position in the CDR at which a substitution mutant showed improved binding). Preparation, and screening or selection of this library is discussed further below.

Library scanning mutagenesis also provides a means for characterizing a CDR, in so far as the frequency of clones with improved binding, the same binding, decreased binding or no binding also provide information relating to the importance of each amino acid position for the stability of the antibody-antigen complex. For example, if a position of the CDR retains binding when changed to all 20 amino acids, that position is identified as a position that is unlikely to be required for antigen binding. Conversely, if a position of CDR retains binding in only a small percentage of substitutions, that position is identified as a position that is important to CDR function. Thus, the library scanning mutagenesis methods generate information regarding positions in the CDRs that can be changed to many different amino acid (including all 20 amino acids), and positions in the CDRs which cannot be changed or which can only be changed to a few amino acids.

Candidates with improved affinity may be combined in a second library, which includes the improved amino acid, the original amino acid at that position, and may further include additional substitutions at that position, depending on the complexity of the library that is desired, or permitted using the desired screening or selection method. In addition, if desired, adjacent amino acid position can be randomized to at least two or more amino acids. Randomization of adjacent amino acids may permit additional conformational flexibility in the mutant CDR, which may in turn, permit or facilitate the introduction of a larger number of improving mutations. The library may also comprise substitution at positions that did not show improved affinity in the first round of screening.

The second library is screened or selected for library members with improved and/or altered binding affinity using any method known in the art, including screening using BIAcore surface plasmon resonance analysis, and selection using any method known in the art for selection, including phage display, yeast display, and ribosome display.

Fusion Proteins

As noted in the foregoing, the invention also encompasses fusion proteins comprising one or more fragments or regions from the antibodies (such as huMabJC18) or polypeptides of this invention. A huMabJC18 fusion polypeptide can be created by methods known in the art, for example, synthetically or recombinantly. Typically, the huMabJC18 fusion proteins of this invention are made by preparing and expressing a polynucleotide encoding them using recombinant methods described herein, although they may also be prepared by other means known in the art, including, for example, chemical synthesis.

Conjugation

As noted in the foregoing, this invention also provides compositions comprising huMabJC18 antibodies or polypeptides conjugated (for example, linked) to an agent that facilitate coupling to a solid support (such as biotin or avidin). For simplicity, reference will be made generally to huMabJC18 or antibodies, with the understanding that these methods apply to any of the Dkk-1 binding embodiments described herein. Conjugation generally refers to linking these components as described herein. The linking (which is generally fixing these components in proximate association at least for administration) can be achieved in any number of ways. For example, a direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Labeling Agents

As noted in the foregoing, an antibody or polypeptide of this invention may be linked to any suitable labeling agent (alternatively termed "label"), such as, for example, a fluorescent molecule, a radioactive molecule or any others labels known in the art. Labels are known in the art which generally provide (either directly or indirectly) a signal.

Compositions

As noted in the foregoing, the invention also provides compositions (including pharmaceutical compositions) and kits comprising, e.g., huMabJC18, or, as this disclosure makes clear, any or all of the antibodies and/or polypeptides described herein.

Polynucleotides, Vectors (e.g., Expression) and Host Cells

As noted in the foregoing with several specific embodiments provided, the invention also provides isolated polynucleotides encoding the antibodies and polypeptides of the invention (including an antibody comprising the polypeptide sequences of the light chain and heavy chain variable regions shown in FIG. 1), and vectors and host cells comprising the polynucleotide.

In another aspect, the invention provides polynucleotides encoding any of the antibodies (including antibody fragments) and polypeptides described herein. As those skilled in the art will appreciate, the provided polynucleotides can be made by procedures known in the art.

In another aspect, the invention provides compositions (including pharmaceutical compositions described in more detail in the foregoing and below) comprising any of the polynucleotides of the invention. In an embodiment, the composition comprises an expression vector comprising a polynucleotide encoding huMabJC18 as described herein. In an embodiment, the composition comprises an expression vector comprising a polynucleotide encoding any of the antibodies or polypeptides described herein. In still another embodiment, the composition comprises either or both of the polynucleotides shown in SEQ ID NO: 19 and SEQ ID NO: 28. Expression vectors and administration of polynucleotide compositions are further described herein.

In another aspect, the invention provides methods of making any of the polynucleotides described herein.

Polynucleotides complementary to any such sequences are also encompassed by the present invention. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes an antibody or a portion thereof) or may comprise a variant of such a sequence. Polynucleotide variants contain one or more substitutions, additions, deletions and/or insertions such that the immunoreactivity of the encoded polypeptide is not diminished, relative to a native immunoreactive molecule. The effect on the immunoreactivity of the encoded polypeptide may generally be assessed as described herein. Variants preferably exhibit at least about 70% identity, more preferably at least about 80% identity and most preferably at least about 90% identity to a polynucleotide sequence that encodes a native antibody or a portion thereof.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, or 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J. (1990) Unified Approach to Alignment and Phylogenes pp. 626-645 Methods in Enzymology vol. 183, Academic Press, Inc., San Diego, Calif.; Higgins, D. G. and Sharp, P. M. (1989) CABIOS 5:151-153; Myers, E. W. and Muller W. (1988) CABIOS 4:11-17; Robinson, E. D., 1971, Comb. Theor. 11:105; Santou, N., Nes, M. (1987) Mol. Biol. Evol. 4:406-425; Sneath, P. H. A. and Sokal, R. R. (1973) Numerical Taxonomy the Principles and Practice of Numerical Taxonomy, Freeman Press, San Francisco, Calif.; Wilbur, W. J. and Lipman, D. J. (1983) Proc. Natl. Acad. Sci. USA 80:726-730.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e. gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e., the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native antibody (or a complementary sequence).

Suitable "moderately stringent conditions" include prewashing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS.

As used herein, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1° k Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75

M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. The skilled artisan will recognize how to adjust the temperature, ionic strength, etc., as necessary to accommodate desired factors such as probe length and the like.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as, e.g., hybridization, amplification and/or database sequence comparison).

The polynucleotides of this invention can be obtained using chemical synthesis, recombinant methods, or PCR. Methods of chemical polynucleotide synthesis are well known in the art and need not be described in detail herein. One of skill in the art can use the sequences provided herein and a commercial DNA synthesizer to produce a desired DNA sequence.

For preparing polynucleotides using recombinant methods, a polynucleotide comprising a desired sequence can be inserted into a suitable vector, and the vector in turn can be introduced into a suitable host cell for replication and amplification, as further discussed herein. Polynucleotides may be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al. (1989).

Alternatively, PCR allows reproduction of DNA sequences. PCR technology is well known in the art and is described in U.S. Pat. Nos. 4,683,195; 4,800,159; 4,754,065; and 4,683,202, as well as PCR: The Polymerase Chain Reaction, Mullis et al. eds., Birkauswer Press, Boston (1994).

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in, e.g., Sambrook et al., (1989).

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp 18, mp 19, pBR322, pMB9, ColE1, pCR1, RP4, phage DNAs, and shuttle vectors such as pSA3 and pAT28. These and many other cloning vectors are available from commercial vendors such as BioRad, Stratagene, and Invitrogen.

Expression vectors generally are replicable polynucleotide constructs that contain a polynucleotide according to the invention. It is implied that an expression vector must be replicable in the host cells either as episomes or as an integral part of the chromosomal DNA. Suitable expression vectors include, but are not limited to, e.g, plasmids, viral vectors, including adenoviruses, adeno-associated viruses, retroviruses, cosmids, and expression vector(s) disclosed in WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

The invention also provides host cells comprising any of the polynucleotides described herein. Any host cells capable of over-expressing heterologous DNAs can be used for the purpose of isolating the genes encoding the antibody, polypeptide or protein of interest. Non-limiting examples of mammalian host cells include, but are not limited to: COS, HeLa, and CHO cells. See also, e.g., WO 87/04462. Suitable non-mammalian host cells include prokaryotes (such as *E. coli* or *B. subtillis*) and yeast (such as *S. cerevisae, S. pombe*; or *K. lactis*). Preferably, the host cells express the cDNAs at a level of about 5 fold higher, more preferably 10 fold higher, even more preferably 20 fold higher than that of the corresponding endogenous antibody or protein of interest, if present, in the host cells. Screening the host cells for a specific binding to $A\beta_{1-40}$ is effected by, e.g., an immunoassay or FACS. A cell overexpressing the antibody or protein of interest can be identified.

The present disclosure is further illustrated by the following examples which should not be construed as further limiting. The contents of all figures, tables and all references, patents and published patent applications cited throughout this disclosure are expressly incorporated herein by reference in their entirety.

EXAMPLES

Example 1

Generation of muMabJC18

Preparation
A. Immunogen

Recombinant human Dkk-1 (rhuDkk-1) obtained from R&D systems (cat no. 1096-DK/CF corresponding to aas2-266 of human Dkk-1 fused with a 10×His tag at the C terminal) was conjugated to KLH using the Pierce Imject Immunogen EDC kit with mcKLH (cat no. 77622). The KLH conjugated protein was prepared by Genovac GmbH and used as the immunogen for a fusion which gave rise to the subclone JC9H3 (JC18).

```
SEQ ID NO: 1
Human Dkk1-(10His) aa sequence
(amino acids in bold italic type represent actual
N-terminus of purified protein)
MALGAAGATRVFVAMVAAALGGHPLLGVSA TLNSVLNSNAIKNLPPPLG

GAAGHPGSAVSAAPGILYPGGNKYQTIDNYQPYPCAEDEECGTDEYCAS

PTRGGDAGVQICLACRKRRKRCMRHAMCCPGNYCKNGICVSSDQNHFRG

EIEETITESFGN DHSTLDGYSRRTTLSSKMYHTKGQEGSVCLRSSDCA

SGLCCARHFWSKICKPVLKEGQVCTKHRRKGSHGLEIFQRCYCGEGLSC

RIQKDHHQASNSSRLHTCQRHHHHHHHHHH

SEQ ID NO: 2
Human Dkk1-(10His) nt sequence
(nucleotide sequence, where nucleotides in
bold italic type are just an estimation for
the sequence as R&D does not provide sequence
info)
ATGGCTCTGGGCGCAGCGGGAGCTACCCGGGTCTTTGTCGCGATGGTA

GCGGCGGCTCTCGGCGGCCACCCTCTGCTGGGAGTGAGCGCCACCTTG

AACTCGGTTCTCAATTCCAACGCTATCAAGAACCTGCCCCCACCGCTG

GGCGGCGCTGCGGGGCACCCAGGCTCTGCAGTCAGCGCCGCGCCGGGA

ATCCTGTACCCGGGCGGGAATAAGTACCAGACCATTGACAACTACCAG

CCGTACCCGTGCGCAGAGGACGAGGAGTGCGGCACTGATGAGTACTGC

GCTAGTCCCACCCGCGGAGGGGACGCAGGCGTGCAAATCTGTCTCGCC

TGCAGGAAGCGCCGAAAACGCTGCATGCGTCACGCTATGTGCTGCCCC

GGGAATTACTGCAAAAATGGAATATGTGTCTTCTGATCAAATCAT

TTCCGAGGAGAAATTGAGGAAACCATCACTGAAAGCTTTGGTAATGAT

CATAGCACCTTGGATGGGTATTCCAGAAGAACCACCTTGTCTTCAAAA

ATGTATCACACCAAAGGACAAGAAGGTTCTGTTTGTCTCCGGTCATCA

GACTGTGCCTCAGGATTGTGTTGTGCTAGACACTTCTGGTCCAAGATC

TGTAAACCTGTCCTGAAAGAAGGTCAAGTGTGTACCAAGCATAGGAGA

AAAGGCTCTCATGGACTAGAAATATTCCAGCGTTGTTACTGTGGAGAA

GGTCTGTCTTGCCGGATACAGAAAGATCACCATCAAGCCAGTAATTCT

TCTAGGCTTCACACTTGTCAGAGACAC

CACCATCACCACCATCACCATCATCAC
```

B. Immunization and Hybridoma Generation

Balb/c mice were immunized intraperitoneally with 50 ug/dose/mouse of KLH-conjugated rhuDkk-1 protein. This dose was repeated on 3 occasions over a 4 week period. 2 days and 1 day before fusion the mice received a final boost of 50 ugs of protein. Spleen lymphocytes were fused with the non secretory sp2/0 myeloma cell line and subjected to HAT selection as previously described (Galfre and Milstein, Methods Enzymol 73 3-46 (1981)). A hybridoma secreting Dkk1-specific IgG was recovered, subcloned and detected using assays described below.

Dkk-1 Specificity (ELISA Assays)

A. Detection

Dkk-1 specific antibodies were detected using the following ELISA based method. rhuDkk-1 protein (R&D systems cat no. 1096 DK/CF) was diluted to 1 ug/ml in coating buffer (Sigma carbonate/bicarbonate coating buffer pH 9.6 Cat No. C-3041 made up according to manufacturers instructions). 100 uls of Dkk-1 was added per well to Nunc Maxisorp 96 well plates and incubated overnight at 4° C. Wells were washed 4× with 250 uls/well of wash buffer (0.05% (v/v) Tween-20 (Sigma Cat no. P2287) in dPBS without Ca/Mg++ (Sigma Cat No. D8537)) then blocked with 200 uls/well of blocking buffer (1% PVA (Sigma cat no. 363170) (weight/volume) in dPBS (Sigma cat no. D8537)) for 2 hrs at room temperature. Blocking buffer was then removed by rapid decanting. Antibodies were diluted by consecutive 2-fold serial dilutions in blocking buffer and applied to each plate at 100 ul per well. Plates were incubated for 1 hour at RT and then washed as described above.

Binding of the test antibody to Dkk was determined by addition of a secondary antibody specific for the antibody species. When murine antibodies were being tested 100 uls/well of an HRP conjugated Goat anti-Mouse IgG (H&L) was used at a dilution of 1 in 4000 in blocking buffer (Jackson ImmunoResearch Cat No. 115-035-146). When humanized antibodies were being tested 100 uls/well of an HRP conjugated Goat anti-Human IgG F(ab')2 was used at a dilution of 1 in 4000 in blocking buffer (Jackson ImmunoResearch Cat No. 109-035-097). The plates were incubated for 30 mins at room temperature then washed 2× as described above. 100 uls of freshly prepared substrate (KPL ABTS Peroxidase Substrate 2-component Cat No. 50-62-00 prepared according to manufacturers instructions) was added per well and the color allowed to develop. Once developed, the plate absorbance was measured at 405 and 490 nm. Absorbance values were presented as the difference between absorbance at both wavelengths. JC18 showed binding to rhuDKK-1, up to 5 ug/ml.

B. Specificity of Binding to Other Human Dkk Homologues

The ability of JC18 to bind to other human Dkk proteins was assessed using the ELISA protocol described above with the exception that plates were also coated with recombinant human Dkk3 (R&D systems Cat No. 1118-DK/CF) and Dkk4 (R&D systems Cat No. 1269-DK/CF). JC18 showed weak binding to human Dkk-4 and no binding to human Dkk-3 up to 5 ug/ml.

TABLE 2

| JC18 (ng/ml) | HUMAN DKK-1 (OD) | HUMAN DKK-3 (OD) | HUMAN DKK-4 (OD) |
|---|---|---|---|
| 5000 | 2.07215 | 0.0289 | 0.5088 |
| 1250 | 2.06405 | 0.0244 | 0.3366 |
| 31 | 1.934 | 0.0226 | 0.24585 |
| 8 | 1.42005 | 0.02255 | 0.14735 |
| 2 | 0.7559 | 0.02065 | 0.07895 |
| 0.5 | 0.2986 | 0.02325 | 0.0431 |
| 0.125 | 0.11785 | 0.02265 | 0.0325 |
| 0.03 | 0.0593 | 0.02345 | 0.02715 |

C. Species Cross Reactivity

The ability of JC18 to bind to other species Dkk proteins was assessed using the ELISA protocol described above with the exception that plates were also coated with recombinant rat Dkk-1(R&D systems Cat No. 4010-DK/CF), mouse Dkk-1 (R&D systems Cat No. 1765-DK/CF), mouse Dkk-2 (R&D systems Cat No. 2435-DK/CF), and mouse Dkk-4 (R&D systems Cat No. 3105-DK/CF). JC18 showed: (1) similar binding to mouse and rat Dkk-1 as human Dkk-1, up to 5 ug/ml; (2) no binding to mouse Dkk-2, up to 5 ug/ml; and (3) weak binding to mouse Dkk-4, up to 5 ug/ml.

Cloning and Sequencing

One million hybridoma cells were homogenized using the QIAshredder spin columns and total RNA was extracted according to RNAeasy Mini kit from QIAGEN. cDNA was synthesized using SuperScript III RT kit from Invitrogen. Variable regions from the Dkk-1 antibodies were cloned using the mouse IgG-Primer Sets from Novagen, which consist of degenerate primers for cloning mouse IgG heavy chain genes and the mouse kappa or lambda light chains. PCR cycling conditions were the followings: 1 cycle at 94° C. for 2 min; five cycles at 94° C. for 30 sec, 44° C. for 30 sec and 68° C. for 60 sec; followed by 25 cycles at 94° C. for 30 sec, 54° C. for 30 sec and 68° C. for 60 sec. The resulting PCR products were cloned into Topo-TA cloning vector from Invitrogen and sequenced. The cloned antibody sequences were confirmed by direct comparison using mass spectrometry (MS) analysis of the cloned antibody sequences and the original antibodies produced from ascites.

The nucleotide sequence and the predicted amino acid sequence of the light and heavy chains of the variable regions of the JC18 wildtype (mouse) monoclonal antibody are provided below.

```
SEQ ID NO: 3
JC18 Light Chain Variable Region nt sequence
GACATTGTGTTGACCCAATCTCCAGCTTCTTTGGCTGTGTCTCTAG

GGCAGAGGGCCACCATCTCCTGCAGAGCCAGCGAAAGTGTTGATGA

CTTTGGCTTAGTTTTATGAACTGGTTCCAACAGAAACCAGGACAGC

CACCCAAACTCCTCATCTATGCTGCATCCAAGCAGGGATCCGGGGT

CCCTGCCAGGTTTAGGGGCAGTGGGTCTGGGTCAGACTTCAGCCTC

ACCATCCATCCTGTGGAGGAGGATGATACTGCAATGTATTTCTGTC

AGCAAAGTAAGGAGGTTCCTCCCACGTTCGGAGGGGGGACCAAGCT

GGAAATAAAA

SEQ ID NO: 4
JC18 Light Chain Variable Region aa sequence
DIVLTQSPASLAVSLGQRATISCRASESVDDFGISFMNWFQQKPGQ

PPKLLIYAASKQGSGVPARFRGSGSGSDFSLTIHPVEEDDTAMYFC

QQSKEVPPTFGGGTKLEIK

SEQ ID NO: 5
JC18 Light Chain Variable Region CDR1 nt
sequence
AGA GCC AGC GAA AGT GTT GAT GAC TTT GGC ATT

AGT TTT ATG AAC

SEQ ID NO: 6
JC18 Light Chain Variable Region CDR1 aa
sequence
RASESVDDFGISFMN

SEQ ID NO: 7
JC18 Light Chain Variable Region CDR2 nt
sequence
GCT GCA TCC AAG CAG GGA TCC SEQ ID NO: 8
JC18 Light Chain Variable Region CDR2 aa
sequence
AASKQGS SEQ ID NO: 9
JC18 Light Chain Variable Region CDR3 nt
sequence
CAG CAA AGT AAG GAG GTT CCT CCC ACG SEQ ID NO: 10
JC18 Light Chain Variable Region CDR3 aa
sequence
QQSKEVPPT SEQ ID NO: 11
JC18 Heavy Chain Variable Region nt sequence
GAAGTGAAACTGGTGGAGTCTGGGGGAGGCTTAGTGAAGCCTGGAG

GGTCCCTGAAACTCTCCTGTGCAGCCTCTGGATTCACTTTCAGTAA

TTATGCCATGTCTTGGGTTCGCCAGACTCCAGAGAAGAGGCTGGAG

TGGGTCGCATCCATTAGTGGTGGTGGTGACACCTACTATCCAGACA

GTGTGAAGGGCCGATTCACCATCTCCAGAGATAATGTCAGGAACAT

CCTCTACCTGCAAATGAGCAGTCTGAGGTCTGAGGACACGGCCATG

TATTACTGTGCAACATCCCTTGAGAACTATGCTATGGACTACTGGG

GTCAAGGAACCTCAATCACCGTCTCCTCA

SEQ ID NO: 12
JC18 Heavy Chain Variable Region aa sequence
EVKLVESGGGLVKPGGSLKLSCAASGFTFSNYAMSWVRQTPEKRLE

WVASISGGGDTYYPDSVKGRFTISRDNVRNILYLQMSSLRSEDTAM

YYCATSLENYAMDYWGQGTSITVSS

SEQ ID NO: 13
JC18 Heavy Chain Variable Region CDR1 nt
sequence
AAT TAT GCC ATG TCT SEQ ID NO: 14
JC18 Heavy Chain Variable Region CDR1 aa
sequence
NYAMS SEQ ID NO: 15
JC18 Heavy Chain Variable Region CDR2 nt
sequence
TCC ATT AGT GGT GGT GGT GAC ACC TAC TAT CCA

GAC AGT GTG AAG GGC

SEQ ID NO: 16
JC18 Heavy Chain Variable Region CDR2 aa
sequence
SISGGGDTYYPDSVKG SEQ ID NO: 17
JC18 Heavy Chain Variable Region CDR3 nt
sequence
TCC CTT GAG AAC TAT GCT ATG GAC TAC SEQ ID NO: 18
JC18 Heavy Chain Variable Region CDR3 aa
sequence
SLENYAMDY
```

Example 2

Generation and Testing of Humanized Anti-Dkk-1 Monoclonal Antibody (huMabJC18) Obtained Through Mutation of muMabJC18

Binding Affinity Determination of the Humanized Antibody and its Variants

General Methods Used in this Example:

A. Expression Vector Used in Clone Characterization

Expression of the Fab fragment of the antibodies was under control of an IPTG inducible lacZ promotor similar to that described in Barbas (2001) *Phage display: a laboratory manual*, Cold Spring Harbor, N.Y., Cold Spring Harbor Laboratory Press pg 2.10. Vector pComb3X), however, modifications included addition and expression of the following additional domains: the human Kappa light chain constant domain and the CHI constant domain of IgG2a human immunoglobulin. Ig gamma-2 chain C region, protein accession number P01859; Immunoglobulin kappa light chain (*Homo sapiens*), protein accession number CAA09181.

B. Small Scale Fab Preparation

Small scale expression of Fabs in 96 wells plates was carried out as follows. Starting from *E. coli* transformed with a Fab library, colonies were picked to inoculate both a master plate (agar LB+Ampicillin (50 µg/ml)+2% Glucose) and a working plate (2 ml/well, 96 well/plate containing 1.5 mL of LB+Ampicillin (50 µg/ml)+2% Glucose). Both plates were grown at 30° C. for 8-12 hours. The master plate was stored at 4° C. and the cells from the working plate were pelleted at 5000 rpm and resuspended with 1 mL of LB+Ampicillin (50 µg/ml)+1 mM IPTG to induce expression of Fabs.

Cells were harvested by centrifugation after 5 h expression time at 30° C., then resuspended in 500 µL of buffer HBS-EP (100 mM HEPES buffer pH 7.4, 150 mM NaCl, 0.005% P20). Lysis of HBS-EP resuspended cells was attained by one cycle of freezing (−80° C.) then thawing at 37° C. Cell lysates were centrifuged at 5000 rpm for 30 min to separate cell debris from supernatants containing Fabs. Supernatants were filtered using 96-well Multiscreen HTS filter plates (Millipore, cat#MSFBN6B50). The supernatants were then injected into the BIAcore plasmon resonance apparatus to obtain affinity information for each Fab. Clones expressing Fabs were rescued from the master plate to sequence the DNA and for large scale Fab production and detailed characterization as described below.

C. Large Scale Fab Preparation

To obtain detailed kinetic parameters, Fabs were expressed and purified from large cultures. Erlenmeyer flasks containing 200 mL of LB+Ampicillin (50 µg/ml)+2% Glucose were inoculated with 5 mL of over night culture from a selected Fab-expressing *E. coli* clone. Clones were incubated at 30° C. until an $OD_{550nm}$ of 1.0 was attained and then induced by replacing the media with 200 ml, of LB+Ampicillin (50 µg/ml)+1 mM IPTG. After 5 h expression time at 30° C., cells were pelleted by centrifugation, then resuspended in 10 mL PBS (pH 8). Lysis of the cells was obtained by two cycles of freeze/thaw (at −80° C. and 37° C., respectively).

Supernatant of the cell lysates were loaded onto Ni-NTA superflow sepharose (Qiagen, Valencia. Calif.) columns equilibrated with PBS, pH 8, then washed with 5 column volumes of PBS, pH 8. Individual Fabs eluted in different fractions with PBS (pH 8)+300 mM Imidazol. Fractions containing Fabs were pooled and dialized in PBS, then quantified by ELISA prior to affinity characterization.

D. Full Antibody Preparation

For expression of full antibodies, heavy and light chain variable regions were cloned in mammalian expression vectors and transfected using lipofectamine into HEK 293 cells for transient expression.

Antibodies were purified with protein A using standard methods.

BIAcore Assays:

The affinity of huMabJC18 to human, mouse or rat Dkk1 was determined by using the BIAcore3000™ surface plasmon resonance (SPR) system (BIAcore Inc., Piscataway, N.J.), equipped with a CM5 sensor chip (BIAcore AB, Uppsala, Sweden). For the huMabJC18-human Dkk1 interaction analysis, reaction surfaces were generated by amine coupling of huMabJC18 to three flow cells (Fc2, Fc3 and Fc4). CM5 chips were activated with N-ethyl-N'-(3-dimethylaminopropyl)-carbodiinide hydrochloride (EDC) and N-hydroxysuccinimide (NHS) according to the supplier's instructions. The huMabJC18 IgG was diluted into 10 mM sodium acetate pH 4.0 and injected over the activated chip at a concentration of 30 µg/ml.

Using variable flow time across the individual chip channels, a range of antibody density was achieved: 200-800 response units (RU). The IgG and reference surfaces were then saturated with goat Fab2 anti-human Fc (Cappel 55053) to prevent nonspecific binding by Dkk-1 to the chip surface. The chip was then blocked with ethanolamine. Assays were performed at 25° C., with a BIAcore running buffer composed of HBS-EP (0.01 M HEPES, pH 7.4, 0.15 NaCl, 3 mM EDTA, 0.005% Surfactant P20)+2 mg/ml BSA+2 mg/ml CM Dextran. A five membered, three fold dilution series starting at 30.9 nM purified human Dkk1 (R&D Systems) protein was injected for 1.5 min at 100 µL/min, and dissociation was monitored for 8 hours. Kinetic association rates ($k_{on}$) and dissociation rates ($k_{off}$) were obtained simultaneously by fitting the data to a 1:1 Langmuir binding model (Karlsson, R. Roos, H. Fagerstam, L. Petersson, B. (1994). Methods Enzymology 6. 99-110) using the BIAevaluation program. Equilibrium dissociation constant (KD) values were calculated as $k_{off}/k_{on}$.

For the interaction analyses of huMabJC18 with mouse or rat Dkk-1, low-levels of huMabJC18 (typically, 100-400 response units) were captured on individual flow cells by goat Fab2 anti-human Fc, which was pre-immobilized to the CM5 chip surface. A goat Fab2 anti-human Fc-saturated flow cell containing no humanized antibody served as reference channel. Mouse or rat Dkk-1 (R&D Systems) was titrated over the chip using 70.1 nM or 30.2 nM as top concentration, respectively, of a three-fold dilution series Association and dissociation phases were monitored at 100 µL/min for 90 seconds and 30 minutes, respectively. Capture surfaces for all experiments were regenerated with two 30 second pulses of 0.75 mM $H_3PO_4$, except for the amine-coupled huMabJC18 surface used in the human Dkk-1 experiment, which was not regenerated.

The binding responses were double-referenced and fit globally to a simple model using BiaEvaluation v.4.0 software. Affinities were deduced from the quotient of the kinetic rate constants ($K_D=k_{off}/k_{on}$).

For screening assays to determine binding and dissociation rates of huMabJC18 variants to human Dkk1, either BIAcore or ProteOn XPR36 (BioRad, Inc.) systems were used. For the BIAcore assay, biotinylated-human Dkk1 was captured on SA (streptavidin) BIAcore chips according to the supplier's instructions. Biotinylated-human Dkk-1 protein was diluted into HBS-EP, and injected over the chip at a concentration of 5 µg/mL. Flow times across the individual chip channels were selected to achieve an antigen density of approximately 500-600 response units (RU). HBS-EP buffer was used as running buffer. Filtered recombinant *E. coli* cell lysates were injected at high temperature (37° C.) for 1 min at 30 ul/min, allowing a 1-5 min dissociation phase. Surfaces were regenerated with 8 mM NaOH+8% ethanol. A positive control Fab (clone 24) was injected twice at the start of the experiment, and again at the end of the assay to assess reproducibility.

For the ProteOn assay, biotinylated human Dkk-1 was injected for 1 min at serial fold dilutions empirically determined to yield different levels of immobilization (150-3000

RU) on five channels of a ProteOn NLC Neutravidin sensor chip. The sixth channel was left unmodified to serve as a reference surface. Recombinant Fabs in filtered *E. coli* lysates were injected at high temperature (37° C.) for 50 sec at 20 µl/min. Running buffer consisted of PBS+1 mg/ml BSA+ 0.005% Tween-20. The ProteOn is configured such that each injection flows over each of the five Dkk-1 channels as well as the reference channel, and six Fab samples can be injected simultaneously. Fab dissociation from the Dkk-1 surface was monitored for 20 min. The chip surface was regenerated with a 30-sec injection of 8% EtOH, 8 mM NaOH. Clone 24 Fab was used as control. Level of binding during association, and rate of dissociation for each clone was very consistent between different ligand channels.

Binding Affinity of huMabJC18 and its Variants to Dkk1

The amino acid sequences of huMabJC18 is as set forth in SEQ ID NO: 40 (HC variable region) and SEQ ID NO: 42 (LC variable region). The binding affinity of huMabJC18 IgG to Dkk-1 determined using BIAcore as described above is shown in Table 3 below.

TABLE 3

Binding affinity of the huMabJC18 IgG to Dkk1 from human, mouse, and rat

| Dkk-1 species | $k_{on}$ (1/Ms) | $k_{off}$ (1/s) | $T_{1/2}$ (h) | $K_D$ (nM) |
|---|---|---|---|---|
| human | $>1.3 \times 10^{6}$* | $<2.0 \times 10^{-6}$^ | >96.27 | <0.002 |
| mouse | $>1.3 \times 10^{6}$* | $<3.9 \times 10^{-5}$^ | >4.94 | <0.03 |
| rat | $>1.3 \times 10^{6}$* | $2.1 \times 10^{-4}$ | 0.92 | <0.1 |

*onrate is too fast to measure
^offrate is too slow to measure
$K_D = k_{off}/k_{on}$
$T_{1/2}$ (s) = ln2/$k_{off}$(1/s)

The amino acid sequences of the CDRs of huMabJC18 variants are shown in Table 4 below. All amino acid substitutions shown in Table 4 are described relative to the sequence of huMabJC18. The hDkk-1 binding affinity of huMabJC18 and its variants are also shown in Table 4.

TABLE 4

Amino acid sequences and kinetic data for huMabJC18 and its variants as determined at 37° C. by BIAcore or Proteon analyses

| Clone | H2 | H3 | L1 | L2 | L3 | $k_{on}$ (1/Ms) | $k_{off}$ (1/s) | $K_D$ (nM) |
|---|---|---|---|---|---|---|---|---|
| huMabJC18 | | | | | | $\geq 1.36 \times 10^{6}$ | $<2.0 \times 10^{-6}$ | $\leq 0.002$ |
| 36H.33L | T54-L56# G57W Q59D | E103R | | | | $5.18 \times 10^{6}$ | $8.55 \times 10^{-5}$ | 0.017 |
| 2G9.33L | T54-L56## G57W F58G Q59D | E103R | | | | n.d. | $2.83 \times 10^{-4}$ | 0.283 |
| 2H10.33L | T54-L56# G57W Q59D | E103Q | | | | n.d. | $1.48 \times 10^{-4}$ | 0.148 |
| 1F10.33L | T54-L56# | E103D | | | | | $8.99 \times 10^{-5}$ | 0.090 |
| 4E8.33L | T54-L56# G57W F58L Q59D | | | | | $1.13 \times 10^{7}$ | $8.55 \times 10^{-5}$ | 0.008 |
| 2E11.33L | | E103R | | | | $2.88 \times 10^{6}$ | $8.55 \times 10^{-5}$ | 0.03 |
| 4F10.33L | | E103K | | | | $2.31 \times 10^{6}$ | $8.55 \times 10^{-5}$ | 0.037 |
| 35H.LA7 | | | E27Q D30S D31S F32S G33Y I34L S35A F36W I37# N38# | | | $8.92 \times 10^{6}$ | $2.85 \times 10^{-2}$ | 3.2 |
| 2E11.LA7 | | E103R | E27Q D30S D31S F32S G33Y I34L S35A F36W I37# N38# | | | $2.47 \times 10^{6}$ | $1.57 \times 10^{-2}$ | 6.4 |

TABLE 4-continued

Amino acid sequences and kinetic data for huMabJC18 and its variants as determined at 37° C. by BIAcore or Proteon analyses

| Clone | H2 | H3 | L1 | L2 | L3 | $k_{on}$ (1/Ms) | $k_{off}$ (1/s) | $K_D$ (nM) |
|---|---|---|---|---|---|---|---|---|
| 4F10.LA7 | | E103K | E27Q D30S D31S F32S G33Y I34L S35A F36W I37# N38# | | | $2.39 \times 10^6$ | $1.69 \times 10^{-2}$ | 7.1 |
| 36H.LA7 | T54-L56# G57W Q59D | E103R | E27Q D30S D31S F32S G33Y I34L S35A F36W I37# N38# | | | $3.24 \times 10^6$ | $1.58 \times 10^{-1}$ | 48.8 |
| 4E8.LA7 | T54-L56# G57W F58L Q59D | | E27Q D30S D31S F32S G33Y I34L S35A F36W I37# N38# | | | $1.9 \times 10^6$ | $1.08 \times 10^{-1}$ | 56.8 |
| L3.1A3 | T54-L56# G57W Q59H | E103R | | | | n.d. | $1.8 \times 10^{-4}$ | 0.184 |
| L3.1B12 | T54-L56# G57W Q59G | | | | | n.d. | $2.1 \times 10^{-4}$ | 0.210 |
| L3.1D7 | T54-L56# G57W Q59R | E103R | | | | n.d. | $1.64 \times 10^{-4}$ | 0.164 |
| L3.1H3 | T54-L56# G57W F58L Q59H | | | | | n.d. | $1.15 \times 10^{-3}$ | 1.15 |
| L3.2H8 | T54-L56# G57W F58L Q59G | E103Q | | | | n.d. | $5.55 \times 10^{-4}$ | 0.555 |
| L3.2H10 | T54-L56# G57W F58L Q59G | E103K | | | | n.d. | $5.69 \times 10^{-4}$ | 0.569 |
| L3.2H12 | T54-L56# G57G F58L Q59G | E103R | | | | n.d. | $1.97 \times 10^{-3}$ | 1.97 |
| L3.4E6 | T54-L56# F58G Q59G | E103R | | | | n.d. | $9.9 \times 10^{-4}$ | 0.99 |
| L3.4E7 | T54-L56# G57W F58G Q59D | E103Q | | | | n.d. | $2.76 \times 10^{-4}$ | 0.276 |

TABLE 4-continued

Amino acid sequences and kinetic data for huMabJC18 and its variants as determined at 37° C. by BIAcore or Proteon analyses

| Clone | H2 | H3 | L1 | L2 | L3 | $k_{on}$ (1/Ms) | $k_{off}$ (1/s) | $K_D$ (nM) |
|---|---|---|---|---|---|---|---|---|
| L3.4E10 | T54-L56# G57W F58G Q59H | E103Q | | | | n.d. | $5.33 \times 10^{-4}$ | 0.533 |
| L3.4H2 | T54-L56# G57W F58G Q59D | E103Q | | | | n.d. | $4.8 \times 10^{-5}$ | 0.048 |
| L3.4H5 | T54-L56# G57W F58G Q59D | T100S E103D | | | | n.d. | $8.08 \times 10^{-4}$ | 0.808 |
| 24 | T54-L56# F58G Q59R | | I37M | G55A | L95S | n.d. | $1.14 \times 10^{-2}$ | 11.4 |
| 24m4 | T54-L56# F58G Q59R | | I37L | G55A | L95S | n.d. | $1.18 \times 10^{-2}$ | 11.8 |
| 24m5 | T54-L56# F58G Q59R | | I37M | S56T | L95S | n.d. | $8.74 \times 10^{-3}$ | 8.74 |
| 24m6 | T54-L56# F58G Q59R | | I37M | | L95S | n.d. | $9.14 \times 10^{-3}$ | 9.14 |
| SL3.1D2 | T54-L56# F58G Q59R | | I37M | G55A | L95S T101L | n.d. | $4.9 \times 10^{-3}$ | 4.9 |
| SL3.1F11 | T54-L56# F58G Q59R | | I37M | G55A | L95S K96W | n.d. | $5.4 \times 10^{-3}$ | 5.4 |
| SL3.1F12 | T54-L56# F58G Q59R | | I37M | G55A | L95S T101Y | n.d. | $5.52 \times 10^{-3}$ | 5.52 |
| SL3.1G2 | T54-L56# F58G Q59R | | I37M | G55A | L95S K96I | n.d. | $8.72 \times 10^{-3}$ | 8.72 |
| SL3.1G9 | T54-L56# F58G Q59R | | I37M | G55A | | n.d. | $9.47 \times 10^{-4}$ | 0.947 |
| SL3.3A10 | T54-L56# F58G Q59R | | I37M | G55A | L95S V98L | n.d. | $5.72 \times 10^{-3}$ | 5.72 |
| SL3.3B11 | T54-L56# F58G Q59R | | I37M | G55A | L95A | n.d. | $1.2 \times 10^{-2}$ | 12 |
| SL3.3C10 | T54-L56# F58G Q59R | | I37M | G55A | L95S P99W | n.d. | $1.21 \times 10^{-2}$ | 12.1 |
| SL3.3F4 | T54-L56# F58G Q59R | | I37M | G55A | L95S K96S | n.d. | $1.18 \times 10^{-2}$ | 11.8 |
| SL3.3H8 | T54-L56# F58G Q59R | | I37M | G55A | L95S P100G | n.d. | $2.29 \times 10^{-2}$ | 22.9 |

TABLE 4-continued

Amino acid sequences and kinetic data for huMabJC18 and its variants as determined at 37° C. by BIAcore or Proteon analyses

| Clone | H2 | H3 | L1 | L2 | L3 | $k_{on}$ (1/Ms) | $k_{off}$ (1/s) | $K_D$ (nM) |
|---|---|---|---|---|---|---|---|---|
| SL3.4A10 | T54-L56# F58G Q59R | | I37M | G55A | L95S K96L | n.d. | $7.3 \times 10^{-3}$ | 7.3 |
| SL3.4C7 | T54-L56# F58G Q59R | | I37M | G55A | L95S Q94H | n.d. | $7.3 \times 10^{-3}$ | 7.3 |
| SL3.4D1 | T54-L56# F58G Q59R | | I37M | G55A | L95S K96M | n.d. | $7.5 \times 10^{-3}$ | 7.5 |
| SL3.4E4 | T54-L56# F58G Q59R | | I37M | G55A | L95S E97D | n.d. | $7.7 \times 10^{-3}$ | 7.7 |
| SL3.4F1 | T54-L56# F58G Q59R | | I37M | G55A | L95S P100S | n.d. | $1.69 \times 10^{-2}$ | 16.9 |
| SL3.4F5 | T54-L56# F58G Q59R | | I37M | G55A | L95G | n.d. | $7.8 \times 10^{-3}$ | 7.8 |
| L2.1B5 | T54-L56# G57W F58G Q59D | | I37M | G55A | L95S | n.d. | $4.42 \times 10^{-3}$ | 4.42 |
| L2.1B11 | T54-L56# G57W Q59D | E103R | I37M | G55A | L95S | n.d. | $2.07 \times 10^{-3}$ | 2.07 |
| L2.1D12 | T54-L56# G57W Q59D | E103Q | I37M | G55A | L95S | n.d. | $2.78 \times 10^{-3}$ | 2.78 |
| L2.1E5 | T54-L56# F58G Q59R | | I37M | G55A | L95S | n.d. | $5.7 \times 10^{-3}$ | 5.7 |
| L2.1F11 | T54-L56# G57W F58L Q59D | E103Q | I37M | G55A | L95S | n.d. | $2.12 \times 10^{-3}$ | 2.12 |
| L2.1G4 | T54-L56# G57W Q59D | Y109K | I37M | G55A | L95S | n.d. | $3.12 \times 10^{-3}$ | 3.12 |
| L2.1G8 | T54-L56# G57W Q59D | | I37M | G55A | L95S | n.d. | $2.55 \times 10^{-3}$ | 2.55 |
| L2.4B10 | T54-L56# G57W F58Y Q59D | | I37M | G55A | L95S | n.d. | $3.45 \times 10^{-3}$ | 3.45 |
| L2.4D11 | T54-L56# G57W F58M Q59D | | I37M | G55A | L95S | n.d. | $3.26 \times 10^{-3}$ | 3.26 |
| L2.4E1 | T54H G55# L56# F58V Q59W | | I37M | G55A | L95S | n.d. | $5.51 \times 10^{-3}$ | 5.51 |
| L2.4G10 | T54-L56# G57W F58L Q59D | E103R | I37M | G55A | L95S | n.d. | $2.76 \times 10^{-3}$ | 2.76 |

TABLE 4-continued

Amino acid sequences and kinetic data for huMabJC18 and its variants as determined at 37° C. by BIAcore or Proteon analyses

| Clone | H2 | H3 | L1 | L2 | L3 | $k_{on}$ (1/Ms) | $k_{off}$ (1/s) | $K_D$ (nM) |
|---|---|---|---|---|---|---|---|---|
| L2.P4.B5 | T54-L56# G57W F58G Q59D | L102Y | I37M | G55A | L95S | n.d. | $5.32 \times 10^{-3}$ | 5.32 |
| L2.P4.C10 | T54-L56# G57W F58G Q59D | E103K | I37M | G55A | L95S | n.d. | $4.31 \times 10^{-3}$ | 4.31 |
| L2.P4.D1 |  | E103D | I37M | G55A | L95S | n.d. | $2.88 \times 10^{-3}$ | 2.88 |
| L2.P4.E7 | T54-L56# G57W F58G Q59D | E103R | I37M | G55A | L95S | n.d. | $5.19 \times 10^{-3}$ | 5.19 |
| L2.P4.H3 | T54-L56# G57W F58L Q59D |  | I37M | G55A | L95S | n.d. | $2.74 \times 10^{-3}$ | 2.74 |

In Table 4, # represents a gap in that position(s); n.d., not determined.

The CDRs are extended CDRs, which include both Kabat and Chothia definitions, except for CDR H1 which is the Kabat definition. Amino acid residues are numbered sequentially (see SEQ ID NO: 28 for numbering of residues in H2 and H3 columns, and SEQ ID NO: 20 for numbering of residues in L1, L2 and L3 columns). All clones have framework and CDR H1 sequences identical to huMabJC18. $K_D = k_{off}/k_{on}$. All $k_{off}$ values were determined in a screening mode except those that are underlined, which were obtained by global analysis of a hDkk-1 concentration series flowed across IgGs captured on the BIAcore chip or ProteOn surface. Underlined $K_D$ values were therefore determined experimentally by measuring $k_{on}$. Other $K_D$ values are theoretical, based on an estimated $k_{on}$ value of $1 \times 10^6$ (1/Ms). Since onrates for all analyzed clones were very fast and thus diffusion limited ($>1 \times 10^6$, and too fast to measure accurately), affinities are most likely even higher than shown.

Interaction of huMabJC18 with Dkk Homologs

HuMabJC18 was analyzed for binding to other available Dkk homologs, including human Dkk-3, human Dkk-4, mouse Dkk-2 and mouse Dkk-4 (R&D Systems). The results are summarized in Table 5.

TABLE 5

Interaction of huMabJC18 with Dkk homologs

| DKK homolog | $k_{on}$ (1/Ms) | $k_{off}$ (1/s) | $T_{1/2}$ (h) | $K_D$ (nM) |
|---|---|---|---|---|
| hDkk-3 | — | — | — | no binding |
| hDkk-4 | $1.50 \times 10^4$ | $1.72 \times 10^{-4}$ | 1.12 | 11 |
| mDkk-2 | $1.80 \times 10^4$ | $1.69 \times 10^{-4}$ | 1.14 | 9 |
| mDkk-4 | $>1.3 \times 10^{6*}$ | $<3.9 \times 10^{-5\char94}$ | >4.94 | <0.03 |

*onrate is too fast to measure
^offrate is too slow to measure

Interaction analyses for huMabJC18 with Dkk-1 homologs were run as described above using goat Fab2 anti-human Fc as pre-immobilized capture reagent. Human Dkk-4, mouse Dkk-2, or mouse Dkk-4 were titrated over the chip, using 76.3 nM, 88.8 nM, or 32.3 nM as top concentration, respectively, in a five-fold dilution series. Human Dkk-3 showed no specific binding response.

JC18 Dkk-1 Binding Antibody

The binding affinities of mouse antibody JC18 to human, mouse or rat Dkk1 (R&D Systems) as determined at 25° C. by BIAcore analysis are shown in Table 6 below. For this assay, polyclonal anti-mouse IgG was amine-coupled to the BIAcore chip. Anti-Dkk-1 antibody JC18 is at 6.53 µg/ml, and was captured for 1 min at 5 µl/min. A five-fold series dilution of human, mouse or rat Dkk-1 (R&D Systems; from 0.4-250 nM) was injected for 1 min at 50-100 µl/min. Dissociation was monitored for 3-5 min. The chip was regenerated with two 30-sec pulses of 100 mM $H_3PO_4$.

TABLE 6

Kinetic data for mouse antibody JC18 binding to human, mouse or rat Dkk-1 as determined by BIAcore at 25° C.

| Dkk-1 species | Kon (1/Ms) | Koff (1/s) | Kd (nM) |
|---|---|---|---|
| human | $3.18 \times 10^6$ | $2.07 \times 10^{-4}$ | 0.65 |
| mouse | $1.74 \times 10^6$ | $2.54 \times 10^{-3}$ | 1.5 |
| rat | $3.8 \times 10^6$ | $2.75 \times 10^{-3}$ | 0.72 |

Sequences for huMabJC18

```
SEQ ID NO: 19
huMabJC18 Light Chain Variable Region nt
sequence
GAGATCGTGCTGACCCAGAGCCCCGCCACCCTGAGCCTGAGCCCT

GGCGAGCGGGCCACCCTGTCCTGCCGGGCCAGCGAGAGCGTGGAC

GACTTCGGCATCAGCTTCATCAACTGGTATCAGCAGAAGCCCGGC

CAGGCCCCCAGACTGCTCATCTACGCCGGCAGCAAGCAGGGCAGC

GGCATCCCCGCCAGGTTCAGCGGCAGCGGCTCCGGCACCGACTTC

ACCCTGACCATCTCCAGCCTCGAACCCGAGGACTTCGCCGTGTAC

TACTGCCAGCAGCTGAAAGAGGTGCCCCCCACCTTCGGCGGTGGG

ACCAAGGTGGAAATCAAA
```

SEQ ID NO: 20
huMabJC18 Light Chain Variable Region aa
sequence
EIVLTQSPATLSLSPGERATLSCRASESVDDFGISFINWYQQKPG

QAPRLLIYAGSKQGSGIPARFSGSGSGTDFTLTISSLEPEDFAVY

YCQQLKEVPPTFGGGTKVEIK

SEQ ID NO: 21
huMabJC18 Light Chain Variable Region CDR1 nt
sequence
CGGGCCAGCGAGAGCGTGGACGACTTCGGCATCAGCTTCATCAAC SEQ ID NO: 22
huMabJC18 Light Chain Variable Region CDR1 aa
sequence
RASESVDDFGISFIN SEQ ID NO: 23
huMabJC18 Light Chain Variable Region CDR2 nt
sequence
GCCGGCAGCAAGCAGGGCAGC SEQ ID NO: 24
huMabJC18 Light Chain Variable Region CDR2 aa
sequence
AGSKQGS SEQ ID NO: 25
huMabJC18 Light Chain Variable Region CDR3 nt
sequence
CAGCAGCTGAAAGAGGTGCCCCCCACC SEQ ID NO: 26
huMabJC18 Light Chain Variable Region CDR3 aa
sequence
QQLKEVPPT SEQ ID NO: 27
huMabJC18 Heavy Chain Variable Region nt
sequence
GAGGTGCAGCTGGTCGAGTCTGGCGGCGGACTGGTGCAGCCTGGC

GGCAGCCTGAGACTGAGCTGCGCCGCCAGCGGCTTCACCTTCAGC

AGCTACGCCATCAGCTGGGTGCGGCAGGCCCCTGGCAAGGGCCTG

GAATGGGTGGCCAGCGTGAGCGGCACCGGCCTGGGCTTCCAGACC

TACTACCCCGACAGCGTGAAGGGCCGGTTCACCATCAGCCGGGAC

AACGCCAAGAACAGCCTGTACCTGCAGATGAACAGCCTGCGGGCC

GAGGACACCGCCGTGTACTACTGCGCCACCTCCCTGGAAAACTAC

GCCTTCGACTACTGGGGCCAGGGAACCACGGTCACCGTCTCCTCA

SEQ ID NO: 28
huMabJC18 Heavy Chain Variable Region aa
sequence
EVQLVESGGGLVQPGGSLRLSCAASGFTFSSYAISWVRQAPGKGL

EWVASVSGTGLGFQTYYPDSVKGRFTISRDNAKNSLYLQMNSLRA

EDTAVYYCATSLENYAFDYWGQGTTVTSS

SEQ ID NO: 29
huMabJC18 Heavy Chain Variable Region CDR1 nt
sequence
AGCAGCTACGCCATCAGC SEQ ID NO: 30
huMabJC18 Heavy Chain Variable Region CDR1 aa
sequence
SSYAIS SEQ ID NO: 49
huMabJC18 Heavy Chain Variable
Region CDR1 aa sequence (Kabat)
SYAIS SEQ ID NO: 50
huMabJC18 Heavy Chain Variable Region CDR1 aa
sequence (Chothia)
GFTFSSY SEQ ID NO: 31
huMabJC18 Heavy Chain Variable Region CDR2 nt
sequence
AGCGTGAGCGGCACCGGCCTGGGCTTCCAGACCTACTACCCCGAC

AGCGTGAAGGGC

SEQ ID NO: 32
huMabJC18 Heavy Chain Variable Region CDR2 aa
sequence
SVSGTGLGFQTYYPDSVKG SEQ ID NO: 51
huMabJC18 Heavy Chain Variable Region CDR2 aa
sequence (Chothia)
SVSGTGLGFQTY SEQ ID NO: 33
huMabJC18 Heavy Chain Variable Region CDR3 nt
sequence
TCCCTGGAAAACTACGCCTTCGACTAC SEQ ID NO: 34
huMabJC18 Heavy Chain Variable Region CDR3 aa
sequence
TSLENYAFDY SEQ ID NO: 52
huMabJC18 Heavy Chain Variable Region CDR3 aa
sequence (short)
SLENYAFDY SEQ ID NO: 35
huMabJC18 Heavy Chain nt sequence with leader
sequence
ATGGAATGGAGCTGGGTCTTTCTCTTCTTCCTGTCAGTAACTACA

GGTGTCCACTCCGAGGTGCAGCTGGTCGAGTCTGGCGGCGGACTG

GTGCAGCCTGGCGGCAGCCTGAGACTGAGCTGCGCCGCCAGCGGC

TTCACCTTCAGCAGCTACGCCATCAGCTGGGTGCGGCAGGCCCCT

GGCAAGGGCCTGGAATGGGTGGCCAGCGTGAGCGGCACCGGCCTG

GGCTTCCAGACCTACTACCCCGACAGCGTGAAGGGCCGGTTCACC

ATCAGCCGGGACAACGCCAAGAACAGCCTGTACCTGCAGATGAAC

AGCCTGCGGGCCGAGGACACCGCCGTGTACTACTGCGCCACCTCC

CTGGAAAACTACGCCTTCGACTACTGGGGCCAGGGAACCACGGTC

ACCGTCTCCTCAGCCTCCACCAAGGGCCCATCGGTCTTCCCCCTG

GCGCCCTGCTCCAGGAGCACCTCCGAGAGCACAGCGGCCCTGGGC

TGCCTGGTCAAGGACTACTTCCCCGAACCGGTGACGGTGTCGTGG

AACTCAGGCGCTCTGACCAGCGGCGTGCACACCTTCCCGGCTGTC

CTACAGTCCTCAGGACTCTACTCCCTCAGCAGCGTAGTGACCGTG

CCCTCCAGCAACTTCGGCACCCAGACCTACACCTGCAACGTAGAT

CACAAGCCCAGCAACACCAAGGTGGACAAGACAGTTGAGCGCAAA

TGCTGTGTCGAGTGCCCACCGTGCCCAGCACCACCTGTGGCAGGA

CCGTCAGTCTTCCTCTTCCCCCCAAAACCCAAGGACACCCTCATG

ATCTCCCGGACCCCTGAGGTCACGTGCGTGGTGGTGGACGTGAGC

CACGAAGACCCCGAGGTCCAGTTCAACTGGTACGTGGACGGCGTG

GAGGTGCATAATGCCAAGACAAAGCCACGGGAGGAGCAGTTCAAC

-continued
AGCACGTTCCGTGTGGTCAGCGTCCTCACCGTCGTGCACCAGGAC

TGGCTGAACGGCAAGGAGTACAAGTGCAAGGTCTCCAACAAAGGC

CTCCCATCCTCCATCGAGAAACCATCTCCAAAACCAAAGGGCAG

CCCCGAGAACCACAGGTGTACACCCTGCCCCCATCCCGGGAGGAG

ATGACCAAGAACCAGGTCAGCCTGACCTGCCTGGTCAAAGGCTTC

TACCCCAGCGACATCGCCGTGGAGTGGGAGAGCAATGGGCAGCCG

GAGAACAACTACAAGACCACACCTCCCATGCTGGACTCCGACGGC

TCCTTCTTCCTCTACAGCAAGCTCACCGTGGACAAGAGCAGGTGG

CAGCAGGGGAACGTCTTCTCATGCTCCGTGATGCATGAGGCTCTG

CACAACCACTACACACAGAAGAGCCTCTCCCTGTCTCCGGGTAAA

SEQ ID NO: 36
huMabJC18 Heavy Chain aa sequence with leader
sequence (*Δa mutations (A329S, P330S) shown
in bold italic)
MEWSWVFLFFLSVTTGVHSEVQLVESGGGLVQPGGSLRLSCAASG

FTFSSYAISWVRQAPGKGLEWVASVSGTGLGFQTYYPDSVKGRFT

ISRDNAKNSLYLQMNSLRAEDTAVYYCATSLENYAFDYWGQGTTV

TVSSASTKGPSVFPLAPCSRSTSESTAALGCLVKDYFPEPVTVSW

NSGALTSGVHTFPAVLQSSGLYSLSSVVTVPSSNFGTQTYTCNVD

HKPSNTKVDKTVERKCCVECPPCPAPPVAGPSVFLFPPKPKDTLM

ISRTPEVTCVVVDVSHEDPEVQFNWYVDGVEVHNAKTKPREEQFNS

TFRVVSVLTVLHQDWLNGKEYKCKVSNKGLPSSIEKTISKTKGQPR

EPQVYTLPPSREEMTKNQVSLTCLVKGFYPSDIAVEWESNGQPEN

NYKTTPPMLDSDGSFFLYSKLTVDKSRWQQGNVFSCSVMHEALHN

HYTQKSLSLSPGK

Glycosylation Site: HC, N296.

SEQ ID NO: 37
huMabJC18 Light Chain nt sequence with leader
sequence
TATGAGTGTGCCCACTCAGGTCCTGGGGTTGCTGCTGCTGTGGCT

ACAGATGCCAGATGTGAGATCGTGCTGACCCAGAGCCCCGCCACC

CTGAGCCTGAGCCCTGGCGAGCGGGCCACCCTGTCCTGCCGGGCC

AGCGAGAGCGTGGACGACTTCGGCATCAGCTTCATCAACTGGTAT

CAGCAGAAGCCCGGCCAGGCCCCCAGACTGCTCATCTACGCCGGC

AGCAAGCAGGGCAGCGGCATCCCCGCCAGGTTCAGCGGCAGCGGC

TCCGGCACCGACTTCACCCTGACCATCTCCAGCCTCGAACCCGAG

GACTTCGCCGTGTACTACTGCCAGCAGCTGAAAGAGGTGCCCCCC

ACCTTCGGCGGTGGGACCAAGGTGGAAATCAAACGAACTGTGGCT

GCACCATCTGTCTTCATCTTCCCGCCATCTGATGAGCAGTTGAAA

TCTGGAACTGCCTCTGTTGTGTGCCTGCTGAATAACTTCTATCCC

AGAGAGGCCAAAGTACAGTGGAAGGTGGATAACGCCCTCCAATCG

GGTAACTCCCAGGAGAGTGTCACAGAGCAGGACAGCAAGGACAGC

ACCTACAGCCTCAGCAGCACCCTGACGCTGAGCAAAGCAGACTAC

-continued
GAGAAACACAAAGTCTACGCCTGCGAAGTCACCCATCAGGGCCTG

AGCTCGCCCGTCACAAAGAGCTTCAACAGGGGAGAGTGT

SEQ ID NO: 38
huMabJC18 Kappa Light Chain aa sequence with
leader sequence
MSVPTQVLGLLLLWLTDARCEIVLTQSPATLSLSPGERATLSCRA

SESVDDFGISFINWYQQKPGQAPRLLIYAGSKQGSGIPARFSGSG

SGTDFTLTISSLEPEDFAVYYCQQLKEVPPTFGGGTKVEIKRTVA

APSVFIFPPSDEQLKSGTASVVCLLNNFYPREAKVQWKVDNALQS

GNSQESVTEQDSKDSTYSLSSTLTLSKADYEKHKVYACEVTHQGL

SSPVTKSFNRGEC

Isotypes of huMabJC18: IgG2(Δa)*, Kappa
Allotypes of huMabJC18: G2(n-), Km3

SEQ ID NO: 39
huMabJC18 Heavy Chain nt sequence without
leader sequence
GAGGTGCAGCTGGTCGAGTCTGGCGGCGGACTGGTGCAGCCTGGC

GGCAGCCTGAGACTGAGCTGCGCCGCCAGCGGCTTCACCTTCAGC

AGCTACGCCATCAGCTGGGTGCGGCAGGCCCCTGGCAAGGGCCTG

GAATGGGTGGCCAGCGTGAGCGGCACCGGCCTGGGCTTCCAGACC

TACTACCCCGACAGCGTGAAGGGCCGGTTCACCATCAGCCGGGAC

AACGCCAAGAACAGCCTGTACCTGCAGATGAACAGCCTGCGGGCC

GAGGACACCGCCGTGTACTACTGCGCCACCTCCCTGGAAAACTAC

GCCTTCGACTACTGGGGCCAGGGAACCACGGTCACCGTCTCCTCA

GCCTCCACCAAGGGCCCATCGGTCTTCCCCCTGGCGCCCTGCTCC

AGGAGCACCTCCGAGAGCACAGCGGCCCTGGGCTGCCTGGTCAAG

GACTACTTCCCCGAACCGGTGACGGTGTCGTGGAACTCAGGCGCT

CTGACCAGCGGCGTGCACACCTTCCCGGCTGTCCTACAGTCCTCA

GGACTCTACTCCCTCAGCAGCGTAGTGACCGTGCCCTCCAGCAAC

TTCGGCACCCAGACCTACACCTGCAACGTAGATCACAAGCCCAGC

AACACCAAGGTGGACAAGACAGTTGAGCGCAAATGCTGTGTCGAG

TGCCCACCGTGCCCAGCACCACCTGTGGCAGGACCGTCAGTCTTC

CTCTTCCCCCCAAAACCCAAGGACACCCTCATGATCTCCCGGACC

CCTGAGGTCACGTGCGTGGTGGTGGACGTGAGCCACGAAGACCCC

GAGGTCCAGTTCAACTGGTACGTGGACGGCGTGGAGGTGCATAAT

GCCAAGACAAAGCCACGGGAGGAGCAGTTCAACAGCACGTTCCGT

GTGGTCAGCGTCCTCACCGTCGTGCACCAGGACTGGCTGAACGGC

AAGGAGTACAAGTGCAAGGTCTCCAACAAAGGCCTCCCATCCTCC

ATCGAGAAACCATCTCCAAAACCAAAGGGCAGCCCCGAGAACCA

CAGGTGTACACCCTGCCCCCATCCCGGGAGGAGATGACCAAGAAC

CAGGTCAGCCTGACCTGCCTGGTCAAAGGCTTCTACCCCAGCGAC

ATCGCCGTGGAGTGGGAGAGCAATGGGCAGCCGGAGAACAACTAC

AAGACCACACCTCCCATGCTGGACTCCGACGGCTCCTTCTTCCTC

TACAGCAAGCTCACCGTGGACAAGAGCAGGTGGCAGCAGGGGAAC

-continued
GTCTTCTCATGCTCCGTGATGCATGAGGCTCTGCACAACCACTAC

ACACAGAAGAGCCTCTCCCTGTCTCCGGGTAAA

SEQ ID NO: 40
huMabJC18 Heavy Chain aa sequence without
leader sequence (*Δa mutations (A329S, P330S)
shown in bold italic)
EVQLVESGGGLVQPGGSLRLSCAASGFTFSSYAISWVRQAPGKGL

EWVASVSGTGLGFQTYYPDSVKGRFTISRDNAKNSLYLQMNSLRA

EDTAVYYCATSLENYAFDYWGQGTTVTVSSASTKGPSVFPLAPCS

RSTSESTAALGCLVKDYFPEPVTVSWNSGALTSGVHTFPAVLQSS

GLYSLSSVVTVPSSNFGTQTYTCNVDHKPSNTKVDKTVERKCCVE

CPPCPAPPVAGPSVFLFPPKPKDTLMISRTPEVTCVVVDVSHEDP

EVQFNVVYVDGVEVHNAKTKPREEQFNSTFRWSVLTVVHQDWLNG

KEYKCKVSNKGLPSSSSIEKTISKTKGQPREPQVYTLPPSREEM

TKNQVSLTCLVKGFYPSDIAVEWESNGQPENNYKTTPPMLDSDGS

FFLYSKLTVDKSRWQQGNVFSCSVMHEALHNHYTQKSLSLSPGK

Glycosylation Site: HC, N296.

SEQ ID NO: 41
huMabJC18 Light Chain nt sequence without
leader sequence
GAGATCGTGCTGACCCAGAGCCCCGCCACCCTGAGCCTGAGCCCT

GGCGAGCGGGCCACCCTGTCCTGCCGGGCCAGCGAGAGCGTGGAC

GACTTCGGCATCAGCTTCATCAACTGGTATCAGCAGAAGCCCGGC

CAGGCCCCCAGACTGCTCATCTACGCCGGCAGCAAGCAGGGCAGC

GGCATCCCCGCCAGGTTCAGCGGCAGCGGCTCCGGCACCGACTTC

ACCCTGACCATCTCCAGCCTCGAACCCGAGGACTTCGCCGTGTAC

TACTGCCAGCAGCTGAAAGAGGTGCCCCCCACCTTCGGCGGTGGG

ACCAAGGTGGAAATCAAACGAACTGTGGCTGCACCATCTGTCTTC

ATCTTCCCGCCATCTGATGAGCAGTTGAAATCTGGAACTGCCTCT

GTTGTGTGCCTGCTGAATAACTTCTATCCCAGAGAGGCCAAAGTA

CAGTGGAAGGTGGATAACGCCCTCCAATCGGGTAACTCCCAGGAG

AGTGTCACAGAGCAGGACAGCAAGGACAGCACCTACAGCCTCAGC

AGCACCCTGACGCTGAGCAAAGCAGACTACGAGAAACACAAAGTC

TACGCCTGCGAAGTCACCCATCAGGGCCTGAGCTCGCCCGTCACA

AAGAGCTTCAACAGGGGAGAGTGT

SEQ ID NO: 42
huMabJC18 Kappa Light Chain aa sequence
without leader sequence
EIVLTQSPATLSLSPGERATLSCRASESVDDFGISFINWYQQKPG

QAPRLLIYAGSKQGSGIPARFSGSGSGTDFTLTISSLEPEDFAVY

YCQQLKEVPPTFGGGTKVEIKRTVAAPSVFIFPPSDEQLKSGTAS

VVCLLNNFYPREAKVQWKVDNALQSGNSQESVTEQDSKDSTYSLS

STLTLSKADYEKHKVYACEVTHQGLSSPVTKSFNRGEC

Example 3

In Vitro Functional Activity of huMabJC18:
Determination of the Effect of JC18 in Wnt Activity
in a Cell-Based Functional Assay A stable U2OS cell line (U2OS TF) containing the Luciferase reporter gene under control of the TK promoter with TCF binding sites was chosen for the cell-based functional assay. The promoter is activated through the Wnt signaling pathway, when cells are treated with Wnt3a conditioned media. This activation is antagonized by Dkk-1. The Dkk-1-mediated inhibition of Wnt signaling, in turn, can be reversed by adding a Dkk-1 neutralizing mAb.

Specifically, JC18 is a monoclonal antibody that binds to mouse and human Dkk-1 with high affinity. Its ability to reverse the inhibition of Wnt 3a signaling by Dkk-1 was examined in U2OS TOPFlash cells. U2OS cells were obtained from the ATCC and stably transfected with TOPFlash plasmid (Upstate), a TCF-luciferase reporter construct. Cells were maintained at 37° C., 5% $CO_2$ in McCoys 5A Media supplemented with 10% fetal calf serum, 1% Pen Strep, and 2 mM Glutamine. U2OS TOPFlash cells were plated in regular growth media at a density of 31,250 cells/$cm^2$ and incubated overnight. Cells were treated with 0.25 ug/ml rhDkk-1 protein or vehicle (PBS, Gibco) and varying concentrations of Dkk-1 mAbs in Optimem (Gibco). After an overnight incubation, cells were lysed with Reporter Lysis Buffer (Promega) and luciferase expression was quantified using Luciferase Reagent (Promega).

HuMabJC18, the fully humanized anti Dkk-1 mAb showed good efficacy in the functional assay with an IC50 of 1.3 nM (Table 7).

TABLE 7

| IC50 values for Dkk-1 Antibody in a Cell-based Functional Assay | |
|---|---|
| Antibody | IC50 |
| huMabJC18 | 1.3 nM |

Example 4

In Vivo Evaluation of Bone Efficacy of muMabJC18
and Mouse Chimera

Female adult C57BL/6 mice are used for the evaluation of skeletal effect of test Dkk-1 antibodies in vivo. The animals are housed at 24° C. with a 12 h light/12 h dark cycle and allowed free access to water and a commercial diet (Purina laboratory Rodent Chow 5001, Purina-Mills, St. Louis, Mo.). The experiments are conducted according to Pfizer animal care-approved protocols, and animals were maintained in accordance with the ILAR (Institute of Laboratory Animal Research) Guide for the Care and Use of Laboratory Animals. The mice are treated with either vehicle or antibodies by oral gavage once or twice per week for various weeks. At the conclusion of the studies, the mice are euthanized and the serum is harvested for the measurements of free antibody and free Dkk-1 levels. In addition, bone samples are harvested for assessing the changes in bone mass and bone formation by peripheral quantitative computed tomography (pQCT), micro-CT, and histomorphometry.

The right femurs are scanned by pQCT (Stratec XCT Research M; Norland Medical Systems, Fort Atkison, Wis., USA) with software version 5.40. A 1-mm-thick cross-section of each distal femoral metaphysis is taken at 2.5 mm proximal to the distal end (~1.5 mm to the growth plate, a cancellous bone enriched site), and 1-mm-thick cross-section of each femoral diaphysis is taken at 8 mm proximal from the distal end (a cortical bone enriched site) with a voxel size of 0.10 mm. Volumetric bone content, density and area are determined for total, trabecular and cortical bone.

The right femurs are scanned by a microCT machine (Micro-CT40, Scanco Medical, Auenring 6-8, Bassersdorf, Switzerland) with software version 3.1. A cross section of distal femur metaphysis (a total of 50 slices in thickness of 16-µm each, total thickness=0.8 mm) is taken at 2.3 to 3.1 mm proximal to the distal end (~1.3 to 2.1 mm from the growth plate) for the determination of trabecular bone volume.

The left femurs are processed for histomorphometric assessment on cancellous bone. Briefly, the left femurs are dehydrated in graded concentrations of ethanol and embedded undecalcified in methyl methacrylate. Longitudinal frontal sections of the distal femur are cut at 4- and 10-µm thickness using a Reichert-Jung Polycut S microtome (Leica Corp., Heidelberg, Germany). The 4 µm sections are stained with a modified Masson's Trichrome stain and the 10-µm sections remained unstained. All histomorphometric measurements are performed in cancellous bone tissue of the distal femoral metaphyses in an area between 0.375 and 0.875 mm proximal to the growth plate-epiphyseal junction using an image analysis system (Osteomeasure, Inc., Altanta, Ga.). Cancellous bone volume as a percentage of bone tissue area and osteoclast surface as a percentage of total cancellous perimeter are measured in 4 µm thick, stained sections. Trabecular number, thickness and separation are calculated. Fluorochrome-based indices of bone formation including the percentage of cancellous bone surface with a double fluorochrome label (mineralizing surface), mineral apposition rate, bone formation rates (bone surface and tissue volume referent) are obtained in 10-µm thick, unstained sections.

Study Protocol and Results in Intact Mouse Model

A. Effect of Anti Mouse Dkk-1 Monoclonal Antibody (JC18) in Intact Mouse Model

Figure 1B:
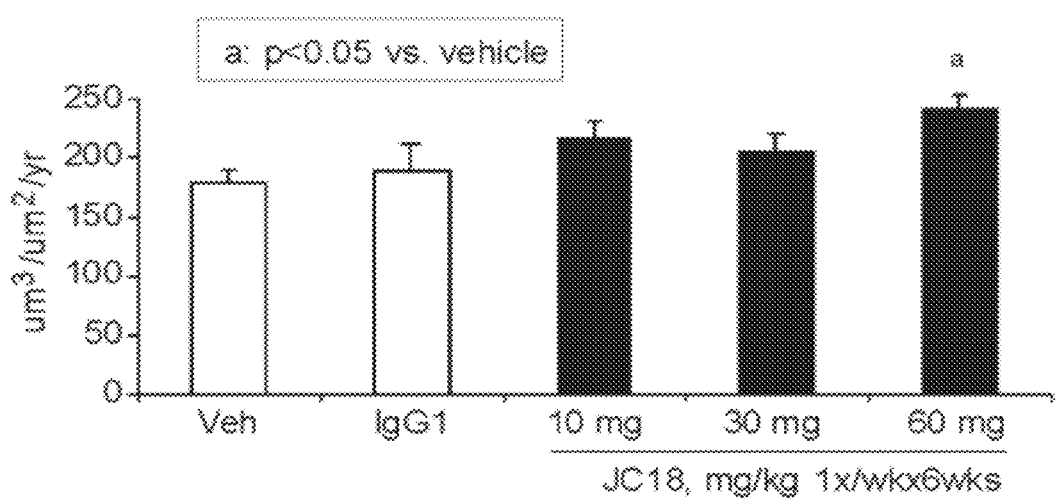

Female adult C57BL/6 mice were orally dosed with vehicle or mouse IgG1 or JC18 at 10, 30, and 60 mg/kg, once per week for 6 weeks. Both right and left femurs were collected from each mouse at necropsy. The right femurs were analyzed using pQCT and the left femurs were analyzed using histomorphometric method. Total BMD of distal femurs was significantly increased by JC18 treatment at all dose levels (FIG. 1A). JC18 also increased bone formation rates significantly at 60 mg/kg dose level in mice (FIG. 1B).

B. Effect of Mouse Chimera of Dkk-1 Monoclonal Antibody (Mouse Chimera—Chimeric Human-Mouse Antibody) in Intact Mouse Model Intact female C57BL/6 mice at 4 months of were treated with mouse chimera at 0, 0.001, 0.01, 0.1, 1, 3, 10, and 30 mg/kg, weekly for 6 weeks. One group of mice was treated with mouse chimera at 5 mg/kg, twice per week for 6 weeks. Right distal femur of each animal was analyzed using pQCT. As shown in FIG. 2, mouse chimera increased total BMD at doses from 1 to 30 mg/kg compared with vehicle treatment.

```
SEQ ID NO: 43
chimeric antibody (hu-mu):
chimeric huMabJC18Lvar-mouse kappa aa sequence
EIVLTQSPATLSLSPGERATLSCRASESVDDFGISFINWYQQKPGQ

APRLLIYAGSKQGSGIPARFSGSGSGTDFTLTISSLEPEDFAVYYC

QQLKEVPPTFGGGTKVEIKRADAAPTVSIFPPSSEQLTSGGASWCF

LNNFYPKDINVKWKIDGSERQNGVLNSWTDQDSKDSTYSMSSTLTL

TKDEYERHNSYTCEATHKTSTSPIVKSFNRNEC
```

```
-continued
SEQ ID NO: 44
chimeric antibody (hu-mu):
chimeric huMabJC18Hvar-mouseIgG1 constant aa
sequence
EVQLVESGGGLVQPGGSLRLSCAASGFTFSSYAISWVRQAPGKGLE

WVASVSGTGLGFQTYYPDSVKGRFTISRDNAKNSLYLQMNSLRAED

TAVYYCATSLENYAFDYWGQGTTVTVSSAKTTPPSVYPLAPGSAAQ

TNSMVTLGCLVKGYFPEPVTVTWNSGSLSSGVHTFPAVLQSDLYTL

SSSVTVPSSTWPSETVTCNVAHPASSTKVDKKIVPRDCGCKPCICT

VPEVSSVFIFPPKPKDVLTITLTPKVTCVVVDISKDDPEVQFSWFV

DDVEVHTAQTQPREEQFNSTFRSVSELPIMHQDWLNGKEFKCRVNS

AAFPAPIEKTISKTKGRPKAPQVYTIPPPKEQMAKDKVSLTCMITD

FFPEDITVEWQWNGQPAENYKNTQPIMNTNGSYFVYSKLNVQKSNW

EAGNTFTCSVLHEGLHNHHTEKSLSHSPGK

SEQ ID NO: 45
chimeric antibody (hu-mu):
huMabJC18Lvar nt sequence
GAGATCGTGCTGACCCAGAGCCCCGCCACCCTGAGCCTGAGCCCTG

GCGAGCGGGCCACCCTGTCCTGCCGGGCCAGCGAGAGCGTGGACGA

CTTCGGCATCAGCTTCATCAACTGGTATCAGCAGAAGCCCGGCCAG

GCCCCCAGACTGCTCATCTACGCCGGCAGCAAGCAGGGCAGCGGCA

TCCCCGCCAGGTTCAGCGGCAGCGGCTCCGGCACCGACTTCACCCT

GACCATCTCCAGCCTCGAACCCGAGGACTTCGCCGTGTACTACTGC

CAGCAGCTGAAAGAGGTGCCCCCCACCTTCGGCGGTGGGACCAAGG

TGGAAATCAAA

SEQ ID NO: 46
chimeric antibody (hu-mu):
mouse kappa nt sequence
GCTGATGCTGCACCAACTGTATCCATCTTCCCACCATCCAGTGAGC

AGTTAACATCTGGAGGTGCCTCAGTCGTGTGCTTCTTGAACAACTT

CTACCCCAAAGACATCAATGTCAAGTGGAAGATTGATGGCAGTGAA

CGACAAAATGGCGTCCTGAACAGTTGGACTGATCAGGACAGCAAAG

ACAGCACCTACAGCATGAGCAGCACCCTCACGTTGACCAAGGACGA

GTATGAACGACATAACAGCTATACCTGTGAGGCCACTCACAAGACA

TCAACTTCACCCATTGTCAAGAGCTTCAACAGGAATGAGTGTTAG

SEQ ID NO: 47
chimeric antibody (hu-mu):
huMabJC18Hvar nt sequence
GAGGTGCAGCTGGTCGAGTCTGGCGGCGGACTGGTGCAGCCTGGCG

GCAGCCTGAGACTGAGCTGCGCCGCCAGCGGCTTCACCTTCAGCAG

CTACGCCATCAGCTGGGTGCGGCAGGCCCCTGGCAAGGGCCTGGAA

TGGGTGGCCAGCGTGAGCGGCACCGGCCTGGGCTTCCAGACCTACT

ACCCCGACAGCGTGAAGGGCCGGTTCACCATCAGCCGGGACAACGC

CAAGAACAGCCTGTACCTGCAGATGAACAGCCTGCGGGCCGAGGAC

ACCGCCGTGTACTACTGCGCCACCTCCCTGGAAAACTACGCCTTCG

ACTACTGGGGCCAGGGAACCACGGTCACCGTCTCCTCA
```

-continued

SEQ ID NO: 48
chimeric antibody (hu-mu):
mouse IgG1 CH1-CH2-CH3 nt sequence

GCCAAAACGACACCCCCATCTGTCTATCCACTGGCCCCTGGATCTG

CTGCCCAAACTAACTCCATGGTGACCCTGGGATGCCTGGTCAAGGG

CTATTTCCCTGAGCCAGTGACAGTGACCTGGAACTCTGGATCCCTG

TCCAGCGGTGTGCACACCTTCCCAGCTGTCCTGGAGTCTGACCTCT

ACACTCTGAGCAGCTCAGTGACTGTCCCCTCCAGCCCTCGGCCCAG

CGAGACCGTCACCTGCAACGTTGCCCACCCGGCCAGCAGCACCAAG

GTGGACAAGAAAATTGTGCCCAGGGATTGTGGTTGTAAGCCTTGCA

TATGTACAGTCCCAGAAGTATCATCTGTCTTCATCTTCCCCCCAAA

GCCCAAGGATGTGCTCACCATTACTCTGACTCCTAAGGTCACGTGT

GTTGTGGTAGACATCAGCAAGGATGATCCCGAGGTCCAGTTCAGCT

GGTTTGTAGATGATGTGGAGGTGCACACAGCTCAGACGCAACCCCG

GGAGGAGCAGTTCAACAGCACTTTCCGCTCAGTCAGTGAACTTCCC

ATCATGCACCAGGACTGGCTCAATGGCAAGGAGTTCAAATGCAGGG

TCAACAGTGCAGCTTTCCCTGCCCCCATCGAGAAAACCATCTCCAA

AACCAAAGGCAGACCGAAGGCTCCACAGGTGTACACCATTCCACCT

CCCAAGGAGCAGATGGCCAAGGATAAAGTCAGTCTGACCTGCATGA

TAACAGACTTCTTCCCTGAAGACATTACTGTGGAGTGGCAGTGGAA

TGGGCAGCCAGCGGAGAACTACAAGAACACTCAGCCCATCATGAAC

ACGAATGGCTCTTACTTCGTCTACAGCAAGCTCAATGTGCAGAAGA

GCAACTGGGAGGCAGGAAATACTTTCACCTGCTCTGTGTTACATGA

GGGCCTGCACAACCACCATACTGAGAAGAGCCTCTCCCACTCTCCT

GGTAAATGA

C. Ovariectomized Mouse Model

Female adult C57BL/6 mice are subjected to sham or ovariectomized (OVX) surgery for the evaluation of skeletal effect of test Dkk-1 antibodies in an estrogen deficient condition, which mimic postmenopausal bone loss. The animals are housed at 24° C. with a 12 h light/12 h dark cycle and allowed free access to water and a commercial diet (Purina laboratory Rodent Chow 5001, Purina-Mills, St. Louis, Mo.). The experiments are conducted according to Pfizer animal care-approved protocols, and animals were maintained in accordance with the ILAR (Institute of Laboratory Animal Research) Guide for the Care and Use of Laboratory Animals. The mice are treated with either vehicle or antibodies by oral gavage once or twice per week for various weeks. At the conclusion of the studies, the mice are euthanized and the bone samples are harvested for assessing the changes in bone mass by peripheral quantitative computed tomography (pQCT), micro CT, and histomorphometry. The methodologies of these measurements have been described in the earlier section.

Study Protocol and Results

Anti Mouse Dkk-1 Monoclonal Antibody (JC18) Prevented Bone Loss Induced by Estrogen Deficiency in OVX Mouse Model.

Female C57BL/6 mice at 4 months of age were subjected to either sham or ovariectomized (OVX) surgeries and treated with either vehicle or JC18 at 0.3, 1, 3, 10, and 30 mg/kg weekly, or JC18 at 15 mg/kg twice weekly for 8 weeks starting the day after surgery. As expected, the mice treated with vehicle exhibited osteopenia at 8 weeks post-OVX as demonstrated by a significant decrease in total BMD (FIG. 3). JC18 dose-responsively increased total BMD as measured by pQCT at distal femurs by 7 to 20% compared with vehicle treatment of OVX mice. In the mice treated with JC18 at 15 mg/kg twice weekly the total BMD was not only higher than vehicle-treated OVX mice but also maintained at the sham control level, indicating that at this dose and dosing regimen JC18 completely prevented the development of osteopenia in OVX mice (FIG. 3).

Example 5 huMabJC18 Increased Bone Mass in Intact Rat Model

Adult female rats received once weekly intravenous administration of huMabJC18 at 0, 0.1, 1, 10, or 100 mg/kg for 6 weeks. Serum osteocalcin, a bone formation biomarker, was increased by 30, 26, and 25% in the rats treated with huMabJC18 at 1, 10, and 100 mg/kg, respectively, at 2 weeks post treatment and it was not different from the control value at 4 weeks post treatment. Serum CTX, a bone resorption marker, did not show consistent changes following treatment. These changes in serum biomarkers support the anabolic action of huMabJC18 on bone. Distal femur BMD and femoral shaft BMC (bone mineral content) were significantly increased by 11 and 16% or 7 and 8%, respectively, in the rats treated with huMabJC18 at doses of 10 and 100 mg/kg, indicating an increase of cancellous and cortical bone mass in these animals.

Example 6

Methods for Understanding the System Dynamics Related to a Monoclonal Antibody Therapy Targeting the Soluble Antigen Dkk-1, an Antagonist of the Wnt-Signaling Pathway Application of a Mechanistic Preclinical Pharmacokinetic/Pharmacodynamic (PK/PD) Model to Select First in Human (FM) Starting Doses of an IgG2 Antibody Osteoporosis is a bone disease characterized by low bone mineral density which leads to bone fragility and subsequently to bone fractures. The majority of pharmacological osteoporosis therapies, including bisphosphonates, calcitonin, HRT and selective estrogen receptor modulators (SERM), prevent bone loss by reducing bone resorption. Restoration of bone mass in patients suffering from osteoporosis is an area of unmet medical need.

Binding of Dkk-1 to the LRP5/6 receptor and Kremen-1/2 co-receptor promotes internalization of the receptor complex resulting in dampening of the Wnt signal (Diarra et al. (2007) Nat Med 13:156-163).

Genetic evidence for a central role of the Wnt pathway in maintaining bone mass has come from the identification of both activating and inactivating mutations in the Wnt receptor LRP5. Inactivation of LRP5 results in a decrease in bone mass and causes the autosomal recessive disorder: osteoporosis pseudoglioma (OPPG) syndrome in humans (Gong et al. (2001) Cell 107:513-523) and a similar phenotype in LRP5 knockout mice (Holmen et al. (2004) J Bone Miner Res 19:2033-2040).

Individuals with HBM have Markedly Reduced Risks of Skeletal Fracture.

A neutralizing Dkk-1 antibody is expected to increase bone mass due to increased bone formation by osteoblasts and, thus, prevent osteoporotic fractures. HuMabJC18 is a humanized prototype anti-Dkk-1 monoclonal antibody for the treatment of osteoporosis, among other disorders. It binds human, mouse, rat and cynomolgus monkey Dkk-1 in vitro with high affinities (Kd<100 pM). It increases bone mass in intact mice and restores bone mass to the osteopenic skeleton of ovariectomized mice, a model of postmenopausal bone loss (Li et al., 2009; manuscript in preparation).

Despite the large numbers of antibodies in development, only a handful of reports using preclinical data to predict the clinical pharmacokinetics or efficacious dose of antibodies have been published (Lobo et al. (2004) J Pharm Sci 93:2645-2668; Agoram, (2009) Br J Clin Pharmacol 67:153-160). Allometric power models are commonly used for interspecies scaling of antibody pharmacokinetics (PK) when linear PK is anticipated (Wang et al. (2008) Clin Pharmacol Ther 84:548-558). However, unlike small molecules, interaction of an antibody with its target often affects the PK of the antibody. Pharmacokinetics (PK) and Pharmacodynamics (PD) are intimately connected and PK/PD understanding requires knowledge of the antibody, target and antibody-target interactions. The highest value comes from linking PK with PD response to predict drug exposure and effect following a given dose (Agoram et al. (2007) Drug Discov Today 12:1018-1024). Mechanistic PK/PD modeling thus offers a rational and effective means of predicting both human PK and clinically efficacious dose of antibodies.

In this study, simultaneous characterization of antibody huMabJC18 target (Dkk-1) in rat and monkey enabled a deep understanding of the pharmacokinetics and the pharmacodynamics of the response. This was coupled with knowledge of target level in healthy vs. diseased subjects, target turnover rates and antibody-target association/dissociation rates for mechanistic predictions of PK/PD in the clinic.

The purpose of the study was to compare and contrast predicted clinical starting doses of an anti-Dkk-1 IgG$_2$ antibody (huMabJC18) obtained by the following calculations: (1) no adverse effect level (NOAEL) in toxicology species, (2) minimum anticipated biological effect level (MABEL) using the classical Duff equation and (3) MABEL using a target-mediated drug disposition (TMDD) model.

Preclinical safety studies in rat and monkey were used to determine NOAEL. A 100-fold safety factor was applied to the NOAEL to generate a recommended starting dose. The classical Duff equation was used to calculate receptor occupancy and the MABEL was defined as the dose which resulted in 10% receptor occupancy. A TMDD model was used to fit free Dkk-1 and antibody concentrations over time in the rat and monkey studies. The model was extrapolated to humans and MABEL was estimated to be the dose which gave 10% reduction in Dkk-1.

Test Materials

Monoclonal anti-Dkk-1 antibodies were made at Genovac (Germany) by immunization of Balb/C mice with full-length recombinant human Dkk-1 protein (R&D Systems, Minneapolis, Minn.). A single mouse IgG1/kappa isotype antibody (JC18) was humanized and affinity matured using a library scanning mutagenesis strategy (Pons et al., 2009; manuscript in preparation). In comparison to the parent mouse antibody, the humanized antibody (huMabJC18) exhibited a >100-fold increase in affinity for both human and mouse Dkk-1.

HDkk-1-V5-6His (human) and rDkk-1-TEV-V5-6His (rat) used in the Dkk-1 kinetic studies were cloned and expressed in-house and qualified as functional by TOP-FLASH assay (Ai et al., 2005).

BIAcore Experiment

Interaction between huMabJC18 and human or mouse or rat or Cynomolgus monkey Dkk-1 were analyzed using a BIAcore 3000™ system equipped with a CM5 sensor chip (BIAcore AB, Uppsala, Sweden). The association and dissociation phases were monitored during the interaction analysis. The binding responses were double-referenced and fit globally to a simple model using BiaEvaluation v.4.0 software. Affinities were deduced from the quotient of the kinetic rate constants ($K_d=k_{off}/k_{on}$).

Animal Studies

All animal studies were conducted in accordance with animal care and use protocols approved by the Institutional Animal Care and Use Committee (IACUC).

Dkk-1 Kinetic Study in Rats hDkk-1-V5-6His was administered as a single intravenous bolus dose to male Sprague Dawley rats (n=3/dose) at 1, 5, 10 and 100 µg/kg. Serial blood samples were collected pre-dose and at 0.083, 0.25, 0.5, 1, 2, 4, 6, 8 and 24 hours post-dose. rDkk-1-TEV-V5-6His was administered as a single intravenous bolus dose to male Sprague Dawley rats (n=3/dose) at 100 µg/kg. Serial blood samples (300 µl) were collected pre-dose and at 0.083, 0.17, 0.33, 0.5, 1, 2, 4 and 6 hours post-dose. Serum was obtained by centrifugation and stored at −20° C. until analysis.

Pharmacokinetic/Pharmacodynamic Study in Rats

Experiments were conducted in female Sprague Dawley rats (n=40, body weight 250-350 g over the course of the study duration, Charles River Laboratories, Wilmington, Mass.). HuMabJC18 was administered once weekly by the intravenous route for six consecutive weeks to female Sprague-Dawley rats (n=8/dose) at 0.1, 1, 10 and 100 mg/kg. One group of rats (n=8) were administered vehicle control (20 mM histidine pH 6.5 with 140 mM NaCl).

Serial blood samples were collected pre-dose and at 1, 3, 8, 24, 48, 72, 168, 240, 336, 408, 504, 576, 672, 744, 840, 912 and 1008 hours post first dose from each treatment group. Serum was obtained by centrifugation and stored at −20° C. until analysis for Dkk-1 and huMabJC18 concentrations.

Bone Mineral Density Determination in Rats

To assess the effect of anti-Dkk-1 mAb treatment on bone mass, the excised right femurs were scanned by peripheral quantitative computed tomography (pQCT, Stratec XCT Research M, Norland Medical Systems, Fort Atkinson, Wis.) with software version 5.40. A 1-mm thick cross section of each distal femoral metaphysis was scanned at 2.5 mm proximal to the distal end, a cancellous bone enriched site, with a voxel size of 0.10 mm. Volumetric total bone mineral density (BMD) was determined as previously described (Ke et al., 2001).

Pharmacokinetic/Pharmacodynamic Study in Cynomolgus Monkeys

The animal care and experimental procedures of this study was conducted in compliance with the U.S. Animal Welfare Act and the conditions specified in The Guide for Care and Use of Laboratory Animals (Institute of Laboratory Animal Research, 1996).

Five male and five female cynomolgus monkeys (*Macaca fascicularis*), 2 to 5 years of age weighing between 3.2 and 5.2 kg (Charles River Primates, BioResearch Facility, Houston, Tex.) were used in this study. Animals (n=1/sex/group) were assigned to 5 groups. HuMabJC18 was administered by slow intravenous injection as a single dose to 4 groups of 1 male and 1 female monkey at doses of 0.1, 1, 10 or 100 mg/kg. The remaining group was administered vehicle control in the same manner.

Whole blood samples (~2 ml) were collected pre-treatment and at 0.1, 0.5, 1, 3, 8, 24, 48, 72, 168, 240, 336, 408, 504, 576 and 672 hours post-dose from each treatment group via femoral venepuncture. Serum was separated from whole blood by centrifugation after which samples were stored at −80° C. until analysis. Samples were later analyzed for Dkk-1 and huMabJC18 concentrations.

Free Dkk-1 Assay

Assay Designs (Ann Arbor, Mich.) human Dkk-1 ELISA System (Cat #900-151) was validated to measure total Dkk-1 in human serum according to the manufacturer's instructions with minor modification: R&D Systems (Minneapolis, Minn.) recombinant human Dkk-1 (Cat#1096-dk-10/cf) was used as assay standards.

To assay free Dkk-1 (unbound to therapeutic antibodies) in rat and monkey serum, anti-Dkk-1 antibodies were used for capturing unbound serum Dkk-1, and reagents from the Assay Designs human Dkk-1 ELISA System (Catalog #900-151) were used for the remaining steps according to the kit's instruction with the following modifications: R&D Systems (Minneapolis, Minn.) recombinant rat Dkk-1 (Cat#4010-dk-10/cf) and human Dkk-1 (Cat #1096-dk-10/cf) were used as assay standards for rat and monkey assays, respectively.

Human serum samples from healthy and diseased subjects were purchased from Bioreclamation Inc. (Nassau, N.Y.).

V5 Tagged Dkk-1 Assay

Serum concentrations of V5 tagged Dkk-1 were determined by an ELISA method. Samples were diluted in a PBS buffer (containing 3% BSA and 0.05% Tween-20) to a final minimum required dilution (MRD) range of ¼ to ¹⁄₄₀, used to reduce background and enable concentrations to fall within the linear range of the assays (0.195-25 ng/ml on assay plate). hDkk-1-V5-6His or rDkk-1-TEV-V5-6His calibration and quality control standards were diluted into the same matrix composition as samples. The 96-well immunosorbent assay plates (Nalgene Nunc, Rochester, N.Y.) were overnight coated at 4° C. with 50 µl of anti-V5 antibody (Invitrogen, Carlsbad, Calif.) at 2 µg/ml then washed with PBS buffer containing 0.05% Tween-20 followed by blocking with PBS buffer containing 3% BSA and 0.05% Tween-20. The diluted samples and standards were added to plates (50 µl/well) and incubated with shaking at room temperature for 1 hour. The plates were then washed with two wash cycles, followed by incubation with a horseradish peroxidase-conjugated anti-Dkk-1 secondary antibody (from Assay Designs kit, Ann Arbor, Mich.) for 1 hour. After washing, the plates were developed by color reaction for ~10 min with 3,3',5,5'-tetramethylbenzidine (TMB) substrate (KPL, Gaithersburg, Md.) then stopped with 2M $H_2SO_4$. Blank matrix OD values were background subtracted after the absorbance OD reading was determined at a wavelength of 450 nm (with subtraction of 650 nm). The V5 tagged Dkk-1 calibration standards were used to construct a standard curve using 4-parameter fitting with uniform weighting in SoftMax Pro 4.8. Serum concentrations of V5 tagged Dkk-1 in unknown samples were interpolated from this standard curve.

Osteocalcin Assay

Serum osteocalcin concentrations were measured by using the Rat-MID™ Osteocalcin ELISA Kit (Nordic Bioscience Diagnostics A/S, Herlev, Denmark).

Free/Partially Free huMabJC18 Antibody Assay for Rat PK/PD Samples

Serum concentrations of huMabJC18 were determined by an electrochemiluminescence (ECL) method using a Meso Scale Discovery (MSD) system (Gaithersburg, Md.). Samples were diluted in a PBS buffer containing 1% BSA to a final minimum required dilution (MRD) of ½ to ¹⁄₁₅₀ followed by an additional 10-4000 fold dilution in order to reduce background interference and to fall within the linear range of the assays (~5-1300 ng/ml on assay plate). HuMabJC18 calibration and quality control standards were diluted into the same matrix composition as samples. 96-well MSD high bind plates (Cat# L11XB-3) were overnight coated at 4° C. with hDkk-1-V5-6His (generated internally) at 5 µg/ml. After inverting the plate to remove the coat, plates were blocked with 1% BSA in PBS. The diluted samples and standards were added to plates (25 µl/well) and incubated with shaking at room temperature for 2 hours. The plates were then washed with three wash cycles with PBS buffer containing 0.05% Tween-20, followed by incubation with a MSD ruthinylated goat anti-human IgG antibody (Cat#R32AJ-1) for 1 hour. After washing, MSD read buffer T (4×) with surfactant (Cat# R92TC-1) was added to each well and immediately read on a MSD Sector Imager 6000. Blank matrix values were background subtracted from the sample values. The anti-Dkk-1 humanized antibody calibration standards were used to construct a standard curve using 4-parameter fitting with $1/y^2$ weighting in the MSD Discovery Workbench v 3.0 software. Serum concentrations of anti-DKK-1 humanized antibody in unknown samples were interpolated from this standard curve.

Free/Partially Free huMabJC18 Antibody Assay for Monkey Samples

Serum concentrations of huMabJC18 were determined by an ELISA method. Samples were diluted in a PBS buffer (containing 3% BSA and 0.05% Tween-20) to a final minimum required dilution (MRD) of ¼ to ¹⁄₁₀₀ followed by an additional 10-500 fold dilution in order to reduce background interference and to fall within the linear range of the assays (~8-100 ng/ml on assay plate). HuMabJC18 calibration and quality control standards were diluted into the same matrix composition as samples. The 96-well immunosorbent assay plates were overnight coated at 4° C. hDkk-1-V5-6His (generated internally) at 1.5 µg/ml and then blocked with PBS (containing 3% BSA and 0.05% Tween-20) after washing with PBS buffer containing 0.05% Tween-20. The diluted samples and standards were added to plates (100 µl/well) and incubated with shaking at room temperature for 1 hour. The plates were then washed with three wash cycles, followed by incubation with biotinylated mouse anti-human $IgG_2$ (Invitrogen, Carlsbad, Calif.) for 1 hour after which horseradish peroxidase-conjugated streptavidin (Jackson ImmunoResearch, West Grove, Pa.) was added and the plate was further incubated for 30 minutes. After washing, the plates were developed by color reaction for ~10 min with 3,3',5,5'-tetramethylbenzidine (TMB) substrate then stopped with 2M $H_2SO_4$. Blank matrix OD values were background subtracted after the absorbance OD reading was determined at a wavelength of 450 nm (with subtraction of 650 nm). The anti-Dkk-1 humanized antibody calibration standards were used to construct a standard curve using 4-parameter fitting with uniform weighting in SoftMax Pro 4.8. Serum concentrations of anti-Dkk-1 humanized antibody in unknown samples were interpolated from this standard curve.

Anti-Drug Antibody (ADA) Assay

Presence of anti-drug antibodies (ADA) against huMabJC18 in rat and monkey was measured with a bridging ligand binding assay (LBA) using the Meso Scale Discovery (MSD) platform (Gaithersburg, Md.). Serum samples (25 µl) diluted 1:10 with assay diluent (3% BSA, 0.05% Tween 20, PBS) were added to a 96-well MSD high bind plate that was coated with huMabJC18 at 1 µg/ml in pH 9.6 carbonate buffer. After incubating for 1 hour at room temperature, the plate was washed and 25 µl of ruthenium labeled huMabJC18 was added to each well at 1 µg/ml and incubated again for 1 hour at room temperature. The plate was washed and following addition of 150 µl of MSD read buffer (2×), the plate was read on a MSD Sector Imager 6000.

Non-Compartmental Pharmacokinetic Analysis

Pharmacokinetic analysis was performed using the WinNonLin Enterprise Edition computer software, Version 5.2 (Pharsight Corp., Cary, N.C.). The terminal phase rate constant ($k_{el}$) was determined by linear regression of the log plasma concentration time profile. The terminal elimination half-life ($t_{1/2}$) was calculated from $0.693/k_{el}$. $C_{max}$, $T_{max}$ and $C_{mm}$ values were obtained directly from recorded data. Area under the serum-concentration time curve ($AUC_{0-tlast}$) was calculated using the linear trapezoidal rule and extrapolated to infinity ($AUC_{0-inf}$) using $k_{el}$. Clearance (CL) was calculated using the relationship dose/$AUC_{0-inf}$. Volume of distribution (Vc) was calculated using the relationship $CL/k_{el}$. Cave was calculated as $AUC_{(1st\ dosing\ interval)}$/tlast of 1st dosing interval.

In the Dkk-1 kinetic study in rats, the elimination half-life value quoted for h-Dkk-1 was a mean of the half-life values determined at 5, 10 and 100 µg/kg dose levels. Insufficient data points were available to calculate an elimination half-life value at the 1 µg/kg dose level. For r-Dkk-1 the elimination half-life was calculated from a naïve pool analysis of the 3 rats at 100 µg/kg, which was the only dose administered.

Pharmacokinetic/Pharmacodynamic Analysis

A preliminary non-compartmental analysis (Jusko, 1992) of individual rat and monkey antibody concentration versus time data was conducted, revealing non-linear pharmacokinetics of the antibody. A mechanistic target-mediated drug disposition model (Mager and Jusko, 2001) was used to describe the PK/PD profile of huMabJC18 in rats and monkeys (FIG. 5). In brief, the TMDD model assumes that saturable high affinity binding of the antibody (huMabJC18) to the target (Dkk-1) is responsible for the observable nonlinear pharmacokinetic behavior. Antibody in the central compartment (volume V1) binds (rate constant, $k_{on}$) to free Dkk-1 to form an antibody-Dkk-1 receptor complex. Once formed the complex may dissociate (rate constant, $k_{off}$) or the antibody-Dkk-1 complex may be eliminated (rate constant, $k_{el,complex}$). Unbound antibody can also be directly eliminated from the central compartment at a first order rate ($k_{el}$). The model was extended to account for antibody distribution to non-specific tissue sites which are described by the rate constants $k_{12}$ and $k_{21}$.

The model was implemented as the following set of differential equations:

$$\frac{dC_{mAbserum}(nM)}{dt} = -k_{el} * C_{mAbserum} - k_{12} * C_{mAbserum} + k_{21} * C_{mAbtissue} - k_{on} * C_{mAbserum} * C_{target} + k_{off} * C_{complex} \quad (1)$$

$$\frac{dC_{mAbtissue}(nM)}{dt} = -k_{21} * C_{mAbtissue} + k_{12} * C_{mAbserum} \quad (2)$$

$$\frac{dC_{target}(nM)}{dt} = k_{el,target} * C_{target_{t=0}} - k_{el,target} * C_{target} - k_{on} * C_{mAbserum} * C_{target} + k_{off} * C_{complex} \quad (3)$$

$$\frac{dC_{complex}(nM)}{dt} = -k_{off} * C_{complex} + k_{on} * C_{mAbserum} * C_{target} - k_{el,complex} * C_{complex} \quad (4)$$

Where $C_{mAbserum}$ is equal to free concentrations of huMabJC18, $K_d = k_{off}/k_{on}$ and $[mAb_{total}] = C_{mAbserum} + C_{complex}$ and $[Target_{total}] = C_{target} + C_{complex}$.

The system of differential equations was solved numerically in the NONMEM software, version V, running in a DOS shell under Windows XP utilizing Compaq Visual Fortran version 6.6. ADVAN 8 TOL=3 was used for this stiff problem. The free Dkk-1 compartment was initialized with a unit dose at t=0 and by setting F3 (free Dkk-1) to the estimated free Dkk-1 concentration at t=0. Variability in Dkk-1 response in the vehicle monkeys was characterized using a fourth order polynomial model:

$Y = A*TIME^4 - B*TIME^3 + C*TIME^2 - D*TIME + DKK0$ where A, B, C and D are constants determined from vehicle data and fixed in the model and Dkk0 is equal to the concentration of Dkk-1 pre-dose (t=0 hr.) This was implemented in the $ERROR block in NONMEM with an additive effect of drug.

Variability in Dkk-1 response in the vehicle rats was characterized using a simple cosine function: F=Baseline+Amplitude*Cos((Time-Peak Time)*(2*π/24)) (Chakraborty et al. (1999) J Pharmacokinet Biopharm 27:23-43) with a multiplicative effect of drug.

The goodness-of-fit was assessed from the precision of the parameter estimates and correlation matrix of the parameters provided by the $COV subroutine in NONMEM, visual inspection for a random spread of weighted residual against time and predicted concentrations, together with visual inspection of the individual subject predicted versus actual concentration-time plots for a lack of systematic bias at any points in time.

Simulations of Dkk-1 and huMabJC18 concentrations in osteoporosis patients were performed using the TMDD model in Berkeley-Madonna (v8.3.9, University of California, Berkeley, Calif.). The parameters used in the human simulations are shown in Table 14. PK, target and complex parameters were scaled from rat and monkey to human via the principles of allometry using a simple power model of the form: $Y = a BW^b$, where Y is the parameter of interest, BW is the body weight, a is the allometric co-efficient and b is the allometric exponent. For scaling of half-life b was assumed to equal 0.25, for the elimination and absorption rate constants ($k_{el}$ and $k_{el}$) b was assumed to equal −0.25 and for volume of distribution b was assumed to equal 1 (Wang et al., 2008).

Estimates of the predicted clinical starting dose derived from these three approaches differed by over 5 orders of magnitude. The highest starting dose was derived from the NOAEL calculation (1 mg/kg). The lowest starting dose was derived from the MABEL calculation which employed the Duff equation (0.00003 mg/kg). The starting dose derived from the MABEL calculation which employed the TMDD model fell near the middle of this range (0.03 mg/kg).

BIAcore Data

A summary of the in vitro Dkk-1 binding kinetics of huMabJC18 versus human, mouse, rat and monkey Dkk-1 determined with BIAcore surface binding technology are shown in Table 8. HuMabJC18 binds human, mouse and rat Dkk-1 with high affinity ($K_d < 2$ pM, $<30$ pM and $<100$ pM, respectively). In most cases, on rates ($k_{on}$) were too fast and off rates ($k_{off}$) were too slow to be measured precisely by the BIAcore instrumentation. HuMabJC18 also binds to cynomolgous monkey Dkk-1, although a $K_d$ could not be determined due to impurity of the Dkk-1 sample.

TABLE 8

In vitro Dkk-1 binding kinetics of huMabJC18

| Dkk-1 species | $k_{on}$ (1/Ms) | $k_{off}$(1/s) | $T_{1/2}$ (hr) | $K_d$ (nM) |
|---|---|---|---|---|
| Human | >1.3e6[a] | <2.0e-6[b] | >96.27 | <0.002 |
| Mouse | >1.3e6[a] | <3.9e-5[b] | >4.94 | <0.03 |
| Rat | >1.3e6[a] | 2.1e-4 | 0.92 | <0.1 |
| Monkey | —[c] | <6.0e-5[b] | >5 | —[d] |

[a]onrate is too fast to measure precisely
[b]offrate is too slow to measure precisely
[c]onrate could not be determined due to mass transport limitation and impure sample
[d]not determined Dkk-1 Expression in Pre-Menopausal, Post-Menopausal, Osteopenic and Osteoporotic Women The concentrations of Dkk-1 in serum samples from pre-menopausal (n=50), post-menopausal (n=50), osteopenic (n=50) and osteoporotic (n=50) women are shown in Table 9. There was no significant difference in Dkk-1 concentrations between pre- and post-menopausal women in the sample set tested, suggesting that age does not affect Dkk-1 concentrations. There was a significant difference (p<0.01) between Dkk-1 levels in pre-menopausal women (mean 2.2 ng/ml) compared to samples from osteopenic women (T score −2.2, mean Dkk-1 9.0 ng/ml) and osteoporotic women (T-score −3.0, mean Dkk-1 10.5 ng/ml). These values were included in the PK/PD model to predict efficacious dose of huMabJC18 in osteoporotic women.

TABLE 9

Dkk-1 concentrations in pre-menopausal, post-menopausal, osteopenic and osteoporotic female subjects

| Subject | N | Age | T-Score[a] | Serum Dkk-1 (ng/ml) | P-value |
|---|---|---|---|---|---|
| Pre-menopausal | 50 | 33.3 ± 13 | >−1.0 | 2.2 ± 2.2 | — |
| Post-menopausal | 50 | 54.7 ± 4.4 | >−1.0 | 2.9 ± 4.3 | 0.35 |
| Osteopenic | 50 | 61.3 ± 10.6 | −2.2 ± 0.5 | 9.0 ± 4.3 | <0.01 |
| Osteoporotic | 50 | 67.4 ± 7.7 | −3.0 ± 0.5 | 10.6 ± 6.5 | <0.01 |

[a]A normal T-score is >−1.0, osteopenia is defined as a T-score of <−1.0 and >−2.5, osteoporosis is defined as a T-score of −2.5 or lower.

Figure 6:
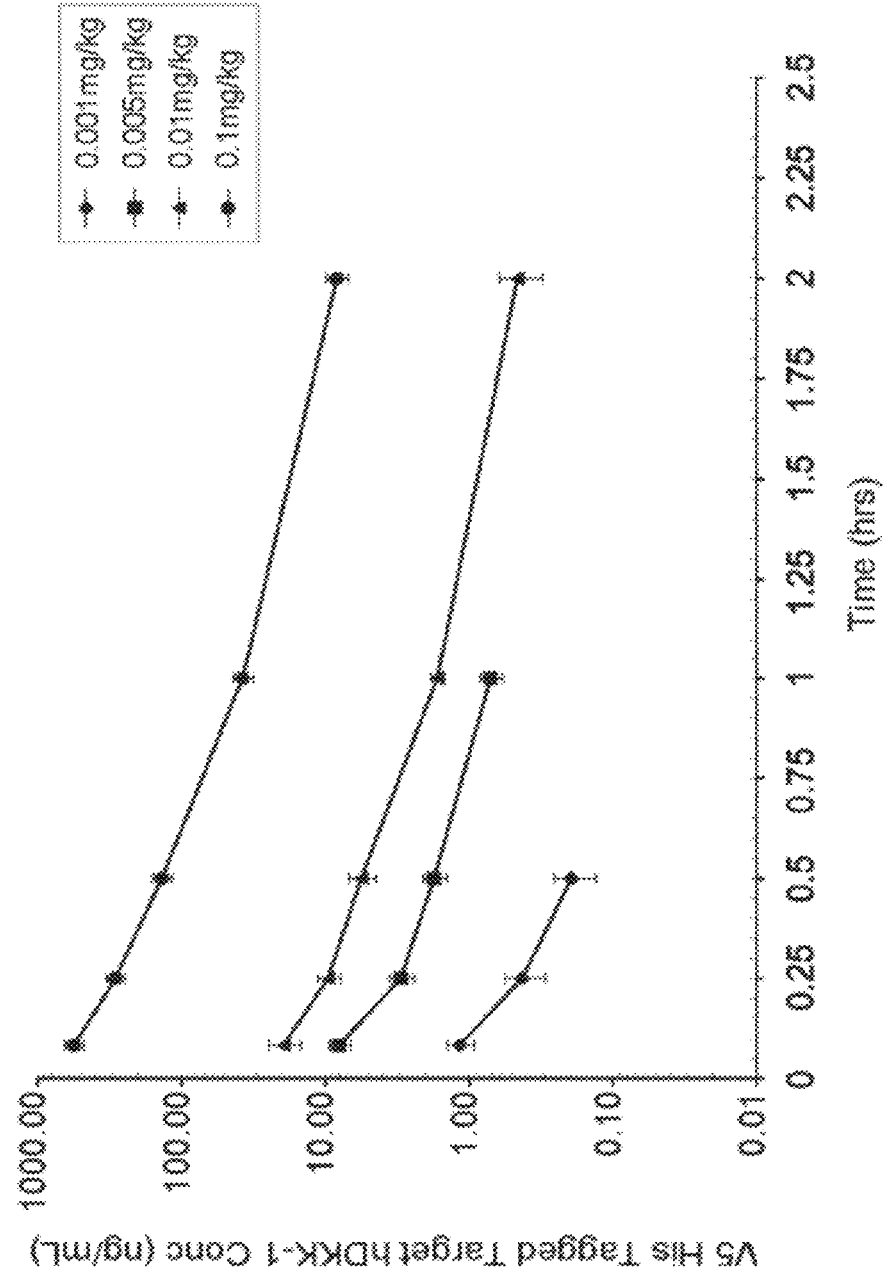
FIG. 6 shows a graph of serum concentrations of V5-His tagged h-DKK-1 in rat following single intravenous administration at 1, 5, 10 and 100 ug/kg. At time points >0.5 hr at 0.001 mg/kg, >1 hr at 0.005 mg/kg and >2 hr at 0.01 and 0.1 mg/kg samples were below the quantifiable limit of the assay method and were not included in the plot.
Figure 8A:
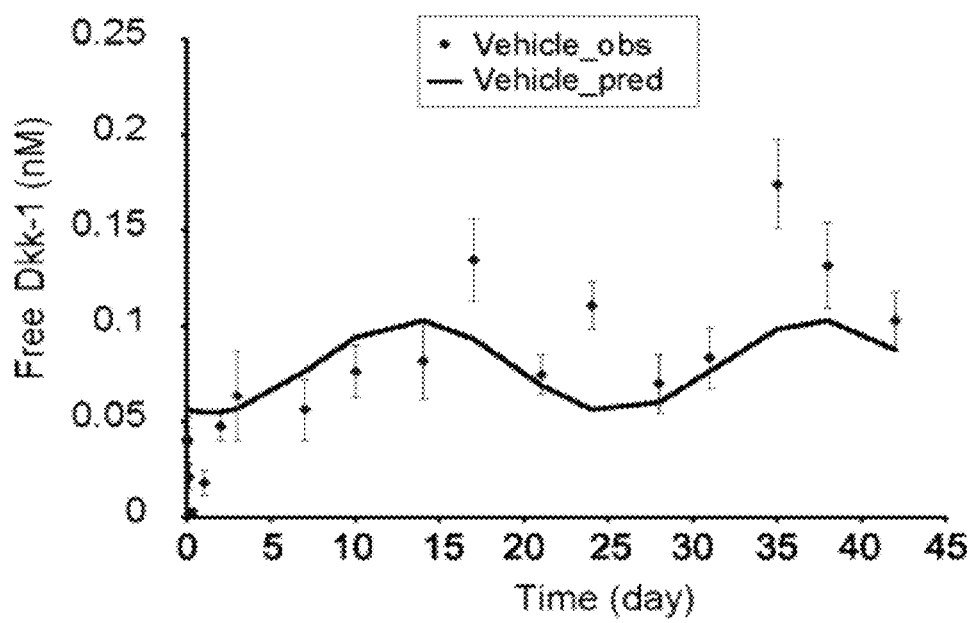
FIGS. 8A-E show graphs of observed and model predicted free Dkk-1 concentrations versus time following weekly intravenous administration of huMabJC18 to Sprague-Dawley rats. Symbols represent the mean observed data (±SE) and lines represent the predicted profiles from the model. Samples with anti-huMabJC18 antibodies detected were removed from the analysis.
Figure 8B:
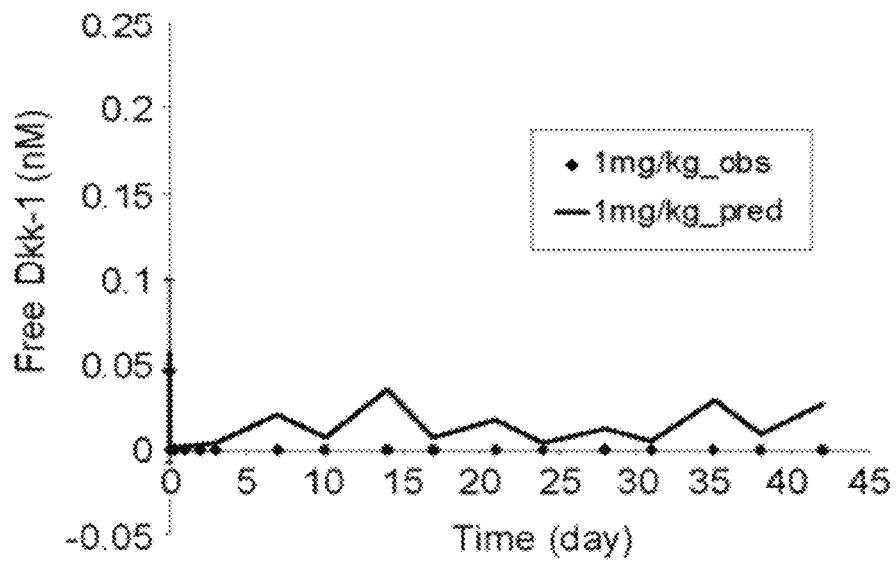
Figure 8C:
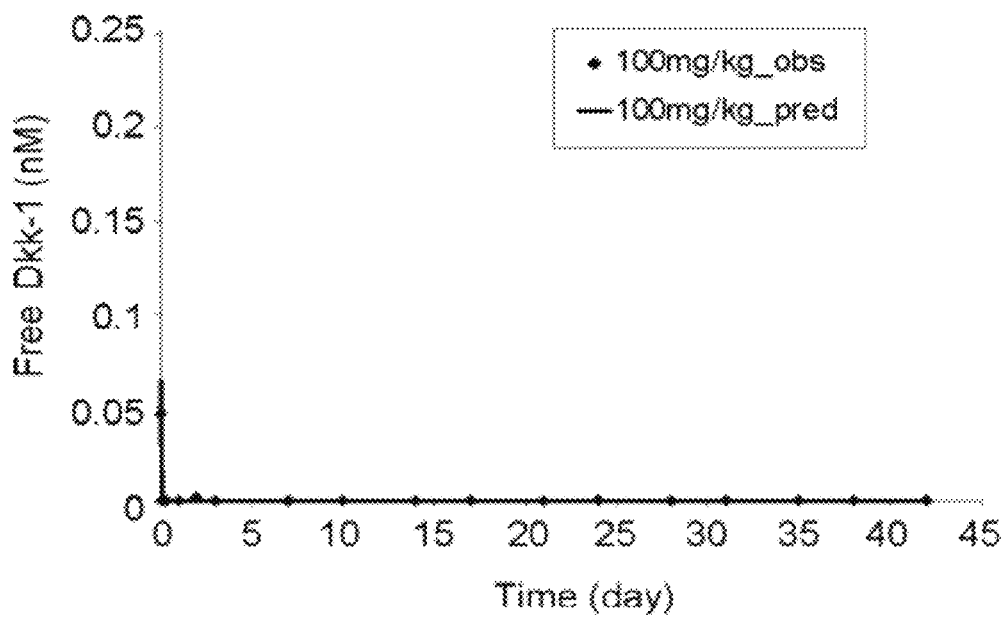
Figure 8D:
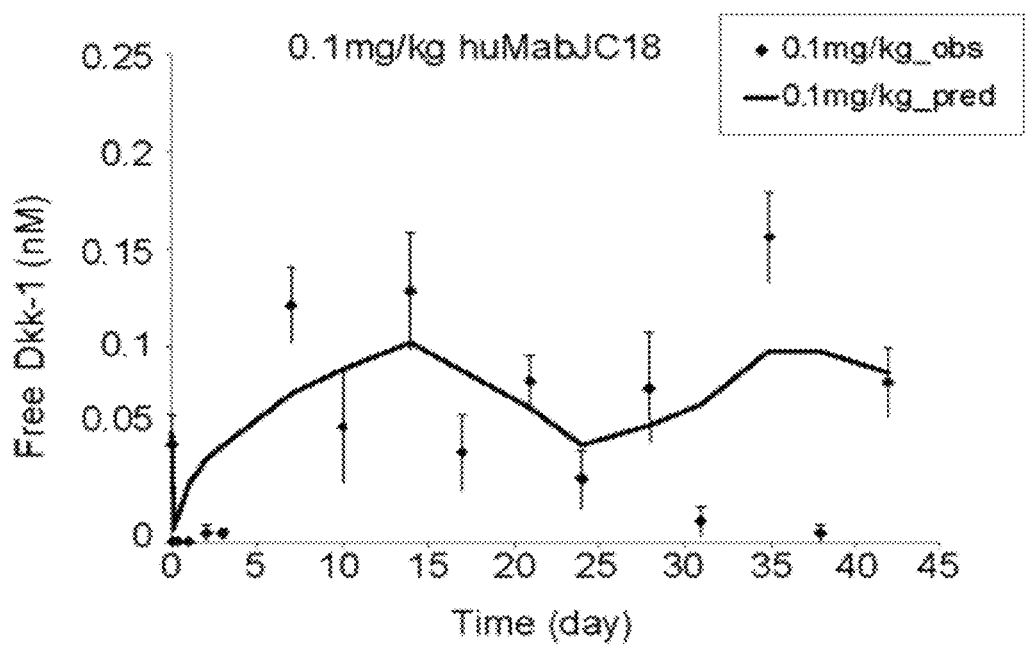
Figure 8E:
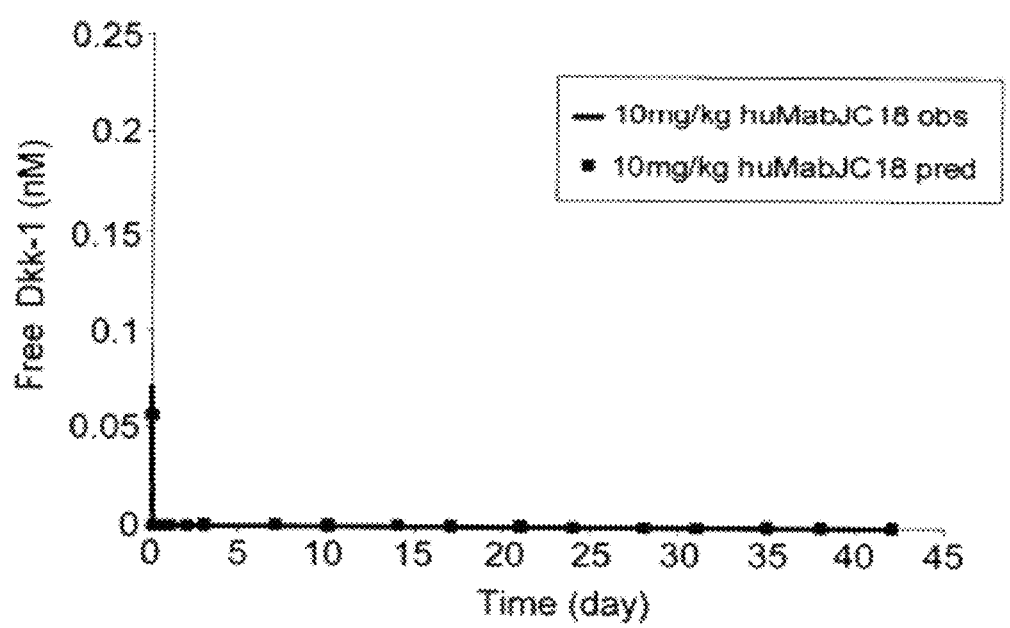
Figure 10A:
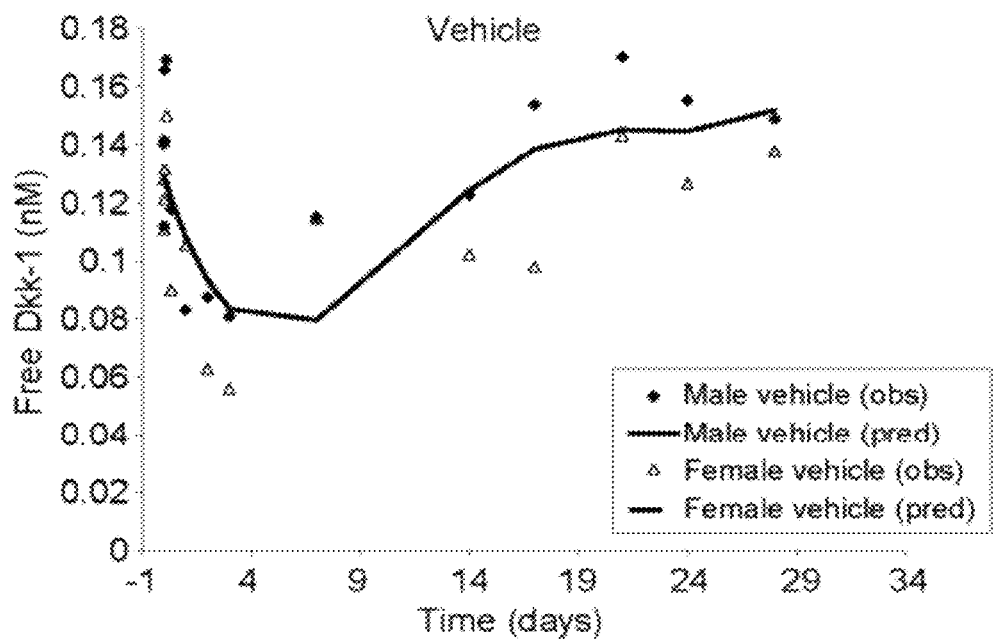
Figure 10B:
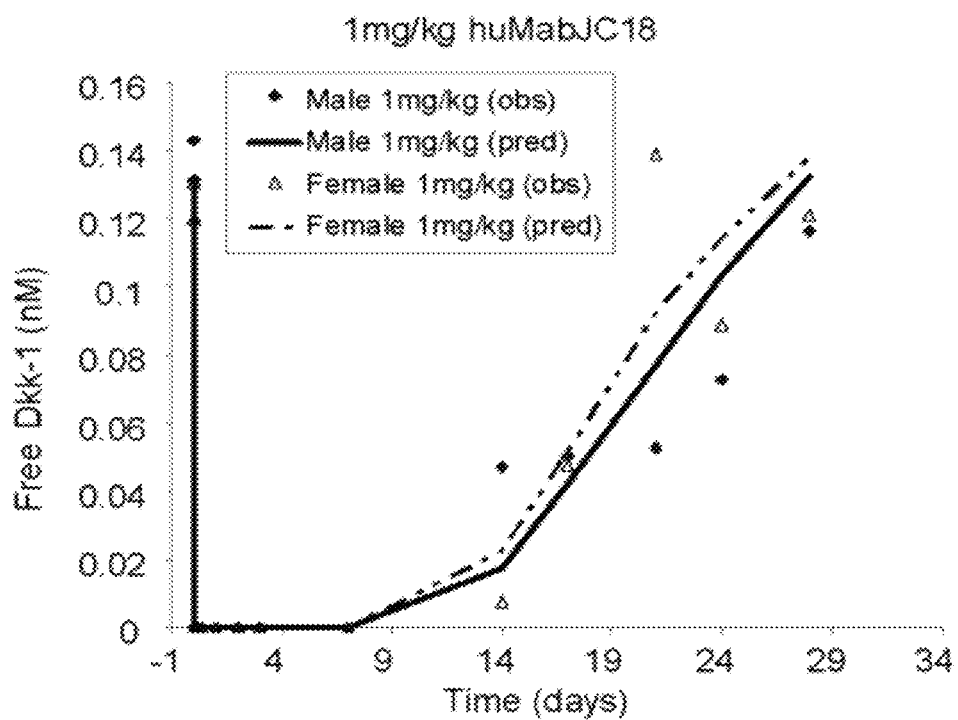
Figure 10E:
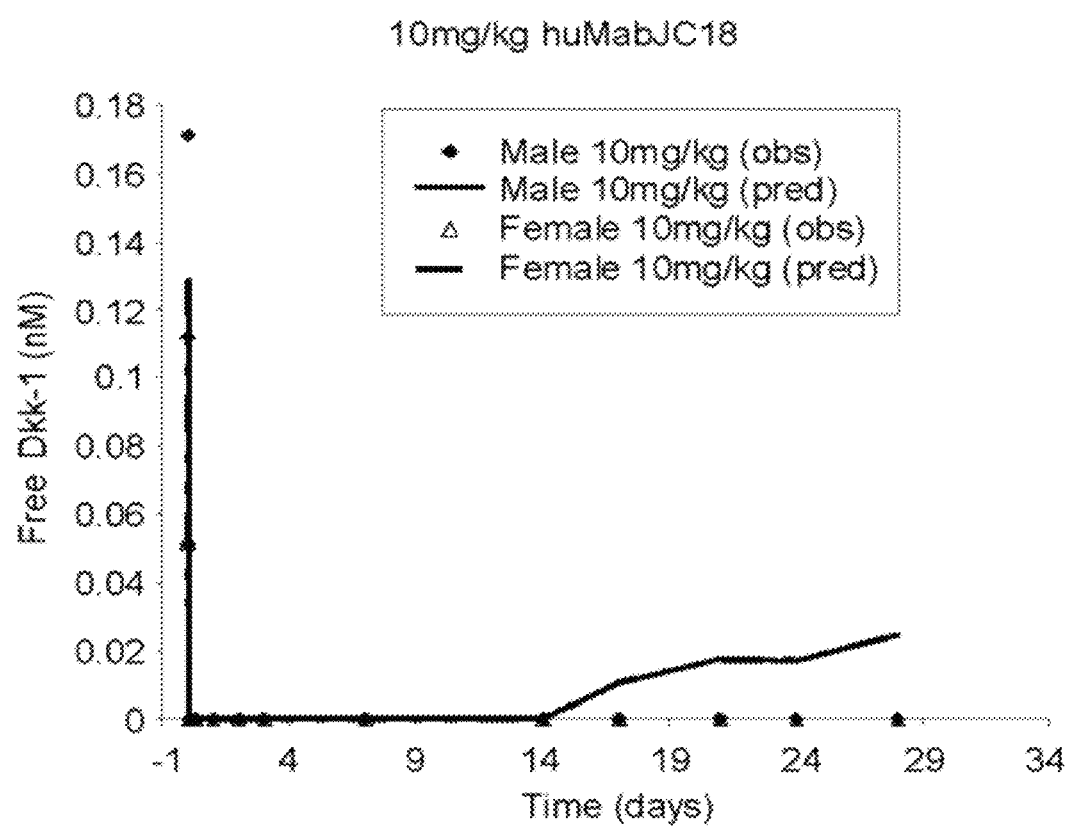

Dkk-1 Target Kinetics in Rat:

V5-His tagged human (h-) Dkk-1 and rat (r-) Dkk-1 were administered to male Sprague-Dawley rats by intravenous bolus administration at 1, 5, 10 and 100 µg/kg (h-Dkk-1) or 100 µg/kg (r-Dkk-1). h-Dkk-1 kinetics were linear over the dose range tested. The mean elimination half-life was 22.3±6.4 min for h-Dkk-1 (FIG. 6) and 34 min for r-Dkk-1.

Rat Pharmacokinetics and Pharmacodynamics

The mean free/partially free huMabJC18 concentration versus time profiles following weekly intravenous administration to female Sprague-Dawley rats are shown in FIG. 7. Non-compartmental pharmacokinetic parameters are shown in Table 10. The pharmacokinetics of huMabJC18 were non-linear across the dose range with supra-proportional increases in AUC with dose up to 10 mg/kg. This indicates a higher rate of clearance at the lower doses (0.1 and 1 mg/kg) compared with the higher doses (10 and 100 mg/kg). At later time points, serum huMabJC18 concentrations in some of the rats were lower than expected or below the limit of quantitation of the assay. Rat anti-huMabJC18 antibodies were confirmed in these samples using a qualitative anti-drug antibody (ADA) assay and data from these rats were removed from the analysis and the plots.

TABLE 10

Non-compartmental pharmacokinetic parameters for free/partially free huMabJC18 concentrations in Sprague Dawley rats following intravenous administration of huMabJC18[a]

| Dose (mg/kg) | AUC 0-168 hrs (µg · hr/mL) | $C_{max}$[b] (µg/ml) | $C_{ave}$[c] (µg/ml) | $C_{min}$[d] (µg/ml) |
|---|---|---|---|---|
| 0.1 | 21.2 ± 2.20 | 1.81 ± 0.156 | 0.127 ± 0.0133 | <LLOQ |
| 1 | 850 ± 88.8 | 24.6 ± 1.60 | 5.06 ± 0.528 | 0.205 ± 0.172 |
| 10 | 13300 ± 1000 | 252 ± 29.7 | 79.0 ± 5.94 | 38.7 ± 8.50 |
| 100 | 141000 ± 18700 | 2660 ± 313 | 841 ± 110 | 439 ± 116 |

[a]Values reported as mean ± standard deviation
[b]$T_{max}$ = 1 hr for every rat except in 100 mg/kg group where Tmax = 3 hr for one rat.
[c]$C_{ave}$ = AUC$_{(1st\,dosing\,interval)}$/tlast of 1$^{st}$ dosing interval (not for entire duration of study due to sparse sampling).
[d]$C_{min}$ = 1$^{st}$ dosing interval (0-168 hrs).

Mean free Dkk-1 concentrations in the same study are plotted in FIGS. 8A-8E. Free Dkk-1 concentrations decreased rapidly following administration of huMabJC18 to rat. At all but the lowest dose, free Dkk-1 concentrations remained suppressed for the duration of the study.

Cynomolgous Monkey Pharmacokinetics and Pharmacodynamics

Individual free/partially free serum huMabJC18 concentration versus time profiles in cynomolgous monkeys are shown in FIGS. 9A and 9B, and non-compartmental pharmacokinetic parameters of huMabJC18 in cynomolgous monkey are shown in Table 11. The pharmacokinetics of huMabJC18 were non-linear over the dose range tested with higher rates of clearance and shorter half-life values observed at the lower doses. The half-life of huMabJC18 in cynomolgous monkeys ranged from 1-13 days across the dose range.

TABLE 11

Mean non-compartmental pharmacokinetic parameters for free/partially free huMabJC18 concentrations in Cynomolgus monkeys following single intravenous administration (n = 1/sex/dose group)

| Dose (mg/kg) | AUC (0-tlast) (μg·hr/mL) | AUC (0-inf) (μg·hr/mL) | CL (mL/day/kg) | Vc (L/kg) | Terminal $t^{1/2}$ (day) | Cmax (μg/mL) |
|---|---|---|---|---|---|---|
| 0.1 | 36.4 | 37.2[a] | 64.6[a] | 46.3[a] | ~1[a] | 2.32 |
| 1 | 1720 | 1810 | 13.8 | 41.3 | 2.6, 4.4[b] | 22.3 |
| 10 | 48100 | 55900 | 4.56 | 41.1 | 12.5 | 242 |
| 100 | 643000 | 845000 | 2.85 | 32.5 | 13.3 | 3040 |

[a] n = 1 due to AUC(0-inf) >120% AUC(0-tlast).
[b] Individual $t^{1/2}$ values reported due to calculations from different time intervals.

Loss of exposure in the 1 mg/kg group around 14 days and in one monkey in the mg/kg group around 21 days post dose is likely to be due to formation of anti-huMabJC18 antibodies and these data were removed from the analysis and the plots. However, this could not be confirmed using a qualitative ADA assay.

Mean serum concentrations of free Dkk-1 in the same study in cynomolgous monkeys are shown in FIGS. 10A-10E. Free Dkk-1 concentration decreased rapidly following dosing of huMabJC18. Duration of Dkk-1 suppression was dose dependent and returned to baseline at the lower doses. At the highest doses, Dkk-1 remained suppressed for the entire dosing interval.

PK/PD Modeling

A mechanistic TMDD model (Mager and Jusko, 2001) was used to simultaneously fit free huMabJC18 and free Dkk-1 concentrations over time (FIG. 5) in both the monkey and the rat. This model was chosen as it accounts for antibody non-target specific elimination, target synthesis and turnover, and complex formation and elimination. Observed versus predicted PK/PD profiles of huMabJC18 and Dkk-1 in rat are shown in FIGS. 7 and 8A-E and in monkey are shown in FIGS. 9A-B and 10A-E. Parameter estimates from the TMDD model for rat and monkey are shown in Table 12.

TABLE 12

Estimated PK/PD Parameters in Monkey and Rat

| Parameter | Estimate from Rat Model | CV (%) | Estimate from Monkey Model | CV (%) |
|---|---|---|---|---|
| $V1_{mAb}$ (L/kg) | 0.147 | 1.74 | 0.052 | 2.02 |
| $k_{el\ mAb}$ (day$^{-1}$) | 0.278 | 3.52 | 0.051 | 1.54 |
| $t_{1/2\ mAb}$ (day)[a] | 2.5 | Derived | 13.6 | Derived |
| $k_{12}$ (day$^{-1}$) | 1.03 | 5.82 | 0.285 | 2.70 |
| $k_{21}$ (day$^{-1}$) | 0.842 | 9.73 | 0.277 | 1.25 |
| $k_{on}$ (nM$^{-1}$ day$^{-1}$)[b] | 49.4 | Fixed | 316 | Fixed |
| $k_{off}$ (day$^{-1}$)[b] | 1.72 | Fixed | 16.2 | Fixed |
| $K_d$ (pM)[c] | 34.8 | Derived | 51.3 | Derived |
| $k_{el\ target}$ (day$^{-1}$) | 93.1 | 1.05 | 39 | 2.18 |
| $t_{1/2\ target}$ (min)[a] | 11 | Derived | 26 | Derived |
| $k_{el\ complex}$ (day$^{-1}$) | 9.54 | 1.75 | 0.613 | 1.57 |
| $t_{1/2\ complex}$ (hr)[a] | 1.74 | Derived | 26.4 | Derived |

[a] Secondary parameter calculated as $t_{1/2} = 0.693/k_{el}$
[b] $k_{on}$ and $k_{off}$ were determined in a previous run where $COV could not be obtained in NONMEM. In the final run, $k_{on}$ and $k_{off}$ estimates were fixed to these values and $COV was achieved.
[c] Secondary parameter calculated as $K_d = k_{off}/k_{on}$ The estimates of volume of distribution (V1) and half-life from the PK/PD model in rat and monkey are consistent with the pharmacokinetics of an $IgG_2$ antibody in rat and monkey (Peppard and Orlans, 1980; Hinton et al., 2004). The estimate of rat in vivo potency ($K_d$=34.8 pM) is consistent with the value obtained in vitro in the rat ($K_d$<100 pM, see BIAcore data above). The Dkk-1 half-life estimates (26 min in monkey and 11 min in rat) determined from the Dkk-1 $k_{el}$ are similar to the values estimated from the V5-his tagged h-Dkk-1 and r-Dkk-1 turnover studies (22.3 min and 34 min respectively, see target kinetics section above). The half-life of the complex (estimated from the complex $k_{el}$) is intermediate between the estimated half-life of the antibody, huMabJC18 and the target, Dkk-1.

Figure 11:
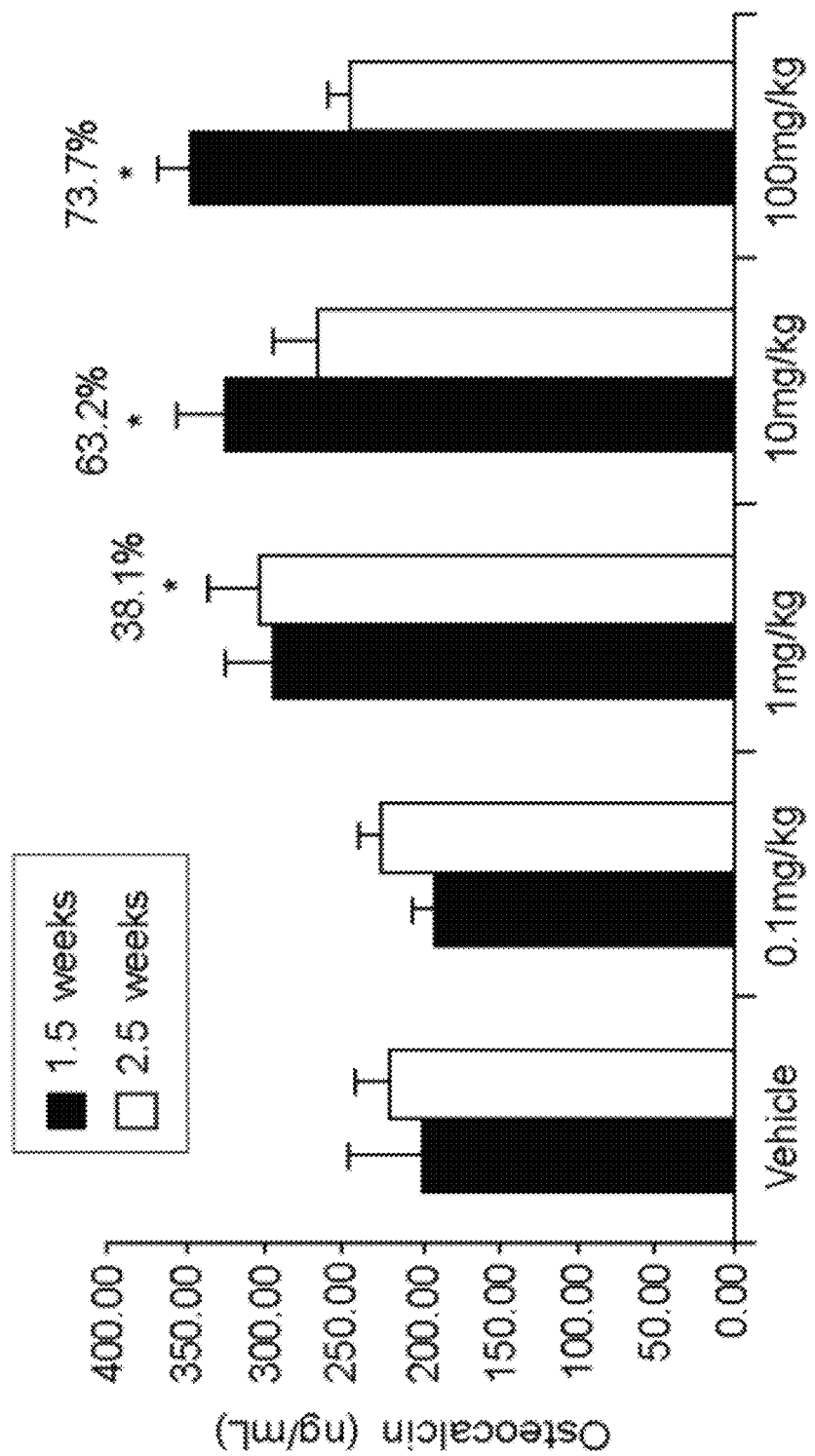
FIG. 11 shows a graph of mean osteocalcin concentrations (±SE) at 1.5 and 2.5 weeks post first dose following weekly intravenous administration of huMabJC18 to Sprague-Dawley rats. * indicates p<0.05 vs. vehicle

Bone Biomarkers in Rat:

In addition to the target Dkk-1, other biomarkers were quantitated in the rat study including osteocalcin, which is a well established biomarker of bone formation, and bone mineral density (BMD), which is a validated biomarker of osteoporosis (see, e.g., *Primer on the Metabolic Bone Diseases and Disorders of Mineral Metabolism* (Rosen C J ed) pages 152-163 and 174-179, American Society for Bone and Mineral Research, Washington D.C). A plot of osteocalcin concentration versus dose at 1.5 and 2.5 weeks post first dose in the rat study are shown in FIG. 11. There is a statistically significant (p<0.05) increase in osteocalcin concentrations in the 1 mg/kg/week dose group at 2.5 weeks post first dose and in the 10 and 100 mg/kg/week dose groups at 1.5 weeks post dose.

As shown in Table 13, total bone mineral density was significantly increased in the rats treated with the huMabJC18 at 10 and 100 mg/kg/week by 11% and 16%, respectively, as compared with vehicle control.

TABLE 13

Changes in total bone mineral density (BMD) at dista femurs in female rats treated for six weeks with huMabJC18[a]

| Group | Vehicle | 0.1 mg | 1 mg | 10 mg | 100 mg |
|---|---|---|---|---|---|
| BMD | 675 ± 18 | 677 ± 22 | 713 ± 28 | 746 ± 24* | 784 ± 19** |

[a] Data are expressed as mean ± SE.
*p<0.05 vs. Vehicle;
**p < 0.01 vs. Vehicle.

Female rats were treated with huMabJC18 at various doses weekly for 6 weeks by intravenous injection. BMD was measured at the end of the study.

Human PKPD Simulations

The mechanism based PK/PD (TMDD) model (FIG. 5) was used to simulate the PK/PD of huMabJC18 in humans and to predict an efficacious dose for treatment of osteoporosis, among other disorders. Literature reported values of $IgG_2$ antibody PK parameters (non-target mediated) were combined with knowledge of Dkk-1 target kinetics and huMabJC18-Dkk-1 complex kinetics obtained from the monkey and rat PK/PD modeling (Table 14) to inform the human PK/PD simulations.

TABLE 14

Parameter estimates used in human PK/PD simulations

| Parameter | Value | Reference/Source |
|---|---|---|
| mAb SC bioavailability (%) | 75 | (Tang et al., 2004) |
| mAb SC absorption rate constant (day−1) | 0.5 | (Tang et al., 2004; Agoram et al., 2007) |
| mAb volume of distribution (mL/kg) | 50 | (Tang et al., 2004; Agoram et al., 2007) Allometric scaling from rat and monkey |
| mAb (non-specific) elimination rate constant (day−1) | 0.03 | (Tang et al., 2004; Hayashi et al., 2007) Allometric scaling from rat and monkey |
| Dkk-1 levels in osteoporosis patients (ng/ml) | 10.6 ± 6.5 | |
| Dkk-1 half-life (min) | 49 | Allometric scaling from rat and monkey |
| mAb-Dkk-1 association rate ($k_{on}$, nM−1day−1) | 112.3 | Human BIAcore data |
| mAb-Dkk-1 dissociation rate ($k_{off}$, day−1) | 0.1728 | Human BIAcore data |
| mAb-Dkk-1 elimination rate constant (day−1) | 0.3 | Allometric scaling from monkey |

Figure 12:
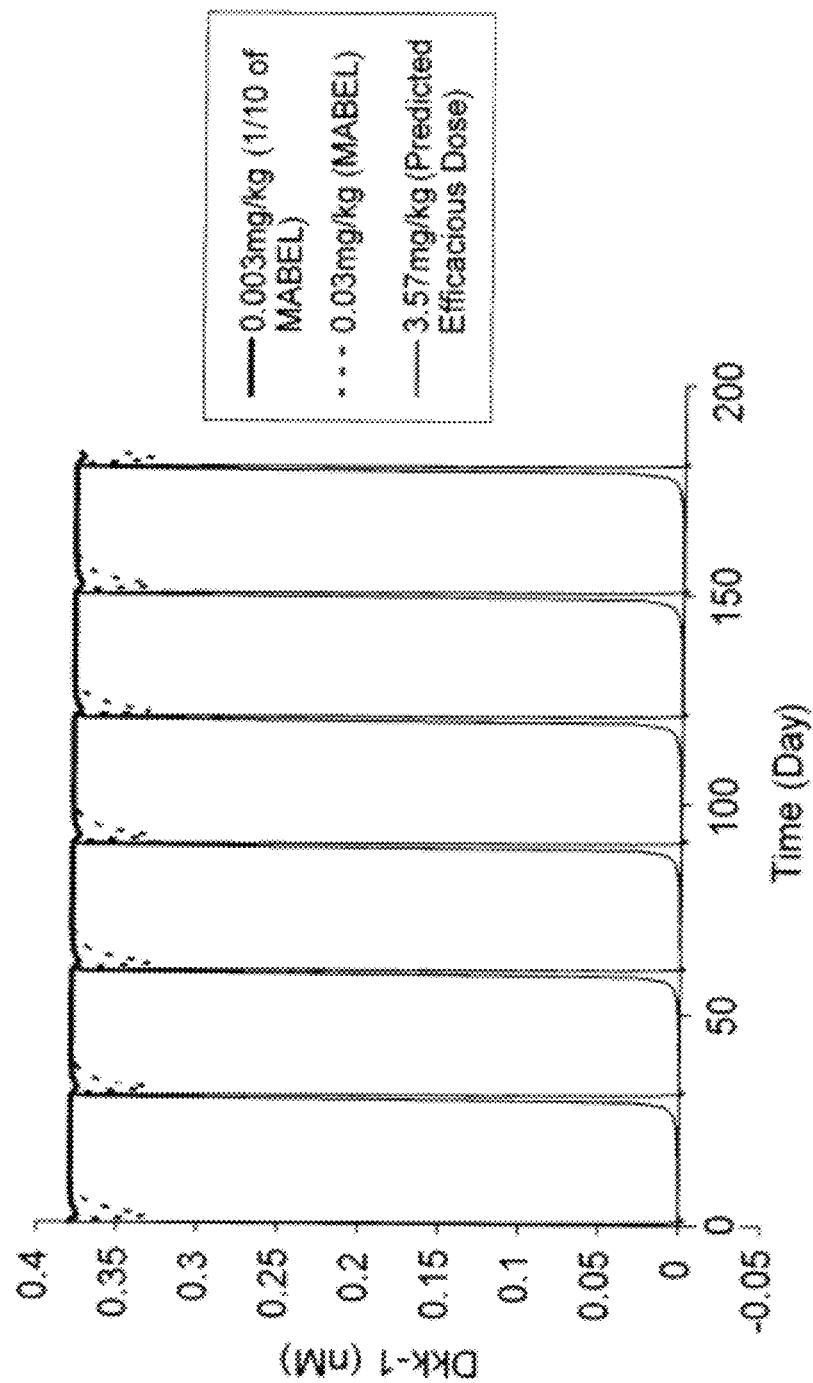
FIG. 12 shows a graph of predicted free Dkk-1 concentrations in humans following subcutaneous administration of huMabJC18 1/month for 6 months. Three different doses were tested: 0.003 mg/kg which represents 1/10 of MABEL or a no effect dose, 0.03 mg/kg which represents MABEL and 3.57 mg/kg which represents predicted efficacious dose for osteoporosis.

Prior experiments in an OVX mouse disease model indicated that 50% reduction in Dkk-1 was required for a statistically significant increase in bone mineral density (data not shown). The predicted efficacious dose of huMabJC18 to reduce Dkk-1 by >50% over the dosing interval is 3.57 mg/kg given once monthly. The projected dose has uncertainty associated with it due to uncertainty around the kinetics of endogenous Dkk-1 and the high sensitivity of Dkk-1 suppression (and thus dose) to this parameter. The dose predicted to give minimum anticipated biological effect (MABEL) was 0.03 mg/kg. This dose is predicted to transiently reduce Dkk-1 levels by <20% followed by return to baseline. A dose of 0.003 mg/kg (1/10 of MABEL) was predicted to have no effect. These human simulations of Dkk-1 concentration are shown in FIG. 12 and should be of high value in dose setting in the clinic.

Figure 13:
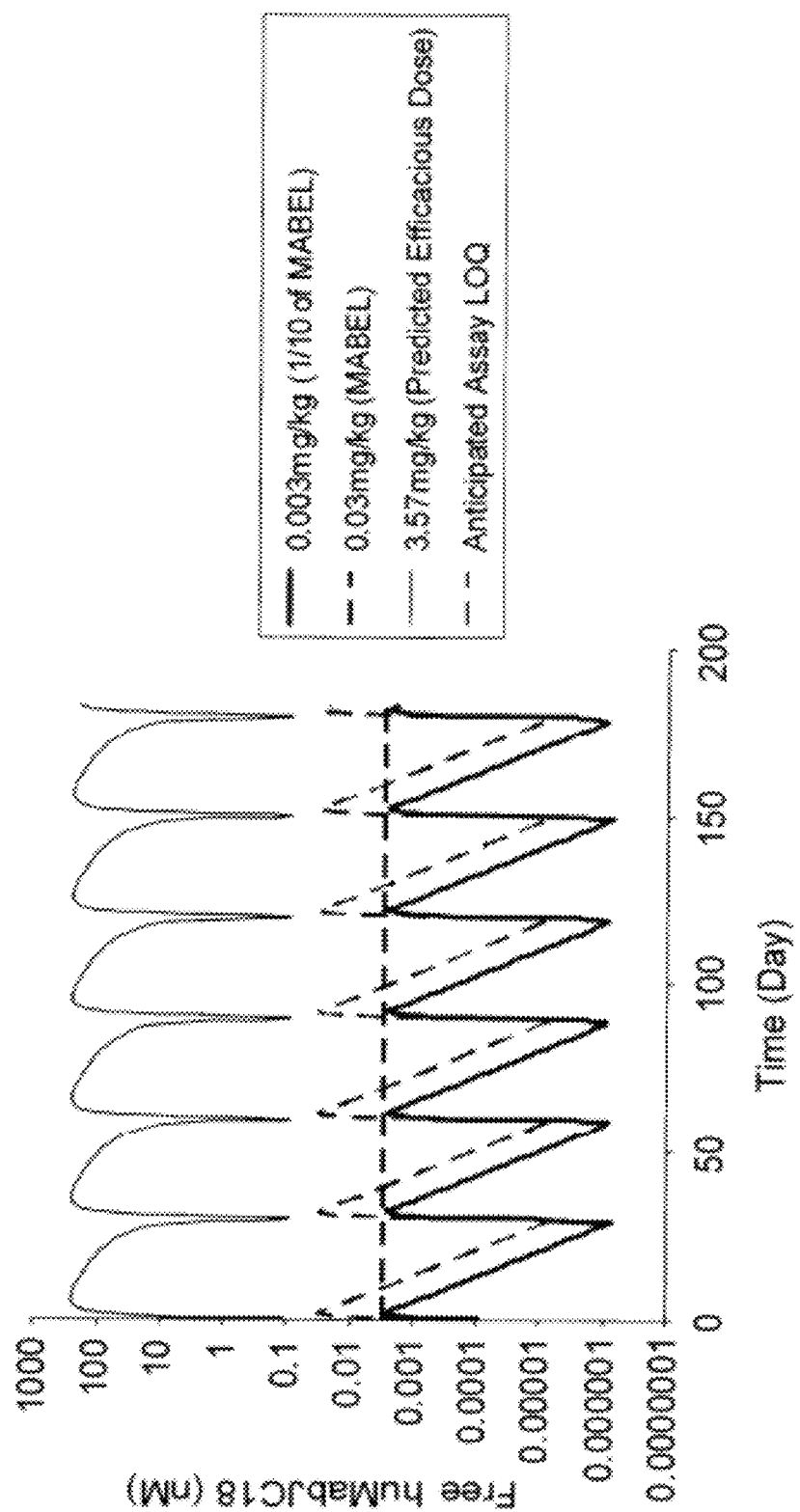
FIG. 13 shows a graph of predicted free huMabJC18 concentrations in humans following subcutaneous administration of huMabJC18 1/month for 6 months. Three different doses were tested: 0.003 mg/kg which represents 1/10 of MABEL or a no effect dose, 0.03 mg/kg which represents MABEL and 3.57 mg/kg which represents predicted efficacious dose for osteoporosis. Anticipated Limit of Quantitation (LOQ) of the bioanalytical assay is shown to represent the futility of dosing lower than predicted MABEL.

Non-linear pharmacokinetics of huMabJC18 are predicted across the dose range encompassing MABEL (0.03 mg/kg) and the predicted efficacious dose (3.57 mg/kg). This is due to TMDD and is shown in FIG. 13.

Target Understanding

Data in mice indicate that Dkk-1 is a master regulator of bone remodeling (Diarra et al. (2007) Nat Med 13:156-163) and Dkk-1 baseline levels are approximately 5 times higher in disease state (ovariectomised, OVX) mice compared with healthy mice (in-house data). Dkk-1 levels have also been shown to be elevated in bone marrow plasma and peripheral blood of multiple myeloma patients with bone lesions (Tian et al., 2003). A sensitivity analysis showed that predicted human dose of an anti-Dkk-1 monoclonal antibody (huMabJC18) was highly sensitive to Dkk-1 baseline levels. The higher the baseline Dkk-1 levels, the greater the concentration of antibody required to reduce Dkk-1. The baseline levels of the target are often known from prior clinical measurements, however the lack of this information for Dkk-1 prompted establishment of reference ranges for human Dkk-1 levels in both healthy subjects and the patient population (osteopenic and osteoporotic patients) that could be used for more informative dose predictions at different stages of clinical development. The analysis showed that Dkk-1 levels were higher in osteopenic and osteoporotic women (T-score<−1) compared with healthy women.

The rate of turnover of target ligands can vary from minutes to days which can have a significant impact on efficacious dose and even potential of the target to be perturbed for clinical benefit. Some ligands have similar kinetics across species, but for others the turnover is not predictable a priori. Meno-Tetang et al. (Meno-Tetang and Lowe (2005) Basic Clin Pharmacol Toxicol 96:182-192) showed that IgE turnover rates range from 5-8 hr in mouse to 2.7 days in man which markedly affected the predictions of human effect of an anti-IgE antibody. For Dkk-1 a sensitivity analysis confirmed that predicted dose of an anti-Dkk-1 monoclonal antibody (huMabJC18) was sensitive to Dkk-1 half-life with a higher molar excess of antibody required at higher target turn-over rates. No information was available on Dkk-1 turnover rates from the literature and therefore experiments were completed in-house using V5-his tagged human and rat Dkk-1 given intravenously to rat. These experiments indicated that Dkk-1 had a high rate of turnover (half-life of 22.3 min for h-Dkk-1 and 34 min for r-Dkk-1) and that human and rat forms of Dkk-1 have similar turnover rates in the rat. The rapid turnover rate of Dkk-1 was later confirmed by using PK/PD modeling to estimate Dkk-1 half-life in rats and monkeys dosed with huMabJC18.

PK/PD Understanding of huMabJC18 in Rat and Monkey

In the rat and monkey studies, huMabJC18 exhibited non-linear pharmacokinetics with higher rates of clearance and shorter elimination half-life values at lower doses. This is indicative of target mediated drug disposition (TMDD) where interaction of an antibody with its pharmacological target influences disposition at lower doses (Tabrizi et al. (2006) Drug Discov Today 11:81-88.; Wang et al. (2008) Clin Pharmacol Ther 84:548-558). This pathway is saturated at higher doses because of the finite expression of the target. Upon saturation of the target mediated pathway, typical IgG FcRn catabolic clearance mechanisms predominate, which gives the antibody its characteristic long half-life. TMDD is more common for monoclonal antibodies directed against proteins expressed on cell membranes where receptor mediated endocytosis results in drug elimination. However, TMDD can also be observed with soluble targets: omalizumab and denosumab are antibodies for soluble targets (IgE and receptor activator of NFkB respectively) which exhibit non-linear elimination kinetics (Hayashi et al., 2007; Marathe et al., 2008).

Empirical PK/PD models consisting of a PK model to describe systemic drug concentrations, which is used as a forcing function to describe PD, are often not appropriate for characterizing TMDD as they do not account for the interdependency of PK and PD. A single model describing drug PK, target dynamics and their interaction was proposed by Mager at al (Mager and Jusko (2001) J Pharmacokinet Pharmacodyn 28:507-532). This model accounts for specific and non-specific distribution and elimination of the drug molecule as well as providing flexibility to account for target dynamics. In other cases where PK and PD have been simultaneously analyzed, this model has been used to provide a direct link between dose, exposure and response (Meno-Tetang and Lowe (2005) Basic Clin Pharmacol Toxicol 96:182-192); Ng et al. (2006) Pharm Res 23:95-103; Wu et al. (2006) J Pharm Sci 95:1258-1268). In this case the TMDD model was used to simultaneously fit antibody, huMabJC18, and target, Dkk-1, concentrations in the rat and monkey following IV administration of huMabJC18 at several dose levels. The model gave an estimation of non-target mediated pharmacokinetics of huMabJC18 that were fairly consistent with typical $IgG_2$ pharmacokinetics in each species (Peppard and Orlans (1980) Immunology 40:683-686; Hinton et al. (2004) J Biol Chem 279:6213-6216). Thus, the elimination half-life was 2.5 days in rat and 13.6 days in monkey. Volume of distribution was approximately equivalent to plasma volume in the monkey (0.052 L/kg) but higher than plasma volume in rat (0.147 L/kg).

The elimination half-life of the target Dkk-1 was estimated to be 11 min in rat and 26 min in monkey from the PK/PD modeling. This was in the same order of magnitude as the elimination half-life of V5-his tagged h-Dkk1 measured in the rat (half-life=25 min). The half-life of the huMabJC18-Dkk-1 complex was estimated to be intermediate between huMabJC18 half-life and Dkk-1 half-life which likely reflects the target mediated clearance mechanism. However, it is possible that binding of the target to the antibody interferes with antibody binding to FcRn and studies are being completed in-house to test this hypothesis.

In the rat, increase in biomarkers of bone formation (osteocalcin and bone mineral density) was observed in addition to decrease in the target biomarker, Dkk-1. This data gave further support to the use of huMabJC18 for treatment of skeletal disorders such as osteoporosis.

Prediction of Human Efficacious Dose and Calculation of MABEL

For monoclonal antibodies, it is becoming widely recognized that rational selection of safe first-in-human doses, on the basis of PK/PD modeling is essential (see, e.g., the UK government website on *Publications policy and guidance: Department of Health—Publications*). A new parameter, minimum anticipated biological effect level (MABEL) involves extrapolation of observed preclinical PK/PD data to clinical prediction on the basis of a PK/PD modeling approach. MABEL has been suggested for consideration in addition to the no adverse effect level (NOAEL) in designing first-in-human dose levels of high risk therapeutics in recent European regulatory guidance (EMEA (2007) Guideline on strategies to identify and mitigate risks for first-in-human clinical trials with investigational medicinal products., in (EMEA ed), London).

To predict the efficacious dose of huMabJC18, the mechanistic TMDD model used for fitting the preclinical data in rat and monkey was adapted for human PK/PD simulations. Literature reported values of $IgG_2$ antibody pharmacokinetic parameters (non-target mediated) were combined with knowledge of Dkk-1 target kinetics and huMabJC18-Dkk-1 complex kinetics obtained from the rat and monkey PK/PD modeling.

In vitro BIAcore values for human Dkk-1 were used to determine association and dissociation rates of the complex ($k_{on}$ and $k_{off}$) in the model. A sensitivity analysis was performed on $k_{on}$ and $k_{off}$, and with the fast on-rates and slow off-rates predicted for this antibody in humans, Dkk-1 suppression and therefore dose is insensitive to fairly large changes in Kd. Indeed at Kd values <10 pM, there is no change in predicted dose. This is because the turnover rate of the huMabJC18-Dkk-1 complex is faster than the off-rate from the receptor. In such cases, affinity maturation steps in candidate selection may be avoided.

Mean Dkk-1 baseline concentrations measured in samples from osteoporotic patients (see results section) were used in the simulations. Dkk-1 was assumed to have a slower turnover rate in human compared with monkey or rat. Therefore, the human Dkk-1 half-life was calculated using allometric scaling of monkey and rat half-life values. This gave an estimated half-life of Dkk-1 in humans of 49 min. It should be noted that because Dkk-1 is a rapidly turned over antigen, overall suppression of Dkk-1, and therefore dose, is highly sensitive to the Dkk-1 half-life value used in the simulations.

The half-life of the huMabJC18-Dkk-1 complex in humans was predicted to be 2.3 days (kel=0.3 day-1) by allometric scaling of the complex half-life which was estimated by the monkey PK/PD model. A shorter complex half-life in humans would be predicted by allometric scaling of the complex half-life estimated by the rat PK/PD modeling. However, a sensitivity analysis was performed and Dkk-1 suppression (and therefore dose) was not sensitive to the change in complex half-life predicted from rat versus monkey.

Prior experiments in OVX mice, a model of postmenopausal bone loss, indicated that approximately 50% reduction in Dkk-1 levels was associated with a statistically significant increase in bone mineral density (data not shown). Therefore, dose predictions for huMabJC18 were made on the basis that Dkk-1 levels needed to be suppressed by >50% from baseline over the dosing interval (1 month). Under this remit and with assumptions stated above, the predicted efficacious dose of huMabJC18 was 3.57 mg/kg given subcutaneously once per month. By simulation, the dose predicted to give minimal effect (MABEL) in humans (<20% reduction in Dkk-1) is 0.03 mg/kg. Non-linear pharmacokinetics are predicted in the clinic (FIG. 13), with huMabJC18 exhibiting a higher clearance and shorter half-life at lower doses due to TMDD.

An alternative approach to predicting human pharmacology is to predict maximal receptor occupancy (RO) using a formula based on equilibrium-drug interaction theory:

$$RO(\%) = \frac{[mAb]}{K_d + [mAb]} \times 100$$

Figure 14:
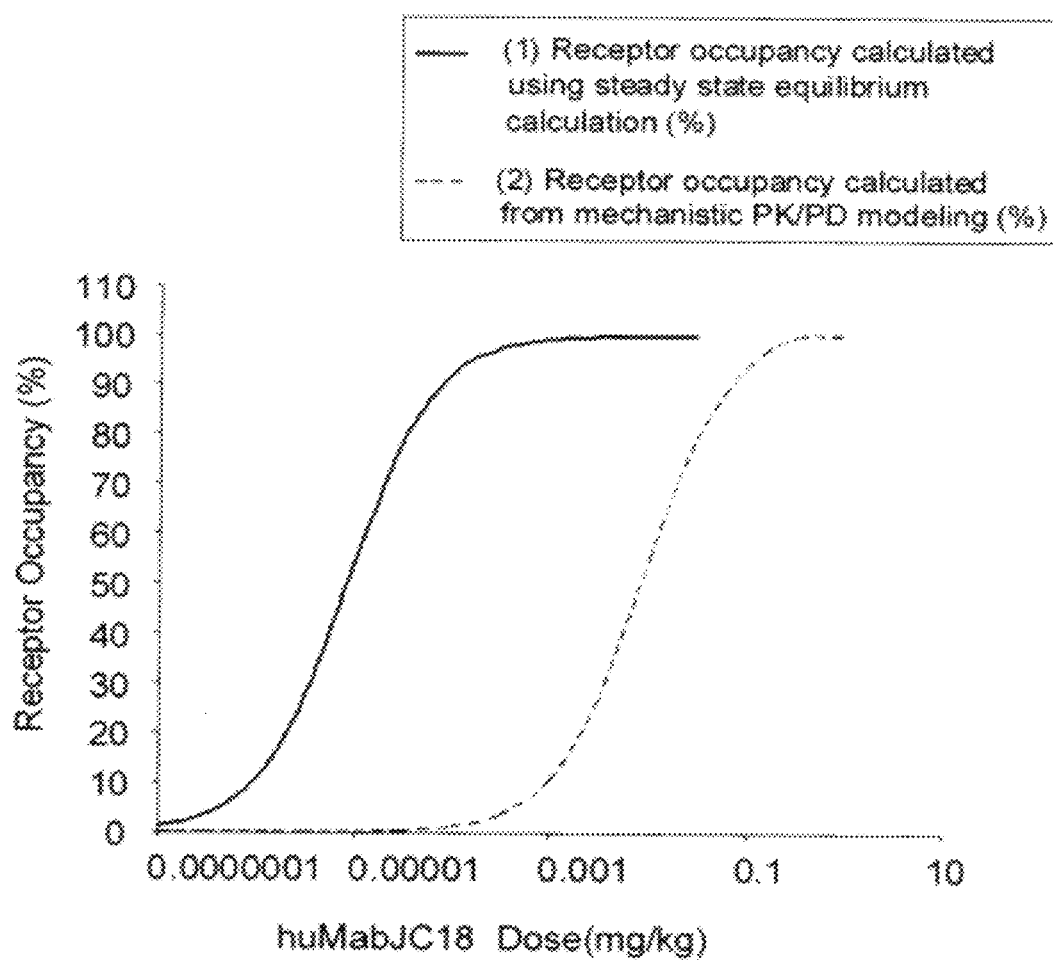
FIG. 14 shows a graph of receptor occupancy calculations for huMabJC18 vs. predicted human dose based on (1) steady state equilibrium method (Duff, 2006) and (2) mechanistic PK/PD (TMDD) model.

(FIG. 14, (Duff (2006) Expert Scientific Group on Phase One Clinical Trials: Final Report, in, Department of Health, UK, London)). Estimation of RO using this method relies on Kd alone and does not take into account target or mAb-target complex kinetics. Dkk-1 has been shown to have a high turnover rate and, binding of Dkk-1 by huMabJC18 changes the kinetics of the target (TMDD). Under these conditions, RO is often not predictable by pharmacological equilibrium approaches and simple $K_d$ based RO calculations have been shown to substantially over predict RO at a particular dose (Agoram (2009) Br J Clin Pharmacol 67:153-160). For Dkk-1, RO calculated using the equilibrium formula estimates an $ED_{50}$ of 0.00001 mg/kg, while the mechanistic PK/PD model estimates an $ED_{50}$ of 0.01 mg/kg (FIG. 14). Use of the equilibrium calculation could result in the selection of doses that are too low in the clinic and delay the progression of a first-in-human study. At the other extreme, the observed NOAEL in rat and monkey (100 mg/kg) is in excess of that required for 100% binding of target to antibody which would not be recommendable for providing clinical starting dose estimates. A PK/PD model based approach to MABEL dose calculations was concluded to be more likely to be predictive for Dkk-1 and ensure the safety and efficiency of clinical studies.

The observed NOAEL (100 mg/kg) is in excess of that required for 100% binding of Dkk-1 to antibody. At the other extreme, the MABEL calculated according to the Duff equation is likely a severe underestimation due to lack of consideration of the rapid turnover of Dkk-1. As such, these methods are not acceptable approaches to setting the starting clinical dose in this instance. In contrast, the TMDD model provided excellent characterization of the preclinical data which indicated the role of target turnover in determining % binding of Dkk-1. Therefore, the MABEL estimate derived from the TMDD model (0.03 mg/kg) will ensure both the safety and efficiency of FIH studies.

In conclusion, huMabJC18 is a humanized prototype anti-Dkk-1 antibody for the treatment of osteoporosis, among other disorders. A mechanistic TMDD model was used to characterize huMabJC18 versus Dkk-1 concentration response relationship in rat and monkey. This model was translated to human to predict efficacious dose and MABEL by incorporating information on target expression and turnover rates. These parameters were found to have more impact on the dose response relationship than affinity for this mechanism.

Deposit Information

Applicants have deposited the heavy and light chain variable regions of the antibody designated as huMAbJC18 herein with the American Type Culture Collection (ATCC) Manassas, Va. 20110-2209 U.S.A. As noted in the foregoing the huMabJC18 HC variable region was deposited on Mar. 19, 2009, and was assigned ATCC Deposit No. PTA-9835, and the huMabJC18 LC variable region was deposited on Mar. 19, 2009, and was assigned ATCC Deposit No. PTA-9836. These deposits were made under the provisions of the Budapest Treaty on the International Recognition of the Deposit of Microorganisms for the Purpose of Patent Procedure and the Regulations thereunder (Budapest Treaty). These deposits will be maintained without restriction in the ATCC depository for a period of 30 years, or 5 years after the most recent request, or for the effective life of the patent, whichever is longer, and will be replaced if the deposits become non-viable during that period. Availability of the deposited materials is not to be construed as a license to practice any aspects of the present disclosure in contravention of the rights granted under the authority of any government in accordance with its patent laws. The foregoing written specification is considered to be sufficient to enable one skilled in the art to practice all aspects of the present disclosure. The present disclosure is not to be limited in scope by the materials deposited since the deposited embodiment is intended as a single illustration of certain aspects of the disclosure and any constructs that are functionally equivalent are within the scope of this disclosure. The deposit of material herein does not constitute an admission that the written description herein is inadequate to enable the practice of any aspect of the disclosure, including the best mode thereof, nor is it to be construed as limiting the scope of the claims to the specific illustrations that it represents. Indeed, various modifications of the disclosure in addition to those shown and described herein will become apparent to those skilled in the art from the foregoing description and fall within the scope of the appendant claims.

The section headings used herein are for organizational purposes only and are not to be construed as limiting the described subject matter in any way. It will be appreciated that there is an implied "about" prior to the temperatures, concentrations, times, etc discussed in the present teachings, such that slight and insubstantial deviations are within the scope of the present teachings herein. In this application, the use of the singular includes the plural unless specifically stated otherwise. Also, the use of "comprise", "comprises", "comprising", "contain", "contains", "containing", "include", "includes", and "including" are not intended to be limiting. It is to be understood that both the foregoing general description and the following detailed description are exemplary and explanatory only and are not restrictive of the invention.

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

What is claimed is:

1. An isolated antibody or immunologically functional fragment thereof, which specifically binds to Dickkopf 1 (Dkk-1) polypeptide comprising (a) heavy chain variable region (VH) complementary determining region one (CDR1) comprising the amino acid sequence shown in SEQ ID NO: 30, 49 or 50, a VH CDR2 comprising the amino acid sequence shown in SEQ ID NO: 32 or 51, and VH CDR3 comprising the amino acid sequence shown in SEQ ID NO: 34 or 52; and (b) a light chain variable region (VL) CDR1 comprising the amino acid sequence shown in SEQ ID NO: 22, a VL CDR2 comprising the amino acid sequence shown in SEQ ID NO: 24, and a VL CDR3 comprising the amino acid sequence shown in SEQ ID NO: 26.

2. The antibody or fragment of claim 1, wherein the heavy chain variable region comprises the amino acid sequence shown in SEQ ID NO: 28 and the light chain variable region comprises the amino acid sequence shown in SEQ ID NO: 20.

3. The antibody or fragment of claim 2, wherein said antibody comprises a light chain comprising the amino acid sequence shown in SEQ ID NO: 42 or 38 and a heavy chain comprising the amino acid sequence shown in SEQ ID NO: 40 or 36, with or without the C-terminal lysine of SEQ ID NO: 40 or 36.

4. An isolated antibody or immunologically functional fragment thereof, which specifically binds to Dickkopf 1 (Dkk-1), wherein the antibody or fragment thereof competes for binding with the antibody of claim 1 for binding to Dkk-1.

5. A composition comprising the antibody or fragment of claim 1 and a pharmaceutically acceptable excipient, diluent or carrier.

6. A method of treating or preventing a loss of bone mass comprising administering to a patient in need thereof an effective amount of the antibody or fragment of claim 1.

7. The method of claim 6, wherein said patient is selected from patients who suffer from osteoporosis, osteopenia, Paget's Disease, periodontitis, rheumatoid arthritis, cancer that metastasizes to bone, multiple myeloma and bone loss due to immobilization.

8. The method of claim 6, wherein increased bone mass is induced in the patient.

* * * * *

SEQUENCE LISTING

<160> NUMBER OF SEQ ID NOS: 52

<210> SEQ ID NO 1
<211> LENGTH: 274
<212> TYPE: PRT
<213> ORGANISM: Homo sapiens

<400> SEQUENCE: 1

Met Ala Leu Gly Ala Ala Gly Ala Thr Arg Val Phe Val Ala Met Val
1               5                   10                  15

Ala Ala Ala Leu Gly Gly His Pro Leu Leu Gly Val Ser Ala Thr Leu
            20                  25                  30

Asn Ser Val Leu Asn Ser Asn Ala Ile Lys Asn Leu Pro Pro Pro Leu
        35                  40                  45

Gly Gly Ala Ala Gly His Pro Gly Ser Ala Val Ser Ala Ala Pro Gly
    50                  55                  60

Ile Leu Tyr Pro Gly Gly Asn Lys Tyr Gln Thr Ile Asp Asn Tyr Gln
65                  70                  75                  80

Pro Tyr Pro Cys Ala Glu Asp Glu Glu Cys Gly Thr Asp Glu Tyr Cys
                85                  90                  95

Ala Ser Pro Thr Arg Gly Gly Asp Ala Gly Val Gln Ile Cys Leu Ala
            100                 105                 110

Cys Arg Lys Arg Arg Lys Arg Cys Met Arg His Ala Met Cys Cys Pro
        115                 120                 125

Gly Asn Tyr Cys Lys Asn Gly Ile Cys Val Ser Ser Asp Gln Asn His
            130                 135                 140

Phe Arg Gly Glu Ile Glu Thr Ile Thr Glu Ser Phe Gly Asn Asp
145                 150                 155                 160

His Ser Thr Leu Asp Gly Tyr Ser Arg Arg Thr Thr Leu Ser Ser Lys
                165                 170                 175

Met Tyr His Thr Lys Gly Gln Glu Gly Ser Val Cys Leu Arg Ser Ser
                180                 185                 190

Asp Cys Ala Ser Gly Leu Cys Cys Ala Arg His Phe Trp Ser Lys Ile
                195                 200                 205

Cys Lys Pro Val Leu Lys Glu Gly Gln Val Cys Thr Lys His Arg Arg
            210                 215                 220

Lys Gly Ser His Gly Leu Glu Ile Phe Gln Arg Cys Tyr Cys Gly Glu
225                 230                 235                 240

Gly Leu Ser Cys Arg Ile Gln Lys Asp His His Gln Ala Ser Asn Ser
                245                 250                 255

Ser Arg Leu His Thr Cys Gln Arg His His His His His His
                260                 265                 270

His His

<210> SEQ ID NO 2
<211> LENGTH: 822
<212> TYPE: DNA
<213> ORGANISM: Homo sapiens

<400> SEQUENCE: 2
atggctctgg gcgcagcggg agctacccgg gtctttgtcg cgatggtagc ggcggctctc      60
ggcggccacc ctctgctggg agtgagcgcc accttgaact cggttctcaa ttccaacgct     120
atcaagaacc tgcccccacc gctgggcggc gctgcgggc acccaggctc tgcagtcagc      180
gccgcgccgg gaatcctgta cccgggcggg aataagtacc agaccattga caactaccag     240
ccgtacccgt gcgcagagga cgaggagtgc ggcactgatg agtactgcgc tagtcccacc     300
cgcggagggg acgcaggcgt gcaaatctgt ctcgcctgca ggaagcgccg aaaacgctgc     360
atgcgtcacg ctatgtgctg ccccgggaat tactgcaaaa atggaatatg tgtgtcttct     420
gatcaaaatc atttccgagg agaaattgag gaaaccatca ctgaaagctt tggtaatgat     480 catagcaccct tggatgggta ttccagaaga accaccttgt cttcaaaaat gtatcacacc     540
aaaggacaag aaggttctgt ttgtctccgg tcatcagact gtgcctcagg attgtgttgt     600
gctagacact tctggtccaa gatctgtaaa cctgtcctga agaaggtca agtgtgtacc      660 aagcatagga gaaaggctc tcatggacta gaaatattcc agcgttgtta ctgtggagaa     720
ggtctgtctt gccggataca gaaagatcac catcaagcca gtaattcttc taggcttcac     780
acttgtcaga gacaccacca tcaccaccat caccatcatc ac                        822

<210> SEQ ID NO 3
<211> LENGTH: 332
<212> TYPE: DNA
<213> ORGANISM: Mus musculus

<400> SEQUENCE: 3
gacattgtgt tgacccaatc tccagcttct ttggctgtgt ctctagggca gagggccacc      60
atctcctgca gagccagcga aagtgttgat gactttggct tagtttttatg aactggttcc     120 aacagaaacc aggacagcca cccaaactcc tcatctatgc tgcatccaag cagggatccg     180 ggtccctgc aggtttaggg gcagtgggt ctgggtcaga cttcagcctc accatccatc       240

-continued

```
ctgtggagga ggatgatact gcaatgtatt tctgtcagca aagtaaggag gttcctccca    300
cgttcggagg ggggaccaag ctggaaataa aa                                  332
```

<210> SEQ ID NO 4
<211> LENGTH: 111
<212> TYPE: PRT
<213> ORGANISM: Mus musculus

<400> SEQUENCE: 4

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asp Phe
            20                  25                  30

Gly Ile Ser Phe Met Asn Trp Phe Gln Gln Lys Pro Gly Gln Pro Pro
        35                  40                  45

Lys Leu Leu Ile Tyr Ala Ala Ser Lys Gln Gly Ser Gly Val Pro Ala
    50                  55                  60

Arg Phe Arg Gly Ser Gly Ser Gly Ser Asp Phe Ser Leu Thr Ile His
65                  70                  75                  80

Pro Val Glu Glu Asp Asp Thr Ala Met Tyr Phe Cys Gln Gln Ser Lys
                85                  90                  95

Glu Val Pro Pro Thr Phe Gly Gly Gly Thr Lys Leu Glu Ile Lys
            100                 105                 110
```

<210> SEQ ID NO 5
<211> LENGTH: 45
<212> TYPE: DNA
<213> ORGANISM: Mus musculus

<400> SEQUENCE: 5

```
agagccagcg aaagtgttga tgactttggc attagtttta tgaac                    45
```

<210> SEQ ID NO 6
<211> LENGTH: 15
<212> TYPE: PRT
<213> ORGANISM: Mus musculus

<400> SEQUENCE: 6

```
Arg Ala Ser Glu Ser Val Asp Asp Phe Gly Ile Ser Phe Met Asn
1               5                   10                  15
```

<210> SEQ ID NO 7
<211> LENGTH: 21
<212> TYPE: DNA
<213> ORGANISM: Mus musculus

<400> SEQUENCE: 7

```
gctgcatcca agcagggatc c                                              21
```

<210> SEQ ID NO 8
<211> LENGTH: 7
<212> TYPE: PRT
<213> ORGANISM: Mus musculus

<400> SEQUENCE: 8

```
Ala Ala Ser Lys Gln Gly Ser
1               5
```

<210> SEQ ID NO 9
<211> LENGTH: 27
<212> TYPE: DNA
<213> ORGANISM: Mus musculus

<400> SEQUENCE: 9
cagcaaagta aggaggttcc tcccacg                                            27

<210> SEQ ID NO 10
<211> LENGTH: 9
<212> TYPE: PRT
<213> ORGANISM: Mus musculus

<400> SEQUENCE: 10

Gln Gln Ser Lys Glu Val Pro Pro Thr
1               5

<210> SEQ ID NO 11
<211> LENGTH: 351
<212> TYPE: DNA
<213> ORGANISM: Mus musculus

<400> SEQUENCE: 11
gaagtgaaac tggtggagtc tgggggaggc ttagtgaagc ctggagggtc cctgaaactc         60
tcctgtgcag cctctggatt cactttcagt aattatgcca tgtcttgggt tcgccagact        120
ccagagaaga ggctggagtg ggtcgcatcc attagtggtg gtggtgacac ctactatcca        180
gacagtgtga agggccgatt caccatctcc agagataatg tcaggaacat cctctacctg        240
caaatgagca gtctgaggtc tgaggacacg gccatgtatt actgtgcaac atcccttgag        300
aactatgcta tggactactg gggtcaagga acctcaatca ccgtctcctc a                351

<210> SEQ ID NO 12
<211> LENGTH: 117
<212> TYPE: PRT
<213> ORGANISM: Mus musculus

<400> SEQUENCE: 12

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asn Tyr
            20                  25                  30

Ala Met Ser Trp Val Arg Gln Thr Pro Glu Lys Arg Leu Glu Trp Val
        35                  40                  45

Ala Ser Ile Ser Gly Gly Gly Asp Thr Tyr Tyr Pro Asp Ser Val Lys
    50                  55                  60

Gly Arg Phe Thr Ile Ser Arg Asp Asn Val Arg Asn Ile Leu Tyr Leu
65                  70                  75                  80

Gln Met Ser Ser Leu Arg Ser Glu Asp Thr Ala Met Tyr Tyr Cys Ala
                85                  90                  95

Thr Ser Leu Glu Asn Tyr Ala Met Asp Tyr Trp Gly Gln Gly Thr Ser
            100                 105                 110

Ile Thr Val Ser Ser
        115

<210> SEQ ID NO 13
<211> LENGTH: 15
<212> TYPE: DNA
<213> ORGANISM: Mus musculus

<400> SEQUENCE: 13
aattatgcca tgtct                                                         15

```
<210> SEQ ID NO 14
<211> LENGTH: 5
<212> TYPE: PRT
<213> ORGANISM: Mus musculus

<400> SEQUENCE: 14

Asn Tyr Ala Met Ser
1               5

<210> SEQ ID NO 15
<211> LENGTH: 48
<212> TYPE: DNA
<213> ORGANISM: Mus musculus

<400> SEQUENCE: 15
tccattagtg gtggtggtga cacctactat ccagacagtg tgaagggc           48

<210> SEQ ID NO 16
<211> LENGTH: 16
<212> TYPE: PRT
<213> ORGANISM: Mus musculus

<400> SEQUENCE: 16

Ser Ile Ser Gly Gly Gly Asp Thr Tyr Tyr Pro Asp Ser Val Lys Gly
1               5                   10                  15

<210> SEQ ID NO 17
<211> LENGTH: 27
<212> TYPE: DNA
<213> ORGANISM: Mus musculus

<400> SEQUENCE: 17
tcccttgaga actatgctat ggactac                                  27

<210> SEQ ID NO 18
<211> LENGTH: 9
<212> TYPE: PRT
<213> ORGANISM: Mus musculus

<400> SEQUENCE: 18

Ser Leu Glu Asn Tyr Ala Met Asp Tyr
1               5

<210> SEQ ID NO 19
<211> LENGTH: 333
<212> TYPE: DNA
<213> ORGANISM: Artificial Sequence
<220> FEATURE:
<223> OTHER INFORMATION: Humanized sequence

<400> SEQUENCE: 19
gagatcgtgc tgacccagag ccccgccacc ctgagcctga gccctggcga gcgggccacc    60
ctgtcctgcc gggccagcga gagcgtggac gacttcggca tcagcttcat caactggtat   120
cagcagaagc ccggccaggc ccccagactg ctcatctacg ccggcagcaa cagggcagc    180 ggcatccccg ccaggttcag cggcagcggc tccggcaccg acttcaccct gaccatctcc   240
agcctcgaac ccgaggactt cgccgtgtac tactgccagc agctgaaaga ggtgcccccc   300
accttcggcg gtgggaccaa ggtggaaatc aaa                              333

<210> SEQ ID NO 20
<211> LENGTH: 111
<212> TYPE: PRT
<213> ORGANISM: Artificial Sequence
```

```
<220> FEATURE:
<223> OTHER INFORMATION: Humanized sequence

<400> SEQUENCE: 20

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asp Phe
            20                  25                  30

Gly Ile Ser Phe Ile Asn Trp Tyr Gln Gln Lys Pro Gly Gln Ala Pro
        35                  40                  45

Arg Leu Leu Ile Tyr Ala Gly Ser Lys Gln Gly Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Leu Lys
                85                  90                  95

Glu Val Pro Pro Thr Phe Gly Gly Gly Thr Lys Val Glu Ile Lys
            100                 105                 110

<210> SEQ ID NO 21
<211> LENGTH: 45
<212> TYPE: DNA
<213> ORGANISM: Artificial Sequence
<220> FEATURE:
<223> OTHER INFORMATION: Humanized sequence

<400> SEQUENCE: 21
cgggccagcg agagcgtgga cgacttcggc atcagcttca tcaac         45

<210> SEQ ID NO 22
<211> LENGTH: 15
<212> TYPE: PRT
<213> ORGANISM: Artificial Sequence
<220> FEATURE:
<223> OTHER INFORMATION: Humanized sequence

<400> SEQUENCE: 22

Arg Ala Ser Glu Ser Val Asp Asp Phe Gly Ile Ser Phe Ile Asn
1               5                   10                  15

<210> SEQ ID NO 23
<211> LENGTH: 21
<212> TYPE: DNA
<213> ORGANISM: Artificial Sequence
<220> FEATURE:
<223> OTHER INFORMATION: Humanized sequence

<400> SEQUENCE: 23
gccggcagca agcagggcag c                                   21

<210> SEQ ID NO 24
<211> LENGTH: 7
<212> TYPE: PRT
<213> ORGANISM: Artificial Sequence
<220> FEATURE:
<223> OTHER INFORMATION: Humanized sequence

<400> SEQUENCE: 24

Ala Gly Ser Lys Gln Gly Ser
1               5
```

<210> SEQ ID NO 25
<211> LENGTH: 27
<212> TYPE: DNA
<213> ORGANISM: Artificial Sequence
<220> FEATURE:
<223> OTHER INFORMATION: Humanized sequence

<400> SEQUENCE: 25
cagcagctga aagaggtgcc ccccacc                                    27

<210> SEQ ID NO 26
<211> LENGTH: 9
<212> TYPE: PRT
<213> ORGANISM: Artificial Sequence
<220> FEATURE:
<223> OTHER INFORMATION: Humanized sequence

<400> SEQUENCE: 26

Gln Gln Leu Lys Glu Val Pro Pro Thr
1               5

<210> SEQ ID NO 27
<211> LENGTH: 360
<212> TYPE: DNA
<213> ORGANISM: Artificial Sequence
<220> FEATURE:
<223> OTHER INFORMATION: Humanized sequence

<400> SEQUENCE: 27
gaggtgcagc tggtcgagtc tggcggcgga ctggtgcagc ctggcggcag cctgagactg    60
agctgcgccg ccagcggctt caccttcagc agctacgcca tcagctgggt gcggcaggcc   120
cctggcaagg gcctggaatg ggtggccagc gtgagcggca ccggcctggg cttccagacc   180 tactacccccg acagcgtgaa gggccggttc accatcagcc gggacaacgc caagaacagc   240
ctgtacctgc agatgaacag cctgcgggcc gaggacaccg ccgtgtacta ctgcgccacc   300
tccctggaaa actacgcctt cgactactgg ggccaggaa ccacggtcac cgtctcctca    360

<210> SEQ ID NO 28
<211> LENGTH: 120
<212> TYPE: PRT
<213> ORGANISM: Artificial Sequence
<220> FEATURE:
<223> OTHER INFORMATION: Humanized sequence

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Ile Ser Trp Val Arg Gln Ala Pro Gly Lys Gly Leu Glu Trp Val
        35                  40                  45

Ala Ser Val Ser Gly Thr Gly Leu Gly Phe Gln Thr Tyr Tyr Pro Asp
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Thr Ser Leu Glu Asn Tyr Ala Phe Asp Tyr Trp Gly Gln
            100                 105                 110

Gly Thr Thr Val Thr Val Ser Ser
        115                 120

```
<210> SEQ ID NO 29
<211> LENGTH: 18
<212> TYPE: DNA
<213> ORGANISM: Artificial Sequence
<220> FEATURE:
<223> OTHER INFORMATION: Humanized sequence

<400> SEQUENCE: 29
agcagctacg ccatcagc                                                   18

<210> SEQ ID NO 30
<211> LENGTH: 6
<212> TYPE: PRT
<213> ORGANISM: Artificial Sequence
<220> FEATURE:
<223> OTHER INFORMATION: Humanized sequence

<400> SEQUENCE: 30

Ser Ser Tyr Ala Ile Ser
1               5

<210> SEQ ID NO 31
<211> LENGTH: 57
<212> TYPE: DNA
<213> ORGANISM: Artificial Sequence
<220> FEATURE:
<223> OTHER INFORMATION: Humanized sequence

<400> SEQUENCE: 31
agcgtgagcg gcaccggcct gggcttccag acctactacc ccgacagcgt gaagggc       57

<210> SEQ ID NO 32
<211> LENGTH: 19
<212> TYPE: PRT
<213> ORGANISM: Artificial Sequence
<220> FEATURE:
<223> OTHER INFORMATION: Humanized sequence

<400> SEQUENCE: 32

Ser Val Ser Gly Thr Gly Leu Gly Phe Gln Thr Tyr Tyr Pro Asp Ser
1               5                   10                  15

Val Lys Gly

<210> SEQ ID NO 33
<211> LENGTH: 27
<212> TYPE: DNA
<213> ORGANISM: Artificial Sequence
<220> FEATURE:
<223> OTHER INFORMATION: Humanized sequence

<400> SEQUENCE: 33
tccctggaaa actacgcctt cgactac                                         27

<210> SEQ ID NO 34
<211> LENGTH: 10
<212> TYPE: PRT
<213> ORGANISM: Artificial Sequence
<220> FEATURE:
<223> OTHER INFORMATION: Humanized sequence

<400> SEQUENCE: 34

Thr Ser Leu Glu Asn Tyr Ala Phe Asp Tyr
1               5                   10
```

<210> SEQ ID NO 35
<211> LENGTH: 1395
<212> TYPE: DNA
<213> ORGANISM: Artificial Sequence
<220> FEATURE:
<223> OTHER INFORMATION: Humanized sequence

<400> SEQUENCE: 35

```
atggaatgga gctgggtctt tctcttcttc ctgtcagtaa ctacaggtgt ccactccgag      60
gtgcagctgg tcgagtctgg cggcggactg gtgcagcctg gcggcagcct gagactgagc     120
tgcgccgcca gcggcttcac cttcagcagc tacgccatca gctgggtgcg gcaggcccct     180
ggcaagggcc tggaatgggt ggccagcgtg agcggcaccg gcctgggctt ccagacctac     240
taccccgaca cgtgaaggg ccggttcacc atcagccggg acaacgccaa gaacagcctg     300
tacctgcaga tgaacagcct gcgggccgag gacaccgccg tgtactactg cgccacctcc     360
ctggaaaact acgccttcga ctactggggc cagggaacca cggtcaccgt ctcctcagcc     420
tccaccaagg gcccatcggt cttccccctg gcgccctgct ccaggagcac ctccgagagc     480
acagcggccc tgggctgcct ggtcaaggac tacttccccg aaccggtgac ggtgtcgtgg     540
aactcaggcg ctctgaccag cggcgtgcac accttcccgg ctgtcctaca gtcctcagga     600
ctctactccc tcagcagcgt agtgaccgtg ccctccagca cttcggcac ccagacctac      660
acctgcaacg tagatcacaa gcccagcaac accaaggtgg acaagacagt tgagcgcaaa     720
tgctgtgtcg agtgcccacc gtgcccagca ccacctgtgg caggaccgtc agtcttcctc     780
ttccccccaa aacccaagga caccctcatg atctcccgga cccctgaggt cacgtgcgtg     840
gtggtggacg tgagccacga agaccccgag gtccagttca actggtacgt ggacggcgtg     900
gaggtgcata atgccaagac aaagccacgg gaggagcagt tcaacagcac gttccgtgtg     960
gtcagcgtcc tcaccgtcgt gcaccaggac tggctgaacg gcaaggagta caagtgcaag    1020
gtctccaaca aggcctccc atcctccatc gagaaaacca tctccaaaac caaagggcag    1080
cccgagaac cacaggtgta caccctgccc ccatcccggg aggagatgac caagaaccag    1140
gtcagcctga cctgcctggt caaaggcttc taccccagcg acatcgccgt ggagtgggag    1200
agcaatgggc agccggagaa caactacaag accacacctc ccatgctgga ctccgacggc    1260
tccttcttcc tctacagcaa gctcaccgtg gacaagagca ggtggcagca ggggaacgtc    1320
ttctcatgct ccgtgatgca tgaggctctg cacaaccact acacacagaa gagcctctcc    1380
ctgtctccgg gtaaa                                                    1395
```

<210> SEQ ID NO 36
<211> LENGTH: 465
<212> TYPE: PRT
<213> ORGANISM: Artificial Sequence
<220> FEATURE:
<223> OTHER INFORMATION: Humanized sequence

<400> SEQUENCE: 36

```
Met Glu Trp Ser Trp Val Phe Leu Phe Phe Leu Ser Val Thr Thr Gly
1               5                   10                  15

Val His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Ala Ile Ser Trp Val Arg Gln Ala Pro Gly Lys Gly Leu
    50                  55                  60
```

-continued

```
Glu Trp Val Ala Ser Val Ser Gly Thr Gly Leu Gly Phe Gln Thr Tyr
 65                  70                  75                  80

Tyr Pro Asp Ser Val Lys Gly Arg Phe Thr Ile Ser Arg Asp Asn Ala
                 85                  90                  95

Lys Asn Ser Leu Tyr Leu Gln Met Asn Ser Leu Arg Ala Glu Asp Thr
                100                 105                 110

Ala Val Tyr Tyr Cys Ala Thr Ser Leu Glu Asn Tyr Ala Phe Asp Tyr
            115                 120                 125

Trp Gly Gln Gly Thr Thr Val Thr Val Ser Ser Ala Ser Thr Lys Gly
        130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Asn Phe Gly Thr Gln Thr Tyr Thr Cys Asn Val
210                 215                 220

Asp His Lys Pro Ser Asn Thr Lys Val Asp Lys Thr Val Glu Arg Lys
225                 230                 235                 240

Cys Cys Val Glu Cys Pro Pro Cys Pro Ala Pro Pro Val Ala Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Gln Phe Asn Trp Tyr Val Asp Gly Val Glu Val His Asn
290                 295                 300

Ala Lys Thr Lys Pro Arg Glu Glu Gln Phe Asn Ser Thr Phe Arg Val
305                 310                 315                 320

Val Ser Val Leu Thr Val Val His Gln Asp Trp Leu Asn Gly Lys Glu
                325                 330                 335

Tyr Lys Cys Lys Val Ser Asn Lys Gly Leu Pro Ser Ser Ile Glu Lys
            340                 345                 350

Thr Ile Ser Lys Thr Lys Gly Gln Pro Arg Glu Pro Gln Val Tyr Thr
        355                 360                 365

Leu Pro Pro Ser Arg Glu Glu Met Thr Lys Asn Gln Val Ser Leu Thr
370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Met Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
450                 455                 460

Lys
465
```

<210> SEQ ID NO 37
<211> LENGTH: 714
<212> TYPE: DNA
<213> ORGANISM: Artificial Sequence
<220> FEATURE:
<223> OTHER INFORMATION: Humanized sequence

<400> SEQUENCE: 37

```
atgagtgtgc ccactcaggt cctggggttg ctgctgctgt ggcttacaga tgccagatgt      60
gagatcgtgc tgacccagag ccccgccacc ctgagcctga gccctggcga gcgggccacc     120
ctgtcctgcc gggccagcga gagcgtggac gacttcggca tcagcttcat caactggtat     180
cagcagaagc ccggccaggc ccccagactg ctcatctacg ccggcagcaa gagggcagc      240
ggcatccccg ccaggttcag cggcagcggc tccggcaccg acttcaccct gaccatctcc     300
agcctcgaac ccgaggactt cgccgtgtac tactgccagc agctgaaaga ggtgcccccc     360
accttcggcg gtgggaccaa ggtggaaatc aaacgaactg tggctgcacc atctgtcttc     420
atcttcccgc catctgatga gcagttgaaa tctggaactg cctctgttgt gtgcctgctg     480
aataacttct atcccagaga ggccaaagta cagtggaagg tggataacgc cctccaatcg     540
ggtaactccc aggagagtgt cacagagcag gacagcaagg acagcaccta cagcctcagc     600
agcaccctga cgctgagcaa agcagactac gagaaacaca agtctacgc ctgcgaagtc      660
acccatcagg gcctgagctc gcccgtcaca aagagcttca caggggaga gtgt             714
```

<210> SEQ ID NO 38
<211> LENGTH: 238
<212> TYPE: PRT
<213> ORGANISM: Artificial Sequence
<220> FEATURE:
<223> OTHER INFORMATION: Humanized sequence

<400> SEQUENCE: 38

Met Ser Val Pro Thr Gln Val Leu Gly Leu Leu Leu Trp Leu Thr
1               5                   10                  15

Asp Ala Arg Cys Glu Ile Val Leu Thr Gln Ser Pro Ala Thr Leu Ser
            20                  25                  30

Leu Ser Pro Gly Glu Arg Ala Thr Leu Ser Cys Arg Ala Ser Glu Ser
        35                  40                  45

Val Asp Asp Phe Gly Ile Ser Phe Ile Asn Trp Tyr Gln Gln Lys Pro
    50                  55                  60

Gly Gln Ala Pro Arg Leu Leu Ile Tyr Ala Gly Ser Lys Gln Gly Ser
65                  70                  75                  80

Gly Ile Pro Ala Arg Phe Ser Gly Ser Gly Ser Gly Thr Asp Phe Thr
                85                  90                  95

Leu Thr Ile Ser Ser Leu Glu Pro Glu Asp Phe Ala Val Tyr Tyr Cys
            100                 105                 110

Gln Gln Leu Lys Glu Val Pro Pro Thr Phe Gly Gly Gly Thr Lys Val
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 39
<211> LENGTH: 1338
<212> TYPE: DNA
<213> ORGANISM: Artificial Sequence
<220> FEATURE:
<223> OTHER INFORMATION: Humanized sequence

<400> SEQUENCE: 39

| | |
|---|---|
| gaggtgcagc tggtcgagtc tggcggcgga ctggtgcagc ctggcggcag cctgagactg | 60 |
| agctgcgccg ccagcggctt caccttcagc agctacgcca tcagctgggt gcggcaggcc | 120 |
| cctggcaagg gcctggaatg gtggccagc gtgagcggca ccggcctggg cttccagacc | 180 |
| tactacccg acagcgtgaa gggccggttc accatcagcc gggacaacgc caagaacagc | 240 |
| ctgtacctgc agatgaacag cctgcgggcc gaggacaccg ccgtgtacta ctgcgccacc | 300 |
| tccctggaaa actacgcctt cgactactgg ggccagggaa ccacggtcac cgtctcctca | 360 |
| gcctccacca agggcccatc ggtcttcccc ctggcgccct gctccaggag cacctccgag | 420 |
| agcacagcgg ccctgggctg cctggtcaag gactacttcc ccgaaccggt gacggtgtcg | 480 |
| tggaactcag gcgctctgac cagcggcgtg cacaccttcc cggctgtcct acagtcctca | 540 |
| ggactctact ccctcagcag cgtagtgacc gtgccctcca gcaacttcgg cacccagacc | 600 |
| tacacctgca acgtagatca caagcccagc aacaccaagg tggacaagac agttgagcgc | 660 |
| aaatgctgtg tcgagtgccc accgtgccca gcaccacctg tggcaggacc gtcagtcttc | 720 |
| ctcttccccc caaaacccaa ggacaccctc atgatctccc ggacccctga ggtcacgtgc | 780 |
| gtggtggtgg acgtgagcca cgaagacccc gaggtccagt tcaactggta cgtggacggc | 840 |
| gtggaggtgc ataatgccaa gacaaagcca cgggaggagc agttcaacag cacgttccgt | 900 |
| gtggtcagcg tcctcaccgt cgtgcaccag gactggctga acggcaagga gtacaagtgc | 960 |
| aaggtctcca acaaaggcct cccatcctcc atcgagaaaa ccatctccaa aaccaaaggg | 1020 |
| cagccccgag aaccacaggt gtacaccctg cccccatccc gggaggagat gaccaagaac | 1080 |
| caggtcagcc tgacctgcct ggtcaaaggc ttctacccca gcgacatcgc cgtggagtgg | 1140 |
| gagagcaatg ggcagccgga gaacaactac aagaccacac tcccatgct ggactccgac | 1200 |
| ggctccttct tcctctacag caagctcacc gtggacaaga gcaggtggca gcaggggaac | 1260 |
| gtcttctcat gctccgtgat gcatgaggct ctgcacaacc actacacaca gaagagcctc | 1320 |
| tccctgtctc cgggtaaa | 1338 |

<210> SEQ ID NO 40
<211> LENGTH: 446
<212> TYPE: PRT
<213> ORGANISM: Artificial Sequence
<220> FEATURE:
<223> OTHER INFORMATION: Humanized sequence

<400> SEQUENCE: 40

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ala Ile Ser Trp Val Arg Gln Ala Pro Gly Lys Gly Leu Glu Trp Val
         35                  40                  45

Ala Ser Val Ser Gly Thr Gly Leu Gly Phe Gln Thr Tyr Tyr Pro Asp
     50                  55                  60

Ser Val Lys Gly Arg Phe Thr Ile Ser Arg Asp Asn Ala Lys Asn Ser
 65                  70                  75                  80

Leu Tyr Leu Gln Met Asn Ser Leu Arg Ala Glu Asp Thr Ala Val Tyr
             85                  90                  95

Tyr Cys Ala Thr Ser Leu Glu Asn Tyr Ala Phe Asp Tyr Trp Gly Gln
            100                 105                 110

Gly Thr Thr Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
            195                 200                 205

Pro Ser Asn Thr Lys Val Asp Lys Thr Val Glu Arg Lys Cys Cys Val
210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Phe Arg Val Val Ser Val
290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415
```

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
            435                 440                 445

<210> SEQ ID NO 41
<211> LENGTH: 654
<212> TYPE: DNA
<213> ORGANISM: Artificial Sequence
<220> FEATURE:
<223> OTHER INFORMATION: Humanized sequence

<400> SEQUENCE: 41
gagatcgtgc tgacccagag ccccgccacc ctgagcctga gccctggcga gcgggccacc    60
ctgtcctgcc gggccagcga gagcgtggac gacttcggca tcagcttcat caactggtat   120
cagcagaagc ccggccaggc ccccagactg ctcatctacg ccggcagcaa gggggcagc    180 ggcatccccg ccaggttcag cggcagcggc tccggcaccg acttcaccct gaccatctcc   240
agcctcgaac ccgaggactt cgccgtgtac tactgccagc agctgaaaga ggtgcccccc   300
accttcggcg gtgggaccaa ggtggaaatc aaacgaactg tggctgcacc atctgtcttc   360
atcttcccgc catctgatga gcagttgaaa tctggaactg cctctgttgt gtgcctgctg   420
aataacttct atcccagaga ggccaaagta cagtggaagg tggataacgc cctccaatcg   480
ggtaactccc aggagagtgt cacagagcag gacagcaagg acagcaccta cagcctcagc   540
agcaccctga cgctgagcaa agcagactac gagaaacaca agtctacgc ctgcgaagtc    600 acccatcagg gcctgagctc gcccgtcaca aagagcttca caggggagag tgt           654

<210> SEQ ID NO 42
<211> LENGTH: 218
<212> TYPE: PRT
<213> ORGANISM: Artificial Sequence
<220> FEATURE:
<223> OTHER INFORMATION: Humanized sequence

<400> SEQUENCE: 42

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asp Phe
            20                  25                  30

Gly Ile Ser Phe Ile Asn Trp Tyr Gln Gln Lys Pro Gly Gln Ala Pro
        35                  40                  45

Arg Leu Leu Ile Tyr Ala Gly Ser Lys Gln Gly Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Leu Lys
                85                  90                  95

Glu Val Pro Pro Thr Phe Gly Gly Gly Thr Lys Val Glu Ile Lys Arg
            100                 105                 110

Thr Val Ala Ala Pro Ser Val Phe Ile Phe Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

```
Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
            210                 215

<210> SEQ ID NO 43
<211> LENGTH: 218
<212> TYPE: PRT
<213> ORGANISM: Artificial Sequence
<220> FEATURE:
<223> OTHER INFORMATION: Chimeric human mouse sequence

<400> SEQUENCE: 43

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asp Phe
            20                  25                  30

Gly Ile Ser Phe Ile Asn Trp Tyr Gln Gln Lys Pro Gly Gln Ala Pro
        35                  40                  45

Arg Leu Leu Ile Tyr Ala Gly Ser Lys Gln Gly Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Leu Lys
                85                  90                  95

Glu Val Pro Pro Thr Phe Gly Gly Gly Thr Lys Val Glu Ile Lys Arg
            100                 105                 110

Ala Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
    210                 215

<210> SEQ ID NO 44
<211> LENGTH: 444
<212> TYPE: PRT
<213> ORGANISM: Artificial Sequence
<220> FEATURE:
<223> OTHER INFORMATION: Chimeric human mouse sequence

<400> SEQUENCE: 44

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Ile Ser Trp Val Arg Gln Ala Pro Gly Lys Gly Leu Glu Trp Val
        35                  40                  45
```

Ala Ser Val Ser Gly Thr Gly Leu Gly Phe Gln Thr Tyr Tyr Pro Asp
 50                  55                  60

Ser Val Lys Gly Arg Phe Thr Ile Ser Arg Asp Asn Ala Lys Asn Ser
 65                  70                  75                  80

Leu Tyr Leu Gln Met Asn Ser Leu Arg Ala Glu Asp Thr Ala Val Tyr
                 85                  90                  95

Tyr Cys Ala Thr Ser Leu Glu Asn Tyr Ala Phe Asp Tyr Trp Gly Gln
            100                 105                 110

Gly Thr Thr Val Thr Val Ser Ala Lys Thr Thr Pro Pro Ser Val
        115                 120                 125

Tyr Pro Leu Ala Pro Gly Ser Ala Gln Thr Asn Ser Met Val Thr
130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Val Thr Val Pro Ser
            180                 185                 190

Ser Thr Trp Pro Ser Glu Thr Val Thr Cys Asn Val Ala His Pro Ala
        195                 200                 205

Ser Ser Thr Lys Val Asp Lys Lys Ile Val Pro Arg Asp Cys Gly Cys
210                 215                 220

Lys Pro Cys Ile Cys Thr Val Pro Glu Val Ser Ser Val Phe Ile Phe
225                 230                 235                 240

Pro Pro Lys Pro Lys Asp Val Leu Thr Ile Thr Leu Thr Pro Lys Val
                245                 250                 255

Thr Cys Val Val Val Asp Ile Ser Lys Asp Asp Pro Glu Val Gln Phe
            260                 265                 270

Ser Trp Phe Val Asp Asp Val Glu Val His Thr Ala Gln Thr Gln Pro
        275                 280                 285

Arg Glu Glu Gln Phe Asn Ser Thr Phe Arg Ser Val Ser Glu Leu Pro
290                 295                 300

Ile Met His Gln Asp Trp Leu Asn Gly Lys Glu Phe Lys Cys Arg Val
305                 310                 315                 320

Asn Ser Ala Ala Phe Pro Ala Pro Ile Glu Lys Thr Ile Ser Lys Thr
                325                 330                 335

Lys Gly Arg Pro Lys Ala Pro Gln Val Tyr Thr Ile Pro Pro Pro Lys
            340                 345                 350

Glu Gln Met Ala Lys Asp Lys Val Ser Leu Thr Cys Met Ile Thr Asp
        355                 360                 365

Phe Phe Pro Glu Asp Ile Thr Val Glu Trp Gln Trp Asn Gly Gln Pro
370                 375                 380

Ala Glu Asn Tyr Lys Asn Thr Gln Pro Ile Met Asn Thr Asn Gly Ser
385                 390                 395                 400

Tyr Phe Val Tyr Ser Lys Leu Asn Val Gln Lys Ser Asn Trp Glu Ala
                405                 410                 415

Gly Asn Thr Phe Thr Cys Ser Val Leu His Glu Gly Leu His Asn His
            420                 425                 430

His Thr Glu Lys Ser Leu Ser His Ser Pro Gly Lys
        435                 440

<210> SEQ ID NO 45
<211> LENGTH: 333
<212> TYPE: DNA
<213> ORGANISM: Artificial Sequence
<220> FEATURE:
<223> OTHER INFORMATION: Humanized sequence

<400> SEQUENCE: 45

```
gagatcgtgc tgacccagag ccccgccacc ctgagcctga gccctggcga gcgggccacc    60
ctgtcctgcc gggccagcga gagcgtggac gacttcggca tcagcttcat caactggtat   120
cagcagaagc ccggccaggc ccccagactg ctcatctacg ccggcagcaa cagggcagc    180
ggcatccccg ccaggttcag cggcagcggc tccggcaccg acttcaccct gaccatctcc   240
agcctcgaac ccgaggactt cgccgtgtac tactgccagc agctgaaaga ggtgcccccc   300
accttcggcg gtgggaccaa ggtggaaatc aaa                                333
```

<210> SEQ ID NO 46
<211> LENGTH: 321
<212> TYPE: DNA
<213> ORGANISM: Artificial Sequence
<220> FEATURE:
<223> OTHER INFORMATION: Chimeric human mouse sequence

<400> SEQUENCE: 46

```
gctgatgctg caccaactgt atccatcttc ccaccatcca gtgagcagtt aacatctgga    60
ggtgcctcag tcgtgtgctt cttgaacaac ttctacccca agacatcaa tgtcaagtgg   120
aagattgatg gcagtgaacg acaaaatggc gtcctgaaca gttggactga tcaggacagc   180
aaagacagca cctacagcat gagcagcacc ctcacgttga ccaaggacga gtatgaacga   240
cataacagct atacctgtga ggccactcac aagacatcaa cttcacccat tgtcaagagc   300
ttcaacagga atgagtgtta g                                             321
```

<210> SEQ ID NO 47
<211> LENGTH: 360
<212> TYPE: DNA
<213> ORGANISM: Artificial Sequence
<220> FEATURE:
<223> OTHER INFORMATION: Chimeric human mouse sequence

<400> SEQUENCE: 47

```
gaggtgcagc tggtcgagtc tggcggcgga ctggtgcagc ctggcggcag cctgagactg    60
agctgcgccg ccagcggctt caccttcagc agctacgcca tcagctgggt gcggcaggcc   120
cctggcaagg gcctggaatg ggtggccagc gtgagcggca ccggcctggg cttccagacc   180
tactaccccg acagcgtgaa gggccggttc accatcagcc gggacaacgc caagaacagc   240
ctgtacctgc agatgaacag cctgcgggcc gaggacaccg ccgtgtacta ctgcgccacc   300
tccctggaaa actacgcctt cgactactgg ggccagggaa ccacggtcac cgtctcctca   360
```

<210> SEQ ID NO 48
<211> LENGTH: 975
<212> TYPE: DNA
<213> ORGANISM: Artificial Sequence
<220> FEATURE:
<223> OTHER INFORMATION: Chimeric human mouse sequence

<400> SEQUENCE: 48

```
gccaaaacga cacccccatc tgtctatcca ctggcccctg gatctgctgc ccaaactaac    60
tccatggtga ccctgggatg cctggtcaag ggctatttcc ctgagccagt gacagtgacc   120
tggaactctg gatccctgtc cagcggtgtg cacaccttcc cagctgtcct ggagtctgac   180
ctctacactc tgagcagctc agtgactgtc ccctccagcc ctcggcccag cgagaccgtc   240
```

-continued

```
acctgcaacg ttgcccaccc ggccagcagc accaaggtgg acaagaaaat tgtgcccagg      300
gattgtggtt gtaagccttg catatgtaca gtcccagaag tatcatctgt cttcatcttc      360
cccccaaagc ccaaggatgt gctcaccatt actctgactc ctaaggtcac gtgtgttgtg      420
gtagacatca gcaaggatga tcccgaggtc cagttcagct ggtttgtaga tgatgtggag      480
gtgcacacag ctcagacgca accccgggag gagcagttca acagcacttt ccgctcagtc      540
agtgaacttc ccatcatgca ccaggactgg ctcaatggca aggagttcaa atgcagggtc      600
aacagtgcag ctttccctgc ccccatcgag aaaaccatct ccaaaccaa aggcagaccg      660
aaggctccac aggtgtacac cattccacct cccaaggagc agatggccaa ggataaagtc      720
agtctgacct gcatgataac agacttcttc cctgaagaca ttactgtgga gtggcagtgg      780
aatgggcagc cagcggagaa ctacaagaac actcagccca tcatgaacac gaatggctct      840
tacttcgtct acagcaagct caatgtgcag aagagcaact gggaggcagg aaatactttc      900
acctgctctg tgttacatga gggcctgcac aaccaccata ctgagaagag cctctcccac      960
tctcctggta aatga                                                       975
```

<210> SEQ ID NO 49
<211> LENGTH: 5
<212> TYPE: PRT
<213> ORGANISM: Artificial Sequence
<220> FEATURE:
<223> OTHER INFORMATION: huMabJC18 Kabat heavy chain CDR1

<400> SEQUENCE: 49

Ser Tyr Ala Ile Ser
1               5

<210> SEQ ID NO 50
<211> LENGTH: 7
<212> TYPE: PRT
<213> ORGANISM: Artificial Sequence
<220> FEATURE:
<223> OTHER INFORMATION: huMabJC18 Chothia heavy chain CDR1

<400> SEQUENCE: 50

Gly Phe Thr Phe Ser Ser Tyr
1               5

<210> SEQ ID NO 51
<211> LENGTH: 12
<212> TYPE: PRT
<213> ORGANISM: Artificial Sequence
<220> FEATURE:
<223> OTHER INFORMATION: huMabJC18 Chothia heavy chain CDR2

<400> SEQUENCE: 51

Ser Val Ser Gly Thr Gly Leu Gly Phe Gln Thr Tyr
1               5                   10

<210> SEQ ID NO 52
<211> LENGTH: 9
<212> TYPE: PRT
<213> ORGANISM: Artificial Sequence
<220> FEATURE:
<223> OTHER INFORMATION: huMabJC18 Chothia heavy chain CDR3

<400> SEQUENCE: 52

Ser Leu Glu Asn Tyr Ala Phe Asp Tyr
1               5